United States Patent
Knox et al.

(10) Patent No.: US 11,931,264 B2
(45) Date of Patent: Mar. 19, 2024

(54) MODULAR HUMERAL HEAD

(71) Applicant: HOWMEDICA OSTEONICS CORP., Mahwah, NJ (US)

(72) Inventors: Kevin P. Knox, Fort Wayne, IN (US); Austin Wyatt Mutchler, Warsaw, IN (US); Michael C. Nelson, Syracuse, IN (US); David R. Stump, Columbia City, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 519 days.

(21) Appl. No.: 17/278,495

(22) PCT Filed: Oct. 1, 2019

(86) PCT No.: PCT/US2019/054023
§ 371 (c)(1),
(2) Date: Mar. 22, 2021

(87) PCT Pub. No.: WO2020/072465
PCT Pub. Date: Apr. 9, 2020

(65) Prior Publication Data
US 2022/0031464 A1 Feb. 3, 2022

Related U.S. Application Data

(60) Provisional application No. 62/740,342, filed on Oct. 2, 2018.

(51) Int. Cl.
*A61F 2/40* (2006.01)
*A61F 2/30* (2006.01)
(52) U.S. Cl.
CPC .......... *A61F 2/4014* (2013.01); *A61F 2/4003* (2013.01); *A61F 2002/30339* (2013.01);
(Continued)

(58) Field of Classification Search
CPC ...................... A61F 2/4003; A61F 2002/4007
See application file for complete search history.

(56) References Cited

U.S. PATENT DOCUMENTS

| 4,310,931 A | 1/1982 | Muller |
| 5,314,479 A | 5/1994 | Rockwood, Jr. et al. |

(Continued)

FOREIGN PATENT DOCUMENTS

| DE | 102008010478 | 8/2009 |
| EP | 1402854 | 3/2004 |

(Continued)

OTHER PUBLICATIONS

International Search Report and Written Opinion for PCT/US2018/024824 dated Jul. 10, 2018 in 12 pages.

(Continued)

*Primary Examiner* — Megan Y Wolf
(74) *Attorney, Agent, or Firm* — DUANE MORRIS LLP

(57) ABSTRACT

A humeral head assembly is provided that includes an articular body and a coupler. The articular body includes a coupling portion disposed on a side of the articular body opposite an articular surface. The coupling portion includes a continuous zone of eccentricity adjustment. The coupler portion optionally includes one or more than one discrete position site. The coupler includes a first portion and a second portion opposite the first portion. The first portion is configured to mate with the coupling portion and the second portion is configured to mate with another member of a joint prosthesis. A coupling portion with the continuous range of eccentricity adjustment can be provided on a bone anchor and the eccentricity of another component can be selected by motion of a coupler, such as a tray for reverse humeral assemblies, along the coupling portion of the anchor.

18 Claims, 73 Drawing Sheets

(52) U.S. Cl.
CPC ............... *A61F 2002/30385* (2013.01); *A61F 2002/30405* (2013.01); *A61F 2002/30433* (2013.01); *A61F 2002/30538* (2013.01); *A61F 2002/3054* (2013.01); *A61F 2002/30604* (2013.01); *A61F 2002/30617* (2013.01); *A61F 2002/4018* (2013.01)

(56) References Cited

U.S. PATENT DOCUMENTS

| | | | |
|---|---|---|---|
| 5,358,526 A | 10/1994 | Tornier et al. | |
| 5,480,451 A * | 1/1996 | Grundei | A61F 2/3609 |
| | | | 623/22.43 |
| 5,910,171 A | 6/1999 | Kummer et al. | |
| 6,187,012 B1 | 2/2001 | Masini | |
| 6,197,062 B1 | 3/2001 | Fenlin | |
| 6,197,063 B1 | 3/2001 | Dews | |
| 6,436,147 B1 | 8/2002 | Zweymuller | |
| 6,530,957 B1 | 3/2003 | Jack | |
| 6,626,946 B1 | 9/2003 | Walch et al. | |
| 6,673,114 B2 | 1/2004 | Hartdegen et al. | |
| 6,676,705 B1 | 1/2004 | Wolf | |
| 6,719,799 B1 | 4/2004 | Kropf | |
| 6,736,851 B2 | 5/2004 | Maroney et al. | |
| 6,749,637 B1 | 6/2004 | Bahler | |
| 6,899,736 B1 | 5/2005 | Rauscher et al. | |
| 6,942,699 B2 | 9/2005 | Stone et al. | |
| 7,175,663 B1 | 2/2007 | Stone et al. | |
| 7,189,261 B2 | 3/2007 | Dews et al. | |
| 7,431,736 B2 | 10/2008 | Maroney et al. | |
| 7,621,961 B2 | 11/2009 | Stone et al. | |
| 7,758,650 B2 | 7/2010 | Dews et al. | |
| 7,819,923 B2 | 10/2010 | Stone et al. | |
| 7,854,768 B2 | 12/2010 | Wiley et al. | |
| 8,002,838 B2 | 8/2011 | Klotz | |
| 8,052,758 B1 | 11/2011 | Winslow | |
| 8,062,376 B2 | 11/2011 | Shultz et al. | |
| 8,070,820 B2 | 12/2011 | Winslow et al. | |
| 8,236,059 B2 | 8/2012 | Stone et al. | |
| 8,246,687 B2 | 8/2012 | Katrana et al. | |
| 8,647,387 B2 | 2/2014 | Winslow | |
| 8,702,804 B2 | 4/2014 | Smith et al. | |
| 8,734,457 B2 | 5/2014 | Bailey et al. | |
| 8,771,362 B2 | 7/2014 | Isch et al. | |
| 8,795,379 B2 | 8/2014 | Smith et al. | |
| 8,876,908 B2 | 11/2014 | Katrana et al. | |
| 8,906,103 B2 | 12/2014 | Stone et al. | |
| 8,968,415 B2 | 3/2015 | Meridew et al. | |
| 9,241,803 B2 | 1/2016 | Stone et al. | |
| 9,283,083 B2 | 3/2016 | Winslow et al. | |
| 9,326,862 B2 | 5/2016 | Smith et al. | |
| 9,408,704 B2 | 8/2016 | Metzger | |
| 9,498,344 B2 | 11/2016 | Hodorek et al. | |
| 9,566,162 B2 | 2/2017 | Isch | |
| 9,693,880 B2 | 7/2017 | Anthony et al. | |
| 10,022,229 B2 | 7/2018 | Cappelletti | |
| 10,070,967 B2 | 9/2018 | Chavarria et al. | |
| 10,226,349 B2 | 3/2019 | Sperling et al. | |
| 10,368,998 B2 | 8/2019 | Chavarria et al. | |
| 10,368,999 B2 | 8/2019 | Greiwe | |
| 10,390,972 B2 | 8/2019 | Rao | |
| 10,433,969 B2 | 10/2019 | Humphrey | |
| 2001/0011193 A1 | 8/2001 | Nogarin | |
| 2002/0156534 A1 | 10/2002 | Kelley et al. | |
| 2003/0028253 A1 | 2/2003 | Stone et al. | |
| 2003/0097183 A1 | 5/2003 | Rauscher et al. | |
| 2004/0064190 A1 | 4/2004 | Ball et al. | |
| 2005/0049713 A1 * | 3/2005 | Garber | A61F 2/34 |
| | | | 623/22.21 |
| 2005/0071014 A1 | 3/2005 | Barnett et al. | |
| 2006/0020344 A1 | 1/2006 | Shultz et al. | |
| 2006/0069445 A1 | 3/2006 | Ondrla et al. | |
| 2007/0162140 A1 | 7/2007 | McDevitt | |
| 2007/0173945 A1 | 7/2007 | Wiley et al. | |
| 2007/0179624 A1 | 8/2007 | Stone et al. | |
| 2007/0225821 A1 | 9/2007 | Reubelt et al. | |
| 2008/0228281 A1 | 9/2008 | Forrer et al. | |
| 2009/0281630 A1 | 11/2009 | Delince et al. | |
| 2009/0312838 A1 | 12/2009 | Klotz | |
| 2011/0060417 A1 | 3/2011 | Simmen et al. | |
| 2011/0060418 A1 | 3/2011 | Bailey et al. | |
| 2011/0295376 A1 | 12/2011 | Winslow | |
| 2012/0143204 A1 | 6/2012 | Blaycock et al. | |
| 2012/0232667 A1 | 9/2012 | Katrana et al. | |
| 2013/0090736 A1 | 4/2013 | Katrana et al. | |
| 2013/0150975 A1 * | 6/2013 | Iannotti | A61F 2/4059 |
| | | | 623/19.11 |
| 2013/0197652 A1 | 8/2013 | Ekelund et al. | |
| 2014/0236304 A1 | 8/2014 | Hodorek et al. | |
| 2014/0277518 A1 | 9/2014 | Iannotti | |
| 2015/0265411 A1 | 9/2015 | Deransart et al. | |
| 2016/0213480 A1 | 7/2016 | Stone et al. | |
| 2016/0262902 A1 | 9/2016 | Winslow et al. | |
| 2016/0324648 A1 | 11/2016 | Hodorek et al. | |
| 2016/0361173 A1 | 12/2016 | Reubelt et al. | |
| 2017/0049573 A1 | 2/2017 | Hodorek et al. | |
| 2017/0056187 A1 | 3/2017 | Humphrey et al. | |
| 2018/0271667 A1 | 9/2018 | Kemp et al. | |
| 2018/0368982 A1 | 12/2018 | Ball | |
| 2019/0274835 A1 | 9/2019 | Wiley et al. | |
| 2021/0228372 A1 | 7/2021 | Knox et al. | |

FOREIGN PATENT DOCUMENTS

| | | |
|---|---|---|
| EP | 1415621 | 5/2004 |
| EP | 1782765 | 5/2007 |
| EP | 2604225 | 6/2013 |
| FR | 2652498 | 4/1991 |
| FR | 2773469 | 7/1999 |
| JP | 2003517337 A | 5/2003 |
| JP | 2009523578 A | 6/2009 |
| JP | 2009297515 A | 12/2009 |
| JP | 2011512926 A | 4/2011 |
| WO | WO 93/09733 | 5/1993 |
| WO | WO 96/17553 | 6/1996 |
| WO | WO 2003/005933 | 1/2003 |
| WO | 2007084939 A2 | 7/2007 |
| WO | WO 2008/000928 | 1/2008 |
| WO | WO 2013/064569 | 5/2013 |
| WO | WO 2014/067961 | 5/2014 |
| WO | 2016094739 A1 | 6/2016 |
| WO | WO 2018/183484 | 10/2018 |
| WO | WO 2019/079104 | 4/2019 |
| WO | WO 2020/072465 | 4/2020 |

OTHER PUBLICATIONS

International Search Report and Written Opinion for PCT/US2019/054023 dated Apr. 1, 2020 in 22 pages.
First Office Action issued in connection in Japanese Patent Application No. 2021-518133, dated May 31, 2022, 6 pages.
First Examination Report issued in connection with Australian Patent Application No. 2022202353, dated Jun. 13, 2023, 5 pages.
Notice of Allowance issued in connection with U.S. Appl. No. 15/938,214, dated Aug. 23, 2021, 13 pages.
First Office Action issued in connection with Japanese Patent Application No. 2022-176514, dated Sep. 5, 2023, 3 pages.

* cited by examiner

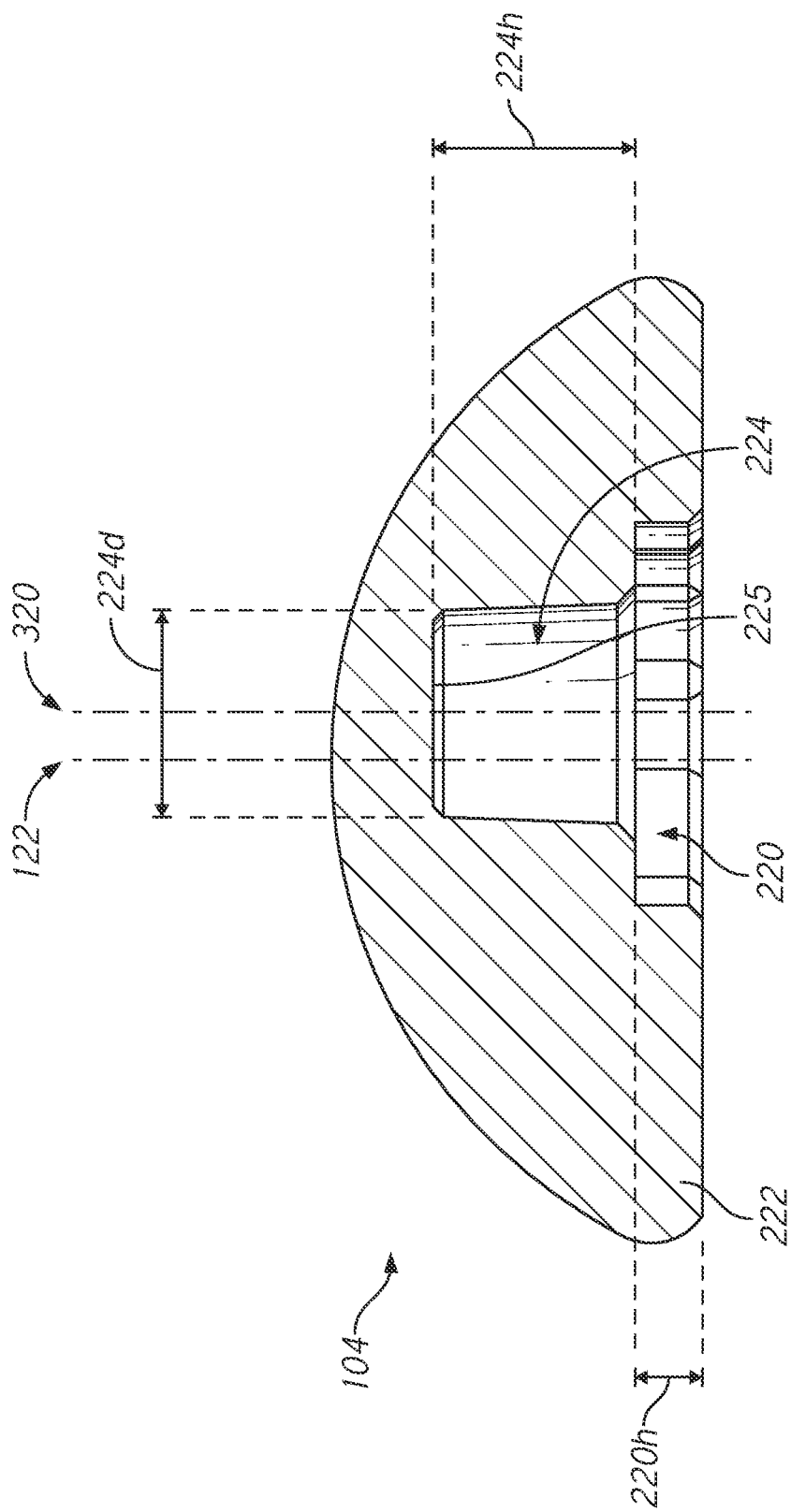

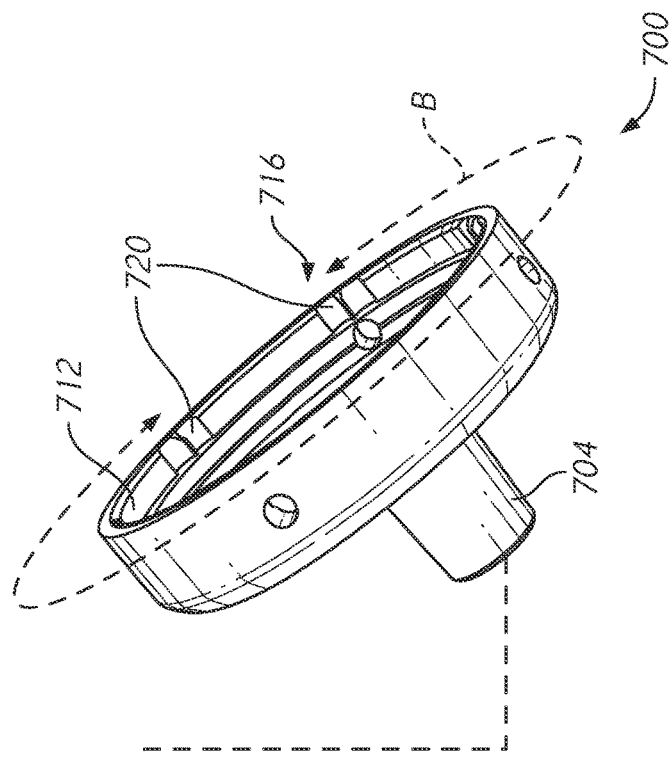
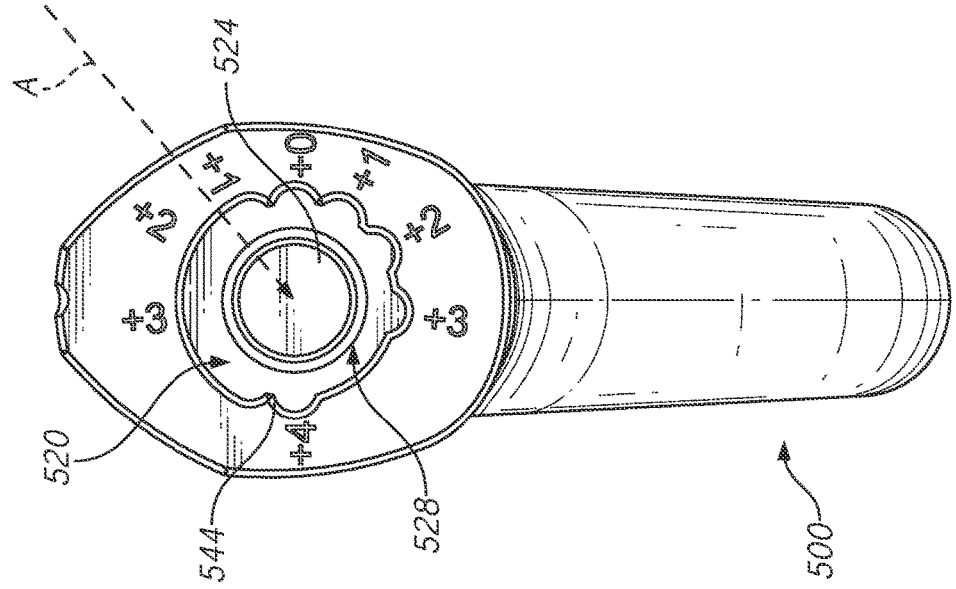
FIG. 14A

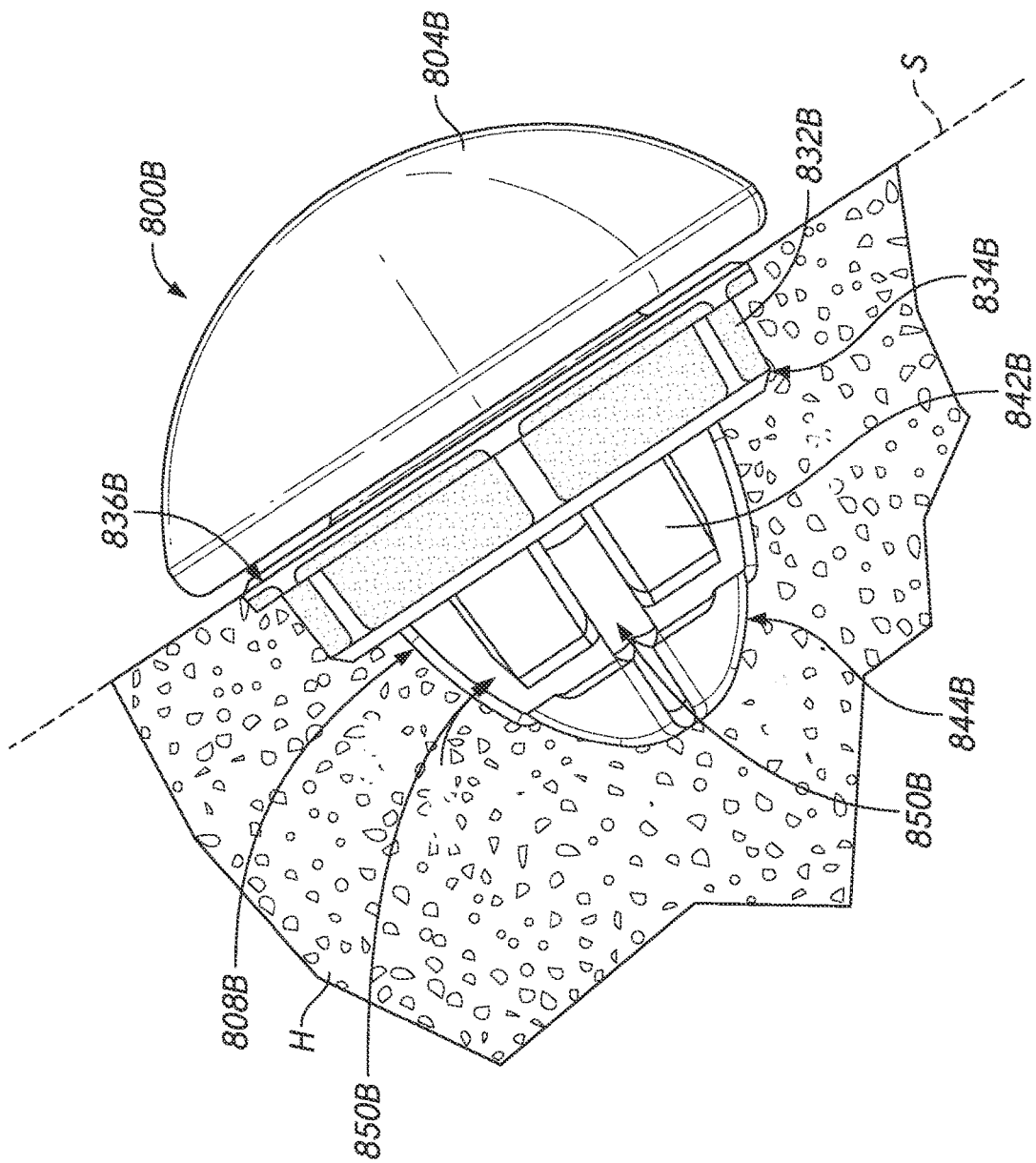

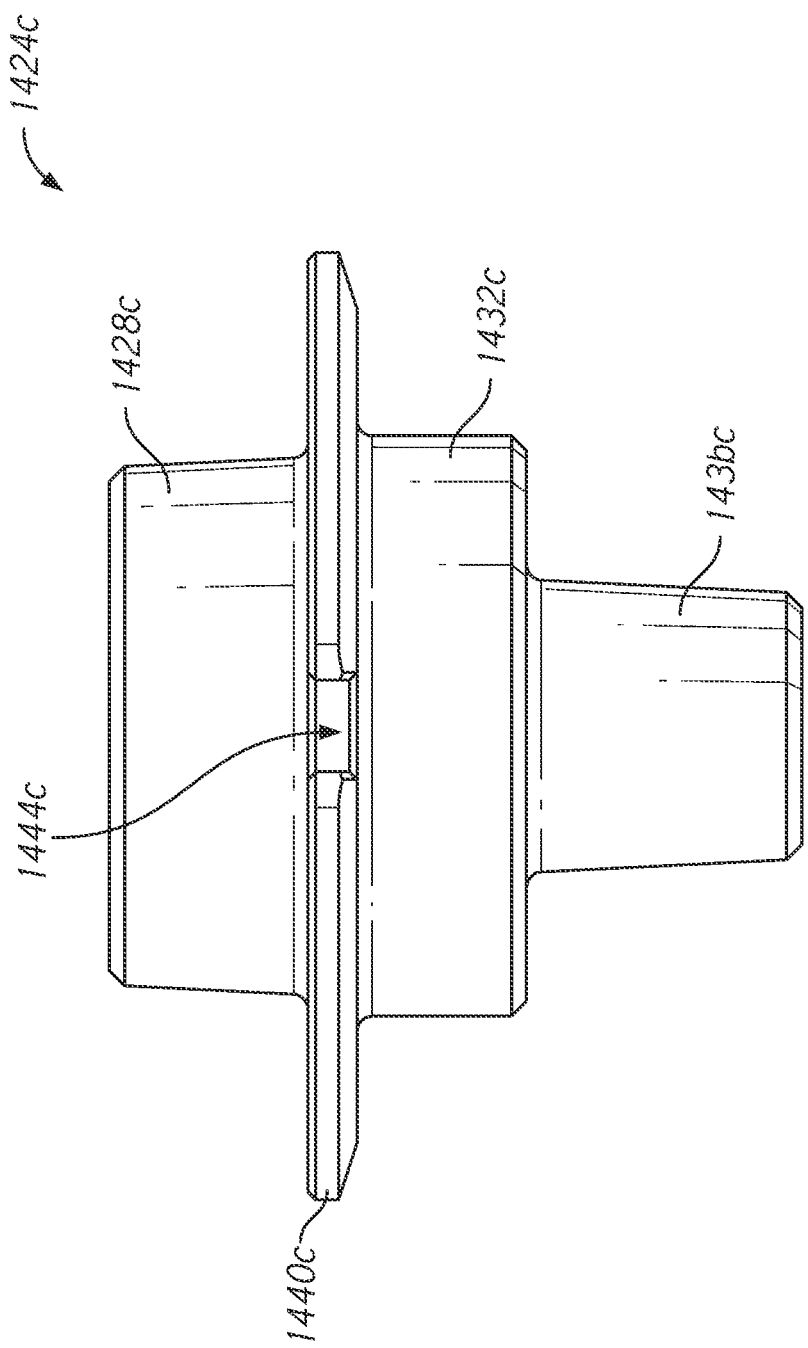

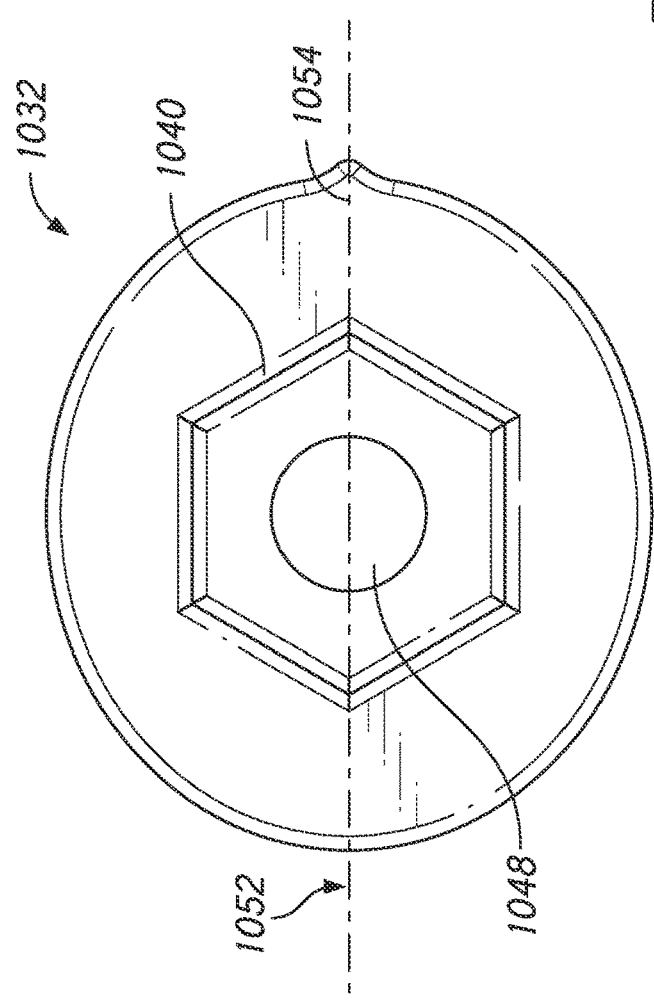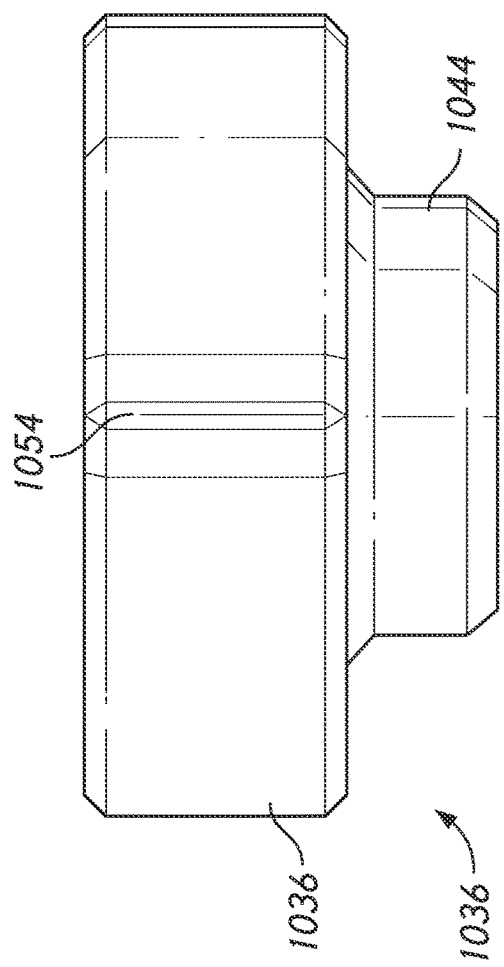

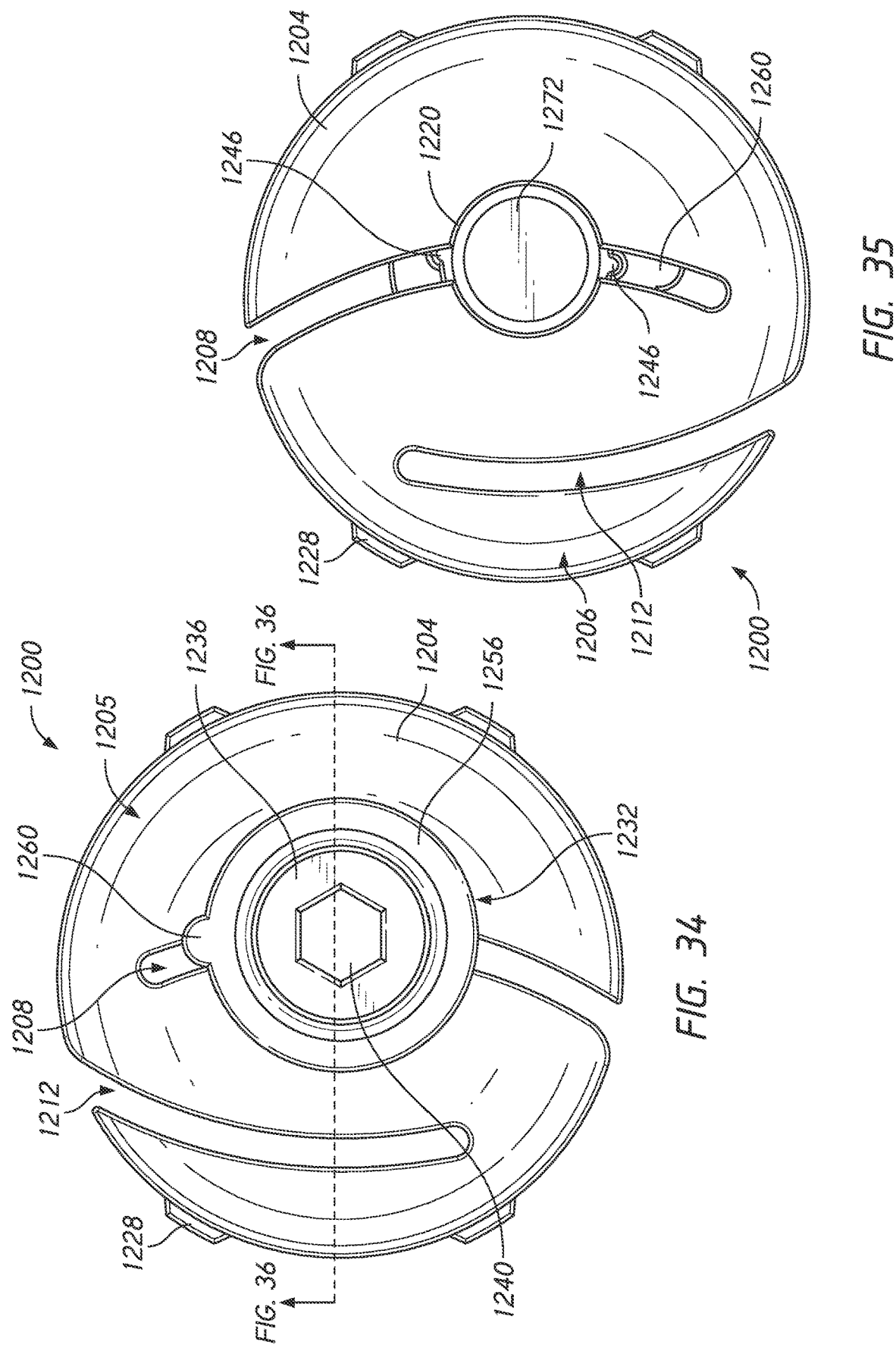

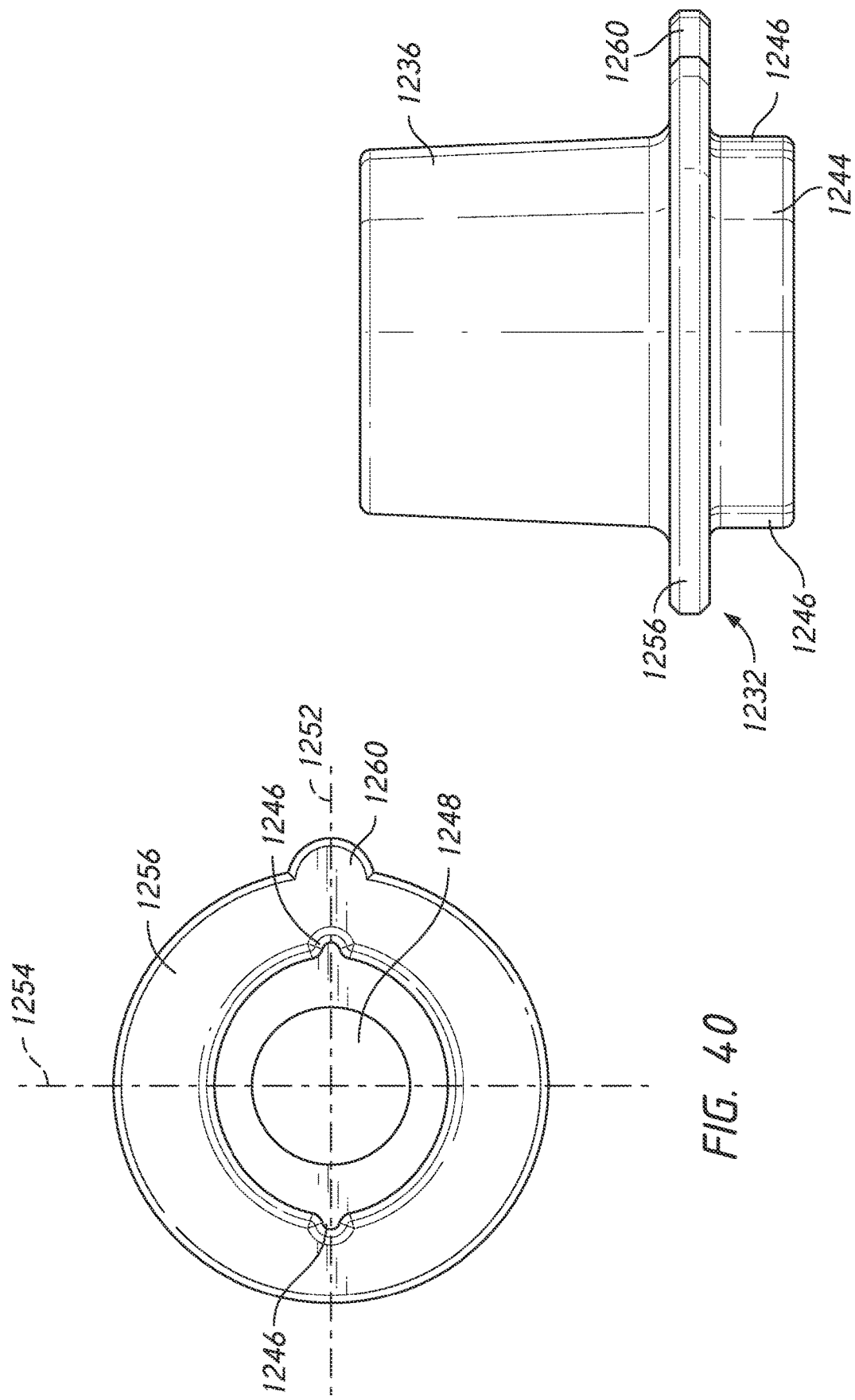

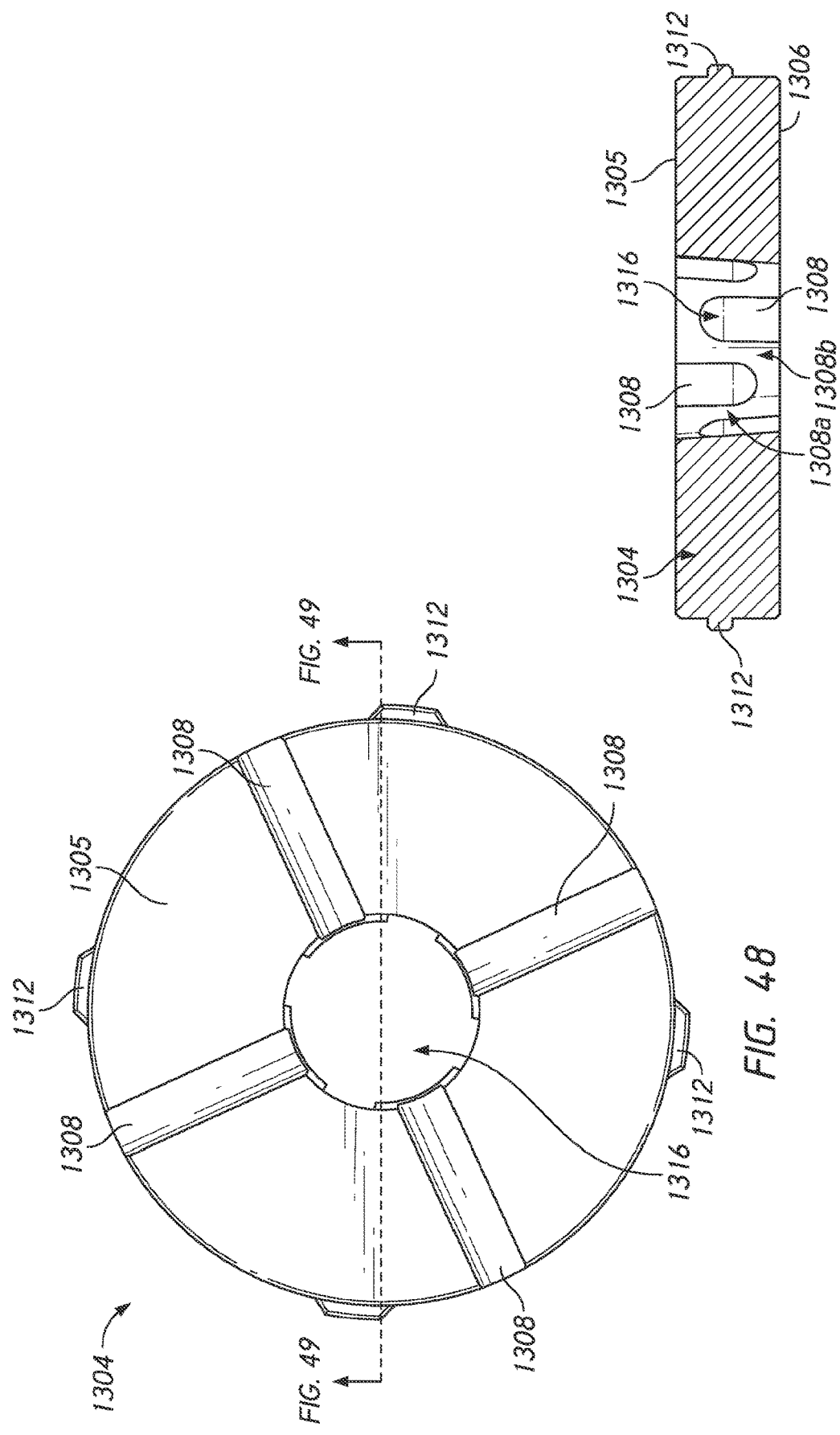

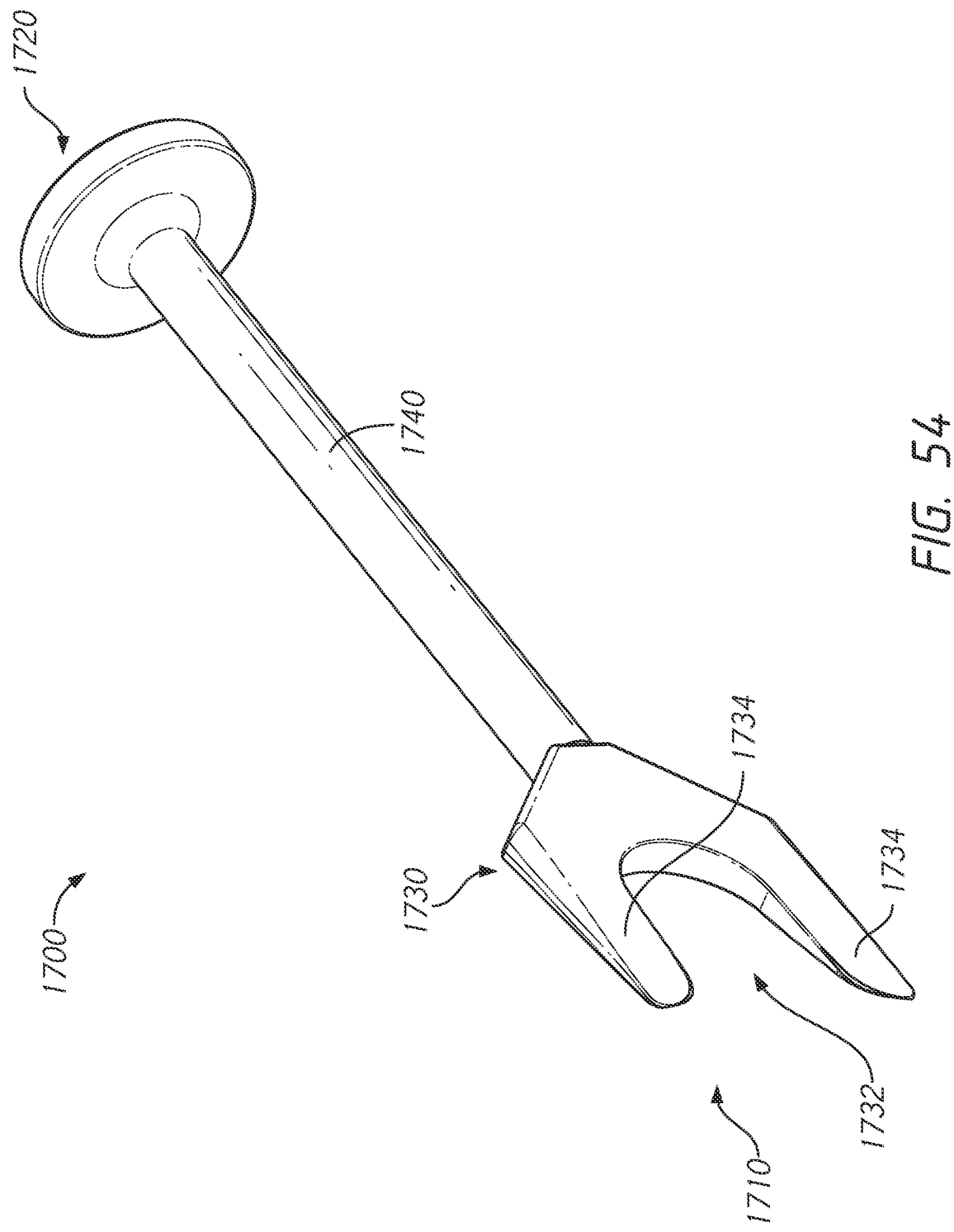

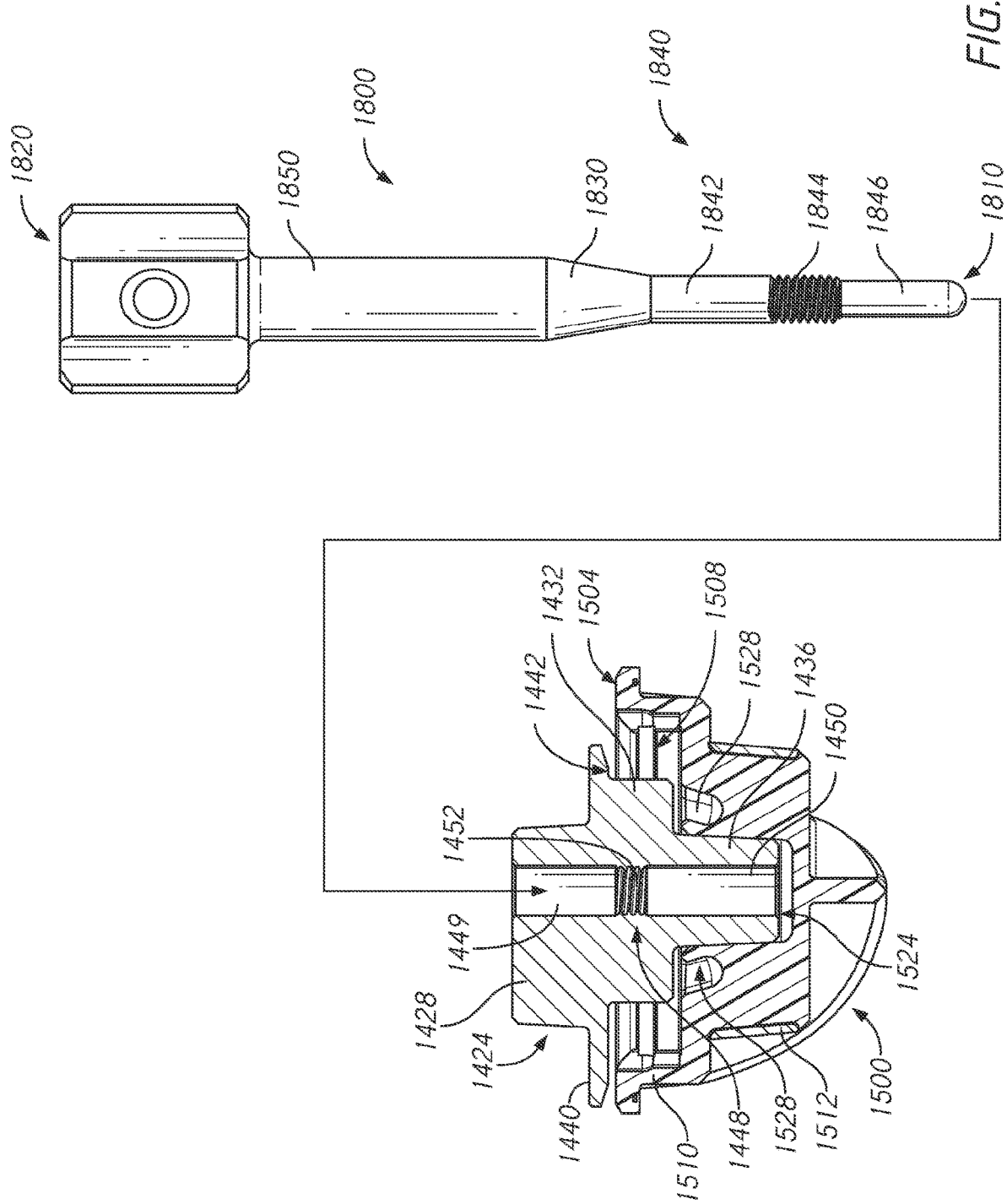

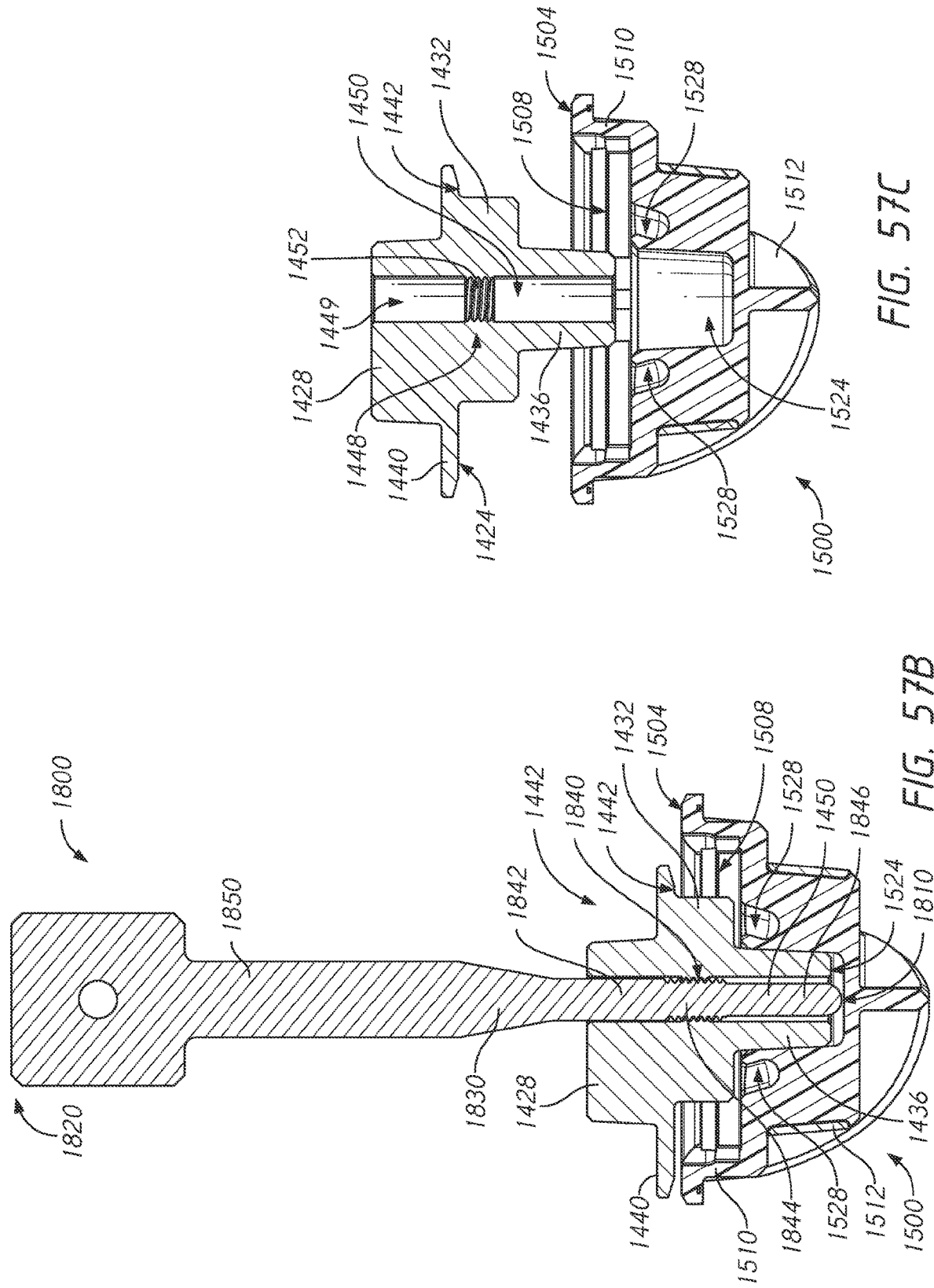

MODULAR HUMERAL HEAD

RELATED APPLICATION

This application is a National Stage Application, filed under 35 U.S.C. 371, of International Patent Application No. PCT/US2019/054023, filed on Oct. 1, 2019, which claims priority to U.S. Provisional Patent Application No. 62/740,342, filed on Oct. 2, 2018, the entireties of which are incorporated herein by reference.

BACKGROUND

Field

The present disclosure relates to humeral head assemblies and components thereof as well as methods for assembling and implanting them.

Description of the Related Art

Skeletal joints have a variety of configurations providing for a wide range of smooth movement of two or more bones relative to each other. For example, in a shoulder joint, an articulating surface at one end of the humerus interacts with an articulating surface at the glenoid cavity of the scapula in a manner similar to a "ball and socket" joint. Joint conditions can develop that cause pain and restrict motion of the shoulder joint. Implanting prosthetic components at one or both articulating surface of the joint can improve such conditions.

A typical anatomical shoulder joint replacement attempts to mimic the natural joint anatomy. For example, a humeral anchor (e.g., a stem or stemless anchor) can be attached to the humerus and a convex humeral head can be assembled to the anchor. Together these structures replace the humeral articulating surface of the shoulder joint. The humeral head can articulate with the native glenoid socket or with a glenoid resurfacing device configured to replace the articulating surface of the glenoid. In either case, the relative position of the humerus to the scapula is dependent on non-skeletal factors such as the condition and location of the soft tissue that connects to the bone and holds the bones in positions relative to each other at rest and during motion.

The position of the humeral head relative to humerus is important to the security of the humeral head assembly and to the kinematics of the joint post operatively.

SUMMARY

There is a need for greater flexibility in component selection and arrangement and providing for desired post-operative humerus and scapula position. There is a further need to increase the control of the degree of post-operative tension in connective tissues. Further there is a desire for humeral anchors that can secure both anatomic and reverse shoulder articular bodies to the humerus while preserving surgeon control over the degree of connective tissue tension. Also, there is a need for enhanced flexibility in placement of a humeral head relative to a humeral anchor for a shoulder joint. There is a need for humeral head assemblies that allow for an articular surface of the head to be either centered on or eccentric from an axis along which the humeral head is coupled with a humeral anchor. There is a need for humeral head assemblies that provide for a range of eccentricity to an assembly axis so that a wide range of patient needs can be met by the assembly.

In one embodiment, a humeral head system is provided that includes an articular body, a coupler and at least one discrete positioning site. The articular body has a convex articular surface and a coupling portion. The coupling portion is disposed on a side of the articular body opposite the convex articular surface. The coupler has a first portion configured to mate with the coupling portion and a second portion opposite the first portion. The second portion is configured to mate with another member of a joint prosthesis. The at least one discrete positioning site is disposed between the coupler and the convex articular surface. The discrete position site providing a fixed rotational position between the articular body and the coupler.

In some embodiments, a coupling portion of the articular body can include a continuous zone of eccentricity adjustment. In some embodiments, the continuous zone of eccentricity adjustment includes at least one discrete position site. The coupler can include a first portion configured to mate with the coupling portion of the articular body.

In some embodiments, the first portion of the coupler includes a tapered protrusion that couples with the articular body by an interference fit. The second portion of the coupler can be tapered. In some examples, the first portion of the coupler is placed in a first configuration against the coupling portion and the rotational position of the coupler to the articular body is adjusted along the continuous zone to allow for selection of different amounts of eccentricity along the continuous zone and the coupler can be secured to the articular body at the coupling portion in a second configuration. In other embodiments, the coupling portion includes a plurality of continuous zones of eccentricity adjustment.

The coupler can also include a collar disposed between the first portion and the second portion thereof, the collar including a protrusion configured to be positionable at least along the continuous zone of eccentricity adjustment. In some examples, the coupling portion includes a radial notch configured to receive the protrusion. Relative rotation of the coupler to the articular body is prevented when the protrusion is received in the notch. The position of the protrusion and the notch can be reversed, such that the coupling portion includes one or a plurality of protrusions at the discrete position site(s) and the collar includes a notch configured to receive a protrusion. In some embodiments, the radial notch is disposed circumferentially adjacent to the continuous zone of eccentricity adjustment. In other embodiments, the radial notch is disposed at a position where no eccentricity is provided between the coupler and the articular body when the protrusion is disposed in the notch.

The coupling portion can include a single radial notch in some embodiments and eccentricity can be provided by selecting a coupler that yields a selected amount of eccentricity.

In some examples, a continuous zone of eccentricity adjustment and the at least one discrete position site are disposed in a same plane. In some embodiments, the plurality of discrete eccentricity positions is disposed on the side of the articular body opposite the convex articular surface and the plurality extends along an angular range opposite the continuous zone of eccentricity adjustment. The continuous range can provide at least 90 degrees of eccentricity. In other embodiments, the continuous range provides from about 90 to about 180 degrees of eccentricity. In some embodiments, the plurality of discrete eccentricity positions includes at least three discrete sites corresponding to positions of eccentricity in a first direction. In some examples, the at least three discrete sites corresponding to positions of eccentricity are disposed between a site corresponding to a position of no eccentricity and a site corresponding to a position of maximum eccentricity. In some embodiments, the position of no eccentricity is 180 degrees rotationally offset from the position of maximum eccentricity.

In some embodiments, a coupling portion includes a discrete eccentricity position in which the first portion of the coupler can be placed in the first configuration against the coupling portion and the rotational position of the coupler to the articular body is fixed. In some examples, the coupling portion includes a plurality of continuous zones of eccentricity adjustment, one of the zones of the plurality being disposed on each side of the discrete eccentricity position. In some embodiments, the coupling portion includes a plurality of discrete eccentricity positions, the continuous zone of eccentricity adjustment being between the discrete eccentricity positions. In some embodiments, the coupling portion includes a plurality of discrete eccentricity positions and a plurality of continuous zones of eccentricity adjustment, the discrete eccentricity positions alternating with the continuous zones of eccentricity adjustment.

The humeral head assemblies described herein can include indicia indicating an amount of eccentricity. The amount of eccentricity can be indicated at predetermined spaced apart locations of the continuous zone. The indicia can be disposed on a side of the articular body opposite the convex articular surface. In some embodiments, the indicia comprise a plurality of markings on the side of the articular body opposite the convex articular surface. The amount of eccentricity provided by a specific rotational position of the coupler relative to the articular body can be provided when the protrusion is aligned with one of the indicia. The amount of eccentricity can be indicated on a side of the articular body opposite the articular surface. For example, a plurality of indicia can be provided on a surface of the side of the articular body opposite the articular surface. A coupler can then be configured to engage with the articular body such that indicia on the coupler is aligned with one of the plurality of indicia to provide the appropriate eccentricity.

In another embodiment, a humeral head assembly is provided that can include an articular body and a coupler. The articular body can include a convex articular surface and a coupling portion. The coupling portion can be disposed on a side of the articular body opposite the convex articular surface. The coupling portion can include a recess extending from the side opposite the convex articular surface toward the convex articular surface. The recess can have an outer periphery having at least one radial notch disposed therealong. The coupler can include a first portion and a second portion. The first portion can be configured to mate with the coupling portion. The coupler can include a radial protrusion disposed thereon. The second portion can be located opposite the first portion and can be configured to mate with another member of a joint prosthesis. The first portion of the coupler can be placed against the coupling portion such that the radial protrusion can be received in the radial notch.

In another embodiment, a humeral head assembly is provided that can include an articular body, a bone anchor, a coupling portion, and a coupler. The articular body can include an articular surface and a coupling portion. The coupling portion can be disposed on a side of the articular body opposite the articular surface. The bone anchor includes a distal end configured to be lodged in a bone and a proximal face. In one embodiment, the coupling portion includes at least one discrete position site disposed between the convex articular surface and the distal end of the bone anchor. The coupling portion can optionally include a continuous zone of eccentricity adjustment between the convex articular surface and the distal end of the bone anchor. The coupler includes a first portion configured to mate with the coupling portion and a second portion opposite the first portion. The second portion is configured to couple the articular body with the bone anchor.

In other embodiments, the bone anchor includes a stem portion configured to be disposed in an intramedullary canal. In other embodiments, the bone anchor includes a stemless anchor configured such that a distal portion resides in the metaphyseal portion or medial of the metaphyseal portion. The coupling portion of the bone anchor can be disposed on a medial surface of the bone anchor. In other embodiments, the bone anchor optionally includes a continuous zone of eccentricity adjustment including an arcuate segment of a circular recess providing for rotation of a radial protrusion of the coupler therein. The bone anchor can include at least one discrete position site that includes a radial notch aligned with the continuous zone of eccentricity adjustment.

In embodiments where the coupling portion is disposed on the bone anchor, a plurality of couplers can be provided in a kit. The couplers can be configured to provide different amounts of eccentricity adjustment when a radial protrusion on the second portion to mate with a radial notch of the coupling portion.

In some embodiments, an articular component of a prosthetic shoulder joint can be assembled by engaging a first end of a coupler with a coupling portion of an articular body. The assembly of the prosthetic shoulder joint can include providing relative rotation of the articular body about the first end of the coupler. The rotation can be along a continuous range of rotational positions, if provided, while the first end is engaged with the coupling portion. The relative rotation can be provide to align the coupler with a radial notch or other discrete position feature. Assembling the articular component can include selecting an amount of eccentricity corresponding to a position within the continuous range of rotational position. Assembling the articular component can include selecting an amount of eccentricity corresponding to one or more notches or other discrete position feature. Assembling the articular component can include selecting a coupler configured to provide an amount of eccentricity when coupled with one radial notch or with one of a plurality of radial notches. Assembling the articular component can include securing the articular body about the first end of the coupler at the selected amount of eccentricity along the continuous zone or at a discrete position feature when combined with a selected coupler.

Assembling the articular component can also include positioning a protrusion of the coupler along the continuous zone, wherein the protrusion is disposed between the first end and a second end of the coupler. In some embodiments, assembling the articular component includes engaging the protrusion in a radial notch of the coupling portion thereby preventing relative rotation of the coupler to the articular body.

In some examples, assembling the articular component includes aligning an alignment feature of a coupler with an eccentricity amount indicator disposed on or adjacent to the coupling portion of the articular body. Assembling the articular component can also include aligning a radial protrusion of the coupler with one of a plurality of indicia of eccentricity disposed on the articular body.

In some embodiments, a plurality of couplers are provided to facilitate discrete positions of or amounts of eccentricity. In other embodiments, the coupling portion includes a plurality of discrete position features, each of the discrete position features providing a different amount of eccentricity for a selected coupler, and where providing relative rotation to align the coupler with a discrete position feature comprises selecting between a discrete position feature corresponding to lesser eccentricity and a discrete position feature corresponding to greater eccentricity.

In another embodiment, an articular component is provided that includes an articular body, a bone anchor, and a coupling portion. The articular body includes an articular surface, e.g., a convex or a concave articular surface. The bone anchor has a distal end configured to be lodged in a bone and a proximal face. The coupling portion optionally has a continuous zone of eccentricity adjustment. The coupling portion can have one or more discrete position sites disposed between the articular surface and the distal end of the bone anchor. A coupler can have a first portion configured to mate with the coupling portion and a second portion opposite the first portion. The second portion configured to couple, directly or indirectly, the articular body with the bone anchor. In some embodiments, the coupler is one of a plurality of couplers with each coupler providing a different degree of eccentricity adjustment when coupled with a discrete position site, e.g., with a radial notch.

In one variation, a method of assembling an articular component of a prosthetic shoulder joint is provided. A first end of a coupler is engaged with a coupling portion. The coupling portion can be on the articular body or on an intermediate coupler to which the articular body is connected. Relative rotation can be provided between the articular body and the coupler about the first end of the coupler. The rotation can be along a continuous range of rotational positions, if provided, while the first end is engaged with the coupling portion. The rotation can align the coupler with a discrete position feature, e.g., a radial notch. The coupler can be selected from a plurality of couplers configured to provide different amounts of eccentricity adjustment when a protrusion thereof is coupled with the discrete position feature. An amount of eccentricity corresponding to a position within the continuous range of rotational position, if provided, can be selected. The articular body is secured about the first end of the coupler at the eccentricity provided by positioning along the continuous range or by coupling a selected coupler with the discrete position feature.

In another embodiment a method of assembling an articular component of a prosthetic shoulder joint is provided. In the method, an end of a coupler of a joint implant is engaged with a coupling portion of another component of the joint implant. Relative rotation is provided between the end of the coupler and the coupling portion of the other component of the joint implant along a continuous range of rotational positions while the end is engaged with the coupling portion of the other component of the joint implant. An amount of eccentricity corresponding to a position within the continuous range of rotational position is selected. The other component of the joint implant is secured to the end of the coupler at the selected amount of eccentricity. In a variation, the coupling portion has one or more discrete position sites, e.g., notches, and the amount of eccentricity is provided by selecting a coupler configured to provide the amount of eccentricity desired.

In some embodiments, a component of the second portion can be expanded from a first periphery to a second periphery. The first periphery can be smaller than the second periphery. The periphery can include a surface or surfaces that are disposed around, e.g., surround a longitudinal axis of the coupler. The coupler can comprise a window providing viewing of offset indicia formed on or opposite the coupling portion.

In one embodiment, an articular component is provided that includes an articular body, a bone anchor, a coupling portion, and a coupler. The articular body has an articular surface. The bone anchor includes a proximal face and a distal end configured to be lodged into a bone. The coupling portion includes a radial notch disposed between the articular surface the distal end of the bone anchor. The coupler includes a first portion that is configured to mate with the coupling portion. The coupler also includes a second portion opposite the first portion that is configured to couple, directly or indirectly, the articular body with the bone anchor.

In one embodiment, a humeral head system is provided that includes an articular body and a coupler. The articular body has a convex articular surface and a coupling portion, the coupling portion disposed on a side of the articular body opposite the convex articular surface. The coupler has a first portion configured to mate with the coupling portion and a second portion opposite the first portion. The second portion is configured to mate with another member of a joint prosthesis. The coupler is configured to provide a fixed rotational position between the articular body and the coupler to provide a selected degree of offset of the articular surface to the other member of the joint prosthesis.

In some embodiments, the coupler has an offset window disposed between the first portion and the second portion of the coupler. In some embodiments, the coupler has a plate extending transverse to the second portion. The offset window has a slot formed in the plate configured to uncover indicia indicative of an extent of eccentricity of the articular body to the other member of the joint prosthesis. In some embodiments, the humeral anchor has the other component of the joint prosthesis. The humeral anchor has indicia of eccentricity, the slot uncovering different indicia in different rotational positions of the coupler to the humeral anchor. The rotational positions are changed by rotation about a longitudinal axis extending through the second portion of the coupler.

In some embodiments, the coupler has a threaded channel extending from a first end surface of the coupler to a second end surface of the coupler. The channel provides access to a surface of one or both of the articular body and the other member of the joint prosthesis. In some embodiments, the threaded channel is formed through the first and second portions of the coupler.

In some embodiments, the coupler has a prying ledge comprising an angled surface disposed between the first portion and the second portion. The prying ledge is responsive to a radial load being applied thereto to direct a longitudinal force along the longitudinal axis of the first portion or the second portion of the coupler. In some embodiments, the prying ledge extends radially between a disc member of the coupler and a periphery of the coupler. The prying ledge is accessible from a periphery of the humeral head system when the humeral head system is fully assembled.

In one variation, a method of disassembling a humeral prosthesis is provided. A periphery of the humeral prosthesis is exposed such that a gap between an articular body and a humeral anchor is accessible. A prying tool can be advanced into the gap. Further advancing the prying tool against a prying ledge formed on a coupler disposed between the articular body and the humeral anchor can be made until contact is made with the prying ledge. A radial load to the prying ledge can be applied at an end of the prying tool. The prying ledge can be angled relative to a direction of application of the radial load. The radial load can result in an axial load causing the articular body to be separated from the humeral anchor.

In another embodiment, a method of disassembling a humeral prosthesis is provided. In the method, an elongate shaft can be advanced through a channel formed in the coupler, the channel extending between a first end of the coupler engaged with the articular body and a second end of the coupler opposite the first end. The elongate shaft can be engaged with the coupler and an end thereof with a surface of the articular body. Opposing loads can be provided to the coupler and the articular body with the elongate shaft to separate the articular body from the coupler. In a variation, engaging the elongate shaft with the coupler includes engaging external threads of the elongate shaft with internal threads of the coupler.

In another embodiment, a method of disassembling a humeral prosthesis is provided. In the method, an elongate shaft can be advanced through a channel formed in the coupler. The channel can extend between a first end of the coupler and a second end of the coupler opposite the first end. The second end of the coupler can be engaged with the humeral anchor. The elongate shaft can be engaged with the coupler and an end thereof with a surface of the humeral anchor. Opposing loads can be provided to the coupler and the humeral anchor with the elongate shaft to separate the coupler form the humeral anchor.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 8B is a cross-sectional view of an articular body of the humeral head assembly of FIG. 2 through plane 8B-8B shown in FIG. 8A;

FIGS. 14A-14C show humeral implant assemblies and components thereof suitable for adjusting offset of a reverse articular body humeral assembly;

FIG. 15 is a schematic view of an anatomic humeral assembly disposed in a resected humerus, shown schematically;

FIGS. 29-31 show a top, side, and perspective view of an actuator configured to engage with the securement portion of FIGS. 27-28 to form the cam assembly of the cam disc assembly shown in FIG. 21;

FIGS. 34-35 show a top and bottom view of the taper cam and slot assembly of FIG. 32;

FIGS. 39-41 show a perspective, top, and side view of an actuator of a cam assembly of the taper cam and slot assembly of FIG. 32;

FIG. 48 is a top view of the coupler of a collet lock assembly;

FIG. 49 is a cross-section taken through plane 49-49 shown in FIG. 48;

FIG. 54 shows a perspective view of a prying tool for separating components of a humeral head assembly, for example components of the humeral head assembly of FIG. 18.

FIGS. 57A-57C illustrate a method of using the coupler separator of FIG. 56 to separate components of the humeral head assembly of FIG. 18.

DETAILED DESCRIPTION

Figure 1A:
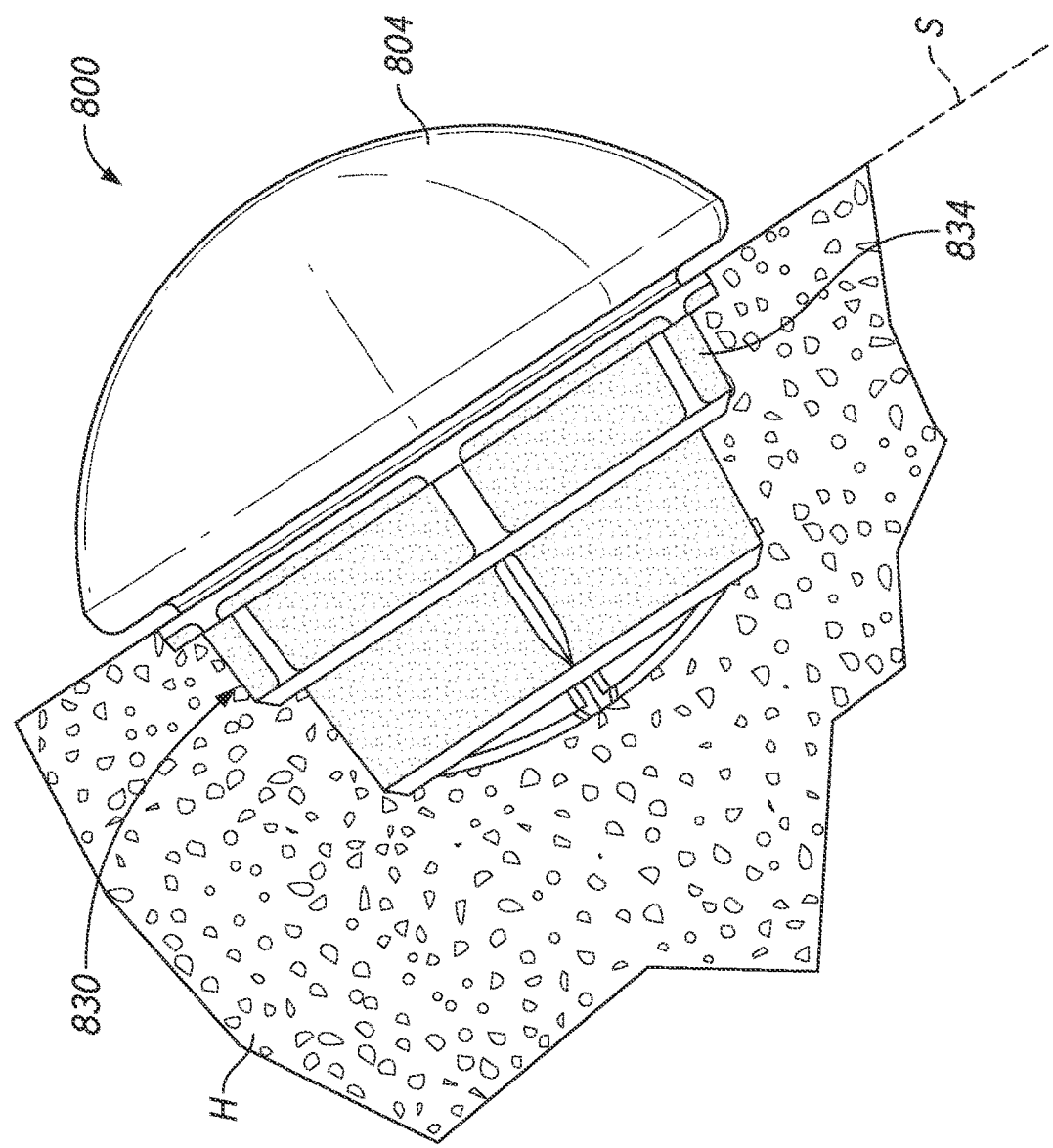
FIG. 1A is a side view of an anchor coupled with an articular body to form a humeral head assembly in an anatomic configuration wherein the anchor is configured to receive the articular body below a humeral resection plane.

This application is directed to orthopedic assemblies that can be applied to long bones in joint arthroplasty. Section I discusses such assemblies in the context of shoulder arthroplasty. The orthopedic assemblies can include a humeral system that can secure an anatomic articular body above a humeral resection plane and can secure a portion of a reverse shoulder articular body below the humeral resection plane. This facilitates a revision procedure and also improves soft tissue accommodation, as discussed below. Section II discusses certain components, systems, and kits including the humeral anchors discussed in Section I for enhancing eccentricity adjustment of articular bodies. Section III discusses variations on the components discussed in Sections I and II. Section IV discusses variations of couplers of the humeral systems discussed in Section I-III. Section V discusses various methods of assembling humeral head and reverse bearing assemblies disclosed herein.

The components and the variations discussed below enable a first portion thereof to be selectively coupled with a second portion to selectively position the first portion aligned with or eccentric to the second portion. The first portion can be co-linear with the second portion. In applications discussed in detail below, the first portion can include an articular body and the second portion can include a bone anchor portion to be coupled to a bone. For example in the context of the shoulder, a humeral head assembly can be provided that enables an articular surface or other aspect of an articular body to be coupled with a humeral anchor in a centered position or in an eccentric position. In some variations, a glenoid anchor could be provided and a shoulder assembly could enable an articular body such as a glenosphere of a reverse shoulder implant to be disposed in a centered or eccentric position relative to the anchor. In further variations, an assembly can be adapted for positioning an articular body of a femoral assembly relative to a femur anchor to provide for centered or eccentric positioning thereof for a hip or a knee assembly. In further variations, an assembly can be adapted for positioning an articular body of a tibial assembly relative to a tibial anchor to provide for centered or eccentric positioning thereof for a knee assembly. The ability to couple the articular surface in a centered or at one or more eccentric positions, or over a range of eccentric positions, allows a surgeon to treat a wider variety of patient anatomy with a kit that has fewer components than was possible in the past.

I. Anchor Configured for Below the Resection Plane Connection with Anatomic and Reverse Articular Bodies FIGS. 1A-1D illustrates a humeral head assembly 800 and a reverse bearing assembly 800A that includes an anchor 830 that can be disposed in a proximal portion of a humerus, e.g., in the metaphyseal portion thereof. The anchor 830 is configured to be able to receive a portion of an articular body below a humeral resection plane within the metaphyseal portion. The anchor 830 advantageously enables a surgeon to reverse the articular surfaces of the shoulder, as discussed below, while accommodating soft tissue of a wide variety of patients.

FIG. 1A shows the anchor 830 coupled with an articular body 804 to form a humeral head assembly 800 in an anatomic configuration. The anchor 830 is disposed at or below the resection surface S. More particularly, the anchor 830 has a first end 832 and a second end 834. The first end 832 can be a proximal end and the second end 834 can be a distal end of the humeral anchor 830. In this context, the distal end is an end that is disposed deeper in the bone when implanted, here in the metaphysis of the humerus.

Figure 1B:
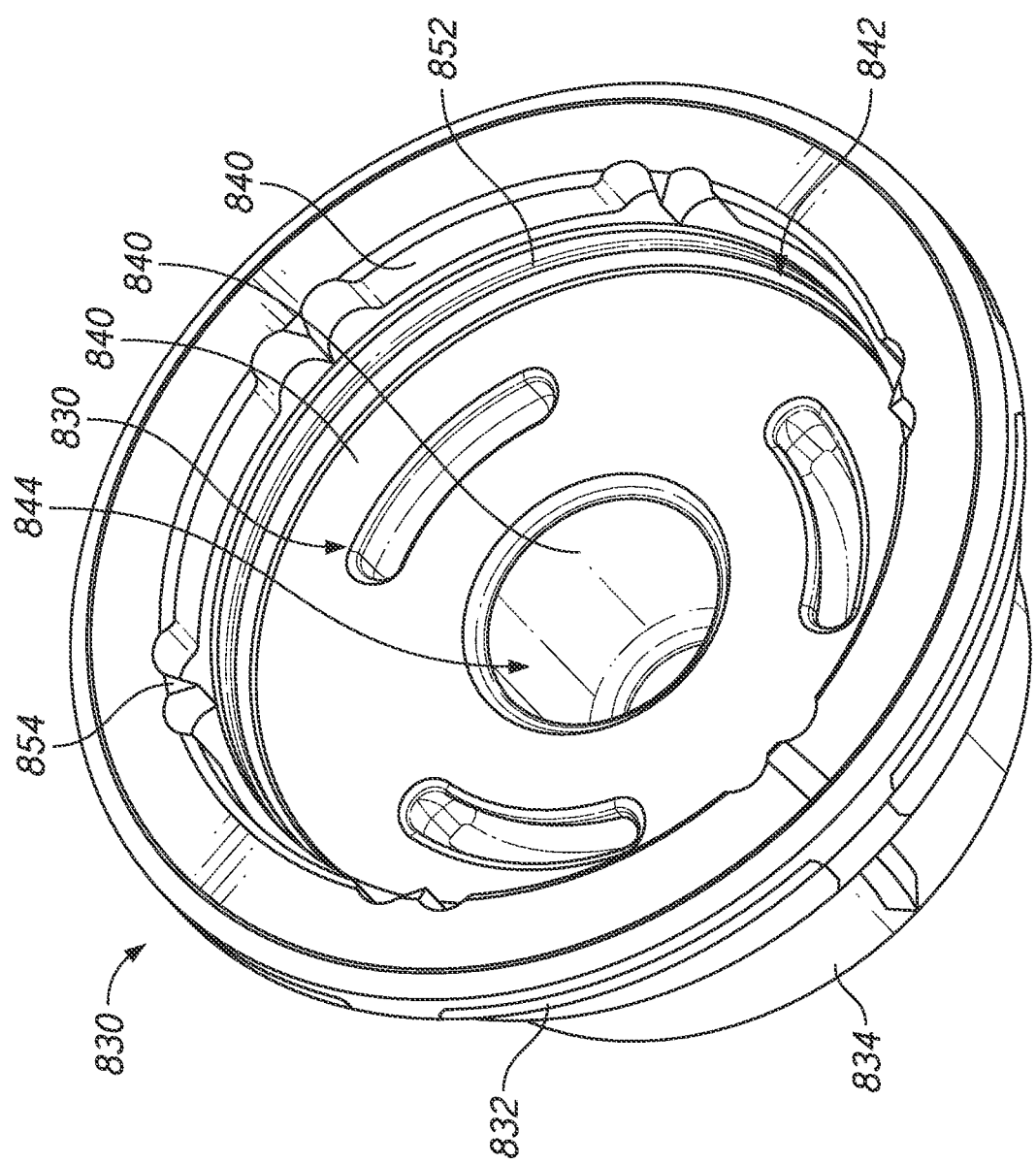
FIG. 1B is a perspective view of an interior surface of the anchor of FIG. 1A.

FIG. 1B shows that an interior surface 840 of the anchor 830 extends between the first end 832 and the second end 834. The interior surface 840 can form a portion of a receiving portion 836 of the anchor 830. The interior surface 840 has a first recess 842 disposed between the first end 832 and the second end 834 and a second recess 844 disposed between the first recess 842 and the second end 834. The first recess 842 is a wider recess disposed near the proximal end of the anchor 830. The second recess 844 is a narrower recess disposed between the first recess 842 and the second end 834. The second recess 842 is configured to receive a coupler 924 (discussed below in FIGS. 16-20) secured to or adapted to be secured to the anatomical articular body 804.

Figure 1D:
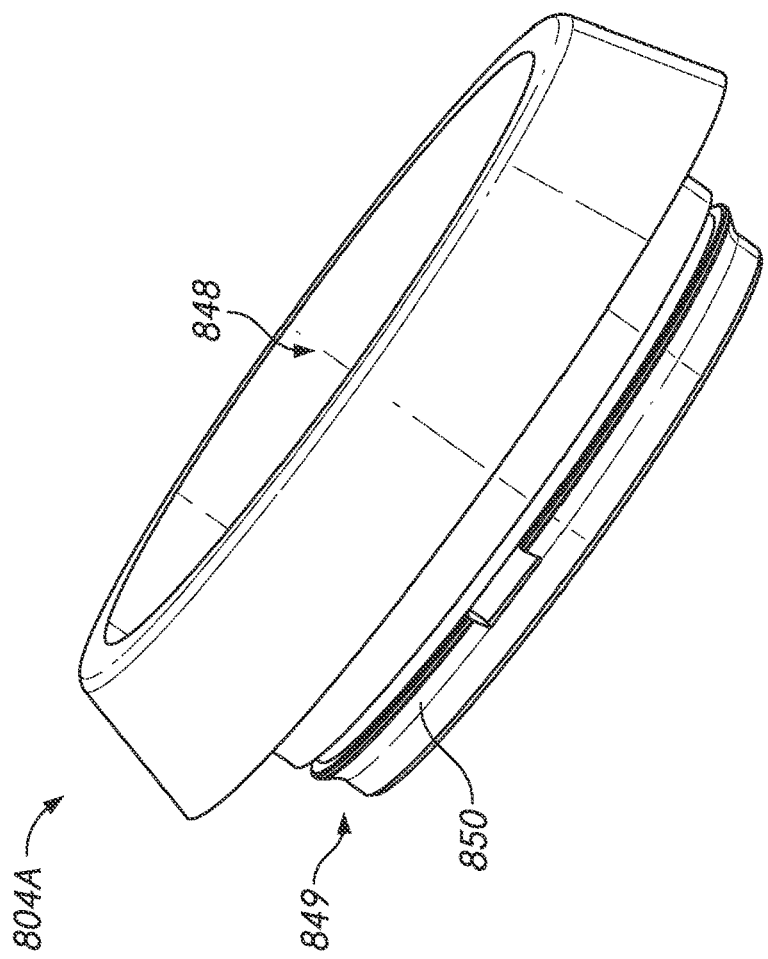
FIG. 1D is a perspective view of another embodiment of a reverse shoulder articular body.
Figure 1C:
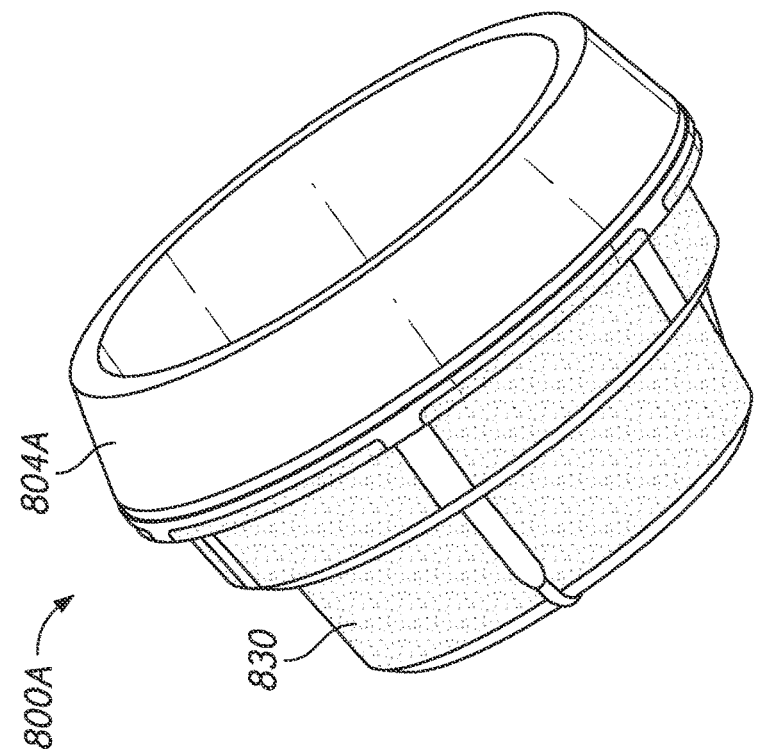
FIG. 1C is a perspective view of an embodiment of a reverse shoulder articular body.

FIG. 1C shows the reverse bearing assembly 800A that can be formed including the anchor 830 and a reverse articular body 804A. The articular body 804A can be coupled directly to the anchor 830. For example, the first recess 842 of the anchor 830 can be configured to secure a coupling portion 846 of the articular body 804A directly to the interior surface interior surface 840. The reverse articular body 804A can include a unitary molded polymeric component with a first portion including a concave articular surface 848 and a second portion including a mating or interface portion 849 that directly couples to the interior surface 840. The coupling can be accomplished by a C-ring 850, an interference fit, or other locking device or in another manner. If present, the C-ring 850 can be received in a slot 852 that extends circumferentially around and radially outward of the first recess 842 in the interior surface 840. In some embodiments, the C-ring 850 can cooperate with one or a plurality of fins 854 that can be disposed about the first recess 842 to provide an interference connection with the articular body 804A. In some examples, the articular body 804A and/or the C-ring 850 can interact with the one or a plurality of fins in the first recess 842 to provide rotational stability. In some embodiments, the C-ring 850 is eliminated and an interference connection employing the fins 854 or other structures can be used alone to secure the articular body 804A in the receiving portion 836.

In the assembled reverse shoulder implant there is an overlap of the interface portion 849 of the reverse articular body 804A and the interior surface 840 of the anchor 830. This provides an advantage in enabling the reverse bearing assembly 800A to fit in patients having a smaller gap between the humerus H and the glenoid of the scapula forming the shoulder joint. For patients with larger gaps, a spacer may be provided to enable the reverse bearing assembly 800A and the corresponding glenoid implant (if present) to occupy the space between the humerus and scapula. This ensures that the shoulder arthroplasty can be achieved without over-tensioning the connective tissues between the humerus and scapula. This ensures that the shoulder joint post-operatively will have as close to pre-morbid biomechanics as possible. The configuration to enable a portion of the reverse shoulder articular body 804A to be disposed below the resection gives the surgeon enhanced ability to treat a wider range of patients.

As noted above, some patients benefit from the reverse shoulder arrangement. Sometimes this follows an initial implantation of an anatomic assembly. To minimize the invasiveness of this revision, the anchor 800 is advantageously configured to mate with either the articular body 804 or with the reverse shoulder articular body 804A. Examples of the reverse shoulder articular body 804A are illustrated in FIGS. 1C and 1D. In particular as discussed in greater detail below, one or a plurality of couplers 924a, 924b, 924c can be provided to enable the articular body 804 to indirectly couple to the anchor 800. The couplers 924a, 924b, 924c can be configured to couple with the second recess 844 and to occupy the first recess 842 of the anchor 830. Thus, the couplers 924a, 924b, 924c can comprises a spacer portion that enables the articular body 804 to mount to the anchor 830 above the resection surface S. Thus, the first recess 842 is included in the anchor 830 to allow an initial anatomic configuration and to enable a surgeon to revise the patient to reverse without having to remove and to install another anchor for a reverse prosthesis.

In some embodiments, the anchor 830 can be configured to receive and/or engage with one or a plurality of the couplers 1424a, 1424b, 1424c. Alternatively, the one or a plurality of couplers 924a, 924b, 924c can be configured to engage with an embodiment of a humeral anchor 1500 described in more detail below. Although the various components of anchors, couplers, and articular bodies are described with reference to the individual components illustrated in each figure, it will be well understood that a humeral head assembly 800 and a reverse bearing assembly 800A can comprise the combination of any of the anchors, couplers, or articular bodies discussed in more detail below.

Figure 1E:
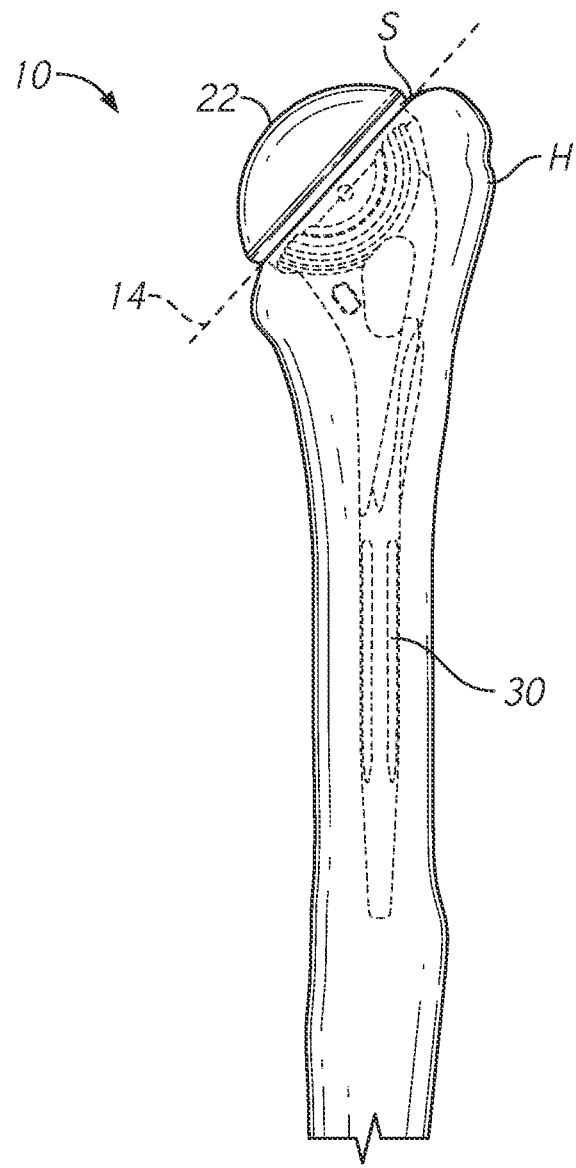
FIG. 1E is a side view of a humerus with a humeral head assembly implanted therein.
Figure 1G:
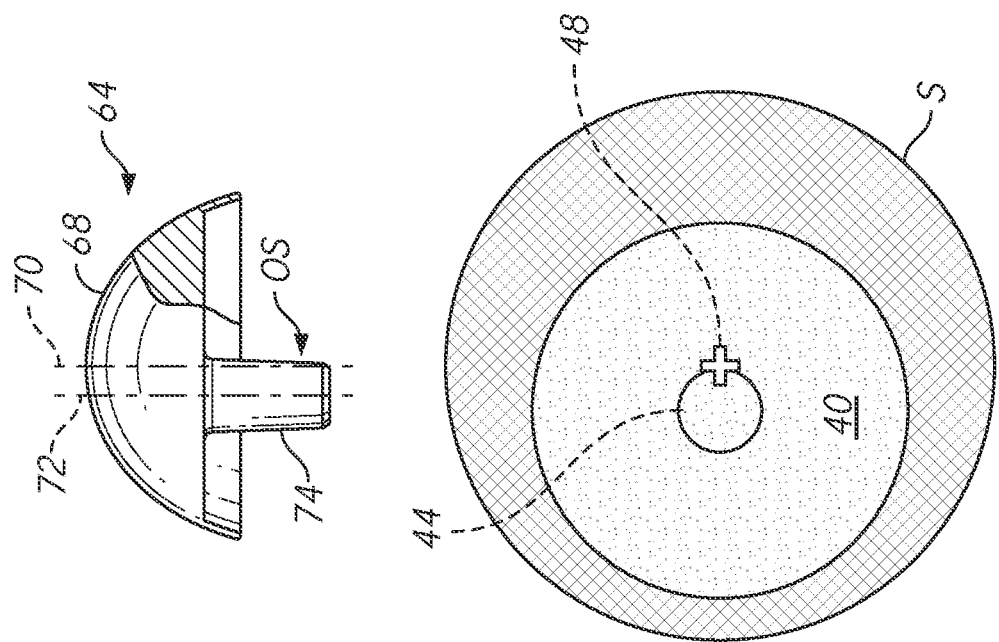
FIG. 1G shows a humeral head having an eccentric coupler and an implantation site that would benefit from coupling with an eccentric coupler humeral head.
Figure 1F:
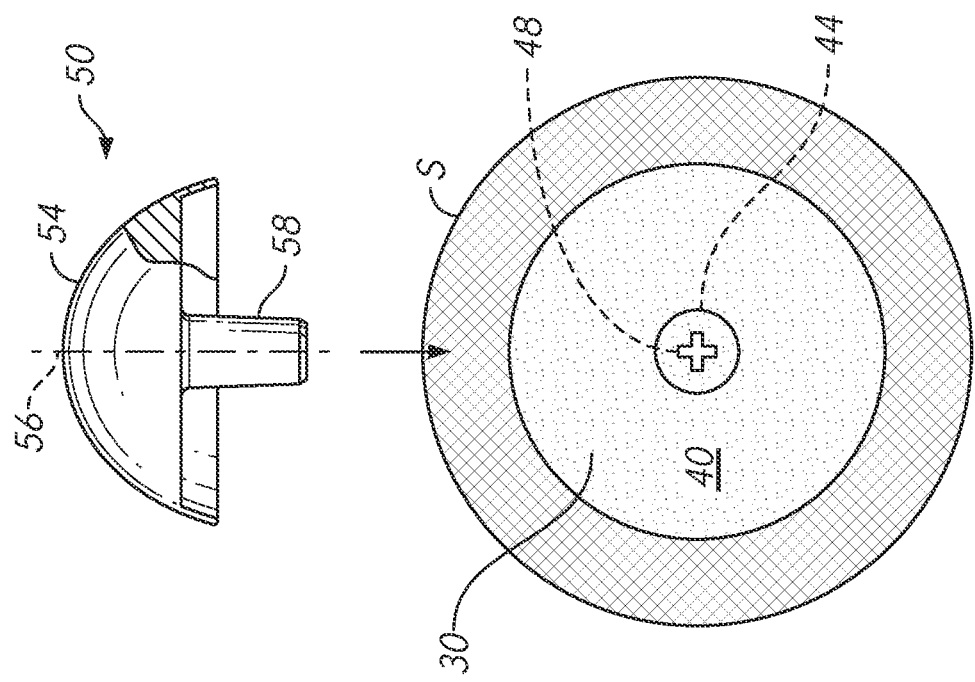
FIG. 1F shows a humeral head having a centered coupler and an implantation site suitable for a centered coupler.
Figure 16:
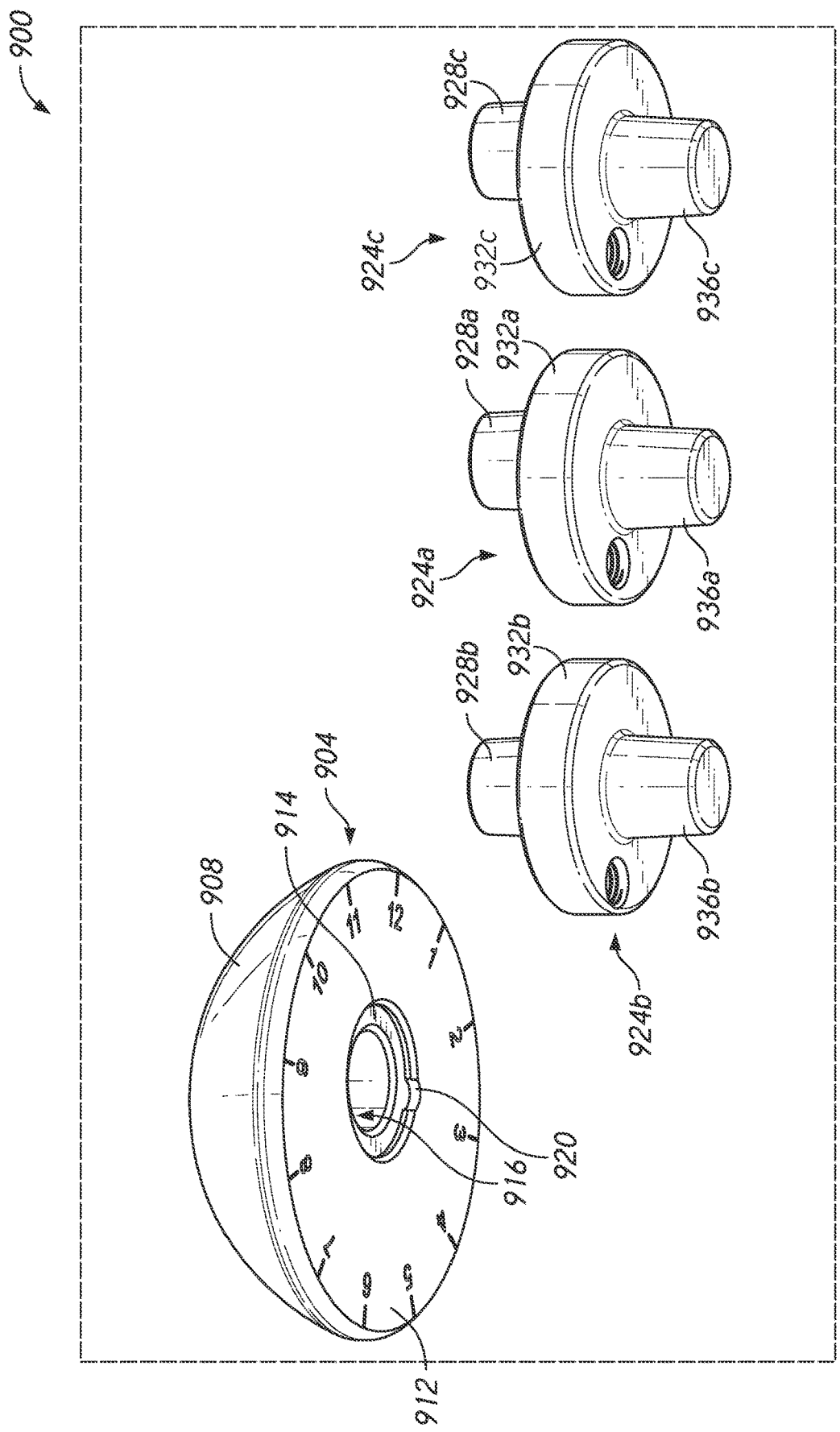
FIGS. 16-16A show a kit including a humeral head and a plurality of couplers that are configured to provide various offsets when mated with the humeral head.

II. Components, Systems, and Kits Facilitating Centered and Eccentric Humeral Assemblies FIGS. 1E-1G show that a joint implant can provide centered or eccentric articular surface configurations. FIGS. 16-17C illustrate components, systems, and kits that can be used with or can incorporate the humeral anchor 830 to provide a variety of degrees of articular surface eccentricity. FIGS. 18-20A illustrate another embodiment of components, systems, and kits that can be used with or can incorporate a humeral anchor 1500 (described in more detail below) to provide a range of directions or degrees of articular surface eccentricity.

FIG. 1E shows an example of a humeral head assembly 10 coupled with a humerus H. In a process of implanting the head assembly 10 in the humerus H, the shoulder joint space is surgically accessed and the humerus is separated from the glenoid cavity of the scapula. The head of the humerus H is separated from the rest of the humerus by cutting, or resecting, along a plane 14. This resection creates an exposed surface S of the proximal humerus H. Thereafter, the intramedullary canal of the humerus (an elongated hollow space in the humerus) is accessed and may be enlarged or otherwise prepared. Thereafter, a stem 30 can be inserted into the canal leaving a coupling face 40 (See FIGS. 1F and 1G) of the stem 30 exposed at or accessible from the surface S. In alternative techniques, a stemless anchor is provided that does not require access to or preparation of the intramedullary canal. An articular body 22 can then be coupled with the stem 30 to form a humeral head assembly coupled with the humerus H, as shown in FIG. 1F.

Whether a stemless (as in FIGS. 1A-1D) or a stemmed humeral anchor (as in FIG. 1E) is used, the coupling face of that anchor, which is disposed at the surface S, may not necessarily be in the center of the surface S. This variable can be addressed by providing a kit having some humeral heads that are centered and some that are eccentric. FIG. 1F shows the stem 30 placed in the humerus H in a centered position. A coupling feature 44 at a center of the coupling face 40 of the stem 30 is aligned with a center 48 of the exposed surface S of the humerus H. In this configuration a humeral head 50 with a centered articular surface 54 can be used to provide good centering of the articular surface 54 to the exposed surface S. A center of the articular surface 54 is intersected by, e.g., is co-linear with, a longitudinal axis 56 of a stem 58 of the humeral head 50. FIG. 1G shows that in some cases, the process of resecting the humerus H and placing the stem 30 results in the coupling feature 44 being off-set from the center 48 of the exposed surface S of the humerus H. In this configuration a humeral head 64 with an eccentric articular surface 68 can be used to provide good centering of the articular surface 68 to the exposed surface S. A center 70 of the articular surface 68 is not intersected by, e.g., is not co-linear with, a longitudinal axis 72 of a stem 74 of the humeral head 64. Rather, there is an offset OS between the center 70 and the longitudinal axis 72. The offset OS shifts the articular surface 68 toward the center 48 of the surface S of the humerus H, which is a preferred placement in many situations.

A kit with a plurality of humeral heads 50, 64 having integral or pre-connected connector can be provided. But, such a kit will contain at least one extra humeral head which is an inefficient approach. The humeral head is a high cost component of a humeral assembly kit. Reducing waste of such components would be beneficial.

FIG. 15 illustrates another example of a humeral head assembly 800B coupled with a Humerus H. The humeral head assembly 800B can include a first recess 834B and a second recess 844B. In some embodiments, the first recess 834B has a greater radius than the second recess 844B. The humeral head assembly 800B can include an exterior surface 808B that includes a first cylindrical portion 832B that is disposed about the first recess 834B. The humeral head assembly 800B can also include a second cylindrical portion 844B that is disposed about the second recess 844B. In some embodiments, the humeral head assembly 800B can include a plurality of rotation control features 850B that are configured to extend radially from the second cylindrical portion 844B. In some examples, each of the plurality of rotation control features 850B are fins that extend radially outward from a central portion of the anchor.

In some embodiments, as will be discussed in more detail below, the articular body 804 can include a receiving portion 836B that is configured to receive a portion of the humeral head assembly 800B below the resection level of the humerus. Placing the receiving portion 836B below the resection level can be beneficial for reducing the amount of hardware between the humerus and the scapula while moving the bones closer together.

Figure 16A:
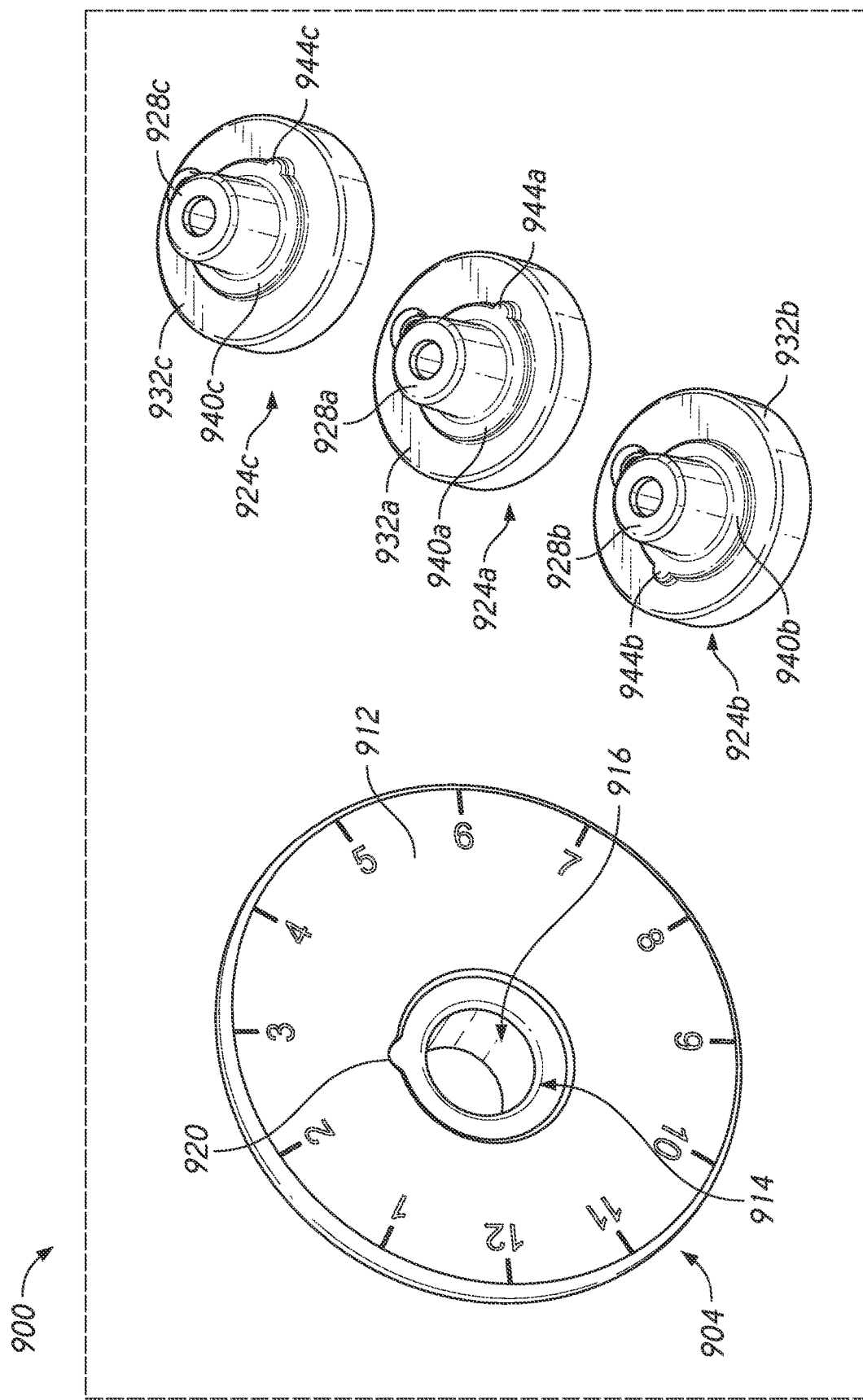

FIGS. 16-17C show embodiments of a humeral head assembly kit 900 in which eccentricity of the assembly can be adjusted by coupling the articular body 904 with one of a plurality of different couplers (e.g. the first coupler 924a, the second coupler 924b, or the third coupler 924c). As shown in FIGS. 16 and 16A, the articular body 904 and the plurality of couplers 924a, 924b, 924c are separable components of the humeral head assembly kit 900. Each of the couplers 924a, 924b, 924c has a discrete engagement position to facilitate the selection of an amount of eccentricity or no eccentricity when a selected one of the couplers 924a, 924b, 924c is engaged with the articular body 904. As discussed further below, the different degrees of eccentricity can be arrived at by selecting one of the couplers 924a, 924b, 924c.

Figure 17A:
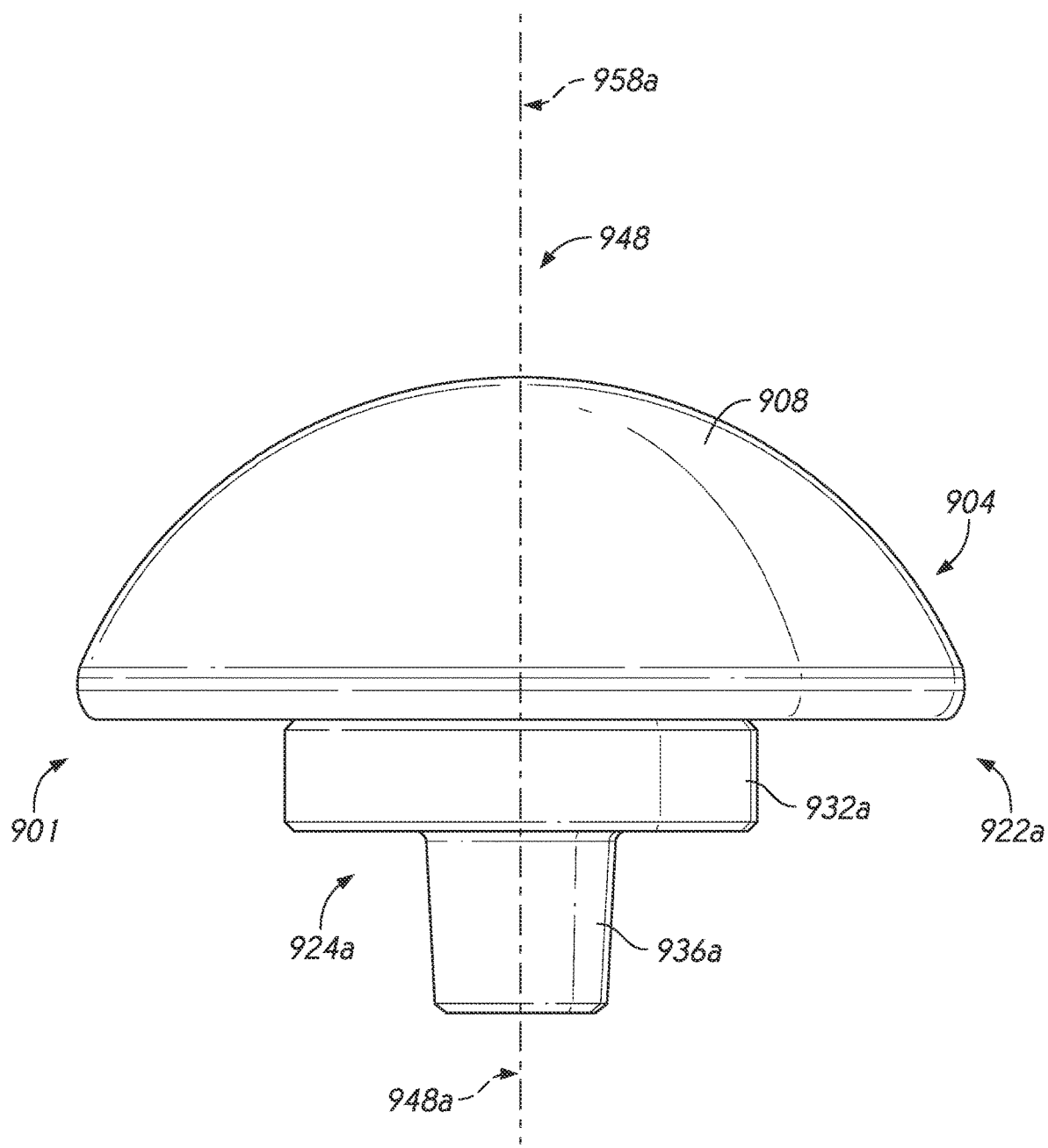
FIGS. 17A-17C show various humeral head assemblies from among the kit of FIGS. 16-16A.
Figure 17B:
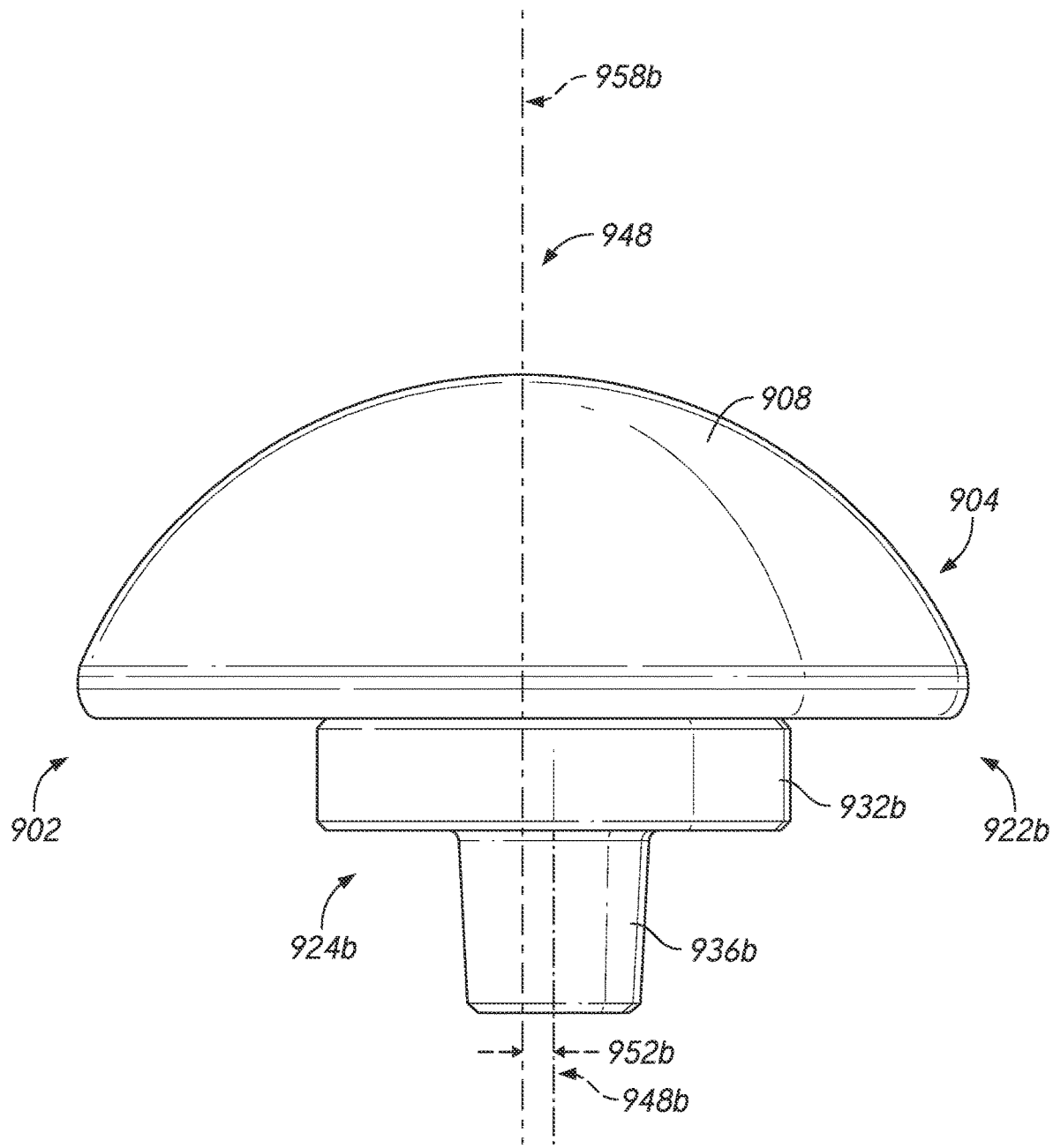
Figure 17C:
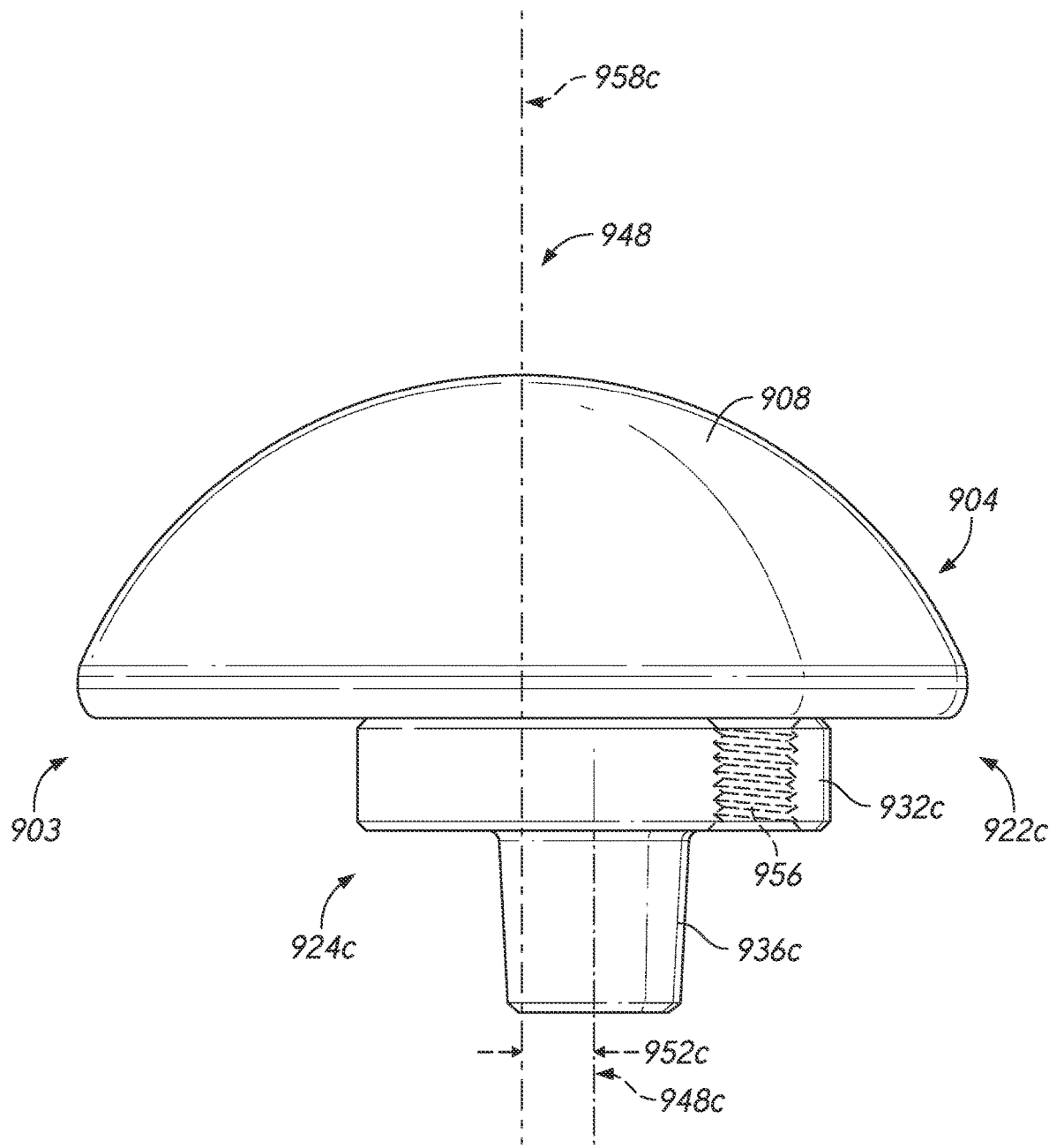

FIGS. 17A-17C illustrate various configurations of humeral assemblies that can be formed from the humeral head assembly kit 900 when the articular body 904 is engaged with a selected one of the couplers 924a, 924b, 924c. FIG. 17A illustrates a humeral head assembly 901 that can be provided where the articular body 904 is coupled with a first coupler 924a. The humeral head assembly 901 corresponds with a centered (or not eccentric) position or configuration. FIG. 17B illustrates a humeral head assembly 902 where the articular body 904 is coupled with a second coupler 924b and corresponds with a low eccentric position or configuration. FIG. 17C illustrates a humeral head assembly 903 where the articular body 904 is coupled with a third coupler 924c and corresponds with a high eccentric position or configuration.

FIGS. 16-17C illustrate various humeral head assemblies similar to a humeral head assembly 100 discussed below and other humeral head assemblies discussed elsewhere in this specification. The discussions of the other humeral head assemblies set forth elsewhere in this specification that are relevant to the discussion of the humeral head assemblies 901, 902, 903 or the kit 900 or the components thereof, e.g., the articular body 904, and to each of the couplers 924a, 924b, 924c, expands upon the present discussion and one skilled in the art will understand that such discussions shall supplement the following discussion of the humeral head assemblies 901, 902, 903 and the kit 900, the articular body 904, and each of the couplers 924a, 924b, 924c.

FIGS. 16 and 16A illustrate that the articular body 904 can have an articular surface 908. The articular surface 908 can be a convex surface. The articular surface 908 can be configured to engage with a concave surface of or at a glenoid of a patient. In some embodiments, as illustrated in FIGS. 16 and 16A, the articular body 904 can also have a coupling portion 912. The coupling portion 912 can be disposed on a side of the articular body 904 opposite the articular surface 908. The humeral head assembly 901, 902, 903 can also include at least one site 920 for discrete positioning of the articular body 904 on each of the couplers 924a, 924b, 924c. In some embodiments, the discrete positioning site is a radial notch 920. In some embodiments, the radial notch 920 can allow for engaging any of the couplers 924a, 924b, 924c to the articular body 904 at the pre-defined position and to prevent relative rotation when engaged. In some embodiments, the one site (e.g. radial notch 920) is disposed in the same plane, e.g., in a plane transverse and normal to the center of the articular surface 908. An amount of eccentricity can be selected by engaging one of the couplers 924a, 924b, 924c with the articular body 904.

The articular body 904 can be configured to engage with and/or be retained by any of the couplers 924a, 924b, 924c. In some embodiments, a selected one of the couplers 924a, 924b, 924c can be coupled with the coupling portion 912 of the articular body 904 to maintain the humeral head assembly 901, 902, 903 in a configuration that is centered or eccentric.

FIGS. 16 and 16A illustrate that the coupling portion 912 can include a first recess 914 disposed within the articular body 904. The first recess 914 can have an open end on a lateral side of the articular body 904. The lateral side is a side of the articular body 904 opposite the articular surface 908. The lateral side faces away from the glenoid when the humeral head assembly 901, 902, 903 is implanted. The second recess 916 can extend into the articular body 904. In some embodiments the second recess 916 can have a closed end. The second recess 916 can be tapered such that the diameter decreases over the length of the second recess 916 to a lesser diameter adjacent to the closed end. The second recess 916 can have a greater diameter toward the coupling portion 912 of the articular body 904.

As discussed above, the articular body 904 can be configured to engage with a plurality of couplers to provide different eccentricities for the humeral head assembly 900. Each of the illustrated couplers 924a, 924b, 924c can include a first portion 928a, 928b, 928c, a disc member 932a, 932b, 932c, and a second portion 936a, 936b, 936c. In some embodiments, the couplers 924a, 924b, 924c can include an engagement portion that comprises a collar 940a, 940b, 940c with a radial protrusion 944a, 944b, 944c.

In some embodiments, the first portion 928a, 928b, 928c each of the couplers 924a, 924b, 924c can be secured within the second recess 916 of the articular body 904. In some examples, the collar 940a, 940b, 940c of each of the couplers 924a, 924b, 924c can be configured to be disposed in the first recess 914. The collar 940a, 940b, 940c can be located between the first portion 928a, 928b, 928c and the disc member 932a, 932b, 932c of each of the couplers 924a, 924b, 924c. The collar 940a, 940b, 940c can be used to position the articular body 904 on or over any of the couplers 924a, 924b, 924c. In some examples, the collar 940a, 940b, 940c can include a radial protrusion 944a, 944b, 944c configured to secure the articular body 904 at the radial notch 920 of the articular body 904. In some embodiments, the radial protrusion 944a, 944b, 944c can extend in a radial direction. The radial protrusion 944a, 944b, 944c can extend in a plane perpendicular to a longitudinal axis of the coupler 924a, 924b, 924c. In some examples, the radial protrusion 944a, 944b, 944c can fix a rotational position relative to the articular body 904 by circumferentially overlapping with a radial edge of the coupling portion 912. Similar to the illustration of FIG. 4A described above, each of the radial protrusions 944a, 944b, 944c can be configured to extend radially outward of a radially inward portion of a circumferential edge of the coupling portion 912.

FIGS. 16-17C show that the couplers 924a, 924b, 924c can include a disc member 932a, 932b, 932c, as discussed above. The disc member 932a, 932b, 932c can be located between the collar 940a, 940b, 940c and the second portion 936a, 936b, 936c of each of the couplers 924a, 924b, 924c. The disc member 932a, 932b, 932c can be used with a stemmed or a stemless anchor, such as the anchor 830 or the anchor 830A. The anchors 830, 830A are also capable of coupling with the reverse articular body 804A as illustrated and described above in FIGS. 1A-1C. As illustrated in FIG. 1B, in some examples, the anchor 830 can include a receiving portion 836. As discussed above, the receiving portion 836 is configured to receive a portion of the humeral head assembly 901, 902, 903 below the resection level of the humerus, e.g., below the surface S. This enables a reverse shoulder articular body 804A to fit more compactly in the shoulder joint space, as discussed above. As mentioned above, the receiving portion 836 of the anchor 830 can beneficially reduce the amount of hardware between the humerus and the scapula for a reverse shoulder assembly. This can allow the humeral head assembly kit 900 to be adapted for use for more patients and also to allow the bones of the humerus and scapula to be moved closer together. In some embodiments of the anatomic humeral head assembly 800, the receiving portion 836 is configured to receive the disc member 932a, 932b, 932c of a selected one of the couplers 924a, 924b, 924c. The couplers 924a, 924b, 924c by virtue of the disc member 932a, 932b, 932c can allow the anchor 830 to be adapted for connection below the resection surface S to also be used for an anatomic configuration. Embodiments of the (e.g. stemless) anchor with a receiving portion adapted for direct connection to the articular body 804A below the resection surface S are discussed in more elsewhere herein. Examples of stemless bone anchors are found in U.S. Provisional Application No. 62/740,333, filed on Oct. 2, 2018, the entirety of which is incorporated by reference herein.

This disc member 932a, 932b, 932c is configured to allow for the coupler 924a, 924b, 924c to be received within a humeral anchor that can secure both anatomic and reverse shoulder articular bodies to the humerus while preserving surgeon control over the degree of connective tissue tension. In some embodiments, the disc member 932a, 932b, 932c is configured to be received within an anchor 830 as illustrated in FIG. 1A. The disc member 932a, 932b, 932c can be positioned between the first portion 928a, 928b, 928c and the second portion 936a, 936b 936c. In some embodiments, the disc member 932a, 932b, 932c can be adjacent to the collar 940a, 940b, 940c. The disc member 932a, 932b, 932c can have a curved profile that is configured to fit within the first recess 842 of the anchor 830 or the anchor 830A. In some embodiments the disc member 932a, 932b, 932c can be circular, however the disc member 932a, 932b, 932c can be any shape that can be received within the first recess 842.

The disc member 932a, 932b, 932c can have an axial length that is longer than the first portion 928a, 928b, 928c, the second portion 936a, 936b 936c, or the collar 940a, 940b 940c. The disc member 932a, 932b, 932c can have an axial length that is shorter than the first portion 928a, 928b, 928c, the second portion 936a, 936b 936c, or the collar 940a, 940b 940c. In some embodiments, the disc member 932a, 932b, 932c can be significantly larger than the collar 940a, 940b, 940c. In one embodiment the disc member 932a, 932b, 932c is circular with a diameter that is greater than the coupling portion 912 of the articular body 904. In some embodiments the disc member 932a, 932b, 932c can have an axial length that is smaller than the axial length of the first recess 842 of the anchor 830 or the anchor 830A. The disc member 932a, 932b, 932c can have a diameter that is smaller than the diameter of the first recess 842 of the anchor 830 or the anchor 830A. This can allow the disc member 932a, 932b, 932c to be retained within the first recess 842 while avoiding contact with the peripheral portion of the interior surface 840 around it. In some embodiments, the axial length of the disc member 932a, 932b, 932c is configured to prevent the exterior surface of the disc member 932a, 932b, 932c from engaging with connection features (e.g. fins 854) that are disposed about the first recess 842. In some embodiments, the disc member 932a, 932b, 932c can have a height that is the same or slightly greater than the height of the first recess 842. As mentioned above, in some examples, when the disc member 932a, 932b, 932c is positioned within the first recess 842, the disc member 932a, 932b, 932c can position the collar 940a, 940b, 940c and the radial protrusion 944a, 944b, 944c at or above the surface S.

The humeral head assembly 901, 902, 903 can include an articular body 904 configured to engage with any one of a plurality of couplers 924a, 924b, 924c. In some examples, each of the couplers 924a, 924b, 924c can include a radial protrusion 944a, 944b, 944c that provides for a discrete eccentricity adjustment position or configuration when engaged with the radial notch 920 on the first recess 914 of the articular body 904. The radial notch 920 can be configured to receive the radial protrusion 944a, 944b, 944c of the collar 940a, 940b, 940c. The profile, outline, edges, or shapes of the radial notch 920 can be concave. The profile, outline, edges, or shapes of the radial protrusion 944a, 944b, 944c can be convex. The radial protrusion 944a, 944b, 944c can be inserted axially into the radial notch 920 of the articular body 904, e.g., along a longitudinal axis of the first portion 928a, 928b, 928c. The matching or inverted configurations, e.g., outline, edges, or shapes, of the radial protrusion 944a, 944b, 944c of the selected coupler 924a, 924b, 924c and the radial notch 920 prevent relative rotation between each of the couplers 924a, 924b, 924c and the articular body 904 when the radial protrusion 944a, 944b, 944c is initially engaged with the radial notch 920. The contact or close adjacency and/or the shape of the radial notch 920 prevents the rotation of the selected coupler 924a, 924b, 924c within or relative to the articular body 904 unless the selected coupler 924a, 924b, 924c, and therefore the radial protrusion 944a, 944b, 944c of the selected coupler 924a, 924b, 924c, is retracted axially away from the articular body 904 to a position where the radial notch 920 is spaced away from the base surface of the first recess 914 and also from the coupling portion 912 of the articular body 904. In this way, the selected coupler 924a, 924b, 924c can at least be radially secured to the articular body 904 when the radial notch 920 initially receives any of the radial protrusion 944a, 944b, 944c. Thereafter a permanent connection between the couplers 924a, 924b, 924c and the articular body 904 is provided by impacting the articular body 904 onto the selected couplers 924a, 924b, 924c to engage mating tapered surfaces.

In some embodiments, the location of the radial protrusion 944a, 944b, 944c and the radial notch 920 can be reversed. In this reversed configuration (not illustrated), the radial protrusion 944a, 944b, 944c discussed above can be instead positioned on a side of the articular body 904 opposite the articular surface 908 while the radial notch 920 discussed above can instead be positioned on the couplers 924a, 924b, 924c. In this reversed example, similar to the embodiment illustrated in FIGS. 16-20, the radial protrusion is configured to provide for a discrete eccentricity adjustment position or configuration when engaged with the radial notch on the coupler. In the reversed embodiment, the radial notch on the coupler can be configured to receive the radial protrusion on the articular surface 908. As with the radial protrusion 944a, 944b, 944c and humeral head assembly 902 discussed above, in the reversed configuration, the matching or inverted configurations of the radial protrusion and the radial notch prevent relative rotation between the coupler and the articular body 904 when the radial protrusion is engaged with the radial notch.

FIGS. 17A-17C illustrate three eccentricity adjustments, positions or configurations that can be achieved by engaging the articular body 904 with a selected one of the couplers 924a, 924b, 924c. Each of the couplers 924a, 924b, 924c, when engaged with the articular body 904, can provide a precise eccentricity adjustment at a pre-determined value. It should be noted that the couplers 924a, 924b, 924c illustrated in FIGS. 17A-17C are only some examples of the eccentricities that the humeral head assembly kit 900 can provide. In some embodiments, engaging the articular body 904 with the selected one of the couplers 924a, 924b, 924c can provide for an eccentricity adjustment of any of, for example, 0 mm, 1 mm, 2 mm, 3 mm, 4 mm, between 0 mm-1 mm, between 1 mm-2 mm, between 2 mm-3 mm, between 3 mm-4 mm, or between 0 mm-4 mm. In some examples, the eccentricity is provided by both the articular body 904 and the selected one of the couplers 924a, 924b, 924c such that when the articular body 904 is engaged with the selected one of the couplers 924a, 924b, 924c it can provide for the selected eccentricity. By having eccentricity provided by both the articular body 904 and the selected one of the couplers 924a, 924b, 924c can help to preserve some strength in the selected one of the couplers 924a, 924b, 924c.

Figure 18:
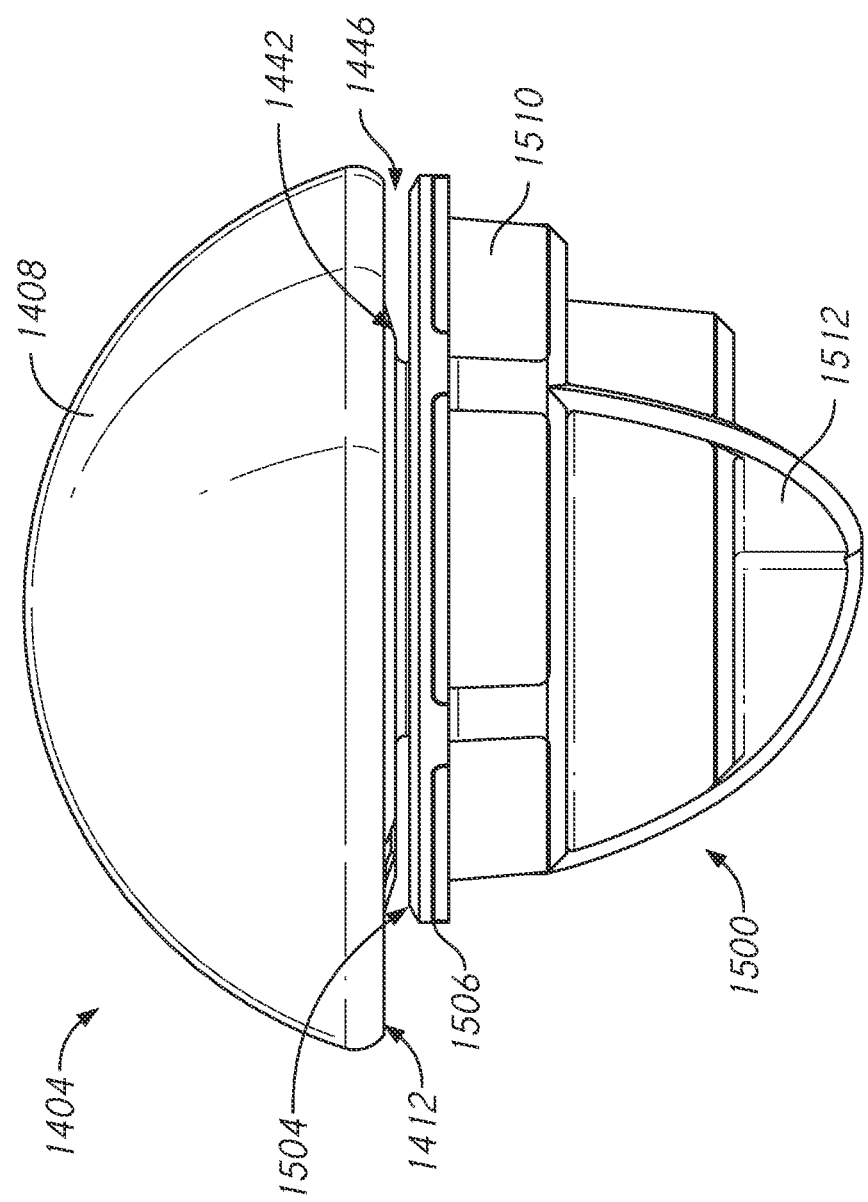
FIG. 18 shows another example of a humeral head assembly and anchor similar to those of FIGS. 1A and 2, the humeral head assembly including a coupler having a window to confirm a selected direction or degree of offset.

FIG. 18 illustrates an example of an embodiment of the humeral head assembly 901 in a first configuration 922a providing a centered (non-eccentric) configuration. As shown, when the articular body 904 is engaged with the coupler 924a, the humeral head assembly 901 will have a first configuration 922a that provides an offset of 0 mm. Thus, the first configuration 922a has a centered or non-eccentric configuration. To provide for a centered (non-eccentric) configuration, in some examples, when the first portion 928a of the coupler 924a is engaged with the articular body 904, the longitudinal axis 948a of the second portion 936a of the coupler 924a aligns with a radius 948 of the articular body 904 that is perpendicular to the lateral side of the articular body 904. In one embodiment, this radius is aligned with a longitudinal axis of the second recess 916 of the articular body 904. In the illustrated embodiment the longitudinal axis 958a of the second recess 916 is offset from the radius 948. A non-eccentric configuration is provided by the asymmetrical configuration of the first portion 928a and the second portion 936a. When the collar 940a and the radial protrusion 944a engage with the first recess 914 and the radial notch 920 respectively, the longitudinal axis 948a of the second portion 936a is aligned with the offset from the longitudinal axis of the second recess 916 but is aligned with the radius 948 of the articular surface 908 such that there is no offset between the radius 948 and the longitudinal axis 948a.

FIG. 17B illustrates an embodiment of the humeral head assembly 902 in a second configuration 922b, providing an example of a low eccentric configuration. As shown, when the articular body 904 is engaged with the coupler 924b, the humeral head assembly 902 can have an eccentric configuration that can, for example, provide an offset of 1.75 mm. In some embodiments, the second configuration 922b provides for an eccentric configuration by engaging the first portion 928b of the coupler 924b with the articular body 904 such that the longitudinal axis 948b of the second portion 936b of the coupler 924b is offset from a radius 948 of the articular body 904 that is perpendicular to the lateral side of the articular body 904. In some examples, the first portion 928b of the coupler 924b aligns with the radius 948 of the second recess 916 while an offset exists between the longitudinal axis 958b of the second recess 916 and the longitudinal axis 948b of the second portion 936b. When the collar 940b and the radial protrusion 944b engage with the first recess 914 and the radial notch 920 respectively, the longitudinal axis of the second portion 936b is not aligned with the radius 948 and the longitudinal axis of the articular surface 908 to provide a 1.75 mm offset.

FIG. 17C illustrates the humeral head assembly 903 in a third configuration 922c that provides for a high eccentric configuration. Similar to FIG. 17B, when the articular body 904 is engaged with the coupler 924c, the humeral head assembly 903 can have an eccentric configuration. In the embodiment illustrated in FIG. 17C, the third configuration 922c can provide a 3.50 mm offset. In some embodiments, the third configuration 922c provides for an eccentric configuration by engaging the first portion 928c of the coupler 924c with the articular body 904 such that the longitudinal axis 948c of the second portion 936c of the coupler 924c is offset from a radius 948 of the articular body 904 that is perpendicular to the lateral side of the articular body 904. In some examples, the first portion 928c of the coupler 924c aligns with the radius 948 of the second recess 916 while there is an offset between the longitudinal axis 958c of the second recess 916 and the longitudinal axis 948c of the second portion 936c. As discussed above, even though the coupler 924c is asymmetrical, when the collar 940c and the radial protrusion 944c engage with the first recess 914 and the radial notch 920 respectively, the longitudinal axis of the second portion 936c is not aligned with the radius 948 and the longitudinal axis of the articular surface 908 to provide a 3.0 mm offset.

In some embodiments, each of the couplers 924a, 924b, 924c can include a threaded channel 956. The threaded channel 956 can be configured to allow for disassembly of the humeral head assembly 903. In some examples, the threaded channel 956 can be configured to receive and/or threadingly engage a tool (e.g. a rod) such that a load can be applied to disassemble, for example, articular body 904 from one of the couplers 924a, 924b, 924c to which the body 904 is coupled.

Figure 18A:
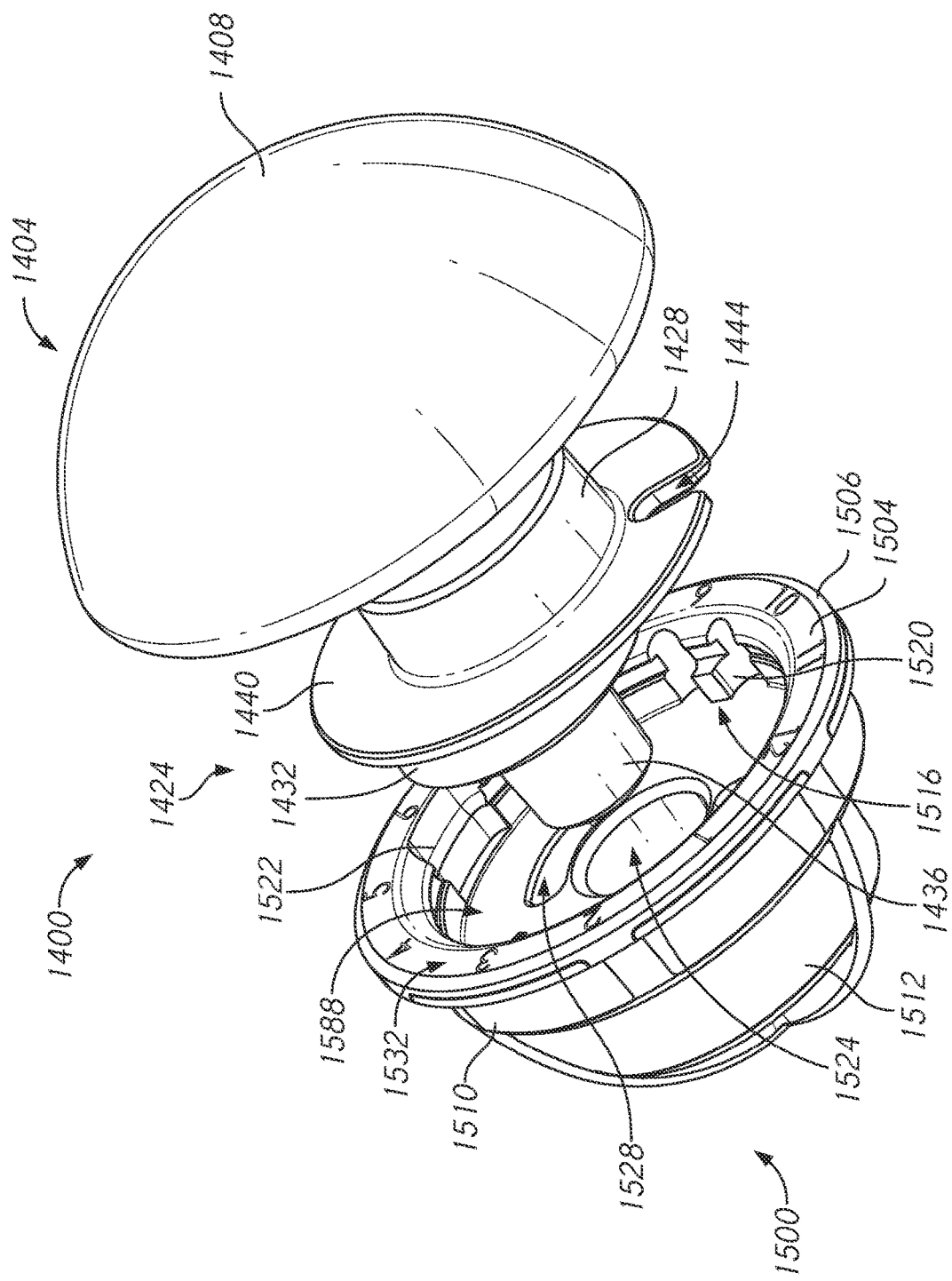
FIG. 18A is an exploded view of components of the humeral head assembly of FIG. 18.

FIGS. 18-20A illustrate another embodiment of a humeral head system in which eccentricity of the system can be adjusted by coupling an articular body with one of a plurality of different couplers. As illustrated in FIG. 18C, the articular body 1404 is configured to be coupled with one of a plurality of different couplers (e.g., the first coupler 1424a, the second coupler 1424b, or the third coupler 1424c). As shown in FIGS. 18A and 18C, articular body 1404 and the plurality of couplers 1424a, 1424b, 1424c are separable components of the humeral head system 1400. Each of the couplers 1424a, 1424b, 1424c is configured to enable a surgeon to select an engagement position to facilitate the selection of an amount or direction of eccentricity or no eccentricity when one of the selected couplers 1424a, 1424b, 1424c is engaged with the articular body 1404. As discussed in more detail below, the different degrees of eccentricity can include a selection of one of the couplers 1424a, 1424b, 1424c. The different degrees or directions of eccentricity can then be further determined by rotational positioning of the couplers 1424b, 1424c relative to an anchor.

FIG. 18C illustrates various configurations of humeral assembles that can be formed from the humeral head system 1400 when the articular body 1404 is engaged with one of the selected couplers 1424a, 1424b, 1424c. For example, the humeral head system 1401 illustrates the articular body 1404 coupled with a first coupler 1424a and corresponds with a centered (or not eccentric) position or configuration. In another example, the humeral head system 1402 illustrates the articular body 1404 coupled with a second coupler 1424b and corresponds with a low eccentric position or configuration. In some embodiments, this can correspond with a nominal 1.5 mm of eccentricity adjustment. In another example, the humeral head system 1403 illustrates the articular body 1404 coupled with a third coupler 1424c and corresponds with a high eccentric position or configuration, which can correspond to a nominal 3.5 mm of eccentricity adjustment. In each of these cases, a change in position of the articular body 1404 can be adjusted by rotating the combination of the body 1404 and the coupler 1424b, 1424c relative to the recess of the second recessed portion 1524 of the anchor 1500. Such rotation can provide eccentricity adjustment of the humeral implant assembly while maintaining the same offset distance between the center of the first recess 1416 in the articular body 1404 and the second recessed portion 1624 in the humeral anchor 1500.

FIGS. 18-20A illustrate various humeral head assemblies similar to the humeral head assembly 100 and other humeral head assemblies discussed elsewhere in this specification. As noted above, the discussions of aspects of the other humeral head assemblies set forth elsewhere in this specification that are relevant to the discussion of the humeral head systems 1400, 1401, 1402, 1403, the articular body 1404, and each of the couplers 1424a, 1424b, 1424c.

Figure 18B:
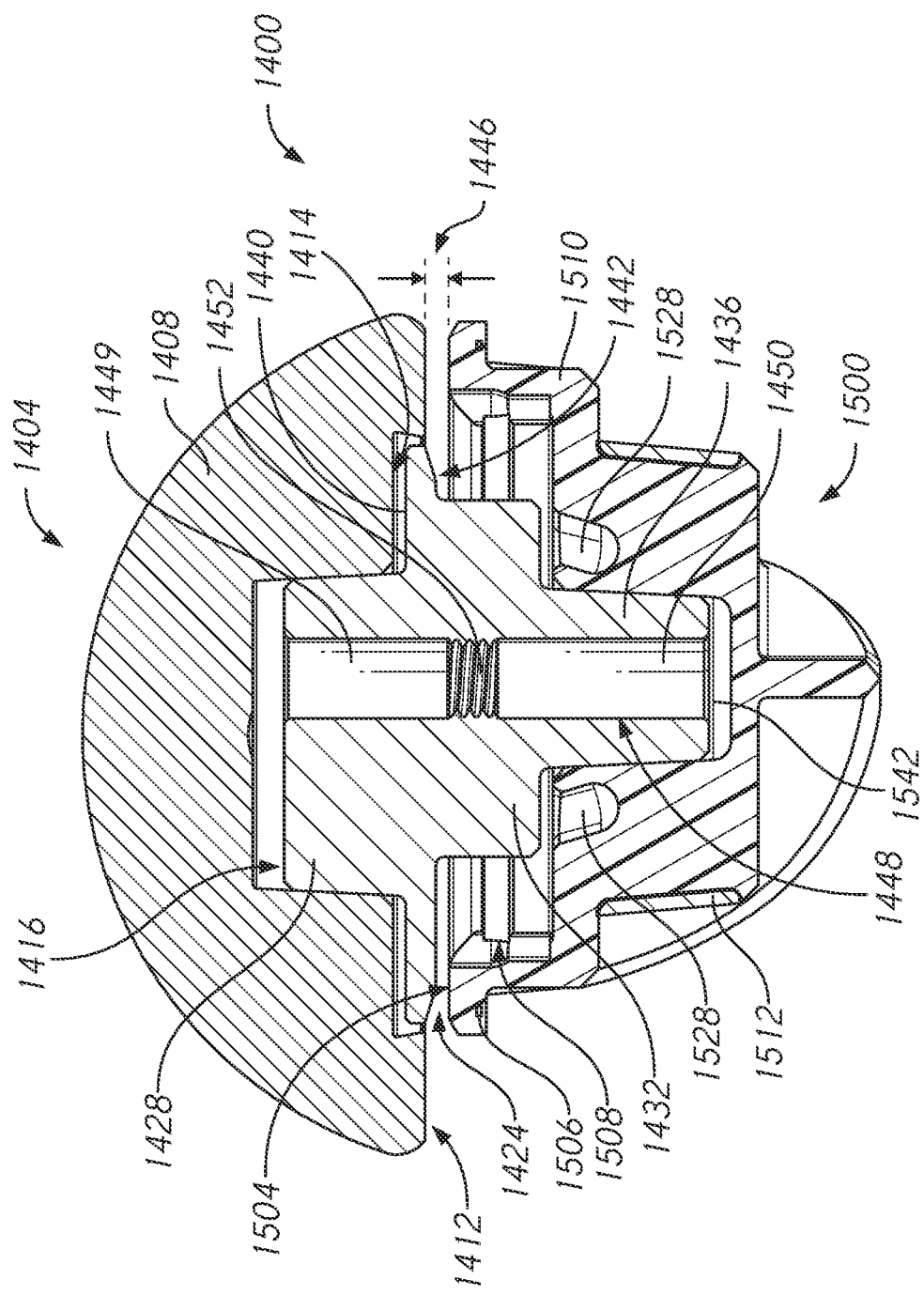
FIG. 18B is a cross-sectional view of the humeral head assembly of FIG. 18.
Figure 18C:
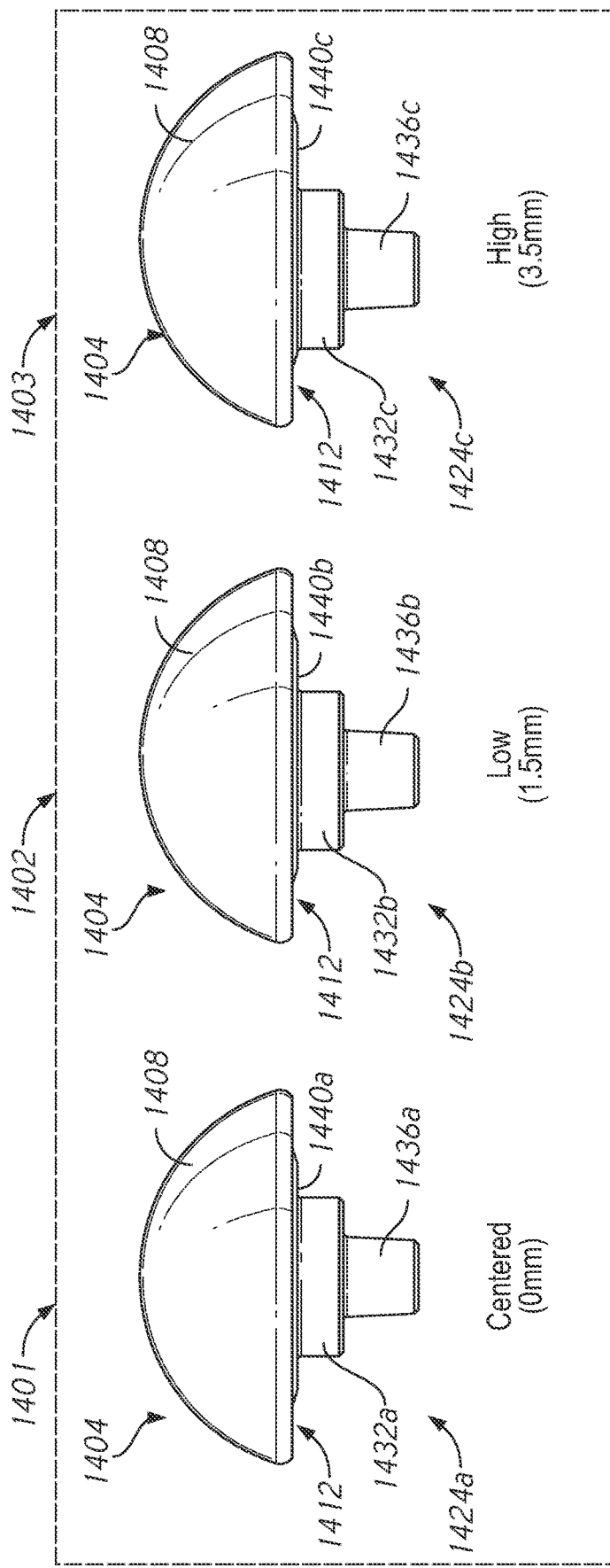
FIG. 18C is a humeral head assembly kit similar to the kit of FIG. 16A.

FIGS. 18 and 18B illustrate a side and cross-sectional view of the articular body 1404 respectively. In some embodiments, the articular body 1404 can have an articular surface 1408. As illustrated, in some examples, the articular surface 1408 can have a convex surface. In some embodiments, the articular surface 1408 can be configured to engage with a corresponding concave surface of or at a glenoid of a patient. In some examples, as illustrated in FIG. 18B, the articular body 1404 can have a lateral side 1412. The lateral side 1412 can be disposed on a side of the articular body 1404 opposite of the articular surface 1408. In some embodiments, the articular body 1404 can include a first recess 1414 and a second recess 1416 that are disposed on the lateral side 1412 and that extend from the lateral side 1412 of the articular body 1404 towards the articular surface 1408 of the articular body 1404. As shown in FIG. 18B, in some examples, the first recess 1414 and the second recess 1416 are centered on the surface of the lateral side 1412. In some embodiments, the radius of the first recess 1414 can be greater than the radius of the second recess 1416. The first recess 1414 and the second recess 1416 can serve a purpose similar to the continuous zone 424 discussed above with regard to the articular bodies 400, 404A in that they allow for engaging any of the couplers 1424a, 1424b, 1424c to the articular body 1404 along a range of positions that are not a pre-defined and to allow rotation when the coupler is inserted into the recesses 1414, 1416 but not fully engaged with the articular body 1404. In some embodiments, the amount of eccentricity can be selected by rotationally positioning one of the couplers 1424b, 1424c relative to the humeral anchor 1500 prior to engaging the coupler with the articular body 1404. The coupler 1424a is rotationally symmetric and thus rotation does not change the eccentricity of the articular body 1404 relative to the anchor 1500.

In some examples, the articular body 1404 can be configured to engage with and/or be retained by any of the couplers 1424a, 1424b, 1424c. Although the following description regarding any of the couplers 1424a, 1424b, 1424c is with regard to providing various amounts of eccentricity, the components of any of the couplers 1424a, 1424b, 1424c (e.g., the first portion 1428, the plate 1440, the disc member 1432, and the second portion 1436, etc.) are generally similar and descriptions of one of the couplers should be understood to describe any of the other couplers as well.

In some embodiments, a selected one of the couplers 1424a, 1424b, 1424c can be coupled with the first recess 1414 and the second recess 1416 of the articular body 1404 to maintain the humeral head system 1401, 1402, 1403 in a configuration that is centered or eccentric following a selection of a degree of eccentricity by choosing one of the couplers 1424a-1424c and thereafter rotating the chosen coupler to the selected position in the anchor 1500. In some embodiments, as illustrated in FIG. 18B, when the various components of the humeral head system 1400 are assembled, the articular body 1404 is engaged with one of the couplers 924a, 924b, 924c. As shown, a gap 1446 is provided between a proximal surface of a collar 1506 and the lateral side 1412 of the articular body 1404. In some embodiments, each of the couplers 924a, 924b, 924c can have a plate 1440 with a ledge 1442 that forms a surface or a boundary between the plate 1440 and the disc member 1432. In some examples, the ledge 1442 forms an angled surface, e.g., a surface at an acute angle to horizontal in view of FIG. 18B. As will be discussed in more detail below, to facilitate the removal of the articular body 1404 from a chosen one of the couplers 924a, 924b, 924c to which the body is attached, a tool can be inserted to engage the ledge 1442 such that a force and/or load can be applied to separate one of the couplers 924a, 924b, 924c from the articular body 1404 to which it is attached.

As noted above, FIG. 18B illustrates that the lateral side 1412 of the articular body 1404 can include the first recess 1414 disposed within the articular body 1404. The first recess 1414 can have an open end on a lateral side 1412 of the articular body 1404. In some embodiments, the first recess 1414 can be straight or tapered such that the radius of the first recess 1414 decreases as it extends into the articular body 1404. As illustrated, the lateral side 1412 is a side of the articular body 1404 opposite to the articular surface 1408. The lateral side 1412 can be configured to face away from the glenoid when the humeral head system 1401, 1402, 1403 is implanted. As discussed above, the second recess 1416 can extend into the articular body 1404. In some embodiments, the second recess 1416 can have a closed end. The second recess 1416 can be tapered such that the diameter decreases over the length of the second recess 1416 to a lesser diameter adjacent to the closed end. The second recess 1416 can have a greater diameter toward the lateral side 1412 of the articular body 1404. As noted above, in some examples, the radius of the first recess 1414 can be greater than the radius of the second recess 1416.

Figure 19:
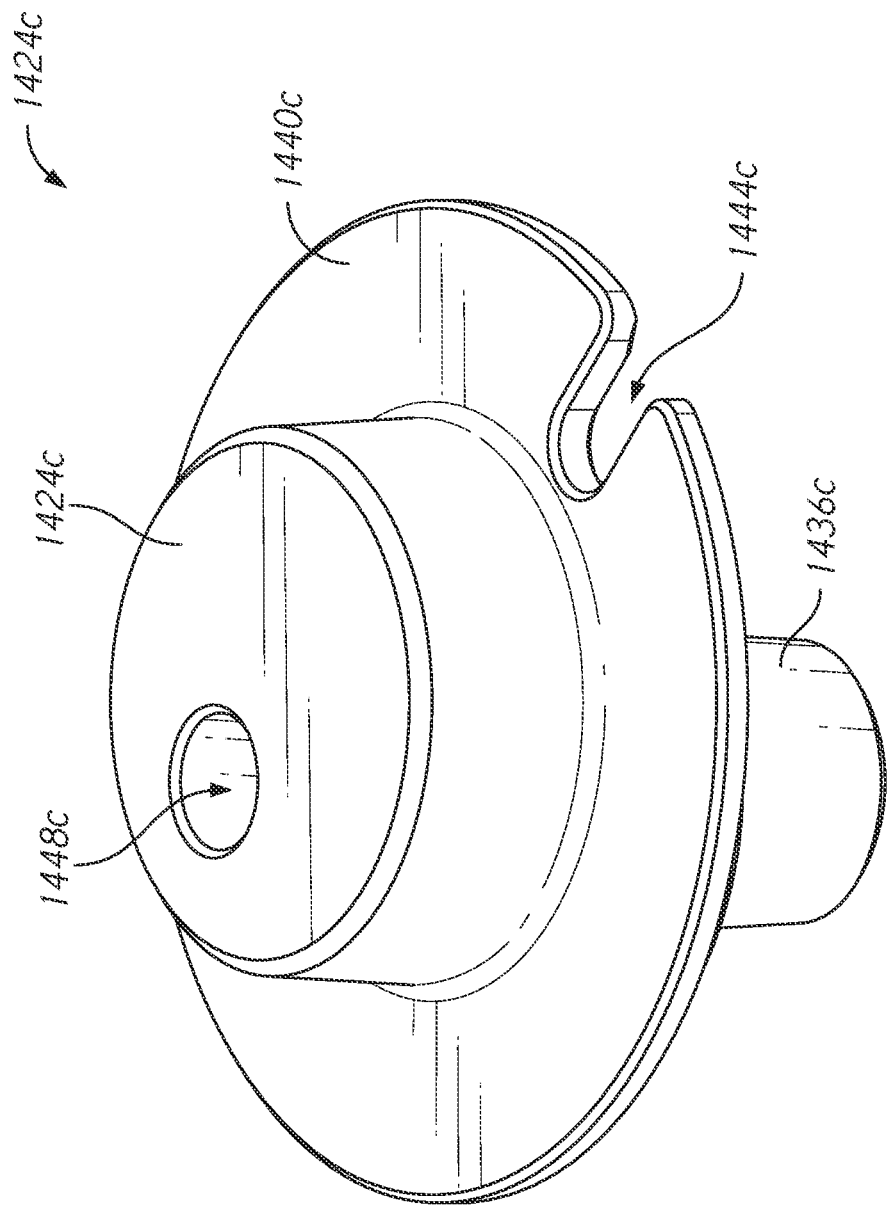
FIGS. 19-19E illustrate an example of a coupler that can be used in the humeral head assembly of FIG. 18, the coupler providing an offset between longitudinal axes of opposite ends of the coupler.
Figure 19A:
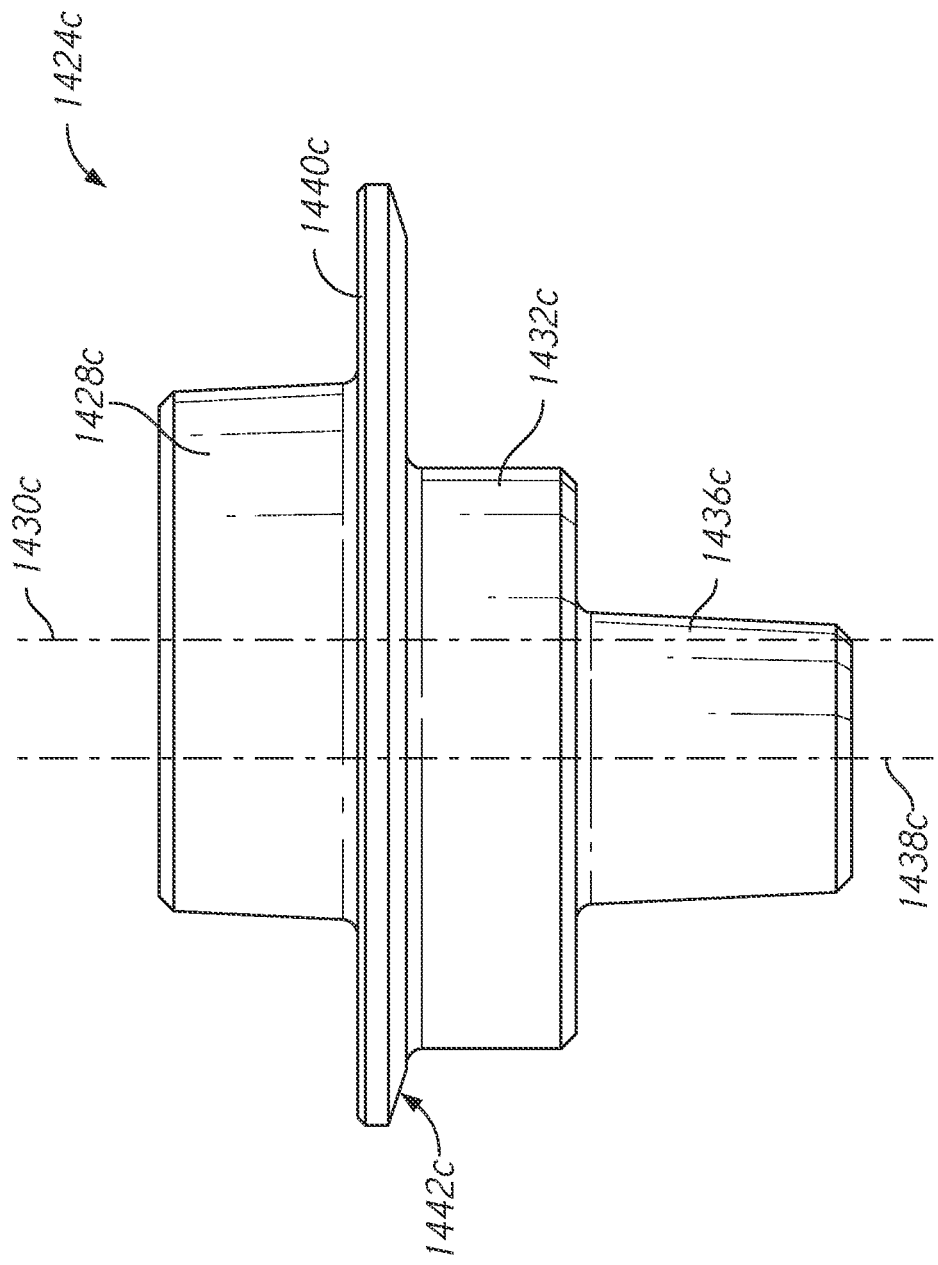
Figure 19B:
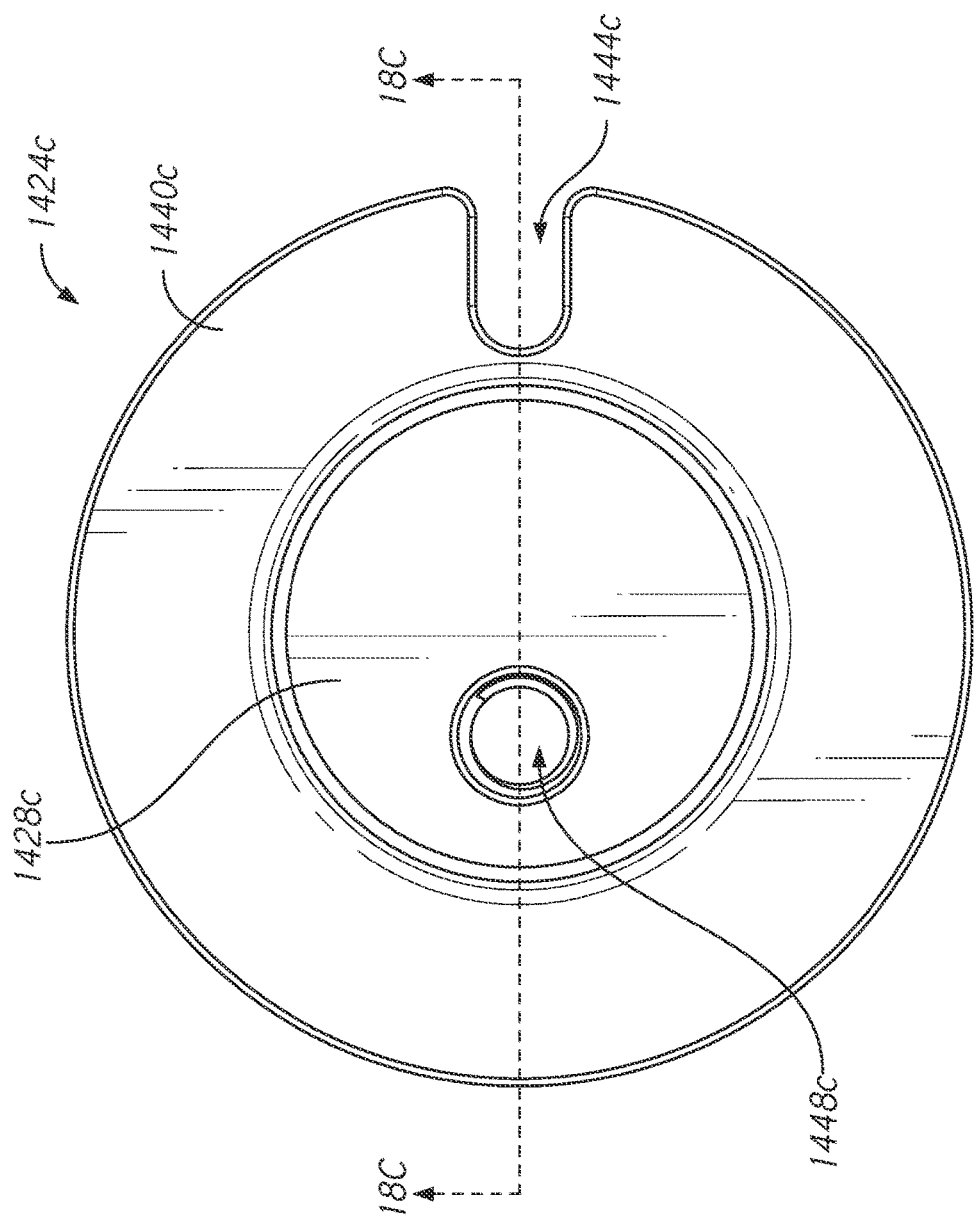

As discussed above, the articular body 1404 can be configured to engage with any one of a plurality of couplers to provide different eccentricities for the humeral head system 1400. A representative embodiment of a coupler 1424 providing an eccentric configuration is illustrated in FIGS. 19-19E. In particular, the coupler 1424c in FIGS. 19-19E provides a relatively high nominal or maximum eccentric position or configuration. In some embodiments, the coupler 1424c can include a first portion 1428c, a disc member 1432c, and a second portion 1436c. In some embodiments, the coupler 1424c can include an engagement portion that comprises a plate 1440c. As illustrated in FIG. 19B, in some examples, the plate 1440c can include a window 1444c that forms a slot in the plate 1440c to uncover an indicium on a corresponding anchor that is indicative of an orientation or a configuration of eccentricity of the articular body 1404 relative to the other member of the joint prosthesis (e.g., the anchor 1500 or to a glenoid component) or a native glenoid in the case of a hemi-arthroplasty.

In some embodiment, the first portion 1428c of the coupler 1424c can be secured within the second recess 1416 of the articular body 1404. As discussed herein, the second recess 1416 can be tapered such that the radius of the second recess 1416 decreases as it extends into the body of the articular body 1404. In some examples, the first portion 1428c is tapered to engage the second recess 1416 of the articular body 1404. In some embodiments, the radius of the first portion 1428c decreases in a proximal direction. In some examples, the plate 1440c of each of the coupler 1424c can be configured to be disposed in the first recess 1414. The plate 1440c can be located between the first portion 1428c and the disc member 1432c of each of the coupler 1424c. In some embodiments, the plate 1440c can be used to position the articular body 1404 on or over any of the coupler 1424c. As will be discussed in more detail below, the plate 1440c can include a window 1444c that is configured to indicate the orientation or configuration of eccentricity of the articular body 1404 relative to a corresponding anchor. As illustrated in FIG. 19B, the window 1444c can form a u-shaped slot that in a portion of the plate 1440c. In some embodiments, the window 1444c can extend inwardly in a radial direction and radially away from, e.g., in a plane perpendicular to, a longitudinal axis of the coupler 1424c.

FIGS. 19-19E show that the coupler 1424c can include a disc member 1432c as discussed above. The disc member 1432c can be located between the plate 1440c and the second portion 1436c of the coupler 1424c. The disc member 1432c of the coupler 1424c can be used with and secured within a stemless anchor, such as the anchor 830, the anchor 830A, or the humeral anchor 1500 discussed above or in a humeral anchor having a stem, e.g., the anchor 500 having a stem portion or a variant thereof omitting the notches 544. In some embodiments, the coupler 1424c (or any of the couplers 1424 described above (e.g., the coupler 1424a or coupler 1424b) can be secured within an anchor with an expandable disc as illustrated in FIGS. 21A-43. For example, instead of the second portion 1436c, the coupler 1424c can include a bottom portion having an expandable disc—similar to the expandable disc 1003 of the coupler 1000—to engage with the first recess 1508 in the humeral anchor 1500 (or any of the proximal openings in the anchors 830, 830A, 500). In some examples, the coupler 1424c (or any of the couplers 1424 described above (e.g., the coupler 1424a or coupler 1424b) can be secured within an anchor with a disc similar to the coupler 1304 illustrated in FIGS. 44-50. For example, in some embodiments, a distal portion of the coupler 1424c can be inserted into a tapered opening 1316 of the coupler 1306 such that the coupler 1306 expands and secures the coupler 1424c within a proximal opening any of the anchors disclosed above.

FIGS. 18-18B illustrate an embodiment of a humeral anchor 1500 that can be configured to engage with the articular body 1404 and coupler 1424 in the humeral head system 1400. In some embodiments, the humeral anchor 1500 is configured to be disposed in a proximal portion of a humerus e.g., in the metaphyseal portion thereof. The humeral anchor 1500 is configured to be able to receive a portion of the coupler 1424 (e.g., the disc member 1432) below a humeral resection plane within the metaphyseal portion. Like the anchor 830, the humeral anchor 1500 advantageously enables a surgeon to reverse the articular surfaces of the shoulder while accommodating soft tissue of a wide variety of patients.

FIG. 18 shows the humeral anchor 1500 coupled with the articular body 1404 to form the humeral head system 1400 in an anatomic configuration. The humeral anchor 1500 is configured to be disposed at or below a resection surface (as illustrated in FIG. 1A). In some embodiments, a recess in a proximal side of the anchor 1500 can have a first recess portion 1508 formed within a cylindrical portion 1510 at a proximal end of the humeral anchor 1500. In some examples, the recess can have a second recess portion 1524 formed within a distal end 1512 of the humeral anchor 1500. The first recess portion 1508 can be disposed between the proximal face 1504 and a bottom surface of the first recess portion 1508. The second recess portion 1524 can be disposed between the first recess portion 1508 and the distal end 1512 of the humeral anchor 1500. In some examples, the first recess portion 1508 forms a wider portion of the recess that is disposed near the proximal end of the humeral anchor 1500. The second recess portion 1524 can form a narrower recess distal to the first recess portion 1508. In some embodiments, the second recess portion 1524 can be tapered such that the radius of the second recess portion 1524 is reduced in a distal direction. As discussed in more detail below, the second recess portion 1524 is configured to receive the coupler 1424 that is secured to or adapted to be secured to the articular body 1404. In some examples, the tapered second recess portion 1524 is configured to engage a tapered second portion 1436 of the coupler 1424.

As illustrated in FIG. 18B, the coupler 1424 and the humeral anchor 1500 are separable components. FIGS. 18A-18B illustrate the disc member 1432 of the coupler 1424 disposed within the first recess portion 1508 of the humeral anchor 1500. As well, the second portion 1436 of the coupler 1424 is seated within the second recess portion 1524 of the humeral anchor 1500.

The humeral anchor 1500 can be configured to be secured in the resected humerus. In some embodiments, the proximal face 1504 of the humeral anchor 1500 can lie in the same plane as the resected humerus such that the cylindrical portion 1510 can secure a base of the coupler 1424 (e.g., the second portion 1436) in the first recess portion 1508 entirely below the surface of the resected humerus. As discussed above, examples of stemless bone anchors are found in U.S. Provisional Application No. 62/740,333, filed on Oct. 2, 2018, the entirety of which is incorporated by reference herein.

As illustrated in FIGS. 18A-18B, in some embodiments, the disc member 1432 of the coupler 1424 is positioned within the cylindrical portion 1510 of the humeral anchor 1500. The disc member 1432 can be positioned such that the distal side of the plate 1440 is adjacent to a surface of a collar 1506 formed on a proximal end of the cylindrical portion 1510. In some examples, the disc member 1432 can be positioned such that a proximal portion of the disc member 1432 is slightly above the proximal face 1504 of the humeral anchor 1500. In some embodiments, the distal surface of the disc member 1432 can lie flush against a bottom surface of the cylindrical portion 1510. As shown in FIG. 18B, by having the cylindrical portion 1510 secure the coupler 1424 at or below the resection level, this can position the base of the plate 1440 at, adjacent to, or just above the resection plane such that the articular body 1404 can be coupled to the coupler 1424 such that the articular body 1404 is flush or near flush with the resection, in some cases leaving a small clearance to assure proper connection between the articular body 1404 and the coupler 1424 and to leave space for tools to enable disassembly of the head from the coupler as needed.

In some examples, the humeral anchor 1500 can include additional connection features. As illustrated in FIG. 18B, a plurality of secondary features 1516 can be formed along the internal surface of the cylindrical portion 1510. These plurality of secondary features 1516 can be configured to provide engagement with a reverse articular component such as the reverse articular body 804A. For example, the plurality of secondary features 1516 can include at least one convex locking feature 1520. In some embodiments, the plurality of secondary features 1516 can include at least one concave locking feature 1522. In some examples, the plurality of secondary features 1516 is formed from alternating convex locking features 1520 and concave locking features 1522. In some embodiments, the plurality of secondary features 1516 are configured to provide rotational stability to the articular body 804A when the humeral anchor 1500 is converted to or initially installed as part of a reverse shoulder system with a reverse shoulder articular body.

In some examples, the disc member 1432 can be configured to engage with the locking features 1520, 1522, e.g., can be configured to include corresponding male or female geometry that is configured to correspond with or engage with the at least one convex locking feature 1520 or the at least one concave locking feature 1522 of the plurality of secondary features 1516 (not illustrated). Such connection could be in lieu of or in addition to the taper connection described above. Further, the engagement features described below in connection with FIGS. 21-50 can be used to connect modified embodiments of the coupler 1424 to an anchor. In some embodiments, the disc member 1432 can be deformed to engage with the plurality of secondary features 1516 (not illustrated). By engaging either the at least one convex locking feature 1520 or the at least one concave locking feature 1522 of the plurality of secondary features 1516 with the outside surface of the disc member 1432, the secondary features 1516 can serve as an anti-rotation feature.

In some embodiments, the humeral anchor 1500 can include a plurality of tooling interfaces 1528. As illustrated in the cross-sectional view of FIG. 18B, each of the plurality of tooling interface 1528 can extend into a portion of the humeral anchor 1500 adjacent to the distal end 1512 from the base of the first recess portion 1508. In some embodiments, the plurality of tooling interfaces 1528 form curved openings that are spaced about the second recess portion 1524. In some examples, the tooling interface 1528 is configured to engage with a tool such that the humeral anchor 1500 can be inserted and/or secured into a cavity of the humerus. The tooling interfaces 1528 can be angled toward the second recess portion 1524

FIG. 18C illustrates three eccentricity adjustments, positions or configurations that can be achieved by engaging the articular body 1404 with a selected one of the couplers 1424a, 1424b, 1424c. Each of the couplers 1424b, 1424c when engaged with the articular body 1404, can provide a nominal eccentricity adjustment level and can provide for adjustment based upon rotation of the coupler relative to the anchor 1500 about an arc defined by the nominal level. The coupler 1424a provide a symmetric arrangement where rotation does not result in a change in position on the resection surface. It should be noted that the couplers 1424b, 1424c illustrated in FIG. 18C are only some examples of the eccentricities that the humeral head system 1400 can provide. In some embodiments, engaging the articular body 1404 with one of the selected couplers 1424a, 1424b, 1424c can provide for a nominal level of eccentricity adjustment of any of, for example, 0 mm, 0.5 mm, 1.0 mm, 1.5 mm, 2.0 mm, 2.5 mm, 3.0 mm, 3.5 mm, 4 mm, between 0 mm-0.5 mm, between 0.5 mm-1.0 mm, between 1.0-1.5 mm, between 1.5 mm-2.0 mm, between 2.0 mm-2.5 mm, between 2.5 mm-3.0 mm, between 3.0 mm-3.5 mm, between 3.5 mm-4.0 mm, or between 0 mm-4.0 mm. Adjustment based upon the nominal level can generally be provided as discussed below. In some examples, the eccentricity is provided by both the articular body and one of the selected couplers 1424a, 1424b, 1424c such that when the articular body is engaged with one of the couplers 1424a, 1424b, 1424c, it can provide for the selected eccentricity. For example, a nominal offset coupler 1242 can be provided. The articular body 1404 can have an off-center recess and continuous or discrete ranges of eccentricity adjustment as discussed in connection with FIGS. 3-12A such that the amount of eccentricity in addition to the direction of eccentricity can be selected. Or, a nominal offset coupler 1242 can be provided and an anchor can have a continuous or discrete range of eccentricity adjustment as discussed in connection with FIGS. 13A-14C such that the amount of eccentricity in addition to the direction of eccentricity can be selected. By having eccentricity provided by two or more of the articular body, the anchor, and one of the couplers 1424a, 1424b, 1424c, strength in the couplers 1424a, 1424b, 1424c can be preserved.

FIGS. 19-19E illustrate an example of an embodiment of the coupler 1424 providing an eccentric configuration (i.e., the coupler 1424c of the humeral head system 1403 illustrated in FIG. 18). As shown, when the articular body 1404 is engaged with the illustrated coupler 1424c, the humeral head system 1400 can have an eccentric configuration that can, for example, provide an offset of 3.5 mm. In some embodiments, the coupler 1424 illustrated in FIGS. 19-19E provides for an eccentric configuration by engaging the first portion 1428c of the coupler 1424c with the articular body 1404 such that, as shown in the side view of FIG. 19A, a longitudinal axis 1438c of the disc member 1432c and the second portion 1436c is offset from a longitudinal axis 1430c of the first portion 1428c that is perpendicular to the lateral side 1412 of the articular body 1404 and extends through a center of the articular surface 1408. In some examples, the first portion 1428c of the coupler 1424c aligns with the second recess 1416 of the articular body 1404 while an offset exists between a longitudinal axis 1430c of the first portion 1428c and the longitudinal axis 1438c of the second portion 1436c. When the plate 1440c and the first portion 1428c engage the first recess 1414 and the second recess 1416 respectively, the longitudinal axis of the second portion 1436c is not aligned with the longitudinal axis of the second recess 1416 of the articular body 1404 (not illustrated). Because of the offset, the rotation of the articular body 1404 and coupler 1424c cause the location of the center of the articular surface 1408 to move relative to the anchor 1500 and therefore relative to the resection surface of the humerus. The motion allows the center of rotation of the humeral head system 1400 to be moved to a position that provides advantageous biomechanical performance for the given patient.

Figure 20:
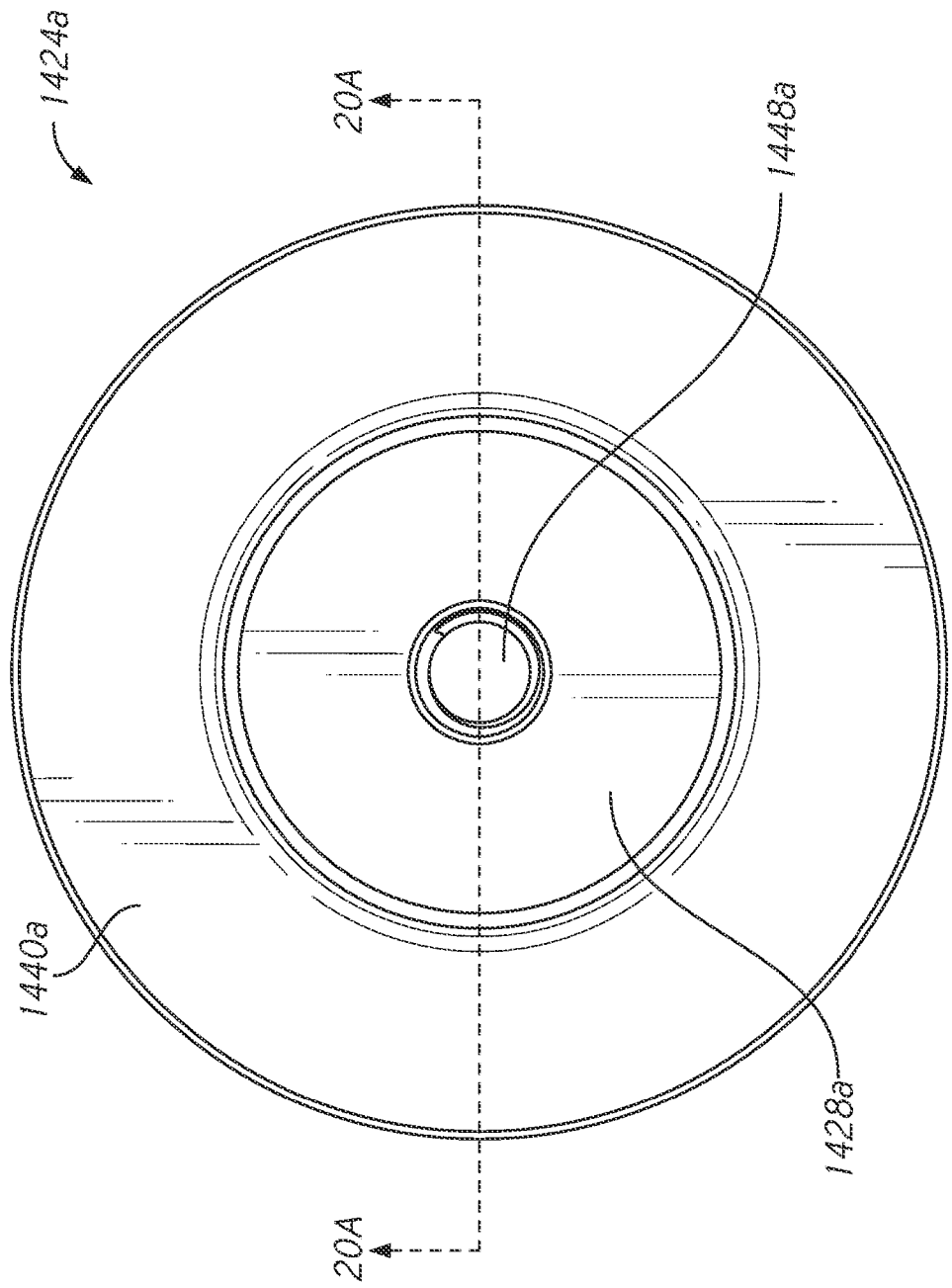
FIGS. 20-20A illustrate another example of a coupler that can be used in the humeral head assembly of FIG. 18, the coupler providing longitudinal axes of opposite ends of the coupler being aligned.
Figure 20A:
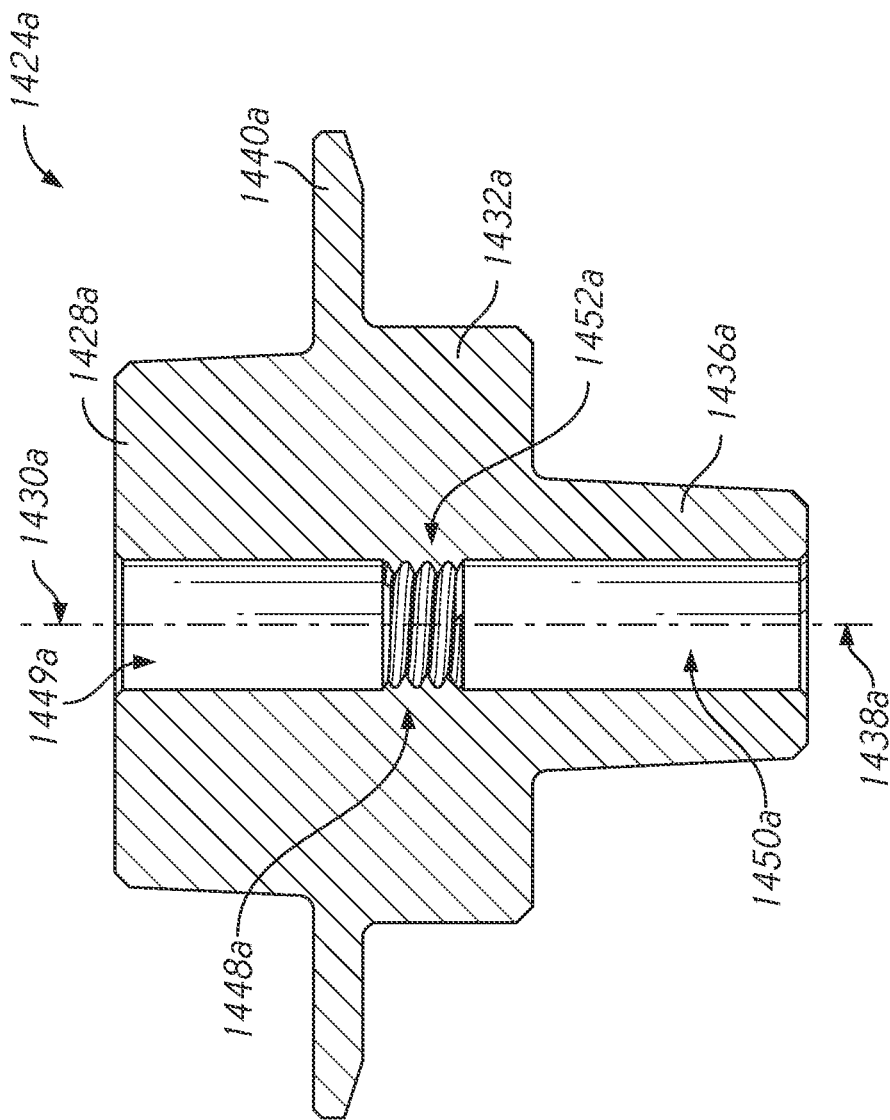

FIGS. 20-20A illustrate an example of an embodiment of the coupler 1424 providing a non-eccentric configuration (e.g., the coupler 1424a of the humeral head system 1401 illustrated in FIG. 18). As shown, when the articular body 1404 is engaged with the coupler 1424a, the humeral head system (e.g. the humeral head system 1401 of FIG. 18) will have a configuration that provides an offset of 0 mm of the center of the articular surface 1408 from the center of the anchor 1500, e.g., from the center of the collar 1506 or of the recess 1524. To provide for a centered (non-eccentric) configuration, in some embodiments, when the first portion 1424a of the coupler 1424a is engaged with the articular body 1404, a longitudinal axis 1438a of the second portion 1436a of the coupler 1424a is aligned with a longitudinal axis of the first portion 1428 that is inserted into and is perpendicular to the lateral side 1412 of the articular body 1404. In some embodiments, the longitudinal axis 1438a of the second portion 1436a is aligned with a longitudinal axis of the second recess 1416 of the articular body 1404 (not illustrated). When the plate 1440a and the first portion 1424a engage with the first recess 1414 and the second recess 1416 respectively, the longitudinal axis 1438a of the second portion 1436a is aligned with the longitudinal axis 1430a of the first portion 1428a and the longitudinal axis of the second recess 1416 of the articular body 1404 such that there is no offset between the longitudinal axis of the second recess 1416 (not illustrated), the longitudinal axis 1438a of the second portion 1436a, and the longitudinal axis 1430a of the first portion 1428a.

In some embodiments, each of the couplers 1424a, 1424b, 1424c can include a channel 1448. As will be discussed in more detail below, the channel 1448 can be configured to allow for disassembly of the humeral head system 1400. In some examples, the channel 1448 can be configured to receive and/or threadingly engage a tool (e.g. an elongate shaft 1840 illustrated in FIG. 56) such that a load can be applied to disassemble, for example, the articular body 1404 from one of the couplers 1424a, 1424b, 1424c to which the articular body 1404 is coupled. In some embodiments, a load can be applied to disassemble one of the couplers 1424a, 1424b, 1424c from the humeral anchor 1500 to which one of the couplers 1424a, 1424b, 1424c is coupled.

Figure 19C:
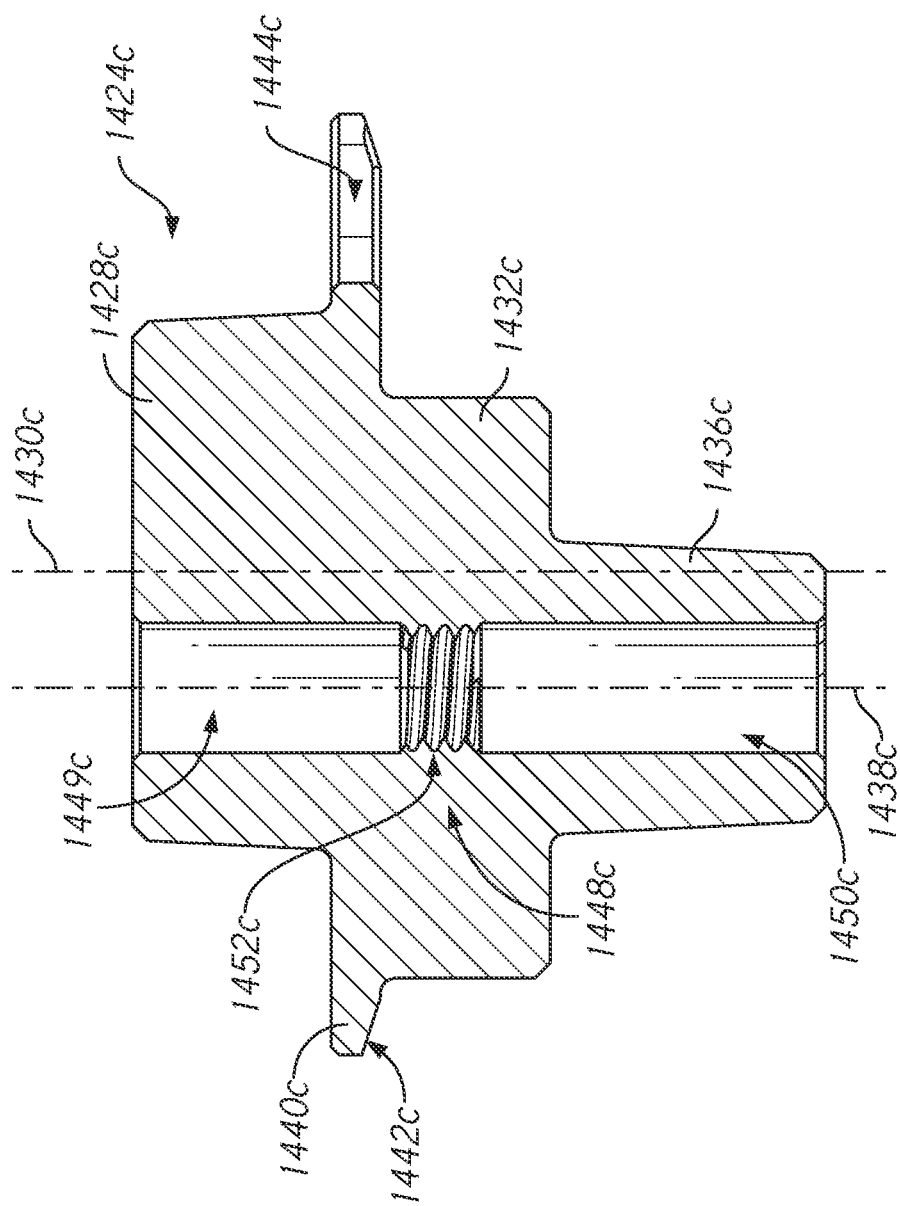
Figure 19E:
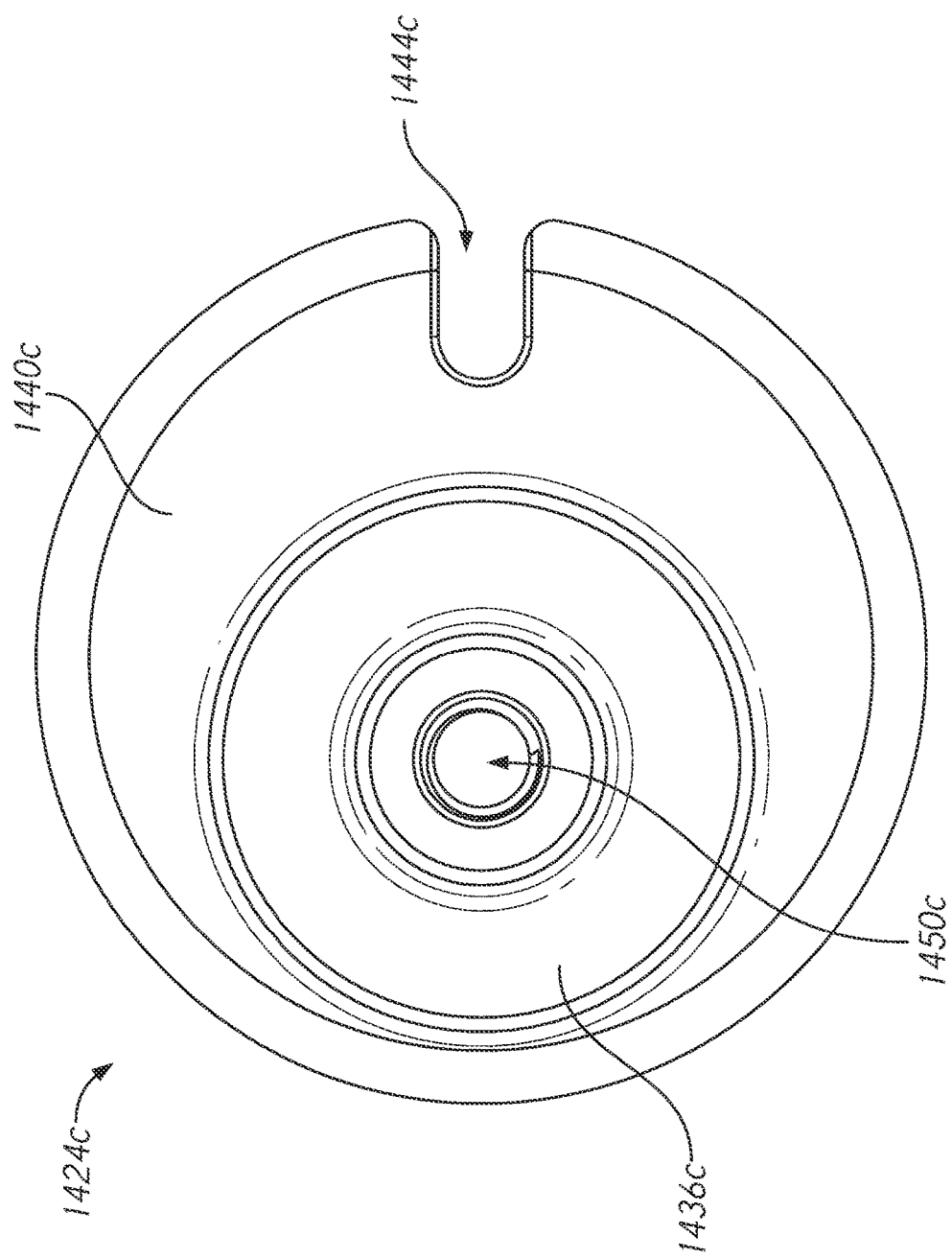

As illustrated in FIGS. 19C and 20A, the channel 1448c, a can include a proximal end 1449 c, a and a distal end 1450c, a. In some embodiments, the proximal end 1449c, a can extend from an opening in the surface of the first portion 1428c, a through a portion of the coupler surrounded by the plate 1440c, a and a portion of the disc member 1432c, a in a distal direction. In some examples, the distal end 1450c, a can extend from an opening in the surface of the second portion 1436c, a through the disc member 1432c, a in a proximal direction. In some embodiments, the channel 1448c, a includes a threaded portion 1452c, a extending between the proximal end 1449c, a and the distal end 1450c, a. In some examples, the channel 1448c, a and the distal end 1450c, a are unthreaded. As will be discussed in more detail, in some embodiments, the tool can be inserted from a proximal end 1449c, a of the channel 1448c, a to extend from the first portion 1428c, a through the disc member 1432c, a and the second portion 1436c, a in a distal direction. In some examples, the tool can be inserted from a distal end 1450c, a of the channel 1448c, a to extend from the second portion 1436c, a through the disc member 1432c, a and the first portion 1428c, a in a proximal direction.

As discussed above, FIGS. 19-19E illustrates an eccentric coupler 1424c. As shown in the cross-sectional view of FIG. 19C, in some embodiments, the channel 1448c of the eccentric coupler 1424c is disposed about the longitudinal axis 1438c of the second portion 1436c. FIGS. 20-20A illustrate a non-eccentric coupler 1424a. As shown in the cross-sectional view of FIG. 20A, in some embodiments, the channel 1448a of the non-eccentric coupler 1424a is disposed about the longitudinal axis 1430a, 1438a of both the first portion 1428a and the second portion 1436a.

III. Humeral Head Assemblies with Adjustable Eccentricity

FIGS. 2-14C illustrate variations of the components and kits of FIGS. 16-17C. For example, although the humeral head assemblies that can be formed by joining a selected one of the couplers 924a, 924b, 924c the articular body 904 result in a single eccentricity position, the articular body 904 could be coupled with a discrete position site to provide the configurations of FIGS. 17A-17C but could also have other connection features that provide for more selection in degree of eccentricity. FIGS. 18-20A illustrate alternative embodiments humeral head assemblies with adjustable eccentricity. As described above, and in more detail below, the eccentricity positions can be indicated by indicia located on the anchor 1500 and as may be observed when using one of the couplers 1424b, 1424c, e.g., through a window that can be rotated to the appropriate position on the relevant anchor to adjust a direction of eccentricity of the coupler.

The following embodiments facilitate providing a centered or a range of eccentric positions of a humeral head relative to a resected humeral surface. The embodiment discussed herein could be used in other orthopedic applications, including for providing centered or eccentric positioning of a glenosphere on a glenoid or scapular anchor, for providing centered or eccentric positioning of a femoral articular body on a femur anchor, for providing centered or eccentric positioning of tibial articular body on a tibial anchor, or for other orthopedic applications.

A. Continuous Adjustment and Discrete Adjustment of a Humeral Head

Figure 2:
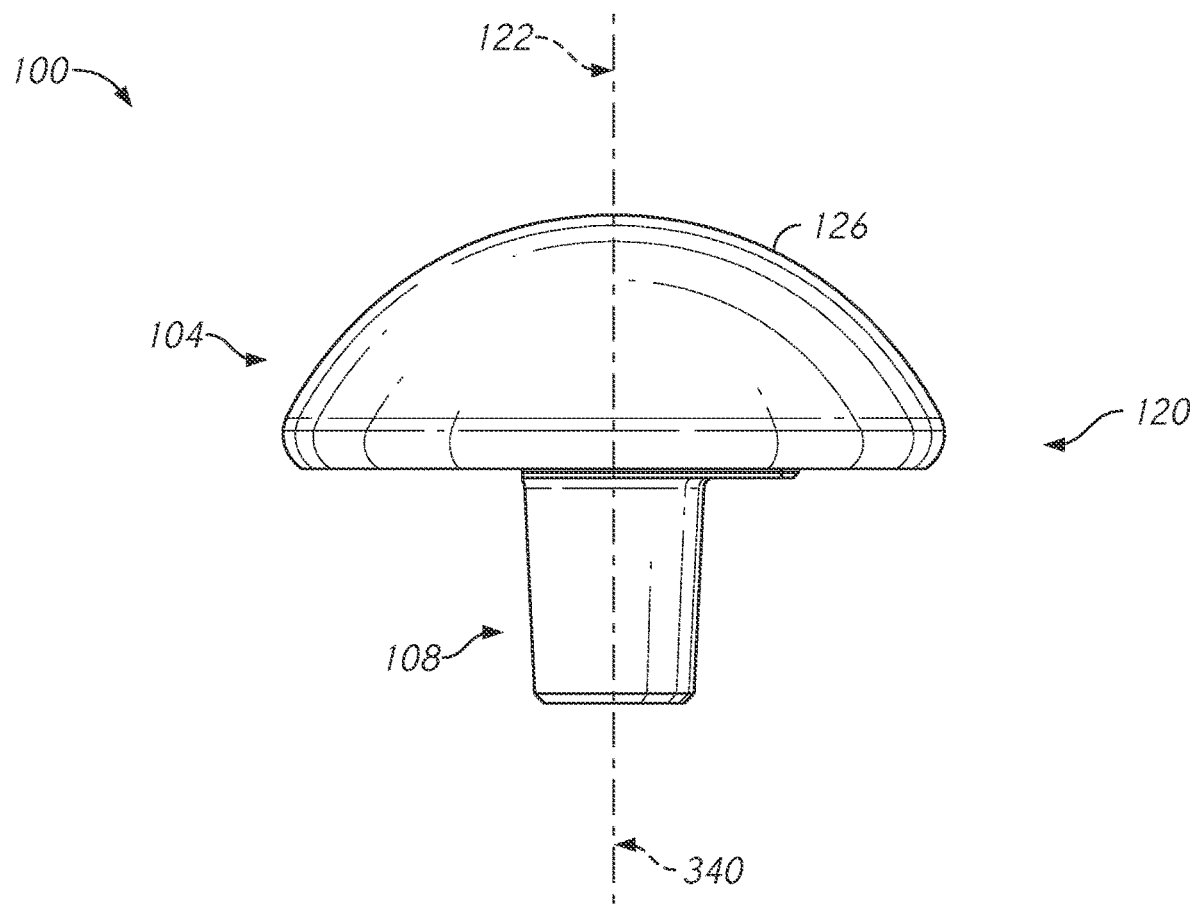
FIG. 2 shows one embodiment of a humeral head assembly, showing a first configuration in which an eccentricity of a portion of a coupler adapted to mate with a humeral anchor to the articular surface of an articular body is zero.
Figure 3:
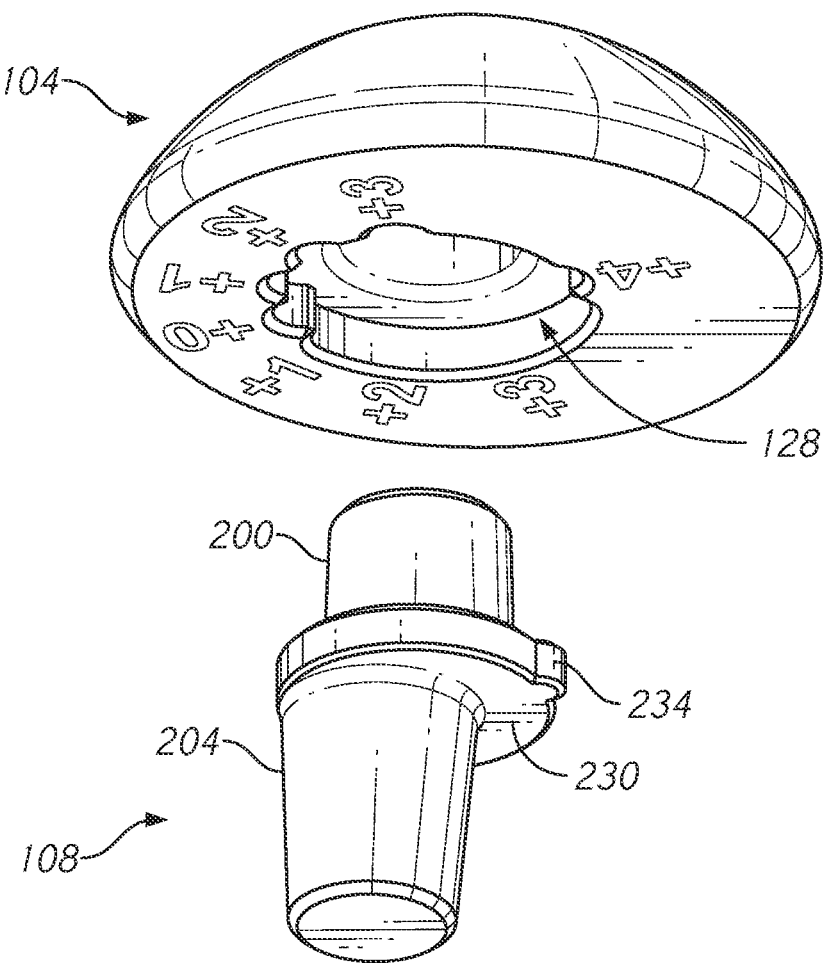
FIG. 3 is an exploded bottom view of the humeral head assembly of FIG. 2
Figure 4A:
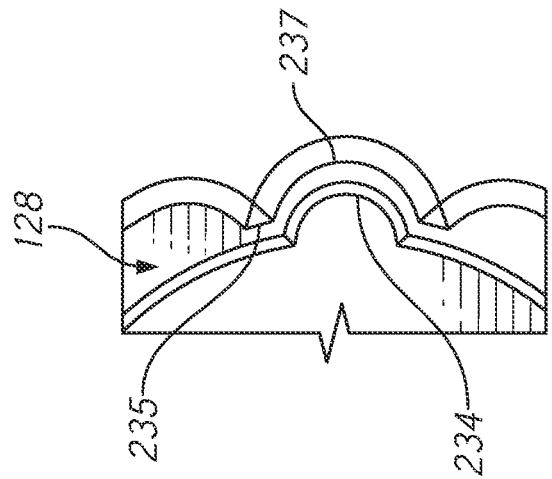
FIG. 4A shows detail 4A of FIG. 4 illustrating radial overlap between a protrusion of a coupler and a circumferential edge of an articular body.
Figure 4:
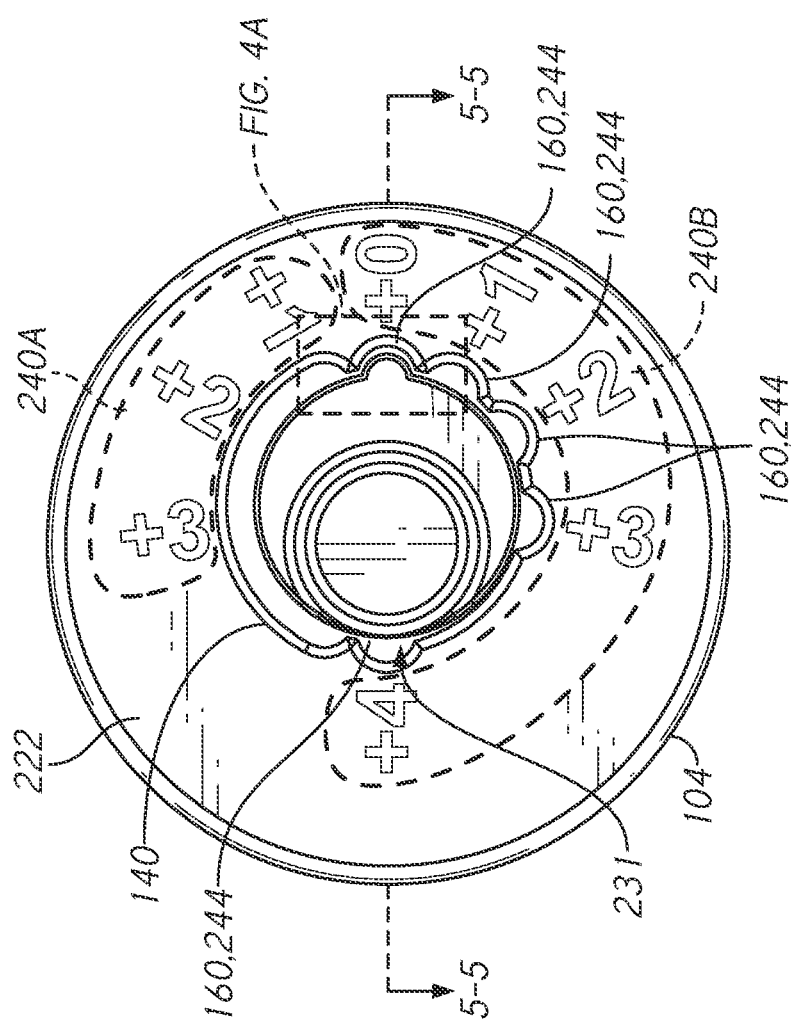
FIG. 4 is a lateral side view of the humeral head assembly of FIG. 2.
Figure 5A:
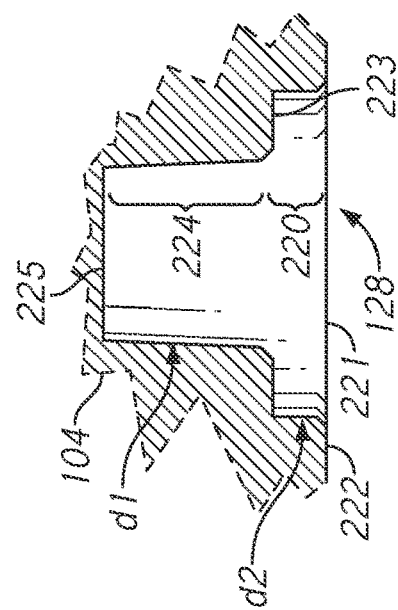
FIG. 5A is a detail view of recesses of a coupling portion of an articular body.
Figure 5:
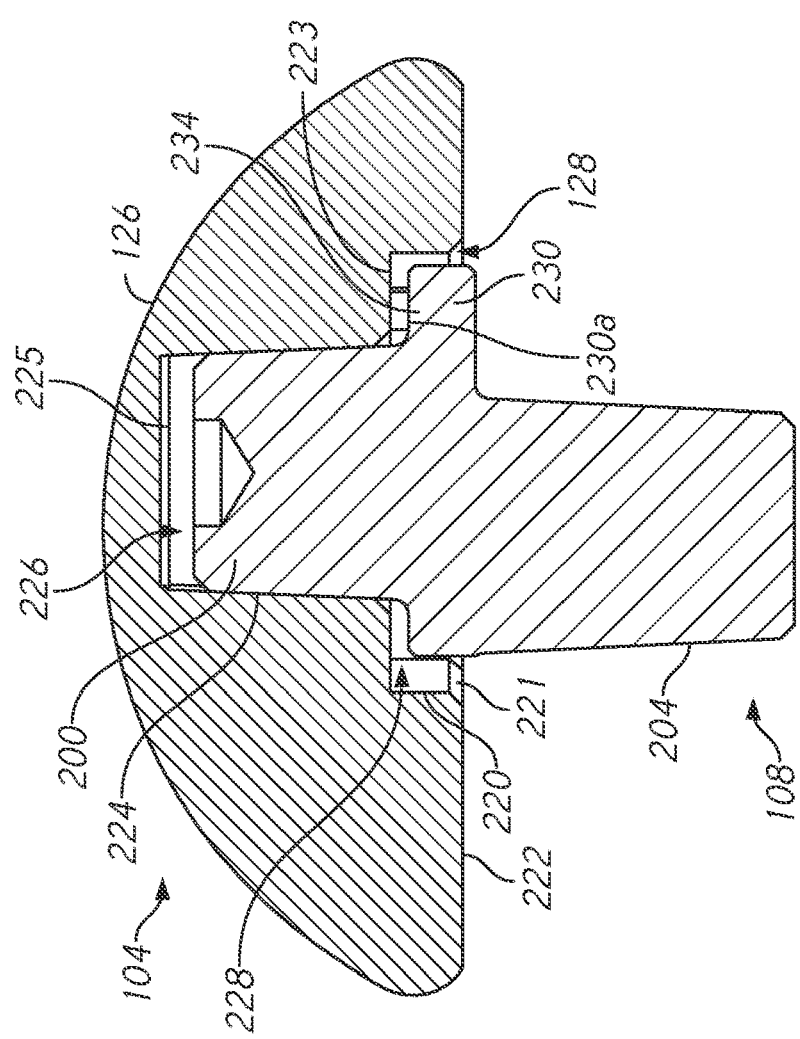
FIG. 5 is a cross-section taken through plane 5-5 shown in FIG. 4.
Figure 6:
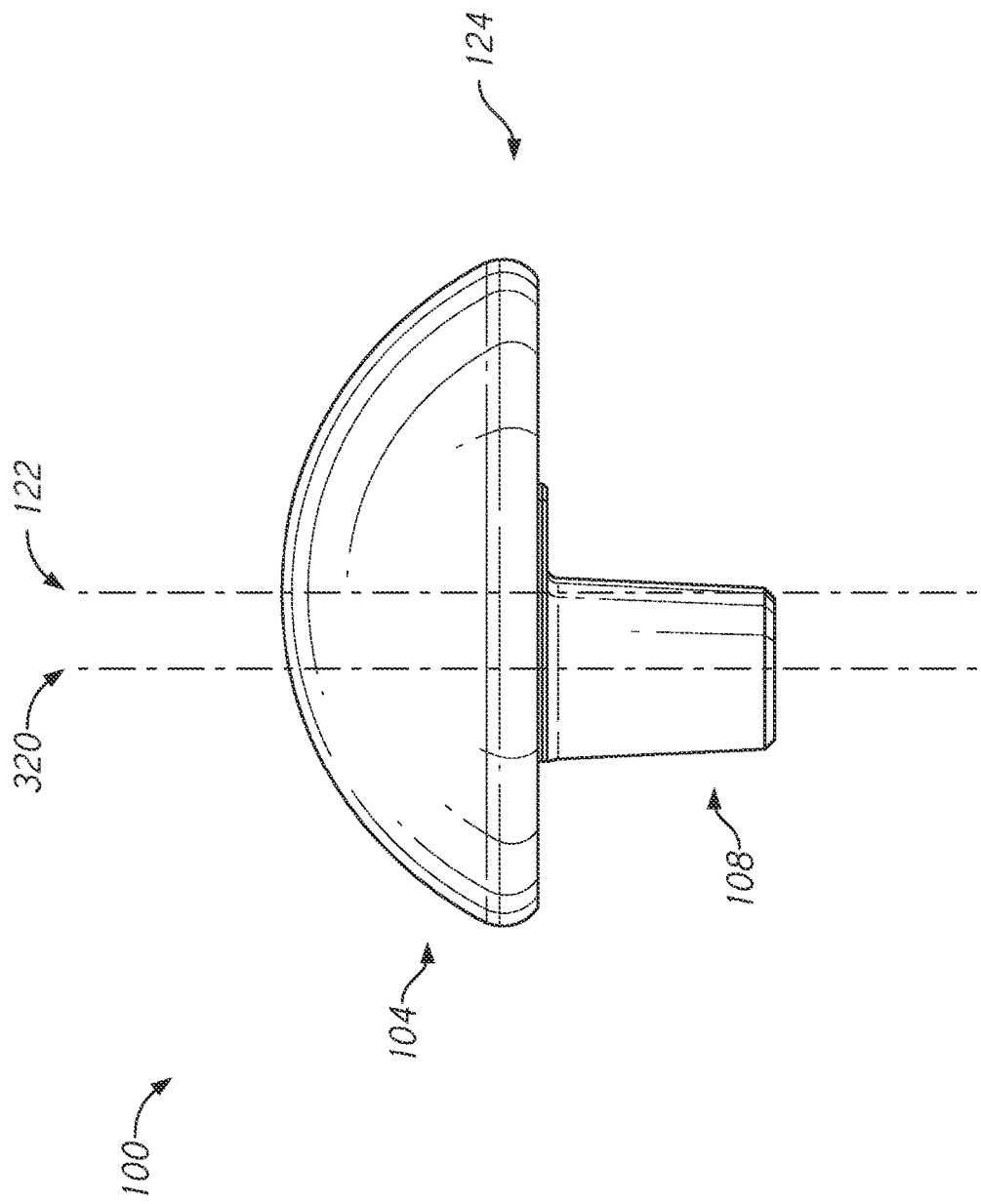
FIG. 6 shows one embodiment of the humeral head assembly of FIG. 2, showing a second configuration in which an eccentricity of the portion of the coupler adapted to mate with a humeral anchor to the articular surface of the articular body is non-zero.

FIGS. 2-11 show embodiments of a humeral head assembly 100 in which eccentricity of the assembly can be adjusted as needed during implantation. FIG. 3 shows that an articular body 104 and a coupler 108 are separable components of the assembly 100. In contrast to the couplers 924a, 924b, 924c, the coupler 108 is not illustrated as having a disc member, similar to the disc members 932a, 932b, 932c. In various combinations, the coupler 108 can be modified to have a disc member to enable the configuration of the humeral head assembly 100 to be used with the anchor 830 or the anchor 830A, discussed above. The articular body 104 and the coupler 108 can be coupled in a number of different positions to facilitate the adjustment of or elimination of eccentricity. As discussed further below, the different positions can include a first pre-defined position (e.g., centered, low, or high eccentricity as discussed above in FIGS. 17A-17C) or a position to be arrived at along a continuous range of adjustment, by selecting a discrete position of one or more discrete positions, or by selecting among these modes of adjustment. FIGS. 2, 4 and 5 illustrate a first configuration 120 of the humeral head assembly 100. The first configuration 120 corresponds to a centered (or not eccentric) position. A modified embodiment of the first configuration 120 can include a combination of the articular body and the coupler 924a, with the radial protrusion 944a aligned to the "+0" position. The articular body 104 advantageously also allows further adjustment as discussed further below. FIG. 6 illustrates a second configuration 124 an embodiment of the humeral head assembly 100. The second configuration 124 corresponds to an eccentric position.

FIG. 2 shows that the articular body 104 can have an articular surface 126. The articular surface 126 can be a convex surface. The articular surface 126 can be configured to engage with a concave surface of or at a glenoid of a patient. FIG. 3 shows that the articular body 104 also has a coupling portion 128. The coupling portion 128 is disposed on a side of the articular body 104 opposite the convex articular surface 126. The coupling portion 128 has a continuous zone 140 of eccentricity adjustment, shown in FIG. 4. For example, shading in FIG. 4 indicates the zone 140, which is an area over which the articular body 104 can be positioned relative to the coupler 108. The humeral head assembly 100 also has at least one site 160 for discrete positioning of the articular body 104 on the coupler 108. There can be one, two, three, four, five, or more than five sites 160. The discrete position site 160 allows for connecting the coupler 108 to the articular body 104 at one or more pre-defined positions and prevents relative rotation when so engaged. In some embodiments, the continuous zone 140 of eccentricity adjustment and the at least one discrete position site 160 are disposed in a same plane, e.g., in a plane transverse a normal to the center of the articular surface 126. An amount of eccentricity can be selected in the continuous zone 140 or in the discrete position site(s) 160 at the same relative axial position of the coupler 108 and the articular body 104. In some examples, the continuous zone 140 of eccentricity adjustment is located between discrete position sites 160. FIG. 4 shows the coupler 108 engaged with the articular body 104 at one of five discrete position sites 160.

FIGS. 3 and 5 shows that the coupler 108 can have a first portion 200 configured to mate with the articular body 104 and a second portion 204 opposite the first portion 200. The first portion 200 can mate with the coupling portion 128 in one embodiment. The second portion 204 can mate with another member of a joint prosthesis (e.g. with the coupling feature 44 of the humeral stem 30 disposed at a surface S of the humerus H or with a stemless humeral anchor). In other applications, the second portion 204 can mate with another anchor member, such as at a glenoid or scapula, at an end of a femur or at an end of a tibia. In some embodiments, the coupler 108 is asymmetrical such that the second portion 204 has a longitudinal axis that is offset from a longitudinal axis of the first portion 200. As will be discussed in more detail below, this offset can form a lateral offset between the center of the articular body 104 and the longitudinal axis of the second portion 204 when the humeral head assembly 100 is in an eccentric configuration, e.g., the second configuration 124.

The articular body 104 can be configured to engage with and/or be retained by the coupler 108. In some embodiments, the coupler 108 can engage with the coupling portion 128 of the articular body 104 to arrange or maintain the humeral head assembly 100 in the first centered (or non-eccentric) configuration 120 or in the second eccentric configuration 124.

FIGS. 5 and 5A illustrate that the coupling portion 128 can include a first recess 220 disposed within the articular body 104. The first recess 220 can have an open end 221 on a lateral side 222 of the articular body 104. The lateral side 222 is a side of the articular body 104 opposite the articular surface 126. The lateral side 222 faces away from the glenoid when the humeral head assembly 100 is implanted. The first recess 220 can extend to a recessed surface 223. A second recess 224 can extend from the recessed surface 223 into the articular body 104. The second recess 224 can have a closed end 225 and a diameter d1 that is less than a diameter d2 of the first recess 220. In some embodiments, the second recess 224 can be tapered such that the diameter decreases over the length of the second recess 224 to a lesser diameter adjacent to the closed end. The second recess 224 can have a greater diameter toward the recessed surface 223 or toward the first recess 220.

In some examples, the first portion 200 of the coupler 108 can be secured within the second recess 224 of the articular body 104. In some embodiments, the coupler 108 can include a collar 230 that can be configured to be disposed in the first recess 220. The collar 230 can be located between the first portion 200 and the second portion 204 of the coupler 108, e.g., at a proximal end of the first portion 200 or at a distal end of the second portion 204. The collar 230 can be used to position of the articular body 104 on or over the coupler 108. In some embodiments, the collar 230 can include a protrusion 234 configured to secure the articular body 104 at any of the discrete position site(s) 160 of the articular body 104. The protrusion 234 extends in a radial direction. The protrusion 234 extends in a plane perpendicular to a longitudinal axis of the coupler 108. The protrusion 234 can fix a rotational position relative to the articular body 104 by circumferentially overlapping with a radial edge (e.g., a portion of a concavity, such as a notch, cavity, or recess) of the coupling portion 128. FIG. 4A shows that the protrusion 234 can be configured to extend radially outward of a radially inward portion 235 of a circumferential edge 237 (e.g., a portion of a concavity, such as a notch, cavity, or recess disposed in the circumferential edge 237) of the coupling portion 128.

In some embodiments, when the first portion 200 of the coupler 108 is engaged with the second recess 224 of the articular body 104, there is a clearance distance 226 between the closed end 225 of the second recess 224 and the top of the first portion 200 such that the top of the first portion 200 does not engage the closed end 225 f the second recess 224. Similarly, in some embodiments, when the collar 230 of the coupler 108 is engaged with the first recess 220 of the articular body 104, there is a clearance distance 228 between the recessed surface 223 and a top (or medial) side 230a of the collar 230 such that the top (or medial side) of the collar 230 does not engage with the recessed surface 223. Further, the coupler 108 can be engaged with the articular body 104 in a first engaged configuration that permits relative rotation, e.g., along the zone 140. In the first engaged configuration the articular body 104 can be merely place or rested on the first portion 200 of the coupler 108. The coupler 108 can be engaged with the articular body 104 in a second engaged configuration that prevents relative rotation and inadvertent disengagement once an amount of eccentricity (or no eccentricity) is selected. The second configuration can be provided by applying an impaction force to the articular body 104 while holding the coupler 108 generally stationary. The clearances distances 226, 228 are each generally greater in the first engaged configuration than in the second engaged configuration due to the impaction force. The lesser (but non-zero) clearance distances 226, 228 in the second engaged configuration can ensure that the coupler 108 and the articular body 104 can be coupled by an interference fit, such as a Morse taper.

FIG. 4 shows that the lateral side 222 of the articular body 104 can have indicia 240A for aiding in positioning the articular body 104 over the coupler 108 along the continuous zone 140. For example, the continuous zone 140 can provide for "+1" "+2" and "+3" to indicate adjustment with progressively more eccentricity. In some embodiments, the indicia 240A corresponds to millimeters of offset (e.g., 1 mm, 2 mm, 3 mm of offset respectively) or can just indicate a progressively greater extent. Because the coupler 108 can be freely movable along the zone 140, eccentricity adjustment between a 0 mm offset and a 4 mm offset positions and also positions between the indicated positions can be provided, including, but not limited to, such as between +1 and +2, e.g., +1.5.

In some embodiments, the plurality of discrete position sites 160 can include radial notches 244 (or other radially extending edges capable of overlap) that provide for discrete eccentricity adjustments. In some embodiments, the radial notches 244 are configured to receive the protrusion 234 of the collar 230. The profile, outline, edges, or shapes of the radial notches 244 can match or invert that of the protrusion 234 such as to provide a fixed position. In one embodiment, the notch 244 can be a negative of the protrusion 234, e.g., the notch 224 can be concave where the protrusion 234 is convex. The concave notch 244 can have a portion that is radially inward of a radially outer portion of the protrusion 234. See FIG. 4A and the corresponding description thereof. The protrusion 234 can be inserted axially into one of the notches 244 in the illustrated embodiment. The matching or inverted configurations, e.g., outline, edges, or shapes, of the protrusion 234 and the notches 244 prevented relative rotation between the coupler 108 and the articular body 104 when the protrusion 234 is engaged with the notch 244. For example, as shown in FIG. 4 an opposing side 231 of the collar 230 disposed away from the protrusion 234 is closely adjacent to or in contact with an inner wall of the first recess 220 (adjacent to the +4 indicia) when the protrusion 234 is in the notch 244 at the +0 indicia. This contact or close adjacency and/or the shape of the notch 244 prevent or prevents the rotation of the coupler 108 within the body 104 unless the coupler 108, and therefore the protrusion 234, is retracted axially away from the body 140 until the protrusion 234 is spaced away from the surface 222. Thus, the coupler 108 is at least radially secured to the articular body 104 when any one of the notches 244 receives the protrusion 234. This condition is referred to above as a first engaged configuration. In other embodiments, a radially oriented detent can be provided between the articular body 104 and the coupler 108. The radial notches 244 of the discrete position site 160 provides for discrete (e.g., "+0", "+1", "+2", "+3", and "+4") eccentricity adjustments. The discrete positions corresponding to the sites 160 can be indicated by indicia 240B. In some embodiments, the markings of the indicia 240B corresponds to millimeters of offset (e.g., 0 mm, 1 mm, 2 mm, 3 mm, and 4 mm of offset respectively). In contrast to the continuous zone 140, the discrete position site 160 provides for adjustments of eccentricity at specific, fixed increments and do not allow for intermediate position, e.g., +1.5.

In one embodiment, one or more radial notches 244 is provided without enclosing the protrusion 234 on both. For example, the notch 244 can provide a radially extending edge that provides a positive stop at one or both ends of the continuous zone 140. In such embodiment, a position such as +0 or +4 can be confirmed by rotating the protrusion 234 into direct circumferential contact with such a notch. For example, in FIG. 4A the circumferential edge 237 extends between two radially inward portions. One of these two portions could be eliminated such that a stop is provided at an end of one or more of continuous zones of eccentricity adjustment. This configuration is elaborated upon in FIG. 12A and in the description thereof.

Figure 7:
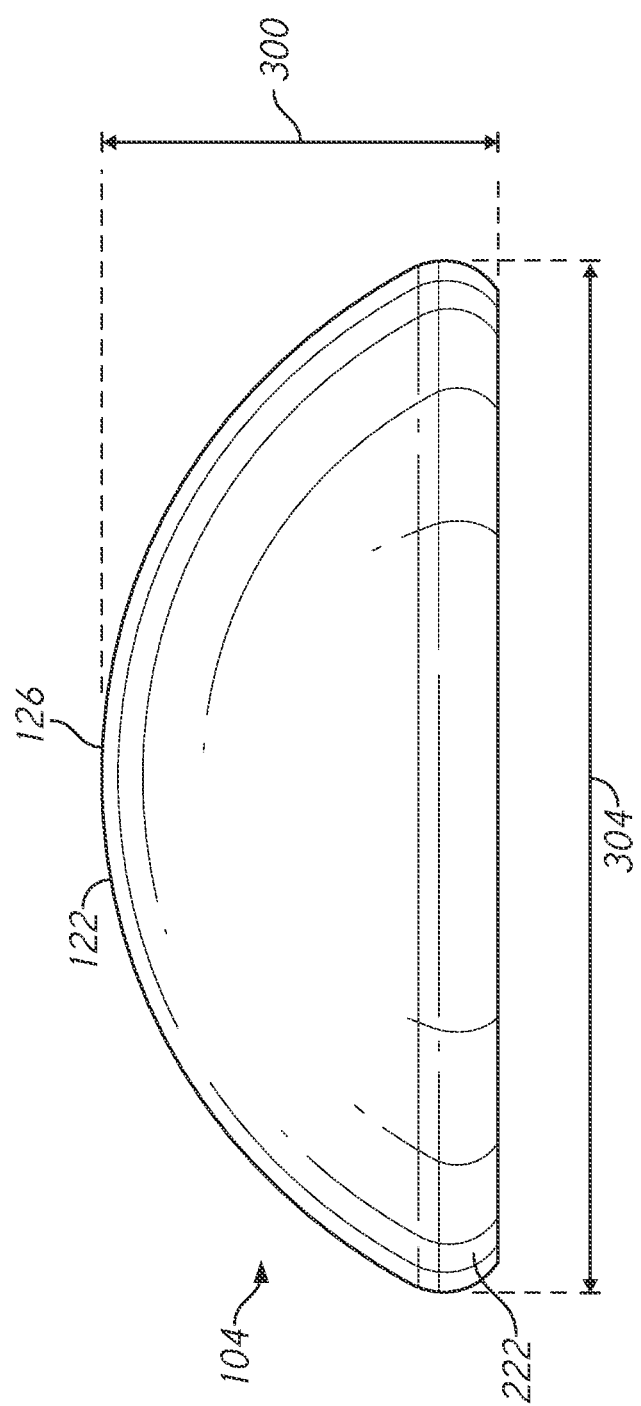
FIG. 7 is a side view of an articular body that can be used in the humeral head assembly of FIG. 2.

FIG. 7-8B illustrate the articular body 104 in greater detail. As discussed above, one side of the articular body 104 includes the articular surface 126. In this embodiment, the articular surface is convex, which presents an anatomical configuration. The articular body 104 has a height 300 and a width 304 that are configured to provide good fit in the shoulder joint space. In some examples, the height 300 of the articular body 104 can be between about 10 mm and about 30 mm, between about 13 mm, and about 27 mm. In some embodiments, the height of the articular body 104 can be about 13.0 mm, about 16.0 mm, about 18.0 mm, about 19.0 mm, about 27.0 mm, etc. The articular body 104 can be made of a variety of materials, such as CoCr, titanium, pyrocarbon, or other advantageous articular material and can include a solid or layered structure.

Figure 8A:
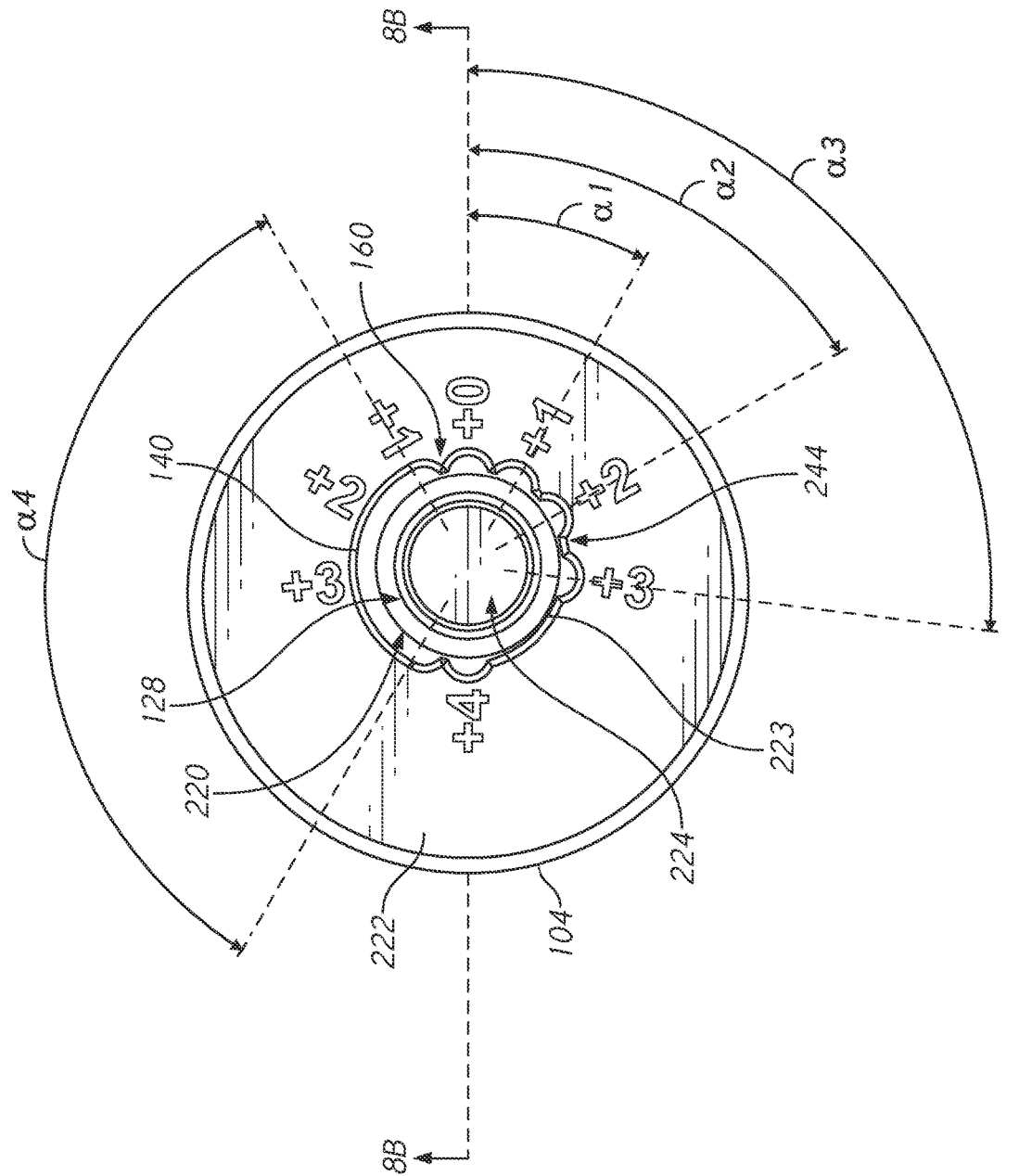
FIG. 8A is a bottom view of an articular body of the humeral head assembly of FIG. 2.

FIG. 8A illustrates further details of the coupling portion 128. As discussed above, the coupling portion 128 includes the first recess 220 in the lateral side 222. The first recess 220 is configured to receive the first portion 200 and the collar 230 of the coupler 108. In some embodiments, the first recess 220 of the coupling portion 128 is offset from the center 122 of the articular body 104. The first recess 220 coupling portion 128 can have an offset of between about 1.95 mm and about 2.05 mm, or can be about 1.95 mm, or about 2.00 mm, or about 2.05 mm from the center 122 of the articular body 104. FIG. 8B shows that in one example, a longitudinal axis 320 of the second recess 224 intersecting the end 225 thereof and extending perpendicular to a plane of the lateral side 222 is offset from the center 122 of the articular surface 126 in this manner or by these amounts.

In the embodiment shown in FIG. 8A, the continuous zone 140 forms an opening configured to accommodate the collar 230 and, for example, the protrusion 234 of the collar 230 through a range of eccentricity adjustments. The coupling portion 128 can include the indicia 240A indicating the amount of eccentricity provided when the protrusion 234 is directed toward any of the various positions along the continuous zone 140 of the coupling portion 128. For example, the coupling portion 128 in FIG. 8A indicates that the articular body 104 can be rotated along the continuous zone 140 to provide between 0 mm-1 mm of eccentricity adjustment (between the "+0" and "+1" indicia 240A); between and including 1 mm-2 mm of eccentricity adjustment (between the "+1" and "+2" indicia 240A); between and including 2 mm-3 mm of eccentricity adjustment (between the "+2" and "+3" indicia 240A); and between 3 mm-4 mm of eccentricity adjustment (between the "+3" and "+4" indicia 240A). In some embodiments, the continuous zone 140 can span an angle $\alpha 4$, providing about 122° 4' of movement. In the illustrated embodiments, eccentricity adjustment results from providing relative rotation between the articular body 104 and the coupler 108. If the coupler 108 is disposed in a humeral, glenoid, scapular, femoral, or tibial anchor on the surface S of the humerus H, glenoid, scapula, femur, or tibia, and is held stationary, rotation of the articular body 104 causes the center 122 of the articular surface 126 of the articular body to move across the surface S. Thus, if the centered configuration 120 is initially provided in the situation illustrated in FIG. 1B, the surgeon can provide eccentricity adjustment by rotating the articular body 104 through a selected degree of rotation to move the center 122 of the articular surface 126 toward the center 48 of the surface S. Thus, the offset illustrated in FIG. 1B can be addressed with the second configuration 124 following some degree of eccentricity adjustment. In some embodiments, the continuous zone 140 can provide at least 90 degrees of eccentricity adjustment. In some examples, the continuous zone 140 can provide from about 90 to about 180 degrees of eccentricity adjustment.

In the embodiment shown in FIG. 8A, each of the discrete position sites 160 is located at a corresponding radial notch 244 configured to receive the protrusion 234 of the collar 230. In some embodiments, at least one of the radial notches 244 is disposed circumferentially adjacent to the continuous zone of eccentricity adjustment. Each of the radial notches 244 can prevent rotation of the articular body 104 relative to the coupler 108, as discussed above, in an engaged configuration. The discrete position sites 160 correspond to indicia 240B indicating the amount of eccentricity provided at each of the discrete position sites 160. For example, the coupling portion 128 in FIG. 8A indicates that the humeral head assembly 100 can be rotated to each of the discrete position sites 160 to provide 0 mm of eccentricity adjustment (at the "+0" indicia 240B); 1 mm of eccentricity adjustment (at the "+1" indicia 240B); 2 mm of eccentricity adjustment (at the "+2" indicia 240B); 3 mm of eccentricity adjustment (at the "+3" indicia 240B); and 4 mm of eccentricity adjustment (at the "+4" indicia 240B). In some embodiments, the position of no eccentricity (e.g. "+0" indicia 240B) is 180 degrees rotationally offset from the position of maximum eccentricity (e.g. "+4" indicia 240B).

In some embodiments, the coupling portion 128 is composed entirely of a continuous zone 140. In some examples, the coupling portion 128 is composed entirely of a continuous zone 140 with a single discrete position site 160, such as at a position corresponding to the centered configuration 120, e.g. at the "+0" radial notch 244 if such embodiment includes discrete position indicia 240B.

In some embodiments, the angle $\alpha 1$ between the "+0" radial notch 244 and the "+1" radial notch 244 is at or about 28° 58'. In some embodiments, the angle $\alpha 2$ between the "+0" radial notch 244 and the "+2" radial notch 244 is at or about 60°. In some embodiments, the angle $\alpha 3$ between the "+0" radial notch 244 and the "+3" radial notch 244 is at or about 97° 11'. In some embodiments, the angle $\alpha 3$ between the "+0" radial notch 244 and the "+4" radial notch 244 is at or about 180°.

FIG. 8A illustrates an eccentricity adjustment between the ranges of 0 mm-4 mm that can be achieved by engaging the coupler 108 with the continuous zone 140 of eccentricity adjustment or with the at least one discrete position site 160 for eccentricity adjustment. The continuous zone 140 can provide eccentricity adjustment through all values in the range of 0 mm-4 mm of eccentricity adjustment while the at least one discrete position site 160 provides precise eccentricity adjustment at pre-determined values (e.g. 0 mm, 1 mm, 2 mm, 3 mm, and 4 mm). In some embodiments, the coupling portion 128 is configured to allow a surgeon to adjust the articular body 104 in a clockwise or a counter-clockwise direction to achieve the desired eccentricity adjustment. This aspect can provide ease of use for the surgeon as the articular body 104 can engage the coupler 108 at any orientation.

FIG. 8B illustrates the first recess 220 and the second recess 224 extending into the articular body 104. The first recess 220 can have a height 220h of between about 2.669 mm and about 2.769 mm, or about 2.669 mm, about 2.719 mm, or about 2.769 mm, etc. As discussed above, the first recess 220 can be formed in or from the lateral side 222 and can form part of the coupling portion 128 in the articular body 104.

The second recess 224 can extend from the first recess 220 into the articular body 104. In some embodiments, the second recess 224 can have a height 224h of about 8.60 mm. In some embodiments, the second recess 224 can have a tapered profile such that the diameter 224d of the second recess 224 decreases as the second recess 224 extends into the articular body 104. The diameter 224d can have a diameter that ranges from about 9.195 mm to about 9.235 mm. The second recess 224 can be configured to engage with the first portion 200 of the coupler 108 in a Morse taper or other form of interference fit. The tapered walls of the second recess 224 can allow the first portion 200 of the coupler 108 to be secured within the articular body 104 such that there is no relative movement between the articular body 104 and the coupler 108, e.g., between the collar 230 and the lateral side 222. In some embodiments, a longitudinal axis 320 of the second recess 224 can be offset from the center 122 of the articular surface 126. In some embodiments the offset is disposed between a longitudinal axis 320 of the second recess 224 and the center 122 of the articular surface 126.

Figure 9:
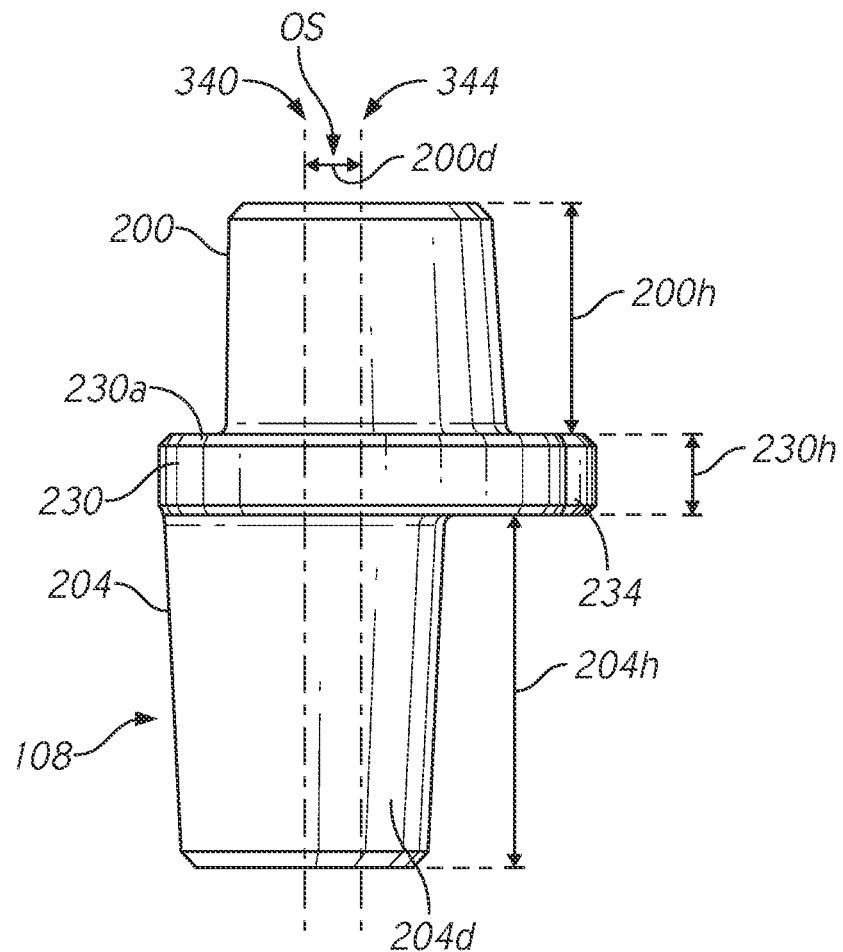
FIG. 9 is a side view of a coupler of the humeral head assembly of FIG. 2.
Figure 11:
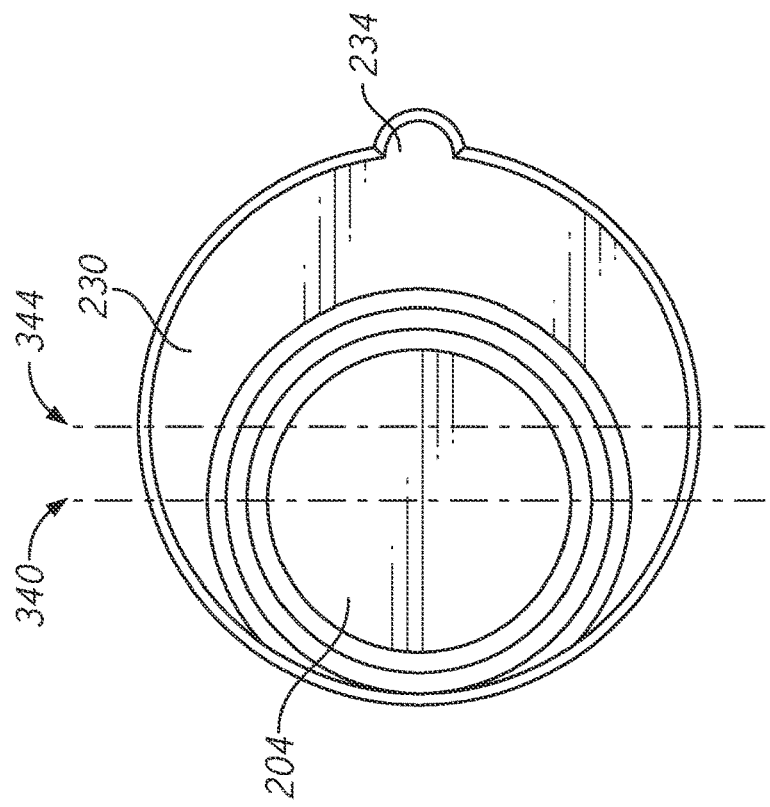
FIG. 11 is a lateral side view of the coupler of FIG. 9.
Figure 10:
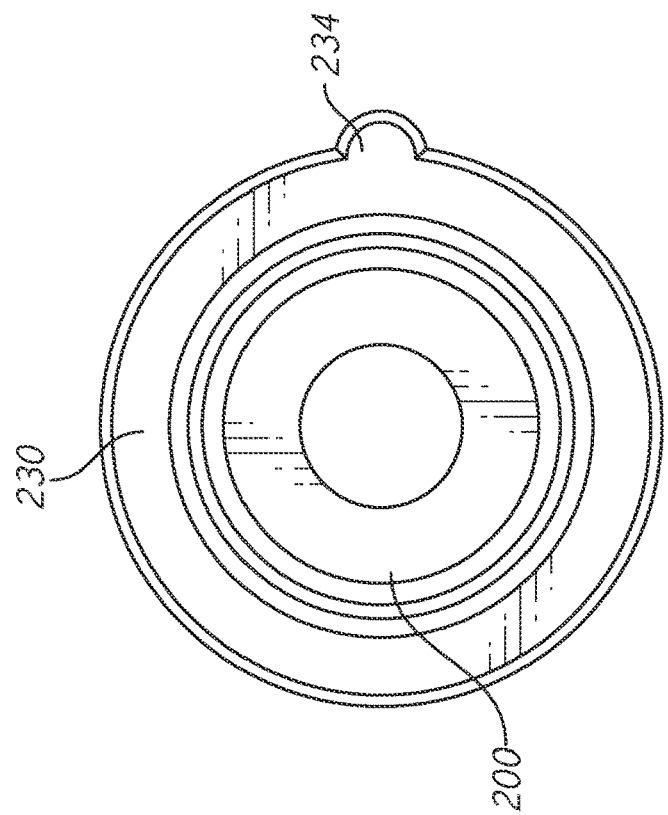
FIG. 10 is a medial side view of the coupler of FIG. 9.

FIGS. 9-11 illustrate various view of an embodiment of the coupler 108. The first portion 200 of the coupler 108 can be configured to engage the articular body 104. In some examples, the first portion 200 can have a height 200h of between about 7.90 mm and about 8.10 mm, or about 7.90, 8.00 mm, or about 8.10 mm. In some embodiments, the first portion 200 can have a diameter 200d at a free end thereof of between 9.205 mm and about 9.235 mm, or about 9.205 mm, about 9.220 mm, about 9.235 mm, etc. In some examples, the diameter 200d of the free end of the first portion 200 is greater than the diameter 224d of the second recess 224 at the end 225 but smaller than the diameter of the recess 224 at the surface 223 such that the first portion 200 can be received and secured within the second recess 224.

The second portion 204 can be configured to mate with another member of a joint prosthesis (e.g. a coupling feature 44 disposed at a surface S of the humerus H, glenoid, scapula, femur, or tibia). In some examples, the second portion 204 can have a height 204h of between about 11.90 mm and about 12.10 mm, or at about 11.90 mm, about 12.00 mm, or about 12.10 mm. In some embodiments, the second portion 204 can have a diameter 204d of between about 9.205 mm and about 9.235 mm, or about 9.205 mm, about 9.220 mm, or about 9.235 mm, etc. In some examples, the diameter 204d can change over its length and range from about 9.205 mm to about 9.235 mm.

The coupler 108 can include the collar 230 at the distal end of the first portion 200. The collar 230 can be configured to fit within the first recess 220 of the articular body 104. In some examples, the collar 230 can have a height of between about 2.45 mm and about 2.55 mm, or at about 2.45 mm, about 2.50 mm, or about 2.55 mm. In some examples, the collar 230 can include the protrusion 234, which as discussed above, is configured to be retained within one of the radial notches 244 of the at least one discrete position sites 160 or to be disposed within or along the continuous range 140.

In some examples, the coupler 108 is asymmetrical such that the second portion 204 had a different longitudinal axis 340 than a longitudinal axis 344 of the first portion 200. The longitudinal axis 340 can be aligned with the center 122 of the articular body 104 (e.g., when the protrusion 234 is aligned with the +0 site 160). When so aligned, the assembly 100 will provide a non-eccentric arrangement as in FIG. 1A. The longitudinal axis 340 can be offset from the center 122 of the articular body 104 (e.g., when the protrusion 234 is not aligned with the +0 site 160). When so offset, the assembly 100 will provide an eccentric arrangement as in FIG. 1B. As illustrated in FIGS. 9-11, the distance between the longitudinal axis 340 of the second portion 204 and the longitudinal axis 344 of the first portion 200 forms an offset OS. In some embodiments, the offset OS can range between about 1.95 mm and about 2.05 mm, or can be about 1.95 mm, or about 2.00 mm, or about 2.05 mm.

In some embodiments, when the coupler 108 is engaged with the articular body 104, the first portion 200 of the coupler 108 aligns with the longitudinal axis 320 of the second recess 224. As discussed above and shown in FIG. 8B, the longitudinal axis 320 of the second recess 224 is offset from the center 122 of the articular surface 124. In some examples, as the coupler 108 is asymmetrical, the longitudinal axis 340 of the second portion 204 may or may not align with the center 122 of the articular surface 124 depending on the arrangement of the humeral head assembly 100. As discussed above in connection with FIGS. 2 and 4-5A, when the humeral head assembly 100 is in the centered configuration 120, the center 122 of the articular surface 124 can be co-linear with the longitudinal axis 340 of the second portion 204. In contrast, when the humeral head assembly 100 is in the eccentric configuration 124 as shown in FIG. 6, the longitudinal axis 340 of the second portion 204 is offset from the center 122 of the articular surface 124. The foregoing shows that the humeral head assembly 100 can provide the configuration of FIG. 1A and a range of eccentric configurations including that of FIG. 1B and thus is a very adaptable assembly and further is able to reduce the complexity of surgical kits and any unused components thereof.

B. Humeral Head with a Plurality of Continuous Adjustment Zones

Figure 12:
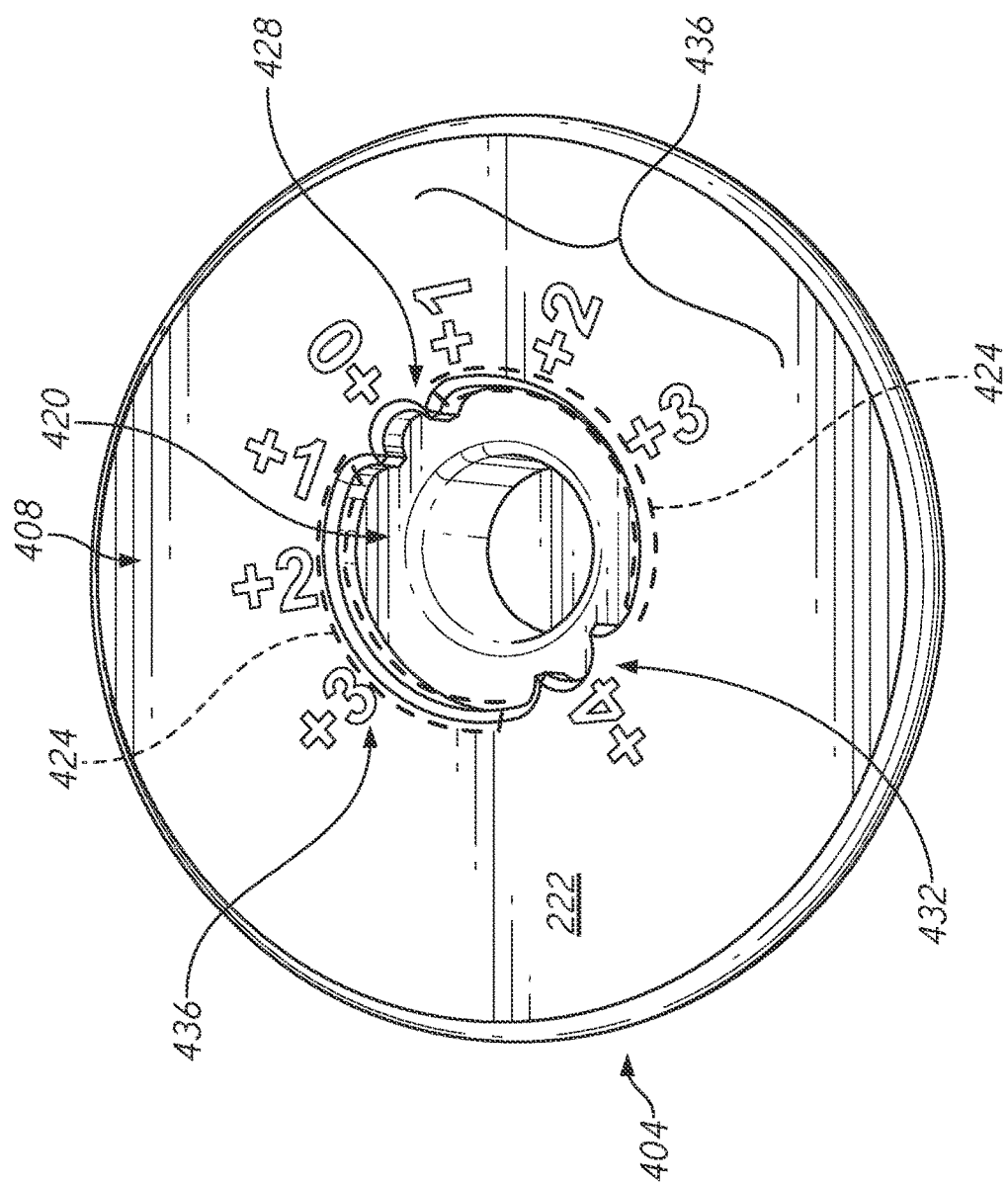
FIGS. 12 and 12A are lateral side views of further embodiments of an articular body suitable for another embodiment of a humeral head assembly.
Figure 12A:
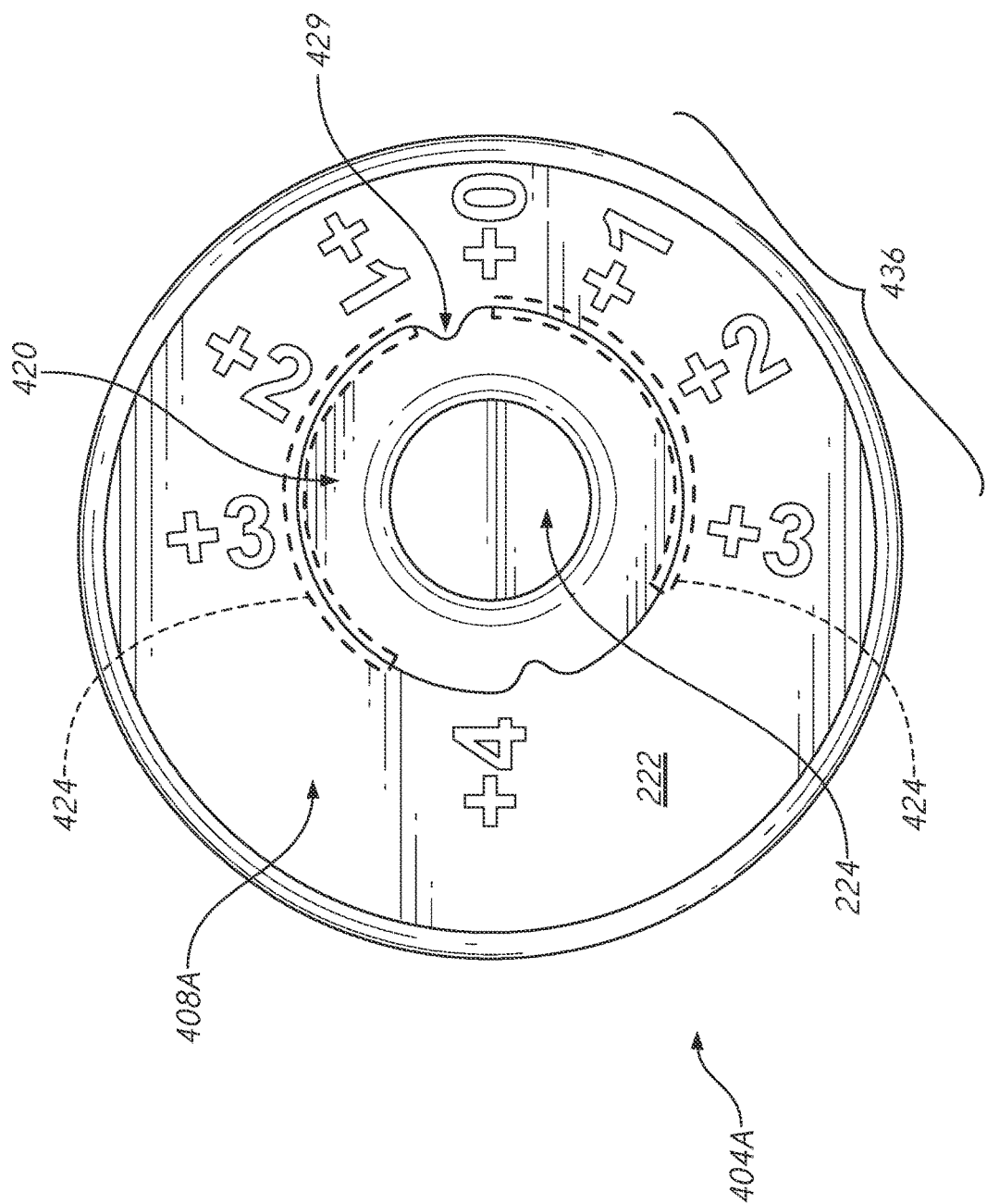

FIGS. 12 and 12A illustrate other embodiments of articular bodies 404, 404A that can form part of a humeral head assembly similar to the humeral head assembly 100. The discussions of the articular body 104 and the humeral head assembly 100 set forth above that are relevant to the discussion of the articular body 404 and to the articular body 404A will not be repeated, but one skilled in the art will understand that such discussions shall supplement the following discussion of the articular body 404.

The articular body 404 has a coupling portion 408, as illustrated in FIG. 12. The coupling portion 408 forms a first recess 420 in the articular body 404. The coupling portion 408 can include a plurality of continuous zones 424 (denoted by shaded regions). The continuous zones 424 can be separated by one or more discrete position sites 428. As with the coupling portion 128, each of the discrete position sites 428 can include a radial notch 432. In some embodiments, the continuous zone 424 of eccentricity adjustment and the one or more discrete position sites 428 are disposed in a same plane, e.g., in a plane parallel to the lateral side 222, located between the side 222 and the articular surface (not shown but located opposite the side 222). In some examples, the continuous zone 424 of eccentricity adjustment is located between discrete eccentricity positions (e.g., discrete position sites 428).

The coupling portion 408 can be configured to engage with the collar 230 of the coupler 108. The plurality of continuous zones 424 form an opening configured to accommodate the collar 230 and, for example, the protrusion 234 of the collar 230 through a range of eccentricity adjustments. The coupling portion 408 can include a plurality of indicia 436 indicating the amount of eccentricity provided at various positions along the continuous zones 424. In the coupling portion 408, the articular body 404 can be rotated in either direction to engage with one of the continuous zones 424 to provide between 0 mm-1 mm of eccentricity adjustment (between the "+0" and "+1" indicia 436); between and including 1 mm-2 mm of eccentricity adjustment (between the "+1" and "+2" indicia 436); between and including 2 mm-3 mm of eccentricity adjustment (between the "+2" and "+3" indicia 436); and between 3 mm-4 mm of eccentricity adjustment (between the "+3" and "+4" indicia 436). In some embodiments, either one of the continuous zones 424 can provide at least 90 degrees of eccentricity. In some examples, either one of the continuous zones 424 can provide from about 90 to about 180 degrees of eccentricity.

In some embodiments, the continuous zones 424 of the plurality of continuous zones are symmetrical. In some embodiments, the continuous zones 424 of the plurality of continuous zone are asymmetrical.

The embodiment of the coupling portion 408 can include two discrete position sites 428 on opposite sides of the coupling portion 408. Each of the discrete position sites 428 form radial notches 432 that are configured to receive the protrusion 234 of the collar 230. In some embodiments, at least one of the radial notches 432 is disposed circumferentially adjacent to the continuous zone of eccentricity adjustment. As discussed above, each of the radial notches 432 can prevent rotation of the articular body 404 relative to the coupler 108. To move from one of the notches 432 to another of the notches or from one of the notches 432 to one of the continuous zones 424, the coupler 108 must be axially disengaged from the articular body 404 such that at least the collar 230 is removed from the first recess 420. In other embodiments, a detent structure can provide mechanical feedback to the user to indicate engagement in a discrete location, e.g., within any of the radial notches 432. Like the continuous zone 424, each of the discrete position sites 428 can include indicia 436 indicating the amount of eccentricity provided at each of the discrete position sites 428. In the embodiment illustrated in FIG. 12, the coupling portion 408 includes two discrete position sites 428—at 0 mm of eccentricity adjustment (at the "+0" indicia 436) and at the 4 mm of eccentricity adjustment (at the "+4" indicia 436). In some embodiments, the position of no eccentricity (e.g. "+0" indicia 436) is 180 degrees rotationally offset from the position of maximum eccentricity (e.g. "+4" indicia 436).

The coupling portion 408 of FIG. 12 differs from the coupling portion 128 in that it includes two continuous zones 424. In this embodiment, a surgeon would be able to confirm through contact with and subsequent engagement in the notches 432 of the discrete position site 360 when the articular body 404 is centered on the coupler 108 and when the articular body 104 is positioned at maximum eccentricity (e.g. 4 mm). Between those ranges, the surgeon is able to freely adjust the position of the articular body 404 about the coupler 108.

FIG. 12A shows further details of the articular body 404A. As discussed the articular body 404A is similar to the articular body 404 except as described differently below. The discussion of the articular body 404 and the other articular bodies are intended to supplement the following discussion and will not be repeated. The articular body 404A includes a coupling portion 408A. The coupling portion 408A includes a first recess 420 and a second recess 224 can extend from the first recess 420. The first recess 420 can be bounded by a plurality of zones or wall segments. The first recess 420 can be bounded by one or a plurality of continuous zones 424. One or both of the continuous zones 424 can extend to an end formed by a stop 429. FIG. 12A shows that a stop 429 can be provided at each end of a first continuous zone 424. The stops 429 can include curved protrusions that extend to peaks disposed into the first recess 420. The peaks of the stops 429 can extend about one-quarter of the width of the first recess 420 from the continuous zones 424 toward the second recess 224. In the illustrated embodiment two continuous zones 424 are provided on opposite sides of the second recess 224.

The continuous zones 424 can be symmetrical about a line intersecting the stops 429, e.g., connecting the peaks of the stops 429. In some embodiments the coupling portion 408A of the articular body 404A is not symmetrical such that the indicia 436 are not spaced apart by the same amount. FIG. 12A shows that the indicia 436 disposed in the portion of the lateral side 222 located in a clockwise direction from +0 correspond to providing 0, 1, 2, or 3 mm of offset. More specifically, when the protrusion 234 of the coupler 108 is advanced into the first recess 420 and is aligned with the +0 of the indicia 436 no additional offset is provided. When the protrusion 234 is advanced into the first recess 420 and is aligned with the +1 of the indicia 436 an additional offset of +1 mm is provided. The indicia 436 that are disposed on the portion of the lateral side 222 located in a clockwise direction from +4 correspond to providing a different range of additional offset. The indicia 436 on this portion of the lateral side 222 indicate a range of adjustment from +1 to +4 mm of additional offset.

The stops 429 differ from the radial notches 432 of the discrete position sites 428 in not being able to enclose the protrusion 234 on both sides when the protrusion 234 is aligned with one of the indicia 436 centered on the radial notches 432. Rather, the engagement of the protrusion 234 is made by contacting one side thereof with one side of the stops 429. An advantage of this is that when the coupler 108 is advanced into the first recess 420 and the protrusion 234 is contacting either one of the stops 429 motion away from the offset position provided at this relative position can be accomplished without having to withdraw the collar 230 out of the first recess 420. Immediate relative rotation of the articular body 404A on the coupler 108 can be provided to move from any of the discrete positions to any other position. The engagement of the protrusion 234 with the stops 429 can be easily confirmed in a tactile manner without requiring any rotational alignment of the protrusion 234 with a notch.

One further variation of an assembly can be provided by modifying the coupler 108 such that the collar 230 has a concave periphery that is configured to either receive the stops 429 or if not aligned therewith to be positional along the continuous zones 424 in the first recess 420. This modification would provide that both sides of the stops 429 would be received within the concave recess of the modified coupler 108 such that in this variation movement from the discrete positions defined by the stops 429 to the continuous zones 424 would require retracting the modified collar of the coupler 108 from the first recess 420.

C. Eccentric Adjustment at an Interface Partially Formed on a Humeral Anchor

Figure 13A:
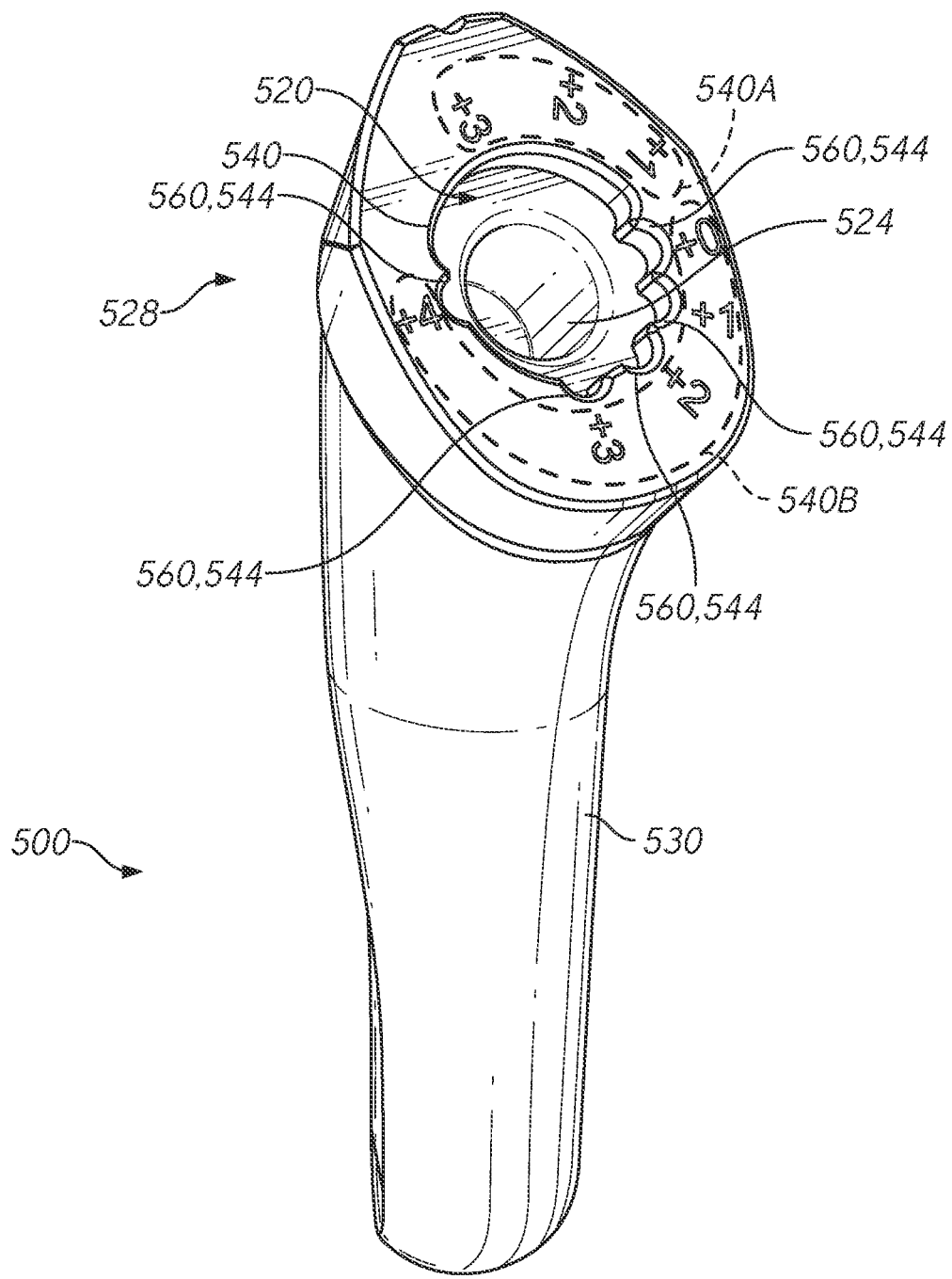
FIGS. 13A-13C illustrate an embodiment of the coupling portion on a surface of a stem.
Figure 13B:
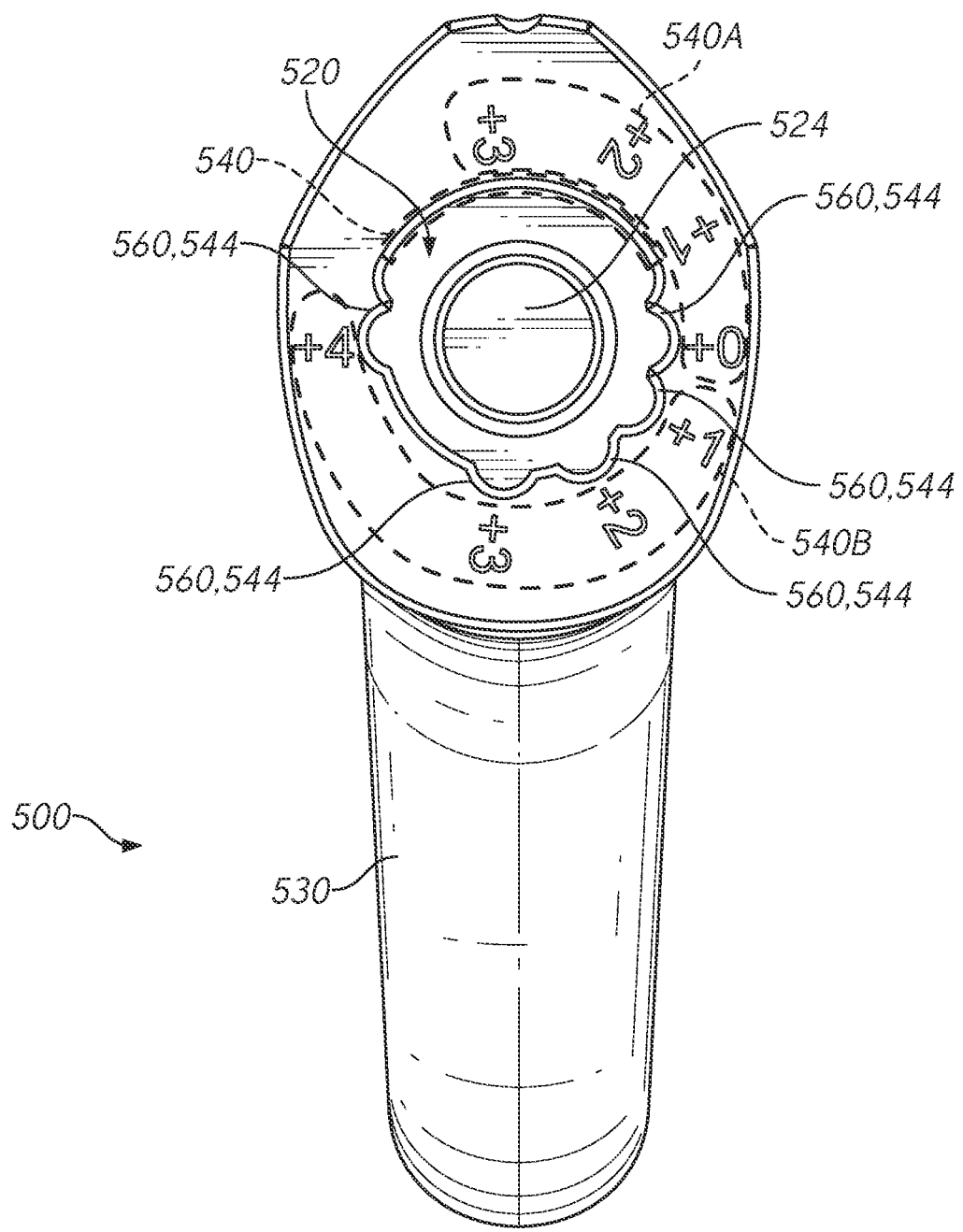
Figure 13C:
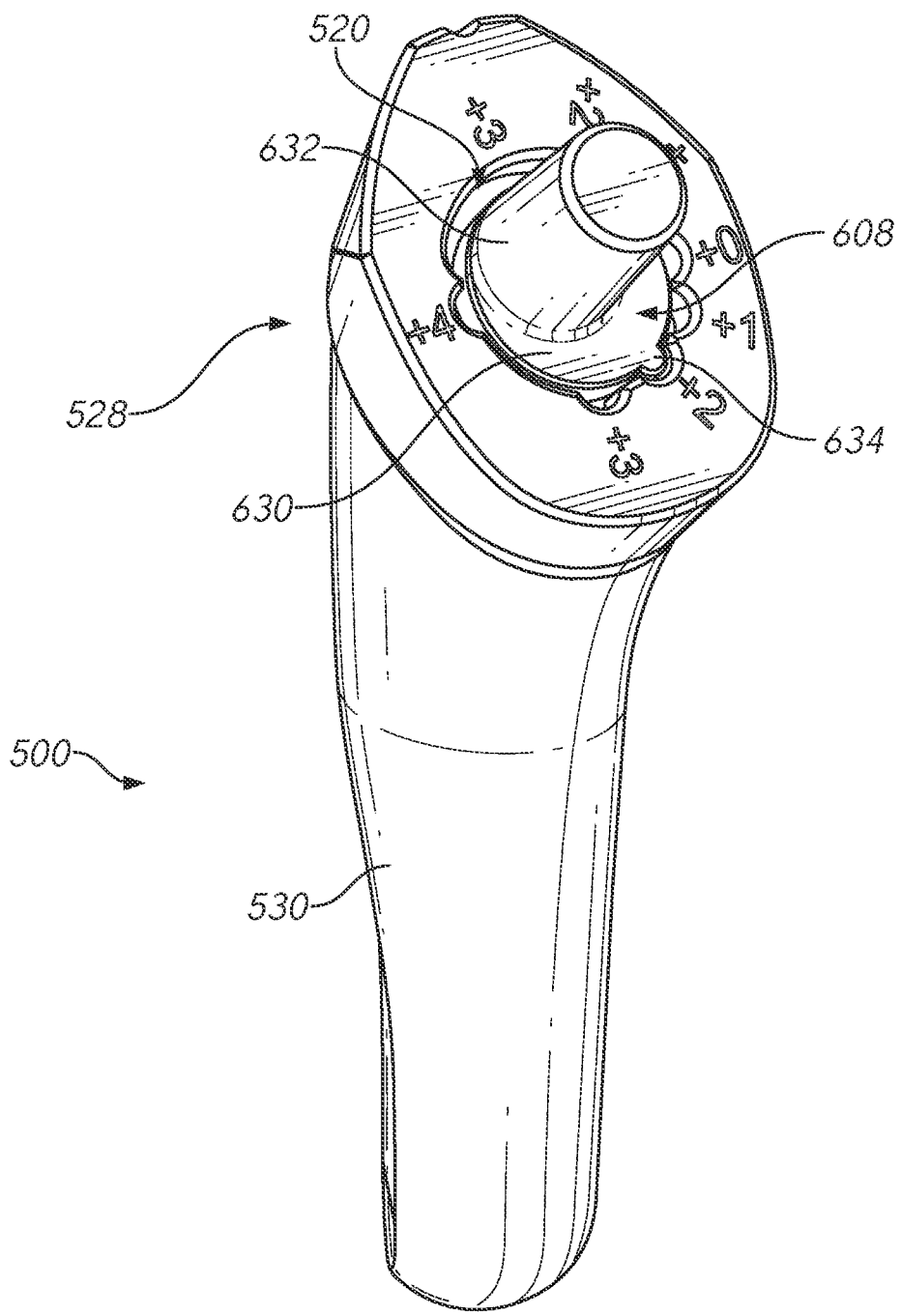

FIGS. 13A-13C illustrate another embodiment of a coupling portion 528. The discussions of the coupling portion 128 set forth above that are relevant to the discussion of the coupling portion 528 will not be repeated, but one skilled in the art will understand that such discussions shall supplement the following discussion of the coupling portion 528.

The coupling portion 528 can be located between the articular surface of an articular body (e.g. articular body 104, articular body 404, articular body 804, articular body 804A) and an end of a bone anchor 500. As discussed above, in some embodiments, the coupling portion can be located on a surface of the articular body (e.g. opposite the convex articular surface). In some embodiments, the coupling portion 528 can be located in an end of the bone anchor 500. In contrast to the bone anchor 830, bone anchor 500 had as tem and is configured for coupling with the coupler 108 and thereby with an anatomic articular body. In various combinations, the bone anchor 500 can be modified to have first and second recesses to enable the articular body 804 and the articular body 804A to be used with the bone anchor 500 for connection below the resection surface, as discussed above. FIGS. 13A-13C illustrate a bone anchor 500 having a stem 530, but in some embodiments, the bone anchor can be stemless. Examples of stemless bone anchors are found in US2016/0324648 and in U.S. 62/368,036, both of which are hereby incorporated by reference herein in their entireties.

The coupling portion 528 illustrated in FIGS. 13A-13C is similar to the coupling portion 128 of the humeral head assembly 100 disclosed above. However, the coupling portion 408 illustrated in FIG. 12, 12A, or any of the other coupling portions disclosed herein can similarly be located in a surface of the bone anchor 500 (e.g. stem or stemless).

The coupling portion 528 forms a first recess 520 in a medial surface of the stem 530. The coupling portion 528 can include a continuous zone 540 and at least one discrete position site 560 (denoted by a shaded region). The coupling portion 528 can include at least one discrete position site(s) 560. As with the coupling portion 128, each of the discrete position sites 560 can include a radial notch 544 or other radially extending edge configured to radially overlap with a portion of a coupler, as discussed below. In some embodiments, the continuous zone 540 of eccentricity adjustment and the at least one discrete position site 560 are disposed in a same plane, e.g., in a plane lateral to but parallel with the medial surface of the stem 530. In some examples, the continuous zone 540 of eccentricity adjustment is located between discrete eccentricity positions (e.g., discrete position sites 560).

The coupling portion 528 can be configured to engage with a collar 630 of a coupler 608 that can be engaged with the coupling portion 528. As noted above with regard to FIGS. 2-11, in contrast to the couplers 924a, 924b, 924c, the 608 is not illustrated as having a disc member, similar to the disc members 932a, 932b, 932c. In various combinations, the coupler 608 can be modified to have a disc member to enable the configuration of the humeral head assembly 100 to be used with the anchor 830 or the anchor 830A, discussed above. In such modifications, the collar 630 may have the same or a larger diameter than the disc member 932a, 932b, 932c. The continuous zone 540 forms an opening configured to accommodate the collar 630 and, for example, a protrusion 634 of the collar 630 through a range of eccentricity adjustments. The coupling portion 528 can include a plurality of indicia 540A indicating the amount of eccentricity provided at various positions along the continuous zone 540. The coupler 608 can be rotated in the coupling portion 528 to provide between 0 mm-1 mm of eccentricity adjustment (between the "+0" and "+1" indicia 540A); between and including 1 mm-2 mm of eccentricity adjustment (between the "+1" and "+2" indicia 540A); between and including 2 mm-3 mm of eccentricity adjustment (between the "+2" and "+3" indicia 540A); and between 3 mm-4 mm of eccentricity adjustment (between the "+3" and "+4" indicia 540A). In some embodiments, the continuous zone 540 can provide at least 90 degrees of eccentricity. In some examples, the continuous zone 540 can provide from about 90 to about 180 degrees of eccentricity.

One or more of the plurality of discrete position sites 560 can include radial notches 544 that are configured to receive the protrusion 634 of the collar 630. In some embodiments, at least one of the radial notches 544 is disposed circumferentially adjacent to the continuous zone of eccentricity adjustment. As discussed above, each of the radial notches 544 can prevent rotation of the coupler 608 relative to the coupling portion 528 in the surface of the stem 530. The notches allow for a first engaged configuration in which rotation is prevented but the coupler 608 and the anchor 500 are not secured in an interference fit and can be easily disengaged. To move from one of the radial notches 544 to another of the notches or from one of the radial notches 544 to the continuous zone 540, the coupler 608 can be axially disengaged from (e.g., moved medially relative to) the medial surface of the stem 530 such that at least the collar 630 is removed from the first recess 520. In other embodiments, a portion of a detent structure can be provided to indicate to the user a rotationally engaged configuration. Like the continuous zone 540, each of the discrete position sites 560 can include indicia 540B indicating the amount of eccentricity provided at each of the plurality of discrete position site 560. In the embodiment illustrated in FIGS. 13A-13C, the coupling portion 528 includes four (4) discrete position sites 560—at 0 mm of eccentricity adjustment (at the "+0" indicia 540B), at 1 mm of eccentricity adjustment (at the "+1" indicia 540B), at 2 mm of eccentricity adjustment (at the "+2" indicia 540B), at 3 mm of eccentricity adjustment (at the "+3" indicia 540B), and at the 4 mm of eccentricity adjustment (at the "+4" indicia 540B). In some embodiments, the position of no eccentricity (e.g. "+0" indicia 540A) is 180 degrees rotationally offset from the position of maximum eccentricity (e.g. "+4" indicia 540A).

In some embodiments, the first recess 520 of the coupling portion 528 opens up to a second recess 524. The second recess 524 can have a smaller diameter than the first recess 520. The second recess 524 can be configured to receive a tapered end portion of the coupler 608. The tapered end portion can be similar to the first portion 200 of the coupler 108. In the illustrated embodiment, the tapered end portion is aligned with a center of the second recess 524. A medial end 632 of the coupler 608 projects medially from the collar 630. The medial end 632 of the coupler 608 is configured to engage a recess in an articular body that can be similar to the articular body 104. The longitudinal axis of the medial end 632 of the coupler 608 is offset from the tapered end (and from the center of the second recess 524) such that rotation of the coupler 608 along the continuous zone 540 or to any of the discrete position sites 560 results in adjustment of the extent of eccentricity (if any) to provide for centering of the articular body over the resected surface of the humerus even if the anchor 500 is not centered on the resected surface.

Figure 14B:
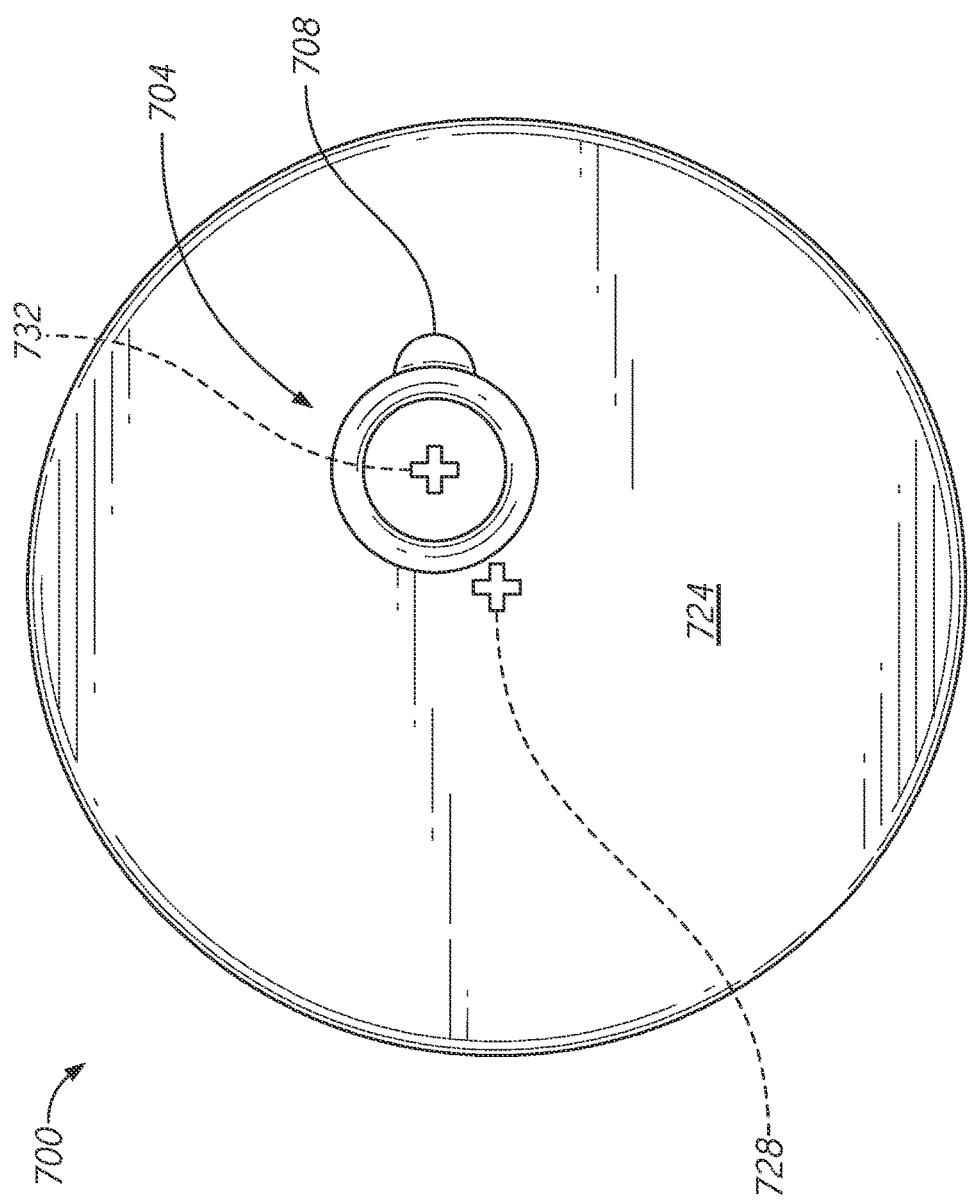
Figure 14C:
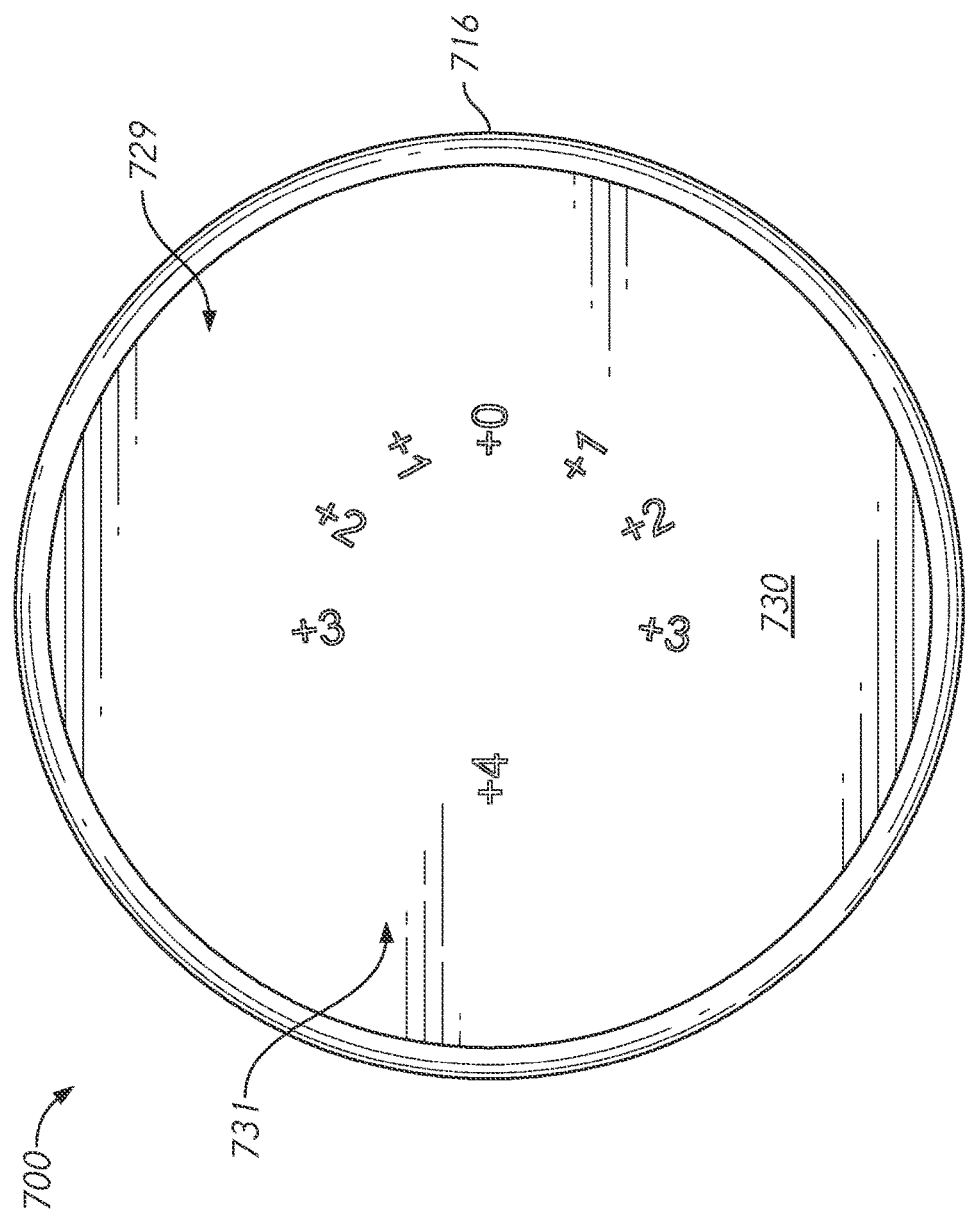

FIGS. 14A-14C show that the foregoing embodiments can also be applied to a reverse shoulder assembly. A reverse shoulder assembly is one in which the natural articular surfaces of the humerus are modified such that a convex articular surface is provided on the scapula and a concave articular surface is provided on the humerus. FIG. 14A show an exploded view of the anchor 500 and a tray 700 of a reverse shoulder assembly. The anchor 500 can have any of the features discussed above. The anchor 500 also can have any combination of continuous and position sites. FIG. 14A shows the notches 544 formed within the first recess 520. The anchor 500 also includes the second recess 524 which extends from the first recess 520 further into the anchor 500.

The tray 700 can have a taper 704 projecting from a humeral facing wall 724 and a recess on the opposite side of the tray 700 from the humeral facing wall 724. The recess can be partly defined by an inner circumference 712 which is surrounded by an inner sidewall 716. The tray 700 can be configured to securely retain an articular body (not shown) which is inserted into the recess in the space surrounded by the inner sidewall 716. The inner sidewall 716 can have one or a plurality of fins 720 disposed about the inner sidewall 716. The fins 720 can be configured to engage an outer sidewall of the articular body to hold the articular body in place in one embodiment. The articular body has a concave articular surface as discussed above.

FIG. 14B shows further details of the tray 700. The tray 700 can be symmetrical, e.g., having a circular outer periphery about the humeral facing wall 724. The tray 700 can have a center 728 from which a radius of the circular periphery can be measured. In various advantageous embodiments the center 728 is disposed offset from a center 732 of the taper 704. The off-set distance between center 728 and the center 732 enables a rotation of the tray 700 relative to the anchor 500 to change the location of the tray 700 (and thereby the articular body coupled therewith) relative to the resected face of the humerus. Thus, even if the anchor 500 is off-set from the center of the humerus the tray 700 can be rotated relative to the anchor 500 to a position in which the center 728 is centered, substantially centered or closer to the of the humerus than the second recess 524 or the taper 704.

The tray 700 can include a protrusion 708 that can be aligned to discrete or continuous zones as discussed further below. FIG. 14C shows the opposite side of the tray 700 shown in FIG. 14B. The side shown in FIG. 14C faces the scapula when the tray 700 is implanted and may be referred to as a medial side. The tray 700 includes a wall 730 that is located opposite the humeral facing wall 724. The wall 730 and the inner sidewall 716 at least partially define a concave space 729 in which an articular insert can be disposed. In one embodiment indicia 731 are provided on the medial side, e.g., on the wall 730 to facilitate alignment of the tray 700 relative to the anchor. The indicia 731 on the wall 730 can be aligned with the indicia on the anchor 500 to provide the off-set position indicated. For example, the protrusion 708 can be placed in the +0 position on the anchor 500 and when so placed the +0 mark of the indicia 731 will be aligned with the +0 on the anchor 500. When the tray 700 is rotated such that the +1 mark of the indicia 731 is moved to the horizontal position (where +0 is in FIG. 14C) the surgeon can know that the protrusion 708 is aligned with +1 in the upper (as depicted in FIG. 14A) continuous zone of the anchor 500. When the tray 700 is rotated such that the +2 mark of the indicia 731 is moved to the horizontal position the surgeon can know that the protrusion 708 is aligned with +2 in the upper continuous zone of the anchor 500. When the tray 700 is rotated such that the inverted +1 mark of the indicia 731 is moved to the horizontal position the surgeon can know that the protrusion 708 is aligned with the inverted +1 in the lower portion of the anchor 500. Visual confirmation on the tray 700 may not be required for discrete zones (as in the lower portion of the anchor 500) but still provides a convenient visual confirmation. Also, the anchor 500 can be provided with upper and lower continuous zones, similar to the arrangements of FIGS. 12 and 12A. The indicia 731 thus can give a visual confirmation of the position of the tray 700 relative to the anchor 500. The visual confirmation enables the surgeon to accurately position the tray 700 and also to make a record during the surgery of the position to enhance the patient's medical record.

A method of implanting a humeral assembly including the anchor 500 and the tray 700 can include surgically exposing the humerus at the shoulder. The humerus is then resected to create the exposed surface S (see FIG. 1). The anchor 500 can thereafter be placed in the humerus by creating a space in the cancellous bone of the humerus for a stemmed anchor. If a stemless anchor is used, less or no additional bone preparation may be required. The tray 700 can be used to provide an adjustment of the position of the tray 700 (and an articular body coupled therewith) if following placement the position of anchor 500 it is determined that some adjustment is needed. For example, the tray 700 can be advanced as indicated by arrow A to be coupled with the anchor 500 by advancing the taper 704 into the second recess 524 until the tray 700 comes to rest on the anchor 500. The tray 700 can be rotationally oriented in either direction of the arrow B as the tray 700 is advanced into first recess 520 and the second recess 524. In one technique the protrusion 708 is initially aligned with the +0 position such that no additional offset is provided, e.g., the center 728 is aligned with the center of the second recess 524. If offset is needed the protrusion 708 can be moved along the continuous zone 540 to +1, +2, +3, or any other position therebetween. The protrusion 708 can be moved to any one of the notch 544, e.g., to the +1, +2, +3, or +4 positions. The position can be visually confirmed by reference to the indicia 731 as discussed above. Once alignment is confirmed the tray 700 can be secured to the anchor 500 by engaging the taper 704 with the walls of the second recess 524, e.g., in a Morse taper connection. The method can include selecting between two continuous zones of adjustment in some embodiments of the anchor 500. After the tray 700 is secured to the anchor 500 a reverse articular body can be coupled with the tray 700 within the inner sidewall 716, e.g., by engaging the fins 720.

Although describe as being combined with the tray 700 in FIG. 14A, the anchor 500 can have two recessed as in the anchor 830 or the anchor 830A such that the articular body 804A can be directly connected to the anchor 500 in a proximal recess, such as the first recess 842.

Although the anchor 500 has been illustrated as configured for implantation in a humerus, the anchor 500 could be adapted for implantation within a glenoid, scapula, femur, or tibia and still provide advantageous positioning of an articular body thereon in a centered or over a range of eccentric positions as discussed herein.

D. Offset Coupler having a Window to Aid Selection of Eccentric Configuration

FIGS. 18-20A illustrate another embodiment of a humeral head system 1400 having a coupling portion 1532. The discussions of the coupling portion 128 and coupling portion 528 will not be repeated, but one skilled in the art will understand that such discussions shall supplement the following discussion of the coupling portion 1532.

In some embodiments, as illustrated in FIG. 18A, the coupling portion 1532 can be located on a proximal face 1504 of the collar 1506 of the humeral anchor 1500. FIGS. 18-18B illustrate a humeral anchor 1500 without a stem, but in some embodiments, the bone anchor can include a stem. Additional examples of stemless bone anchors are found in US2016/0324648 and in U.S. 62/368,036, both of which are hereby incorporated by reference herein in their entireties.

The coupling portion 1532 illustrated in FIG. 18A is generally similar to the coupling portion 128 of the humeral head assembly 100 and the coupling portion 528 disclosed above. However, as shown in FIG. 18A, the coupling portion 1532 does not include any discrete position sites, but instead includes indicia located on the proximal face 1504 of the collar 1506. In some embodiments, the indicia of the coupling portion 1532 is evenly spaced apart on the proximal face 1504 similar to a clock face. As discussed above, in some embodiments, each of the indicia are configured to indicate orientation. As discussed above, the humeral anchor 1500 is configured to engage with the coupler 1424 (e.g., one of the couplers 1424a, 1424b, 1424c). The humeral anchor 1500 includes a first recess portion 1508 that is configured to receive the disc member 1432 (e.g., one of disc member 1432a, 1432b, 1432c) of the coupler 1424 (e.g., one of the couplers 1424a, 1424b, 1424c). As discussed above, the disc member 1432 (e.g., disc members 1432a, 1432b, 1432c) is adjacent to the plate 1440 (e.g., plate 1440b, 1440c) which includes the window 1444 (e.g., window 1444b, 1444c). As with the radial notches discussed above, the window 1444 can be configured to indicate the orientation, direction, or configuration of eccentricity relative to the humeral anchor 1500 provided when one of the couplers 1424a, 1424b, 1424c is inserted into the humeral anchor 1500. In some examples, when the coupler 1424 is inserted in the humeral anchor 1500, the plate 1440 of the coupler 1424 covers all indicia on the coupling portion 1532 except for the indicia selected by the user which is exposed through the window 1444 of the plate 1440.

The coupling portion 1532 can be configured to interact with the plate 1440 of the coupler 1424 such that the window 1444 illustrates indicia corresponding with the orientation or configuration of eccentricity relative to the humeral anchor 1500 provided at various positions along the proximal face 1504 of the collar 1506. FIG. 18A shows that in one embodiment, rotational orientation indicia include numbers in the form of a clock face to indicate twelve discrete rotational positions. While this form of the rotational orientation indicia is intuitive, the indicia can be fewer or more numbers, letters, colors or other indicia or combination of indicia. In some cases, an articular assembly or component to be coupled with the humeral anchor 1500 is asymmetric such that the rotational position thereof relative to the humeral anchor 1500 changes the bio-mechanics of the assembly. The indicia on the proximal face 1504 of the collar 1506 can guide the surgeon on placing the articular assembly or component. The indicia on the humeral anchor 1500 can be used during a trial for a group of articular components or assemblies to indicate a desired position. Then, when the final implant is initially placed in the opened joint space the orientation indicated by the indica can be replicated prior to permanent connection of the final articular component or assembly with the humeral anchor 1500. The indicia and the window 1444 can be used mainly to enable the surgeon to reproduce a direction of eccentricity offset determined during a trial procedure during the surgery. For example, if the trial indicates orienting the eccentricity toward the 2 o'clock indicium, then the surgeon can reproduce that during the procedure by aligning the window 1444 with the 2 o'clock indicium on the coupling portion 1523. In some embodiments, the amount of eccentricity adjustment can be selected by inserting the coupler 1424 into the second recess portion 1524 of the humeral anchor 1500.

Although the humeral anchor 1500 has been illustrated as configured for implantation in a humerus, the humeral anchor 1500 can be adapted for implantation within a glenoid, scapula, femur, or tibia and still provide advantageous positioning of an articular body thereon in a centered or over a range of eccentric positions as discussed herein.

IV. Expandable Couplers for Coupling an Articular Body to a Bone Anchor

The following embodiments provide for coupling an articular body to a humeral anchor using an expandable coupler. The disclosed embodiments can provide for enhanced rotational positional control of the components of the humeral head assembly. As well, the disclosed non-permanent assembly can eliminate tolerance stack-up that is typically associated with conventional connections. Furthermore, the following couplers can be securely engaged to a humeral anchor without the need for impacting the articular body onto the humeral anchor. In some examples, the expandable couplers facilitate removal of portions of the humeral head assembly in a revision procedure, e.g., where an anatomic prosthesis is removed and replaced with a reverse prosthesis.

The embodiments discussed below could be used in other orthopedic applications, including for providing an expandable fixation assembly of a glenosphere on a glenoid or scapular anchor, for providing non-permanent fixation assembly of a femoral articular body on a femur anchor, for providing non-permanent fixation assembly of tibial articular body on a tibial anchor, or for other orthopedic applications.

A. Expanding Coupler with Cam Disc Assembly

Figure 22A:
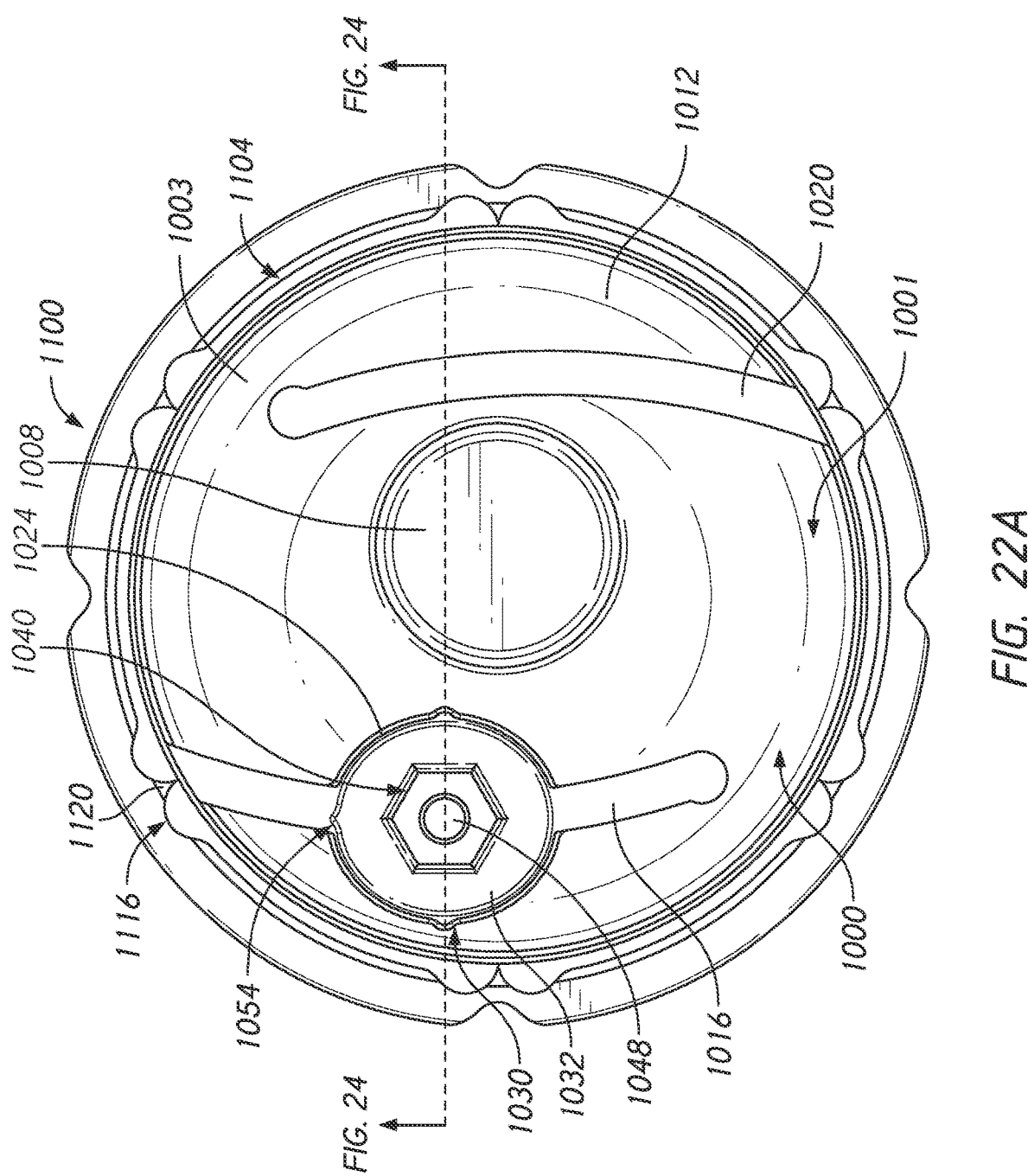
FIG. 22A is a top view of the cam disc assembly engaged with anchor of FIG. 21.
Figure 22B:
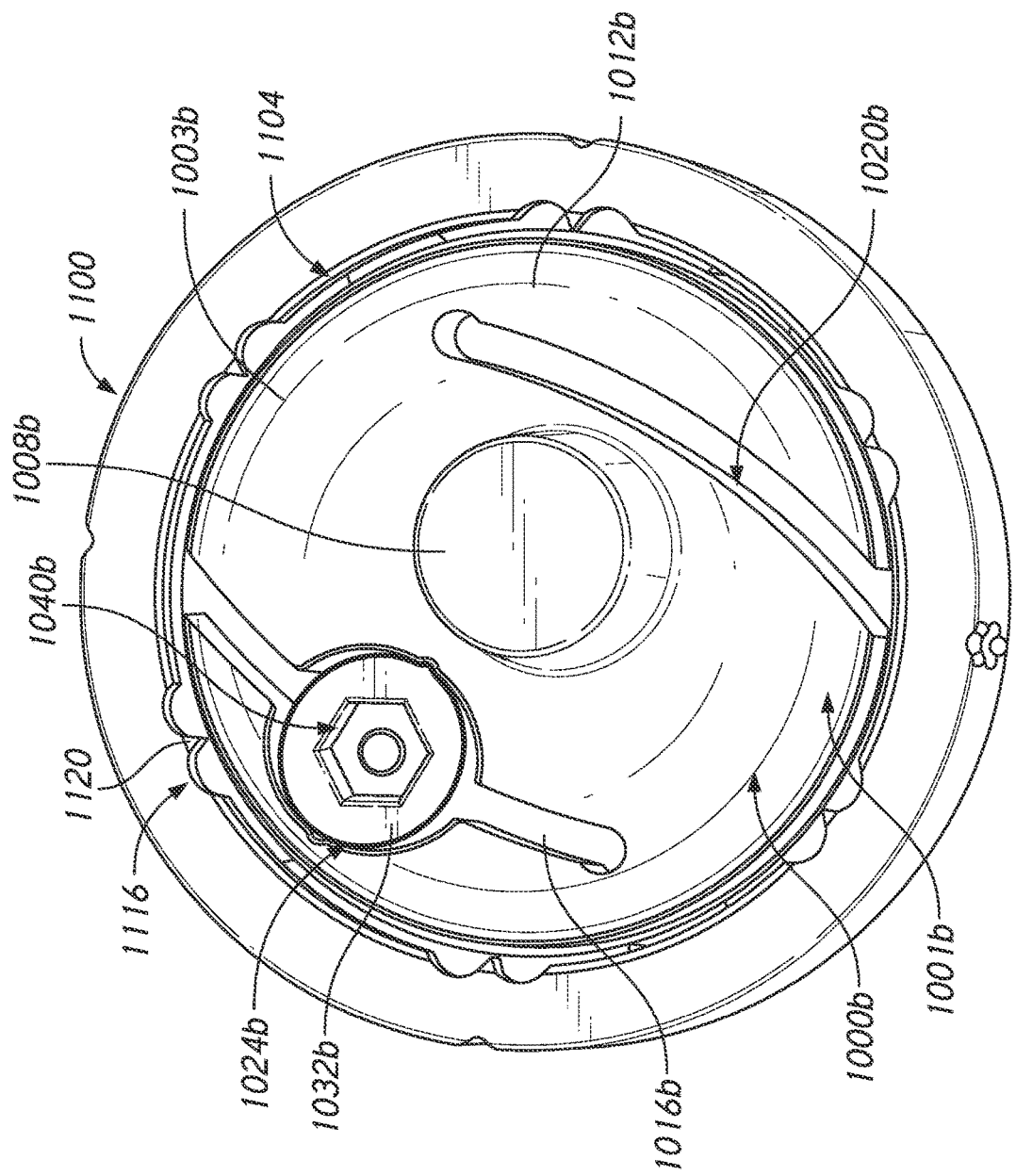
FIG. 22B is a top view of the cam screw assembly engaged with anchor of FIG. 58.
Figure 23:
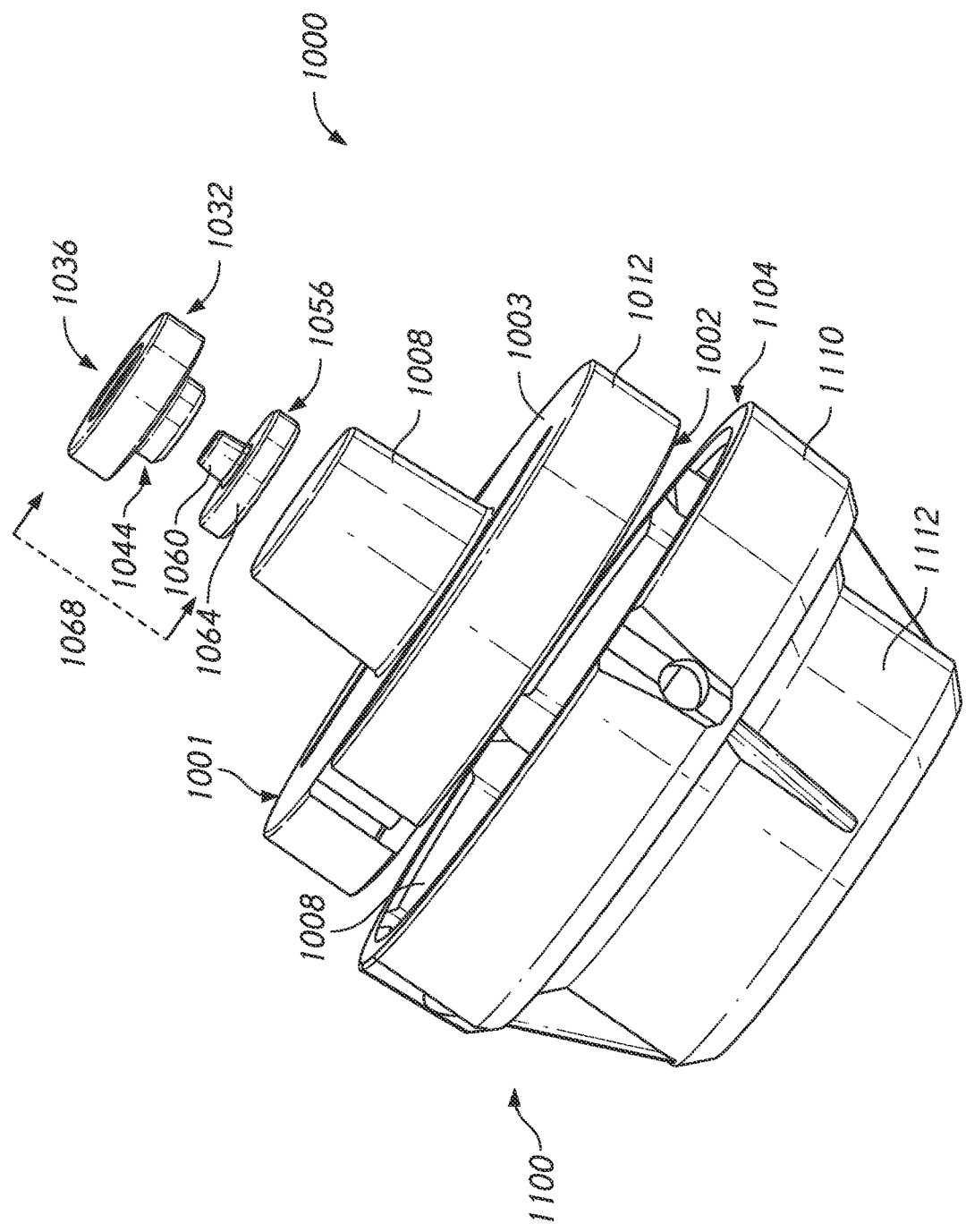
FIG. 23 is an exploded view of the cam disc assembly with anchor of FIG. 21.

FIGS. 21-31 illustrate an embodiment of a coupler 1000 that provides an expandable disc 1003 for coupling an articular body to a humeral anchor. The coupler 1000 includes a cam disc assembly for securing an articular body to a humeral anchor. FIGS. 21-24 show the expandable disc 1003 seated within the recess 1108 of an anchor 1100. As illustrated in FIG. 23, the coupler 1000 and the anchor 1100 are separable components. As will be discussed in further detail below, the coupler 1000, illustrated in FIGS. 25-26, can be configured to engage a humeral head and also be removably secured to the anchor 1100 by actuating a cam assembly 1068. FIGS. 27-31 show a plurality of views of an actuator 1032 and the securement portion 1056 that form the cam assembly 1068. As will be discussed in more detail below, the cam assembly 1068 can be actuated (e.g. rotated) to secure the coupler 1000 to the anchor 1100.

FIGS. 21-24 illustrate the expandable disc 1003 engaged with the anchor 1100. The anchor 1100 can be similar to the anchor 830, e.g., having a recess 1108 similar to the recess 842. The anchor 1100 can include a distal end 1112 and a cylindrical portion 1110 that forms the recess 1108 in the proximal face 1104 of the anchor 1100. As illustrated in connection with the anchor 830 in FIG. 1A and the anchor 830B in FIG. 15, the anchor 1100 is configured to be secured in the resected humerus. In some embodiments, the proximal face 1104 of the anchor 1100 can lie in the same plane as the resected humerus such that the cylindrical portion 1110 can secure a base of the coupler 1000 (e.g. the second portion 1012) in the recess 1108 entirely below the surface of the resected humerus. As discussed above, examples of stemless bone anchors are found in U.S. Provisional Application No. 62/740,333, filed on Oct. 2, 2018, the entirety of which is incorporated by reference herein.

Figure 24:
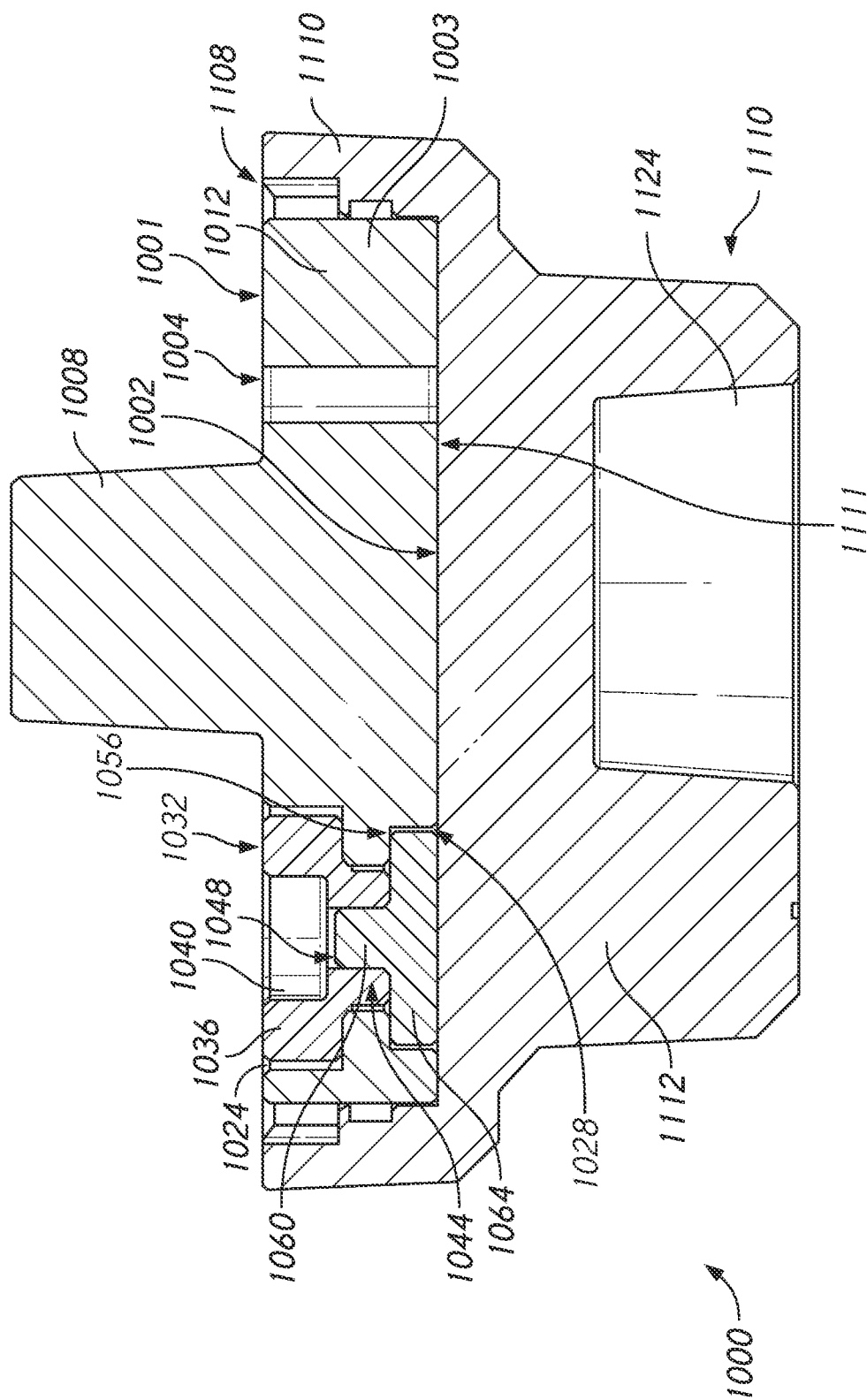
FIG. 24 is a cross-section taken through plane 24-24 shown in FIG. 22.

As illustrated in FIG. 24, in some embodiments, the second portion 1012 of the coupler 1000 is positioned within the cylindrical portion 1110 of the anchor 1100. The second portion 1012 can be positioned such that first surface 1001 slightly below or aligned with the proximal face 1104 of the anchor 1100. In some examples, the second portion 1012 can be positioned such that the first surface 1001 can be slightly above the proximal face 1104 of the anchor 1100. For example, the associated humeral head can be adapted to receive the portion of the second portion 1012 that extends above the proximal face 1104 of the anchor 1100. In some embodiments, the second surface 1002 of the second portion 1012 can lie flush against a bottom surface 1111 of the cylindrical portion 1110. As shown in FIG. 24, by having the cylindrical portion 1110 secure the coupler 1000 at or below the resection level, this can position the base of the first portion 1008 at the resection plane such that the anatomic head can be coupled to the coupler 1000 such that the anatomic head is flush or near flush with the resection.

In some embodiments (not illustrated), the expandable disc 1003 can include a plurality of external engagement portions. The external engagement portions can be similar to external engagement portions 1228 illustrated in FIGS. 32-33 below. The external engagement portions can be configured such that, when the expandable disc 1003 is placed into the cylindrical portion 1110 of the anchor 1100, the external engagement portions can engage the interior surface of the recess 1108 of the anchor 1100 at a position distal to the secondary features 1116 on the interior surface of the cylindrical portion 1110. In some examples, the external engagement portion provide a plurality of spaced apart arcuate contact points. This configuration provides contact areas between the external engagement portions and the interior surface that avoids contact with the secondary features 1116 so that these features are not compacted or otherwise altered by contact with the external engagement portion. In some embodiments, the external engagement portions are configured to engage with, e.g., to be disposed within, the slot 852. The engagement of the external engagement portions with (e.g., disposed within) the slot 852 can prevent the assembly from separating due to overlap between the engagement portions and the material forming the slot 852.

In some examples, the anchor 1100 can include additional connection features. As illustrated in FIGS. 21-22, in some examples, a plurality of secondary features 1116 can be formed along the internal surface of the cylindrical portion 1110. These secondary features 1116 can be configured to provide additional engagement and/or securement with a portion of the coupler 1000. For example, the secondary features 1116 can each include a ridge portion 1120. As will be discussed in more detail below, each of the ridge portions 1120 of the secondary features 1116 can be configured to engage with the outer surface of the second portion 1012 of the coupler 1000 when the coupler 1000 is expanded and secured within the cylindrical portion 1110 of the anchor 1100. In some embodiments the secondary features 1116 are configured to provide rotational stability when the anchor 1100 is converted to secure a reverse shoulder articular body (e.g. articular body 804A). In other embodiments, as will discussed below, the coupler 1000 can include an expandable disc portion (e.g. expandable disc 1003) that is configured to be secured in the cylindrical portion 1110. In some examples, the expandable disc portion can include female geometry or can be deformed to receive the ridge portion 1120 of the secondary features 1116 (not illustrated). By engaging the ridge portion 1120 of the secondary features 1116 with the female geometry on the expandable disc portion of the coupler 1000, the secondary features 1116 can serve as an anti-rotation feature.

FIGS. 21-26 show that the coupler 1000 can include a first portion 1008 and a second portion 1012. In some embodiments, the first portion 1008 can be configured to engage with the articular body of a humeral head assembly while the second portion 1012 can be configured to be removably secured to the cylindrical portion 1110 of the anchor 1100. As illustrated in FIGS. 21, 22, 25 and 26, the second portion 1012 of the coupler 1000 can include an expandable disc 1003 having a first slot 1016 and a second slot 1020. The first slot 1016 can include an opening (e.g. a proximal aperture 1024 and a distal aperture 1028, discussed below) that is configured to receive a cam assembly 1068. As will be discussed in more detail below, the first slot 1016 and second slot 1020 can enable the second portion 1012 of the coupler 1000 to expand in size when the cam assembly 1068 is actuated. In some embodiments, the proximal aperture 1024 can include a plurality of radial notches 1030. As will be discussed in more detail below, each of the radial notches 1030 can be configured to engage a radial protrusion 1054 located on the actuator 1032.

Figure 26:
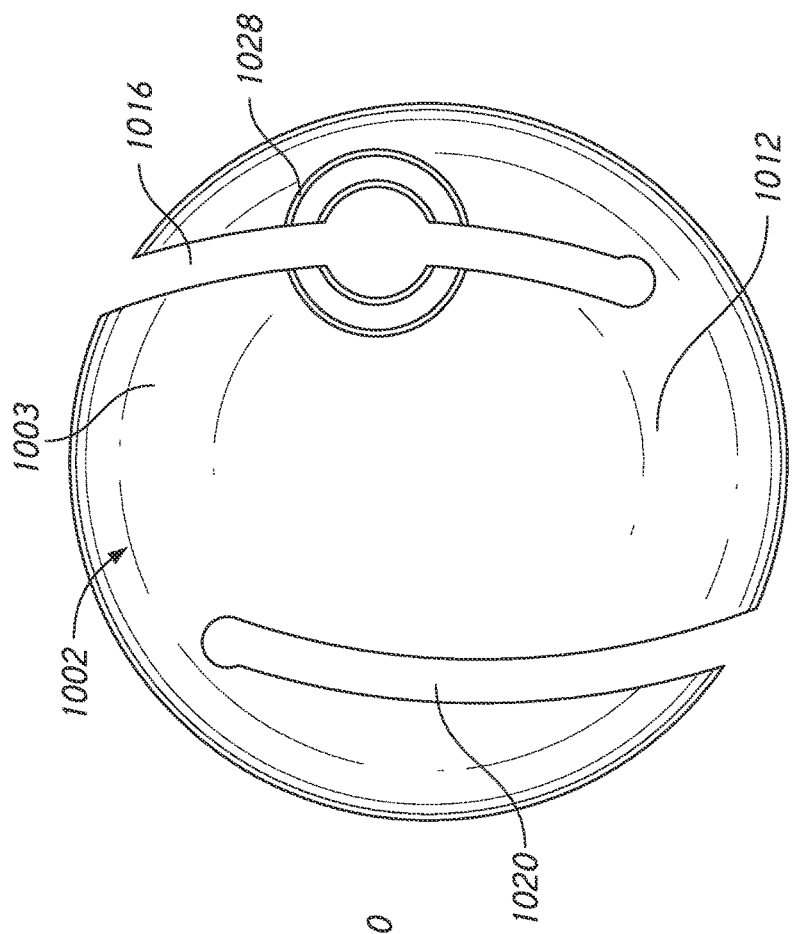
FIGS. 25-26 show a top and bottom view of a coupler of the cam disc assembly shown in FIG. 21.
Figure 25:
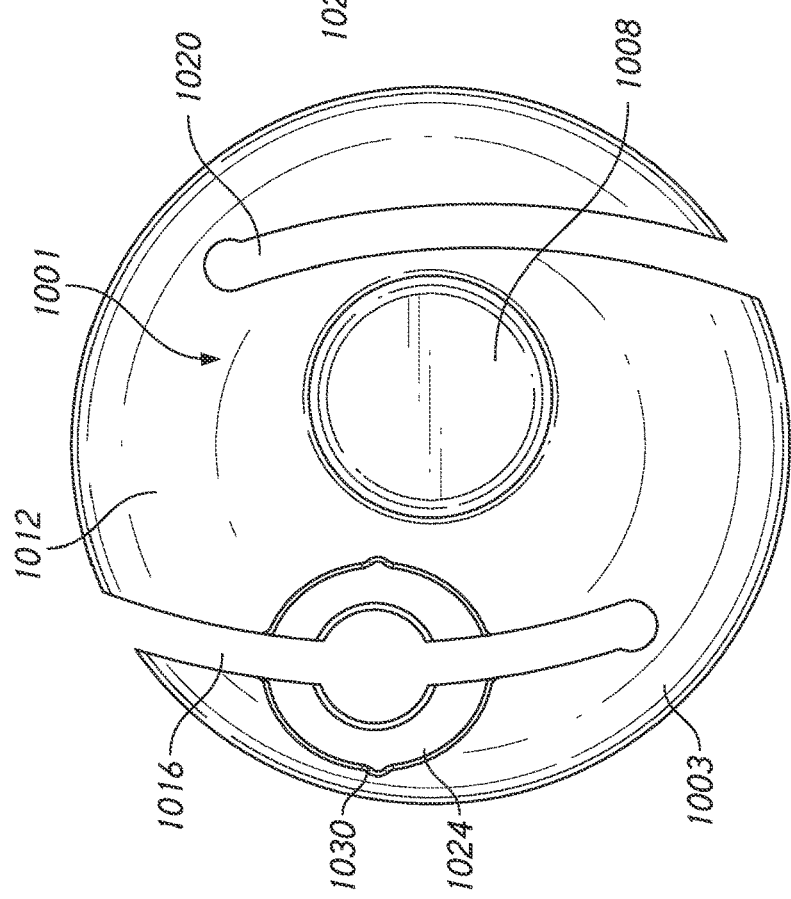

The coupler 1000 can be configured to receive the cam assembly 1068 as illustrated in FIGS. 21-24. In some examples, the cam assembly 1068 can include the actuator 1032 and a securement portion 1056. The actuator 1032 can be configured to be rotated relative to the coupler 1000. In some embodiments, the actuator 1032 is retained in the second portion 1012 of the coupler 1000 by the securement portion 1056. As illustrated in FIGS. 25 and 26, the coupler 1000 can include a proximal aperture 1024 on a first surface 1001 and a distal aperture 1028 on a second surface 1002 of the second portion 1012. FIG. 24 shows a cross-sectional view of the cam assembly 1068 retained within the second portion 1012 of the coupler 1000. In some examples, the proximal end 1036 of the actuator 1032 is retained within the proximal aperture 1024. The actuator 1032 can be secured within the coupler 1000 by engaging the distal end 1044 of the actuator 1032 with the securement portion 1056. In some embodiments, the second portion 1064 of the securement portion 1056 is retained within the distal aperture 1028 of the second portion 1012. To secure the actuator 1032 in place, the second portion 1064 can be press fit into the distal end 1044 of the actuator 1032. In some embodiments, the second portion 1064 can be laser welded or otherwise permanently secured to the distal end 1044 of the actuator 1032 to prevent the cam assembly 1068 from disassembling. In some embodiments, a first portion 1060 of the securement portion 1056 is retained within the channel 1048 in the distal end 1044 of the actuator 1032.

Figure 28:
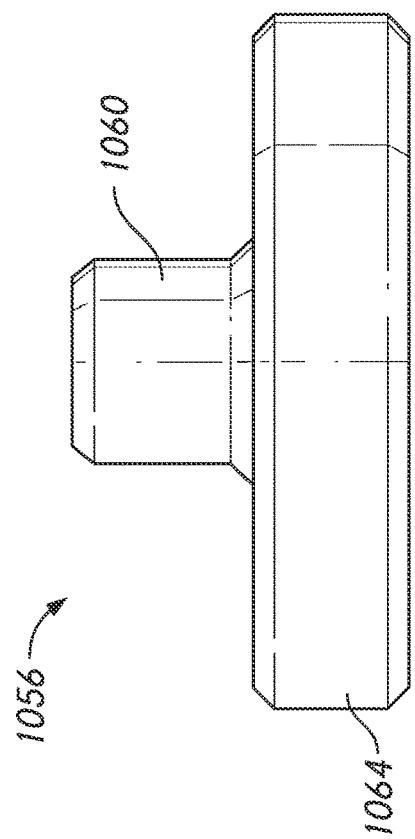
FIGS. 27-28 show a perspective and side view of a securement portion of a cam assembly of the cam disc assembly shown in FIG. 21.
Figure 27:
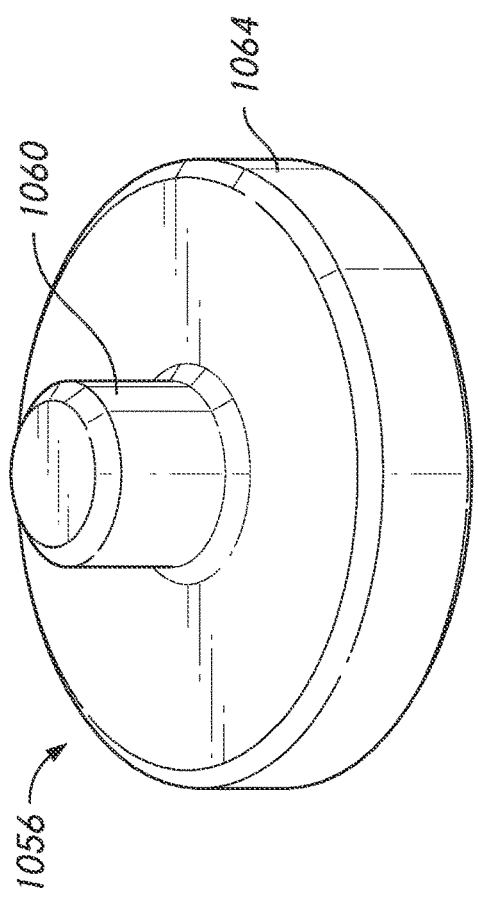
Figure 29:
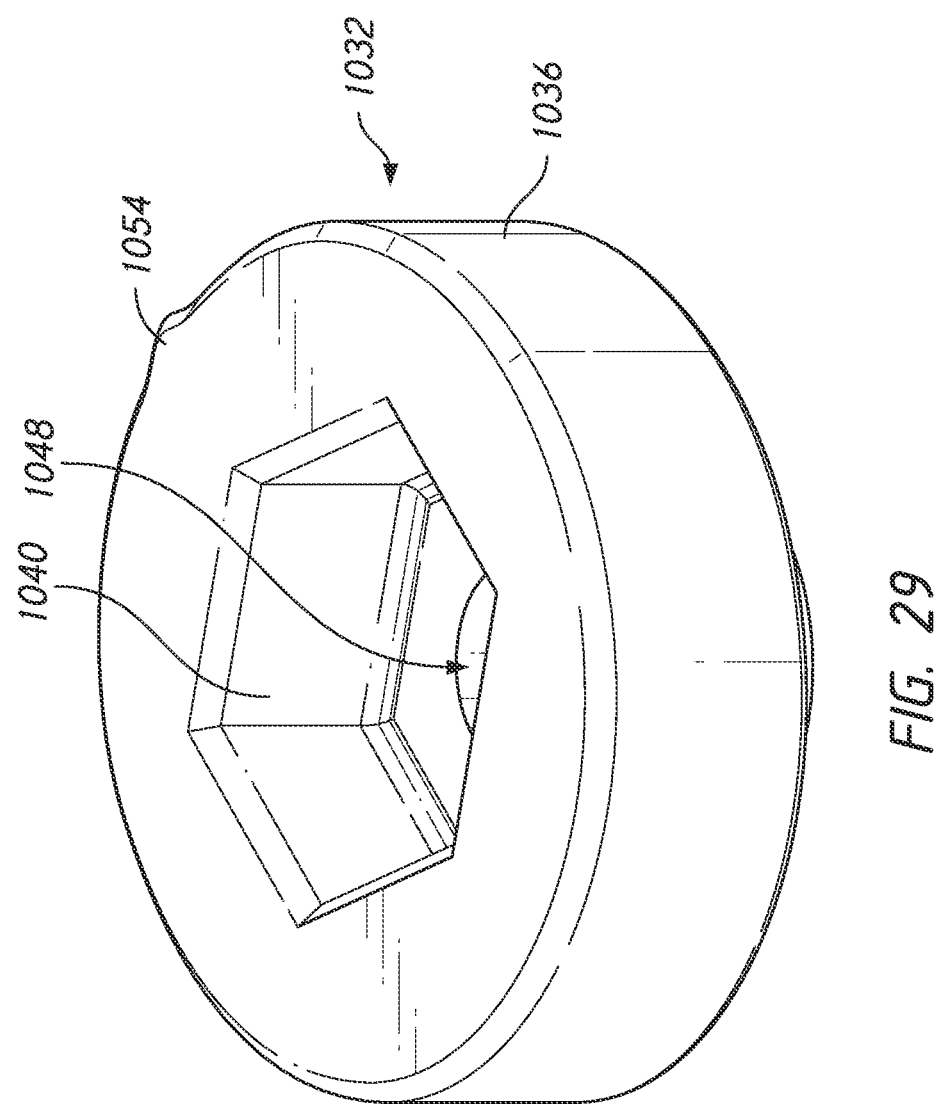

FIGS. 27-28 illustrate a perspective and side view of the securement portion 1056 while FIGS. 29-31 illustrate various views of the actuator 1032. Turning first to the securement portion 1056, in some embodiments the securement portion 1056 includes a first portion 1060 and a second portion 1064. In some examples, the first portion 1060 can be cylindrical and have a smaller radius than the second portion 1064.

FIGS. 30-31 show that the actuator 1032 can include a proximal end 1036 and a distal end 1044. The proximal end 1036 can include a tool interface 1040 extending through a portion of the proximal end 1036. In some embodiments, the tool interface 1040 is configured to engage with a tool such that the actuator 1032 can be rotated. As illustrated in FIGS. 29-30, the tool interface 1040 can have a hexagonal shape. In other embodiments the tool interface 1040 can have other configurations that allows a tool to engage with the actuator 1032, e.g., at least one flat surface or a non-circular shape. As discussed above, in some embodiments, the distal end 1044 of the actuator 1032 can be received in the proximal aperture 1024 of the coupler 1000. The distal end 1044 can be configured to engage the securement portion 1056 such that the actuator 1032 is secured within the coupler 1000 to form the cam assembly 1068. For example, the distal end 1044 can include a channel 1048 extending through the distal end 1044. As noted above, the first portion 1060 of the securement portion 1056 can engage with the channel 1048 to retain the actuator 1032 in the coupler 1000.

In order to secure the coupler 1000 with the anchor 1100 when the cam assembly 1068 is actuated, the actuator 1032 can have an oblong shape (e.g. oval) such that the actuator 1032 is longer along a first axis than a second axis. In the example illustrated in FIG. 30, the actuator 1032 is longest along the major axis 1052. As will be discussed in more detail below, by rotating the actuator 1032, the major axis 1052 of the actuator 1032 will cause the coupler 1000 to expand and engage the anchor 1100. The actuator 1032 can also include a radial protrusion 1054. In some embodiments, the radial protrusion 1054 extends from the actuating surface disposed on an outside of the proximal end 1036 of the actuator 1032. In some examples, the radial protrusion 1054 can have a shape inverse to that of the radial notch 1030 of the proximal aperture 1024. As will be discussed below, the inverse shape of the protrusion to the notch can allow the radial notch 1030 of the proximal aperture 1024 to receive the radial protrusion 1054 of the actuator 1032 in a secure manner.

As discussed above, the coupler 1000 is configured to provide an expandable fixation assembly for an orthopedic application (e.g. humeral head assembly). A portion of the coupler 1000 is configured to fit into the anchor 1100 or into the anchor 830 or the anchor 830A and expand/contract so as to engage the outside perimeter of the coupler 1000 with the interior surface or perimeter of the recess in the anchor

1100. The anchor 830 and the anchor 830A will not be discussed further below but could be substituted for the anchor 1100 in the description of the use of the coupler 1000. As discussed above with regard to FIG. 22, the expandable disc 1003 of the coupler 1000 includes the first slot 1016 and the second slot 1020. The proximal aperture 1024 located on the first surface 1001 of the second portion 1012 is oblong in order to receive the oblong profile of the actuator 1032. In some embodiments, when the actuator 1032 is rotated, the actuating surface at the proximal end 1036 can force the expansion of the proximal aperture 1024 and the associated first slot 1016. In some examples, the actuator 1032 can be rotated 90 degrees such that the radial protrusion 1054 of the actuator 1032 can be retained in one of the radial notches 1030. In some embodiments, either of the radial notches 1030 can be configured to lock the actuator 1032 in place. The expansion of the proximal aperture 1024 and the first slot 1016 can cause the second slot 1020 to compress and to absorb any expansion the rotation of the actuator 1032 provides. In some embodiments, the expansion of the first slot 1016 and the compression of the second slot 1020 can cause the outside perimeter of the second portion 1012 of the coupler 1000 to engage with the inside perimeter of the recess 1108 of the anchor 1100. In some examples, the ridge portions 1120 of the secondary features 1116 can be configured to provide additional engagement points to further secure the coupler 1000 within the anchor 1100. The ridge portion 1120 can be spaced apart from the outer surface of the expandable disc 1003 of the second portion 1012 of the coupler 1000 prior to the expansion thereof. Upon expansion, the expandable disc 1003 can be enlarged to be as large as or larger than a periphery intersecting the peaks of the ridge portion 1120. This can provide interference between the outer periphery of the expandable disc 1003 and the ridge portion 1120 enhancing securement when the ridge portion 1120 is present.

After the coupler 1000 is secured in place, an anatomic articular body, e.g., similar to the articular body 804 can be secured to the coupler at the first portion 1008 of the coupler 1000.

In some embodiments, the coupler 1000 can be disengaged from the anchor 1100 by rotating the actuator 1032 another 90 degrees such that the oblong profile of the actuator 1032 is realigned with the profile of the proximal aperture 1024. In this way, the actuator 1032 no longer expands the proximal aperture 1024 and the first slot 1016 such that the first slot 1016 and the second slot 1020 can return to their original configuration. This enables the expandable disc 1003 of the second portion 1012 to return to an un-expanded configuration.

In a revision procedure, the anatomic articular body (similar to the body 804) can be removed by forcing a wedge into the gap between the first surface 1001 and the side of the articular body opposite the convex articulating surface. The wedge can overcome the interference connection between the first portion 1008 and a tapered recess in the articular body such that the articular body is separated from the coupler 1000. Thereafter the coupler 1000 can be removed by actuating the protrusion 1054 out of the radial notch 1030. After the expandable disc 1003 contracts, the coupler 1000 can be removed.

In one embodiment, the ridge portion 1120 of the anchor 1100 remains out of contact with the expandable disc 1003 of the coupler 1000 when the actuator 1032 is rotated to cause expansion of the expandable disc 1003. A gap extends between the radially inward-most portion of the ridge portion 1120. In a revision procedure, after the anatomic head and the coupler 1000 are removed a reverse articular body similar to the articular body 804A can be inserted into the recess 1108. An interface portion of a distal portion of the reverse articular body, e.g., similar to the interface portion 849 can engage the interior surface of the anchor 1100. The interface portion can include a surface configured to engage the ridge portion 1120 with an interference fit. The interface portion can include a locking device, similar to the C-ring 850. In that case, the interior surface disposed about the recess 1108 can include a radially outward channel to receive a portion of the C-ring. The interface portion can include a locking device that provide both engagement with a C-ring or other locking device and an interference fit with the interface portion.

By configuring the coupler 1000 to be actuated from an enlarged state (with the radial protrusion 1054 engaged into the radial notch 1030) to a smaller configuration (with the radial protrusion 1054 out of the radial notch 1030, e.g., aligned with the first slot 1016) the coupler 1000 can be removed from the recess 1108 without undue force being applied to the anchor 1100. This allows a reverse articular body to be applied with minimal disruption.

The anchor 1100 and the coupler 1000 enable both an anatomic articular body 804 and a reverse articular body 804A to be coupled to the anchor 1100 at the resection plane. The anchor 1100 and the reverse articular body 804A eliminate potential tolerance stackup that would normally arise due to an intervening tray between the reverse insert and the anchor.

B. Expanding Coupler with Screw and Taper Expansion

Figure 21A:
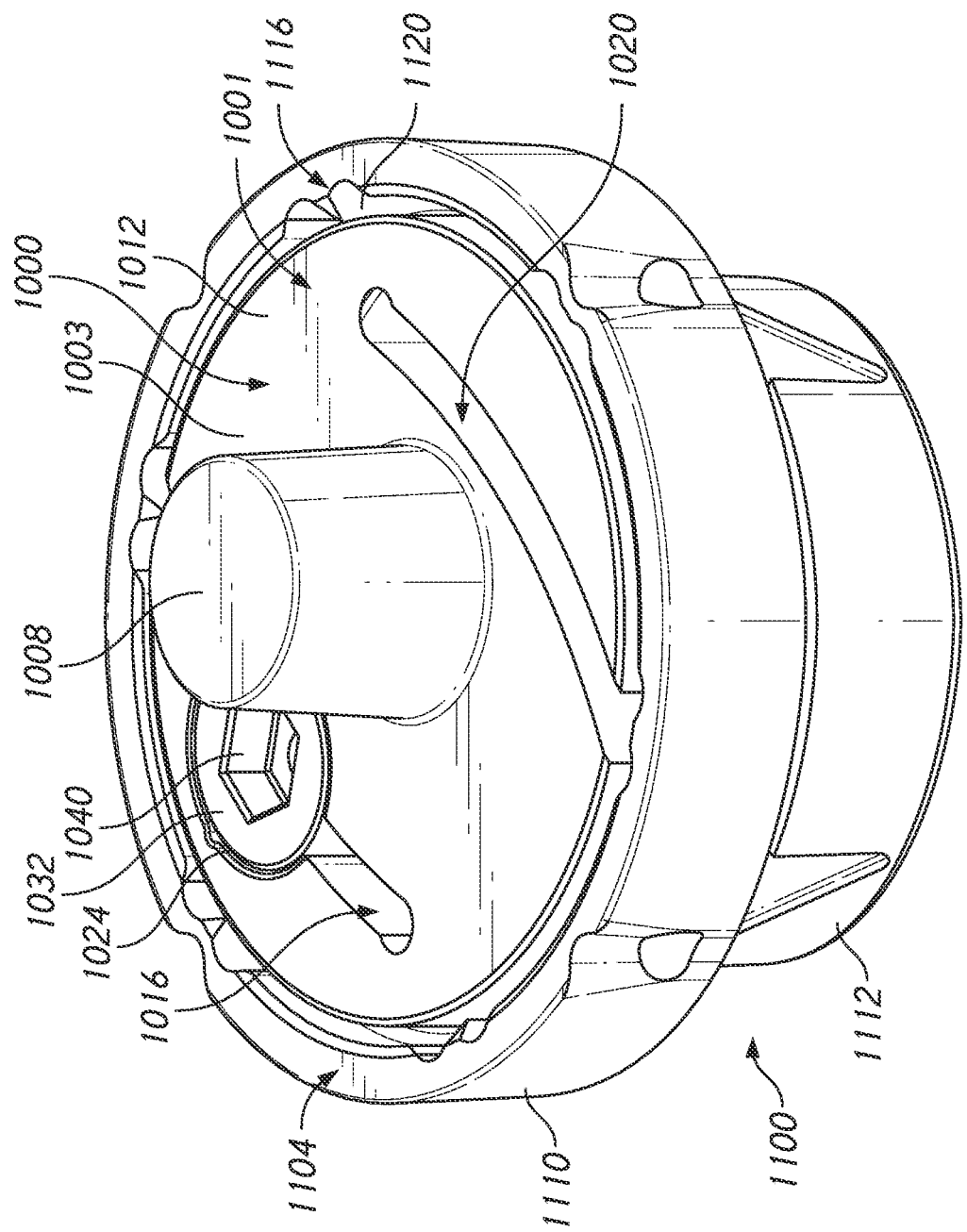
FIG. 21A is a perspective view of a cam disc assembly engaged with an anchor.
Figure 21B:
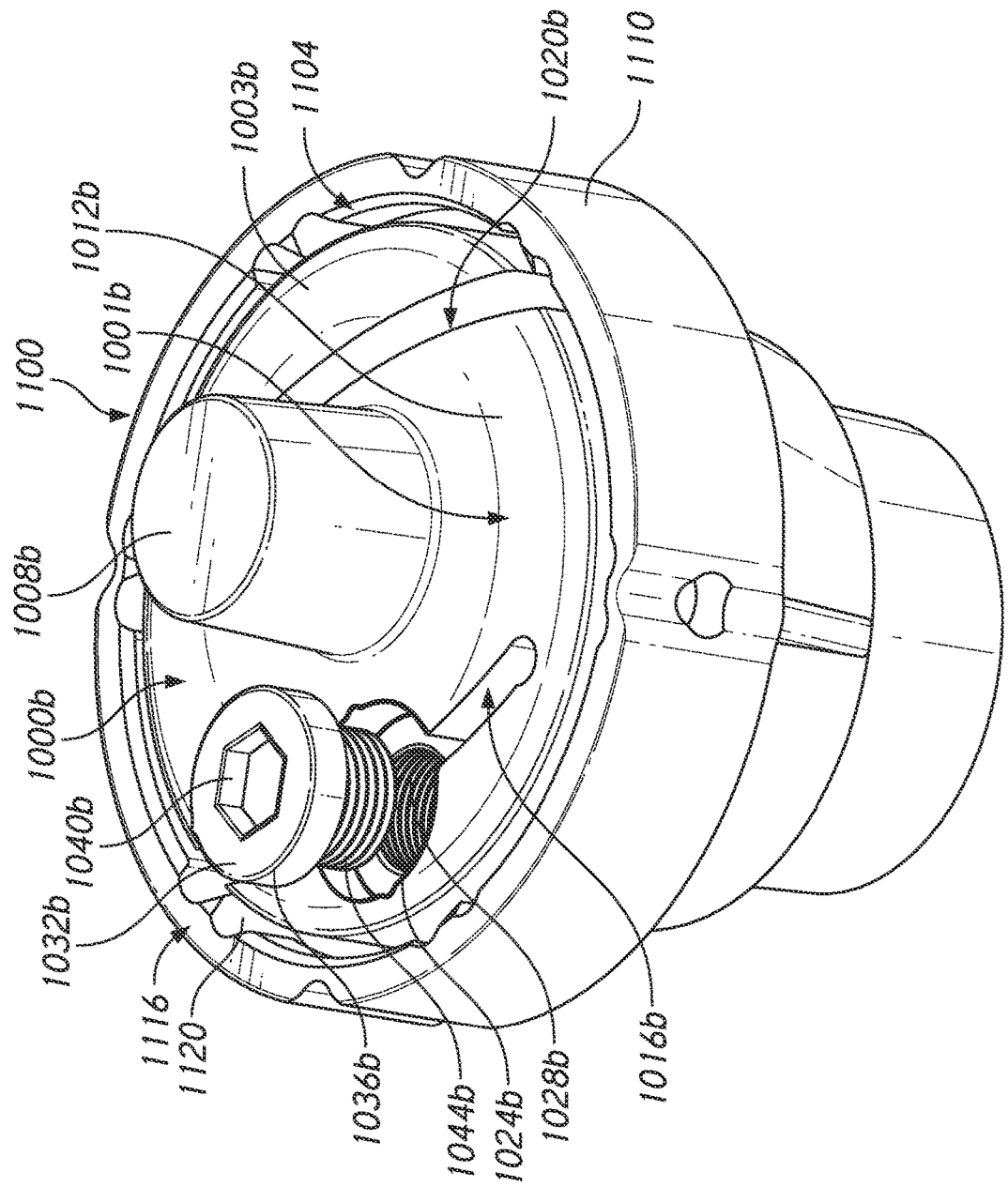
FIG. 21B is a perspective view of a cam screw assembly engaged with an anchor.

FIGS. 21B and 22B illustrate an embodiment of a coupler 1000*b* that is similar to the coupler 1000 illustrated in FIGS. 21A and 22A. The coupler 1000*b* can include an expandable disc 1003*b* for coupling an articular body to a humeral anchor. The coupler 1000*b*, like the coupler 1000, can include an actuator for expanding the coupler 100*b* to secure an articular body to a humeral anchor. As will be discussed in more detail below, the actuator for the coupler 1000*b* comprises a screw 1032*b* adapted to force the expandable disc 1003*b* to expand or to allow the disc 1003*b* to contract.

FIGS. 21B and 22B illustrate the expandable disc 1003*b* seated within the recess 1108 of the anchor 1100 or the anchor 804. The coupler 1000*b* and the anchor 1100 are separable components. The coupler 1000*b* can be configured to engage a humeral head and also be removably secured to the anchor 1100 by actuating the screw 1032*b*. As will be discussed in more detail below, the screw 1032*b* can be actuated (e.g. rotated) to secure the coupler 1000*b* to the anchor 1100.

In some embodiments, the expandable disc 1003*b* is configured to be positioned in the recess 1108 of the anchor 1100. As illustrated in FIGS. 21B and 22B, in some embodiments the second portion 1012*b* of the coupler 1000*b* is positioned within the cylindrical portion 1110, e.g. a proximal recess, of the anchor 1100. The second portion 1012*b* can be positioned such that the first surface 1001*b* is slightly below or aligned with the proximal face 1104 of the anchor 1100. In some examples, the second portion 1012*b* can be positioned such that the first surface 1001*b* can be slightly above the proximal face 1104 of the anchor 1100 if the associated humeral head is adapted to receive the portion of the second portion 1012 that extends above the proximal face 1104 of the anchor 1100. In some embodiments, the second surface of the second portion 1012*b* (not illustrated), opposite the first surface 100*lb*, can lie flush against a bottom surface 1111 of the cylindrical portion 1110. Positioning the distal-most end of the first portion 1008*b* at the resection plane allows the anatomic head is flush or near flush with the resection when the anatomic head is coupled to the coupler 1000*b*.

The expandable disc 1003*b* can include a plurality of external engagement portion similar to the external engagement portions 1228 illustrated in FIGS. 32-33 below. The external engagement portions can be configured such that, when the expandable disc 1003*b* is placed into the cylindrical portion 1110 of the anchor 1100, the engagement portions engage the interior surface of the recess 1108 of the anchor 1100 at a position distal to secondary connection feature 1116 on the interior surface of the cylindrical portion 1110. In some examples, the external engagement portions can include a plurality of spaced apart arcuate contact points, the further structure and user of which is discussed elsewhere herein.

FIGS. 21B and 22B show that the coupler 1000*b*, like the coupler 1000, can include a first portion 1008*b* and a second portion 1012*b*. In some embodiments, the first portion 1008*b* can be configured to engage with the articular body of a humeral head assembly while the second portion 1012*b* can be configured to be removably secured to the cylindrical portion 1110 of the anchor 1100. As illustrated in FIGS. 21B and 22B, the second portion 1012*b* of the coupler 1000*b* can include the expandable disc 1003*b* which includes a first slot 1016*b* and a second slot 1020*b*. The first slot 1016*b* can include an opening (e.g. an aperture 1024*b*, discussed below) that is configured to receive the screw 1032*b*. As will be discussed in more detail below, the first slot 1016*b* and second slot 1020*b* can enable the second portion 1012*b* of the coupler 1000*b* to expand in size when the screw 1032*b* is advanced in the expandable disc 1003*b*. In some embodiments, the screw 1032*b* can be tapered such that the size, e.g., radius, of the head of the screw 1032*b* at a first location adjacent to the proximal end 1036*b* is greater than the radius of the head of the screw 1032*b* at a second location on the head of the screw 1032*b* distal to the first location. The second location can be on the distal end 1044*b* of the head of the screw 1032*b*. In other embodiments, the channel 1028*b* can be tapered such that the size, e.g., radius, of the aperture 1024*b* at a first location at or adjacent to on the first surface 1001*b* is greater than the size, e.g., radius, of the aperture 1024*b* between the first location and the opposite second surface of the expandable disc 1003*b* (not illustrated). In a further embodiment, both the screw 1003 and the channel 1028*b* can be tapered. As will be discussed in more detail below, the tapering of either the screw 1032*b* or the channel 1028*b* is configured such that when the screw 1032*b* is advanced into the channel 1028*b*, the expandable disc 1003*b* of the second portion 1012*b* can expand and engage the coupler 1000*b* into the anchor 1100.

As discussed, the coupler 1000*b* can be configured to receive the screw 1032*b*. In some embodiments, the screw 1032*b* can be configured to rotate relative to the coupler 1000*b*. In some examples, the screw 1032*b* is retained in the second portion 1012*b* of the coupler 1000*b*. As illustrated in FIG. 21B, the coupler 1000*b* can include the aperture 1024*b* on the first surface 1001*b* and a channel 1028*b* that extends through the body of the second portion 1012*b*. In some embodiments, the aperture 1024*b* has a larger radius than the channel 1028*b*. The screw 1032*b* can be secured within the coupler 1000*b* by inserting a distal end 1044*b* of the screw 1032*b* into the channel 1028*b*. As will be discussed in more detail below, the external surface of the distal end 1044*b* of the screw 1032*b* and an internal surface of the channel 1028*b* can be threaded such that the external threading of the screw 1032*b* and the internal threading of the channel 1028*b* can engage as the screw 1032*b* is rotated into the channel 1028*b*.

FIG. 21B illustrates a perspective view of the screw 1032*b*. As discussed above, in some examples, the screw 1032*b* includes the proximal end 1036*b* and the distal end 1044*b*. The proximal end 1036*b* can include a tool interface 1040*b* configured to engage with a tool such that the screw 1032*b* can be rotated. The tool interface 1040*b* can have a hexagonal shape, a flat surface, a non-circular shape or other configurations that allow a tool to drive the screw 1032*b*.

The channel 1028*b* of the second portion 1012*b* can receive distal end 1044*b* of the screw 1032*b*. The threading on the internal surface of the channel 1028*b* is configured to engage with the thread on the external surface of the distal end 1044*b*. When the screw 1032*b* is actuated, the threading on the channel 1028*b* is configured to retain the distal end 1044*b* in the coupler 1000*b*.

As discussed above, the distal end 1044*b* of the screw 1032*b*, the channel 1028*b*, or both are tapered. When the screw 1032*b* is actuated, the expandable disc 1003*b* of the second portion 1012*b* is expanded and engage with the interior surface of the anchor 1100. As discussed earlier, the coupler 1000*b* is configured to provide an expandable fixation assembly for an orthopedic application (e.g. humeral head assembly). A portion of the coupler 1000*b* is configured to fit into the anchor 1100, anchor 830, or the 830A and expand/contract to engage the outside perimeter of the coupler 1000*b* with the interior surface or perimeter of the recess in the anchor 830, 830A, 1100.

As discussed above with regard to FIGS. 21B and 22B, the expandable disc 1003*b* of the coupler 1000*b* includes the first slot 1016*b* and the second slot 1020*b*. The aperture 1024*b* located on the second portion 1012*b* is configured to receive the screw 1032*b*. In some embodiments, when the screw 1032*b* is rotated, the screw 1032*b* can force the expansion of the aperture 1024*b* and the associated first slot 1016*b*. The aperture 1024*b* can expand when either the screw 1032*b* is tapered or the channel 1028*b* is tapered.

In some embodiments, the distal end 1044*b* of the screw 1032*b* is tapered. In some examples, the distal end 1044*b* of the screw 1032*b* can have a first radius adjacent to the proximal end 1036*b* of the screw 1032*b* that is greater than a second radius at a distal end of the distal end 1044*b*. The tapered screw 1032*b* is configured to engage a channel 1028*b*. The channel 1028*b* has a radius that is the same or slightly greater than the second radius but is less than the first radius. The tapered screw 1032*b* is rotated such that the threading on the distal end 1044*b* engages the threading on the channel 1028*b*. In this way, the tapered screw 1032*b* is advanced through the channel 1028*b*. As the radius of the channel 1028*b* is smaller than the second radius of the distal end 1044*b* of the tapered screw 1032*b*, as the screw 1032*b* is advanced through the channel 1028*b*, the channel 1028*b* is expanded to receive the larger radius of the distal end 1044*b*.

In another embodiment, the channel 1028*b* is tapered. In some examples, the channel 1028*b* has a first radius adjacent to the aperture 1024*b* on a first surface 100*lb* of the second portion 1012*b* that is greater than a second radius of the channel 1028*b* between the first surface 1001*b* and a surface of the second portion 1012*b* opposite the first surface 100*lb*. The tapered channel 1028*b* is configured to receive the screw 1032*b*. In this embodiment, the distal end 1044*b* of the head of the screw 1032*b* has a radius that is the same or slightly smaller than the first radius of the head of the screw 1032*b* and greater than the second radius of the head of the screw 1032*b*. The distal end 1044*b* of the screw 1032*b* is rotated such that the threading on the distal end 1044*b* engages the threading disposed in (e.g., distal of) the tapered portion of the tapered channel 1028*b*. In this way, the distal end 1044*b* of the screw 1032*b* is advanced through the tapered channel 1028*b*. As the screw 1032*b* is advanced through the tapered channel 1028*b*, the tapered channel 1028*b* is expanded.

The expansion of the channel 1028*b* also corresponds to expansion of the first slot 1016*b*. This in turn can cause the second slot 1020*b* to compress, if present, and to absorb any at least some of the expansion of the second portion 1012*b*. In some embodiments, the expansion of the first slot 1016*b* and the compression of the second slot 1020*b* can cause the outside perimeter of the second portion 1012*b* of the coupler 1000*b* to engage with the inside perimeter of the recess 1108 of the anchor 1100*b*. The ridge portion 1120 generally is spaced apart from the coupler 1000*b* even in the expanded state of the anchor 1100. In some examples, the ridge portions 1120 of the secondary features 1116 can be configured to provide additional engagement points to further secure the coupler 1000*b* within the anchor 1100. The ridge portion 1120 can be spaced apart from the outer surface of the expandable disc 1003*b* of the second portion 1012 of the coupler 1000*b* prior to the expansion thereof. Upon expansion, the expandable disc 1003*b* can be enlarged to be as large as or larger than a periphery intersecting the peaks of the ridge portion 1120. This can provide interference between the outer periphery of the expandable disc 1003*b* and the ridge portion 1120 enhancing securement when the ridge portion 1120 is present.

After the coupler 1000*b* is secured in place, an anatomic articular body, e.g., similar to the articular body 804 can be secured to the coupler at the first portion 1008*b* of the coupler 1000*b*.

In some embodiments the coupler 1000*b* can be disengaged from the anchor 1100 by rotating the screw 1032*b* to retract the screw 1032*b* in or to withdraw the screw 1032*b* from the channel 1028*b* such that the channel 1028*b* returns to the non-expanded state. This enables the expandable disc 1003*b* of the second portion 1012*b* to return to an un-expanded configuration such that the coupler 1000*b* can be removed.

In one embodiment, a gap extends between the radially inward-most portion of the ridge portion 1120 and the expandable disc 1003*b* of the coupler 1000*b* when the expandable disc 1003*b* is expanded. In a reverse configuration, e.g., in a revision after an anatomic head and the coupler 1000*b* are removed, a reverse articular body 804A can be inserted into the recess 1108. An interface portion 849 of a distal portion of the reverse articular body 804A, can engage the interior surface of the anchor 1100. The interface portion 849 can include a surface configured to engage the ridge portion 1120 with an interference fit. The interface portion 849 can include a locking device, similar to the C-ring 850. In that case, the interior surface disposed about the recess 1108 can include a radially outward channel to receive a portion of the C-ring. The interface portion 849 can include a locking device that provide both engagement with a C-ring or other locking device and an interference fit with the interface portion.

By configuring the coupler 1000*b* to be actuated from an enlarged state to a smaller configuration, the coupler 1000*b* can be removed from the recess 1108 without undue force being applied to the anchor 1100. This allows a reverse articular body to be applied with minimal disruption. The coupler 1000*b* can be removed without applying a transverse load, such as with a wedge tool, between the articular body 804 and the anchor 1100.

The anchor 1100 and the coupler 1000*b* enable the anatomic articular body 804 or the reverse articular body 804A to be coupled to the anchor 1100 at the resection plane. The direct coupling between the anchor 1100 and the articular body 804A eliminates potential tolerance stackup that would normally arise due to an intervening tray between the reverse insert and the anchor.

C. Expanding Coupler with Taper Cam and Slot Assembly

FIGS. 32-43 illustrate a coupler 1200 that provides another embodiment of the expandable coupler for coupling an articular body to a humeral anchor. The coupler 1200 can include a taper cam and slot assembly for securing an articular body to a humeral head anchor. Similar to the coupler 1000 discussed above, the coupler 1200 includes an expandable disc 1204 that can be removably secured to the anchor 1100. As shown in FIGS. 32-43, the coupler 1200 differs from the coupler 1000 in that the cam assembly can be placed within the portion of the coupler (see e.g. the first portion 200 of the coupler 108 or the first portion 1008 of the coupler 1000) that is configured to engage and secure the humeral head assembly.

Figure 32:
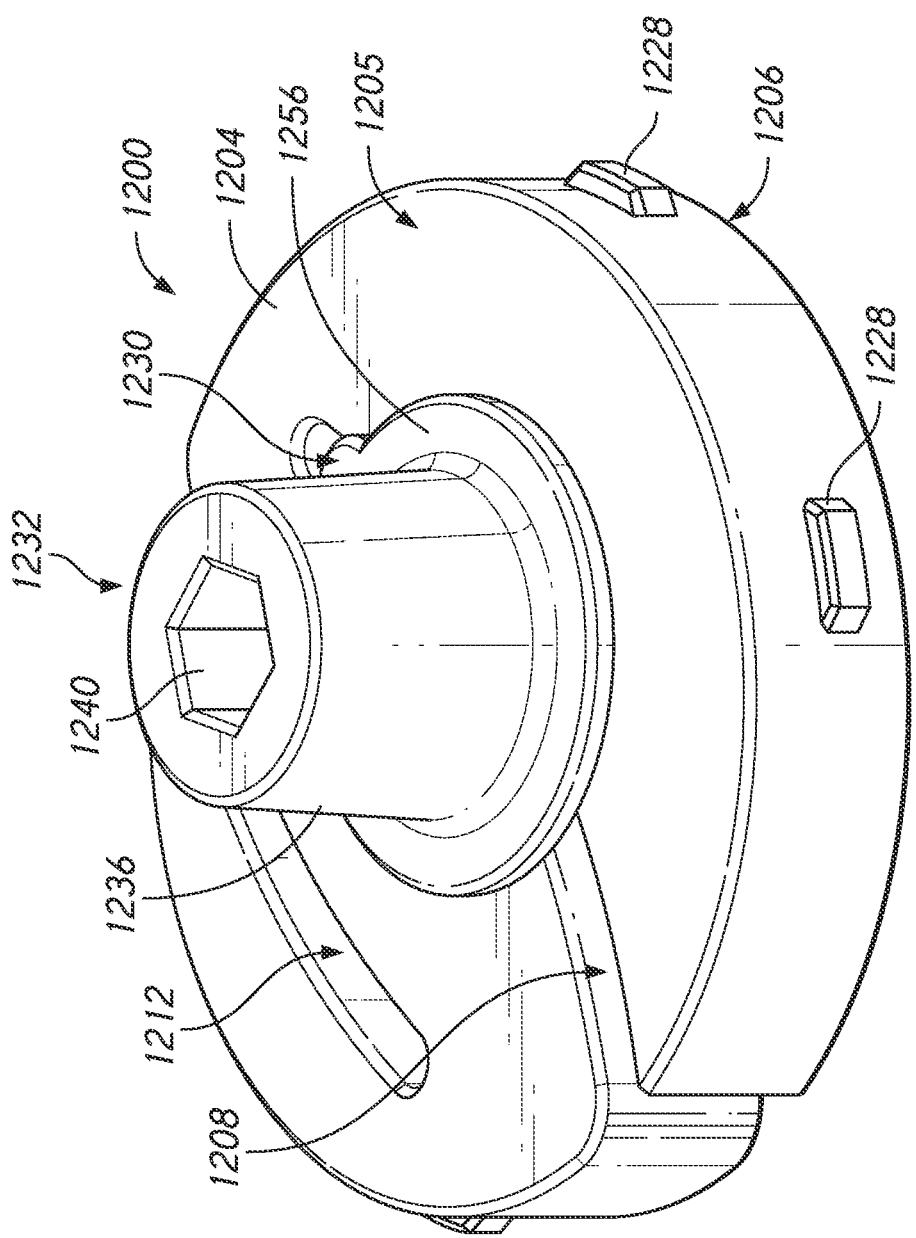
FIG. 32 is a perspective view of a taper cam and slot assembly.
Figure 33:
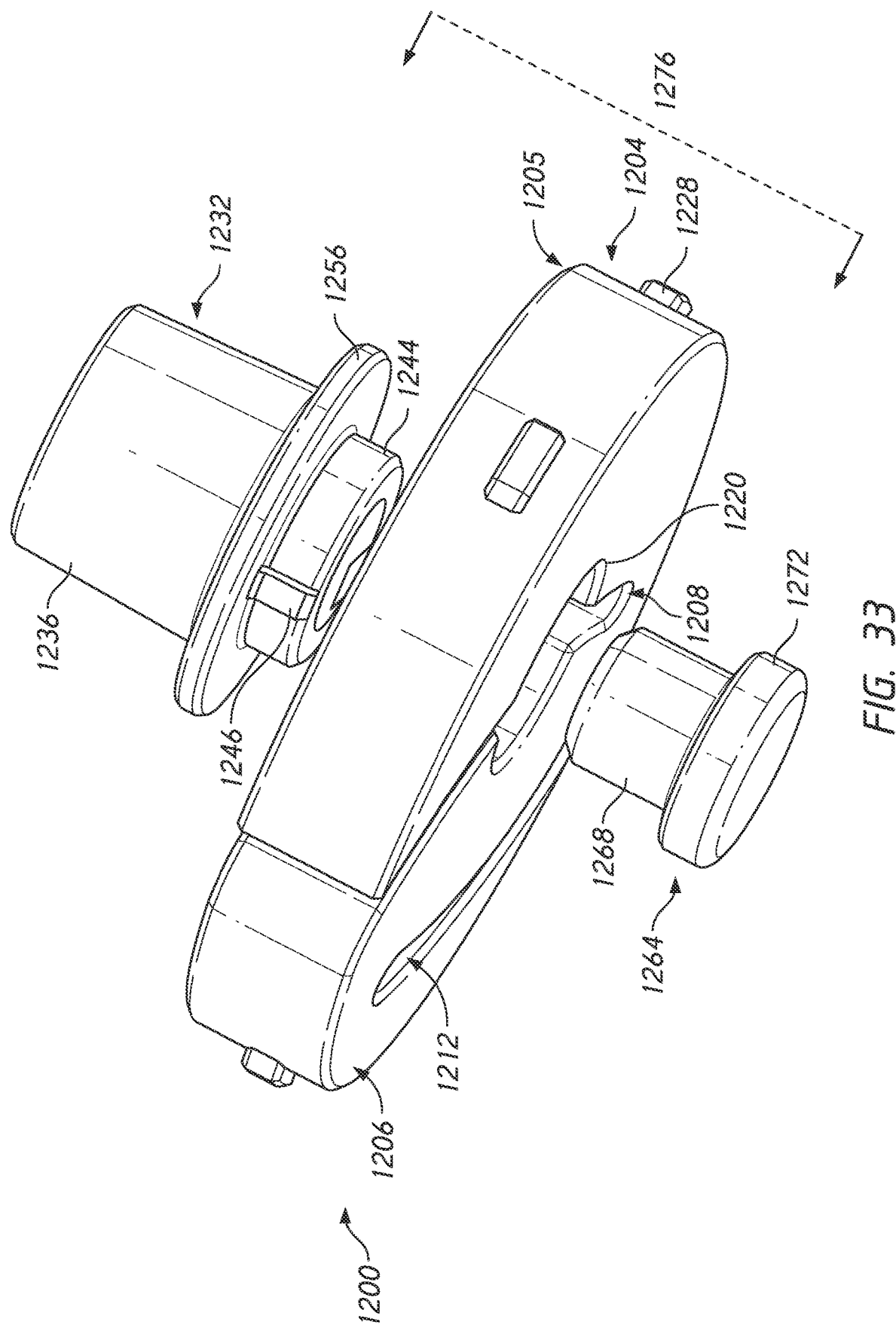
FIG. 33 is an exploded view of the taper cam and slot assembly of FIG. 32.

FIGS. 32-33 illustrate the expandable disc 1204 of the taper cam and slot assembly 1200. In some embodiments, the expandable disc 1204 can be configured to engage with the anchor 1100. As with the expandable disc 1003, the expandable disc 1204 can be received within the cylindrical portion 1110 of the anchor 1100. As with the coupler 1000, the coupler 1200 also can be used with the anchor 830 or with the anchor 830A and one skilled in the art will understand that the discussion of the anchor 830 or the anchor 830A could be substituted for that of the anchor 1100 below. When positioned within the cylindrical portion 1110, the first surface 1205 of the expandable disc 1204 can be slightly below or aligned with the proximal face 1104 of the anchor 1100. In some examples, the expandable disc 1204 can be positioned such that the first surface 1205 can be slightly above the proximal face 1104 of the anchor 1100. For example, the associated humeral head can be adapted to receive the portion of the expandable disc 1204 that extends above the proximal face 1104 of the anchor 1100. In some embodiments, the second surface 1206 of the expandable disc 1204 can lie flush against a bottom surface (e.g. bottom surface 1111) of the cylindrical portion 1110 of the anchor 1100. As noted above, by having the cylindrical portion 1110 secure the expandable disc 1204 at or below the resection level, this can position a distal end 1244 of a proximal end 1236 of an actuator 1232 at the resection plane such that the distal end 1244 of the proximal end 1236 of the actuator 1232 is flush or near flush with the resection. An anatomic articular body 804 can be coupled to the expandable disc 1204 just above the resection plane. For example, a Morse taper can be formed between the articular body 804 and the actuator 1232 of the expandable disc 1204.

In some embodiments, the expandable disc 1204 can include a plurality of external engagement portions 1228. As will be discussed in more detail below, when the expandable disc 1204 is placed into the cylindrical portion 1110 of the anchor 1100, each of the external engagement portions 1228 can be configured to engage the interior surface of the recess 1108 of the anchor 1100 at a position distal to the secondary features 1116 on the interior surface of the cylindrical portion 1110. The external engagement portion 1228 can include a plurality of spaced apart arcuate contact points. This configuration provides contact areas between the external engagement portions 1228 and the interior surface that avoids contact with the secondary features 1116 so that these features are not compacted or otherwise altered by contact with the external engagement portion 1228. In some embodiments, the external engagement portions 1228 are configured to engage with the slot 852 of the anchor 1100 that, as discussed above, can be configured to receive the C-ring 850. The engagement of the external engagement portions 1228 with the slot 852 can provide for a secondary locking mechanism that prevents the assembly from separating.

In some embodiments, the expandable disc 1204 includes a tapered coupler configured as the actuator 1232 and an expandable disc that can include a first slot 1208 and a second slot 1212. The first slot 1208 can include an opening (e.g. a proximal aperture 1216 and a distal aperture 1220) that is configured to receive a cam assembly 1276. As will be discussed in more detail below, the first slot 1208 can expand and the second slot 1212 can contract when the cam assembly 1276 is actuated to a configuration in which the outer periphery is expanded for locking to the anchor 1100. The first slot 1208 can contract and the second slot 1212 can expand when the cam assembly 1276 is actuated to a configuration in which the outer periphery is contracted for disengaging the anchor 1100. In some embodiments, the proximal aperture 1216 of can include a plurality of radial notches 1230. Each of the radial notches 1230 can be configured to engage a radial protrusion 1246 located on the actuator 1232. In some cases, the actuator 1232 also is configured as a taper of the expandable disc 1204 facilitating connection to the actuator/taper of the expandable disc 1204.

Figure 36:
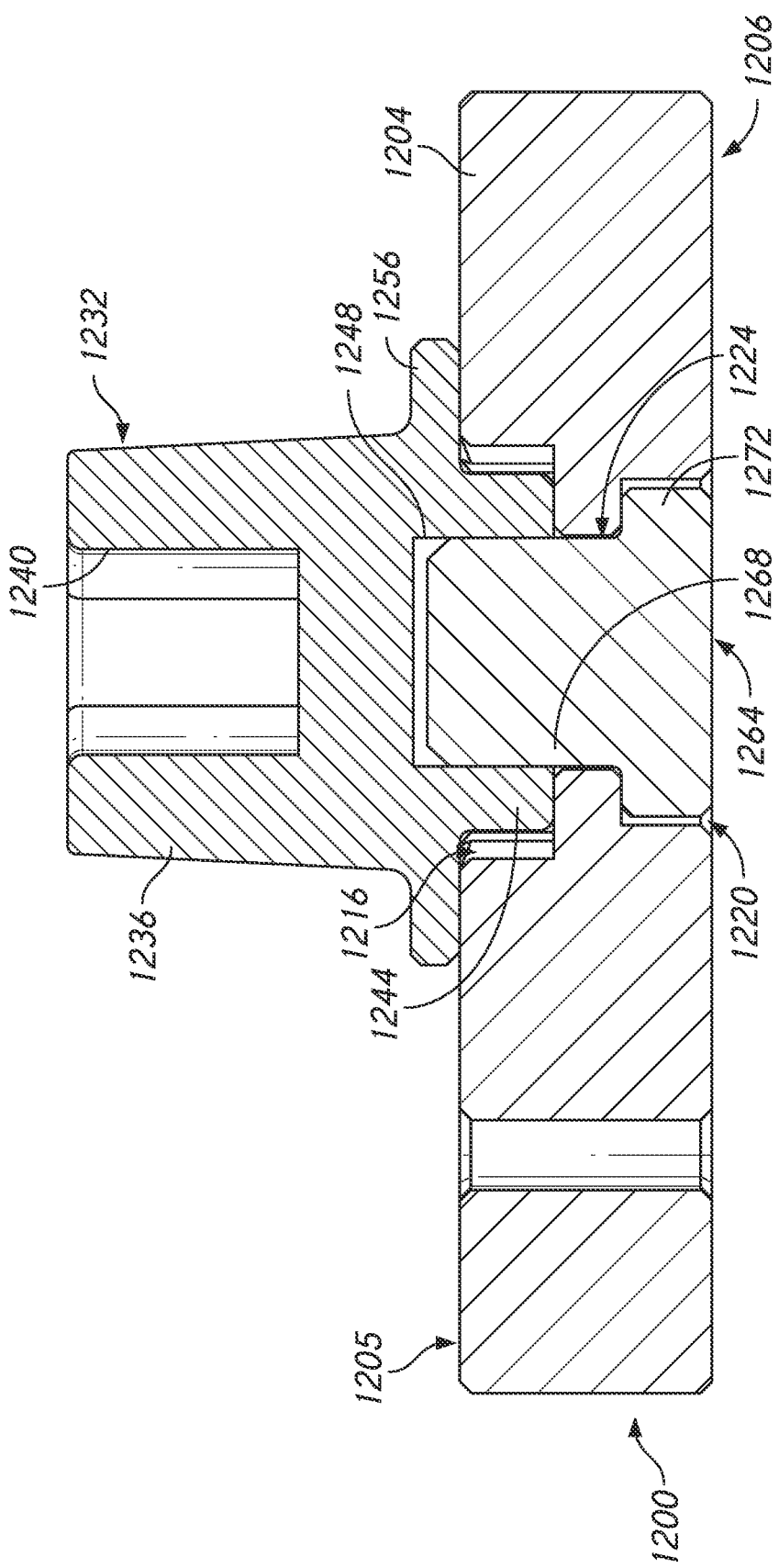
FIG. 36 is a cross-section taken through plane 36-36 shown in FIG. 34.
Figure 38:
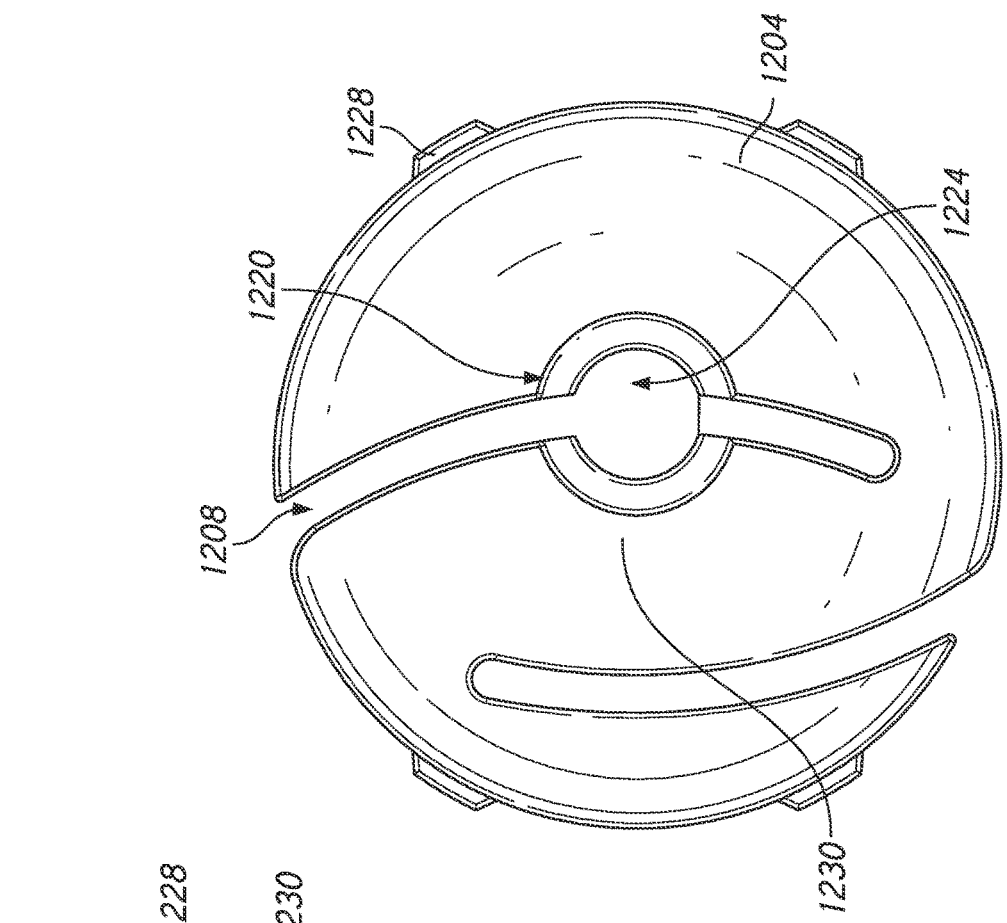
FIGS. 37-38 show a top and bottom view of a coupler of the taper cam and slot assembly of FIG. 32.
Figure 37:
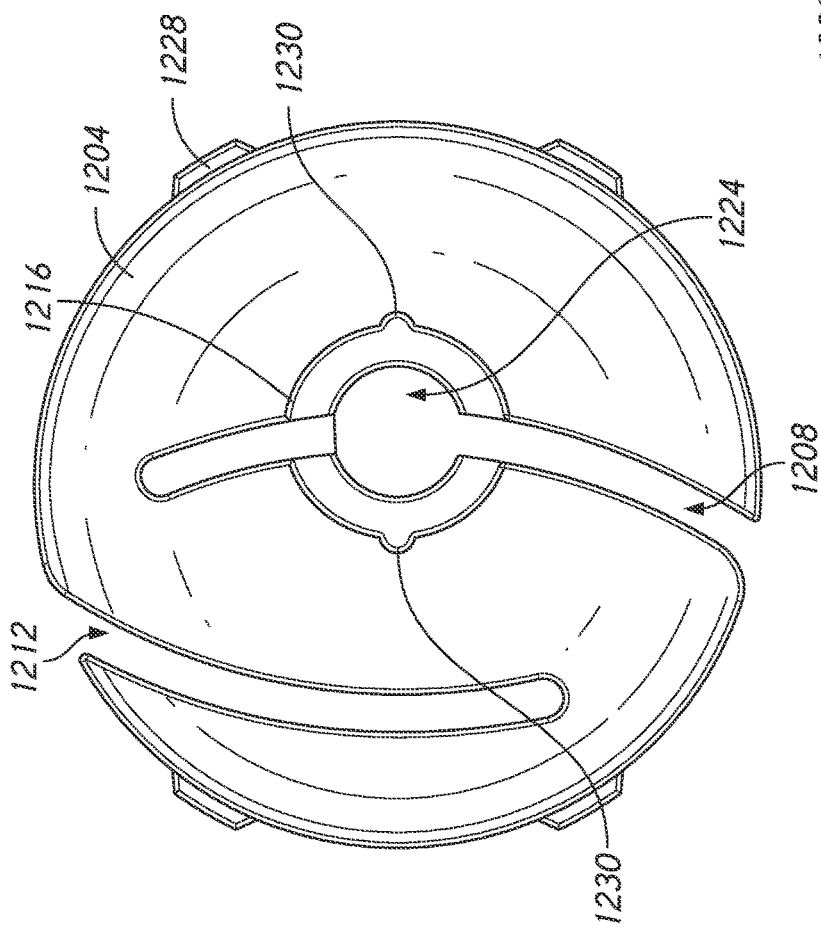

The expandable disc 1204 of the coupler 1200 can be configured to receive the cam assembly 1276 as illustrated in FIGS. 33 and 36. In some examples the cam assembly 1276 can include the actuator 1232 and a securement portion 1264. As discussed above, the actuator 1232 can be configured to rotate relative to the expandable disc 1204 of the coupler 1200. In some embodiments, the actuator 1232 is retained in the expandable disc 1204 by the second portion 1272. FIG. 36 illustrates a cross-sectional view of the cam assembly 1276 retained in the expandable disc 1204. As shown, the coupler 1200 can include a proximal aperture 1216 on a first surface 1205 of the expandable disc 1204 and a distal aperture 1220 on a second surface 1206 of the expandable disc 1204. A distal end 1244 of the actuator 1232 can be retained within the proximal aperture 1216. In some embodiments, the actuator 1232 can be secured within the proximal aperture 1216 of the expandable disc 1204 by engaging the distal end 1244 of the actuator 1232 with the securement portion 1264. In some examples, the second portion 1272 of the securement portion 1264 is retained within the distal aperture 1220 of the expandable disc 1204. In some embodiments, to secure the actuator 1232 in place, the second portion 1272 of the securement portion 1264 can be press fit into the distal aperture 1220 of the expandable disc 1204. In some examples, a first portion 1268 of the securement portion 1264 is retained within the distal opening 1248 in the distal end 1244 of the actuator 1232.

Figure 39:
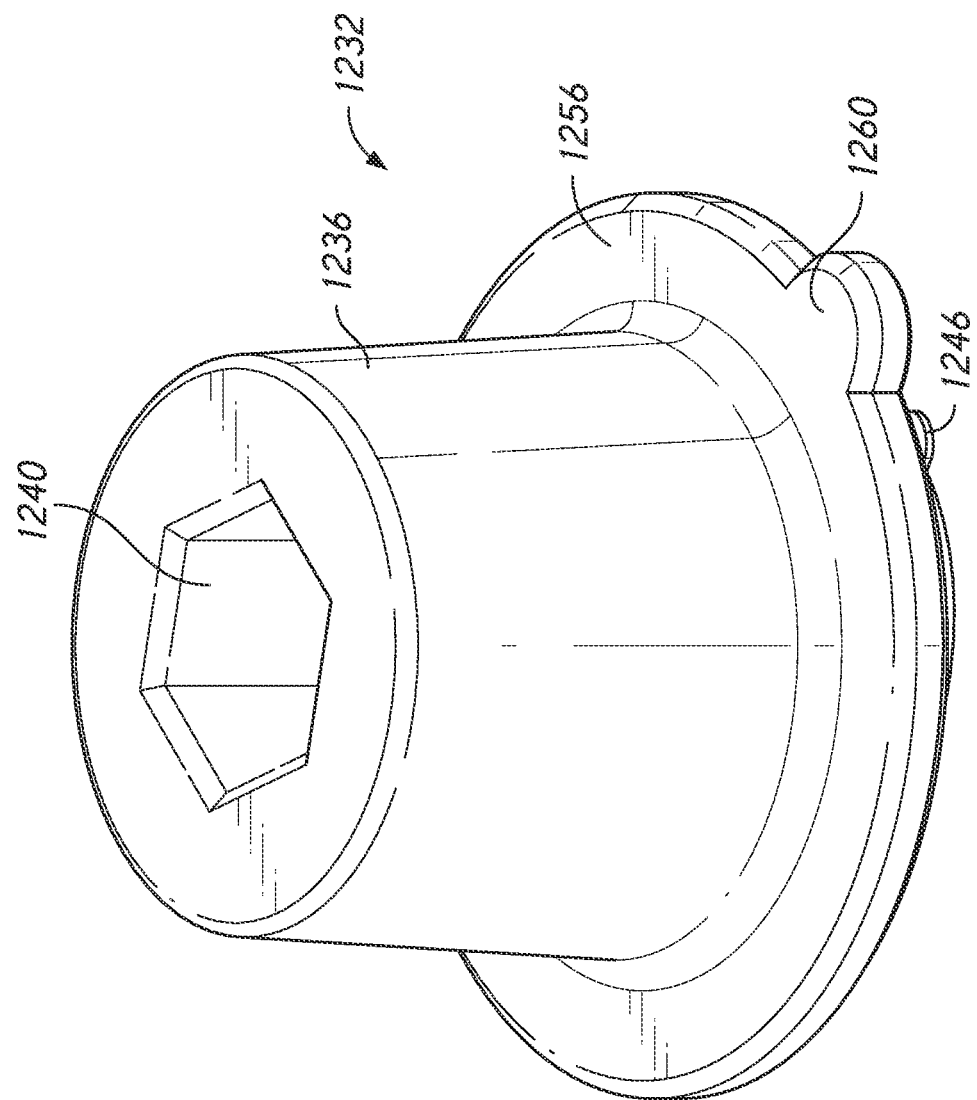
Figure 43:
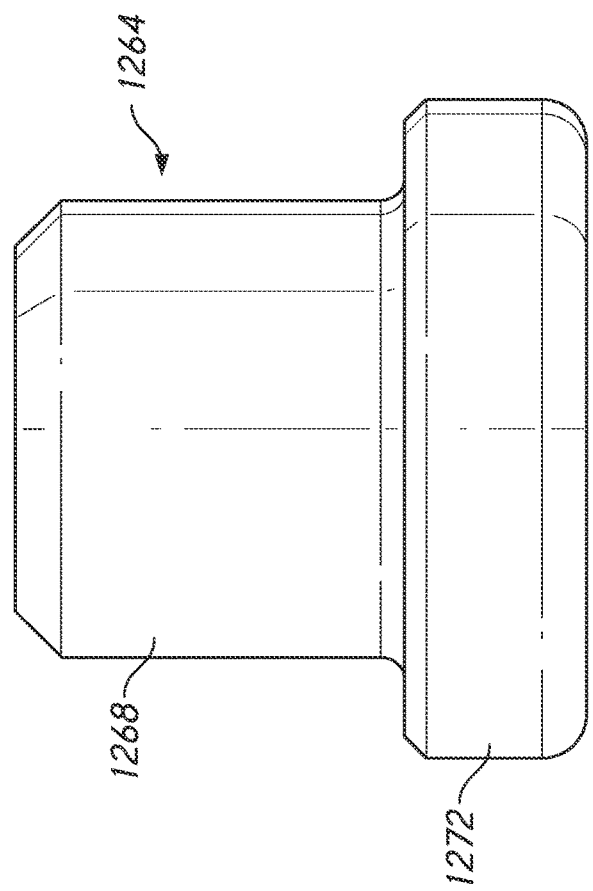
FIGS. 42-43 show a perspective and side view of a securement portion configured to engage with the actuator of FIGS. 39-41 to form the cam assembly of the taper cam and slot assembly of FIG. 32.
Figure 42:
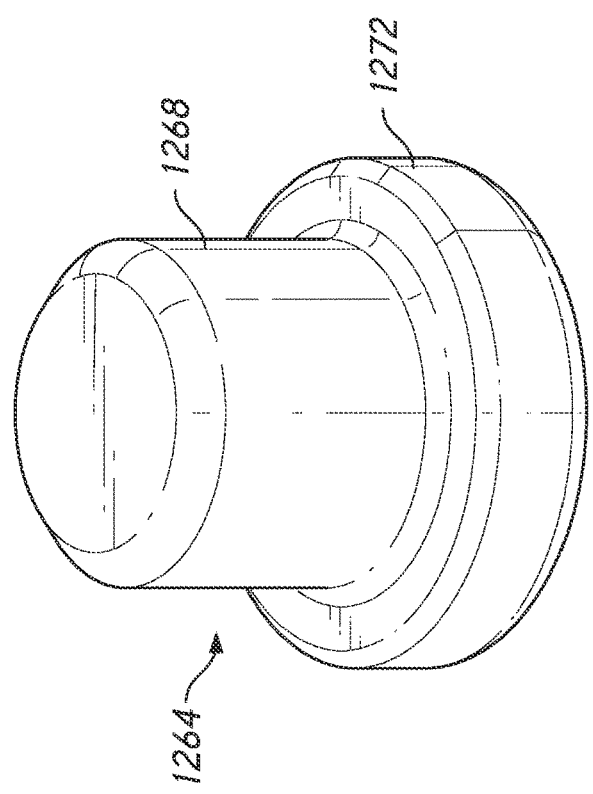
Figure 44:
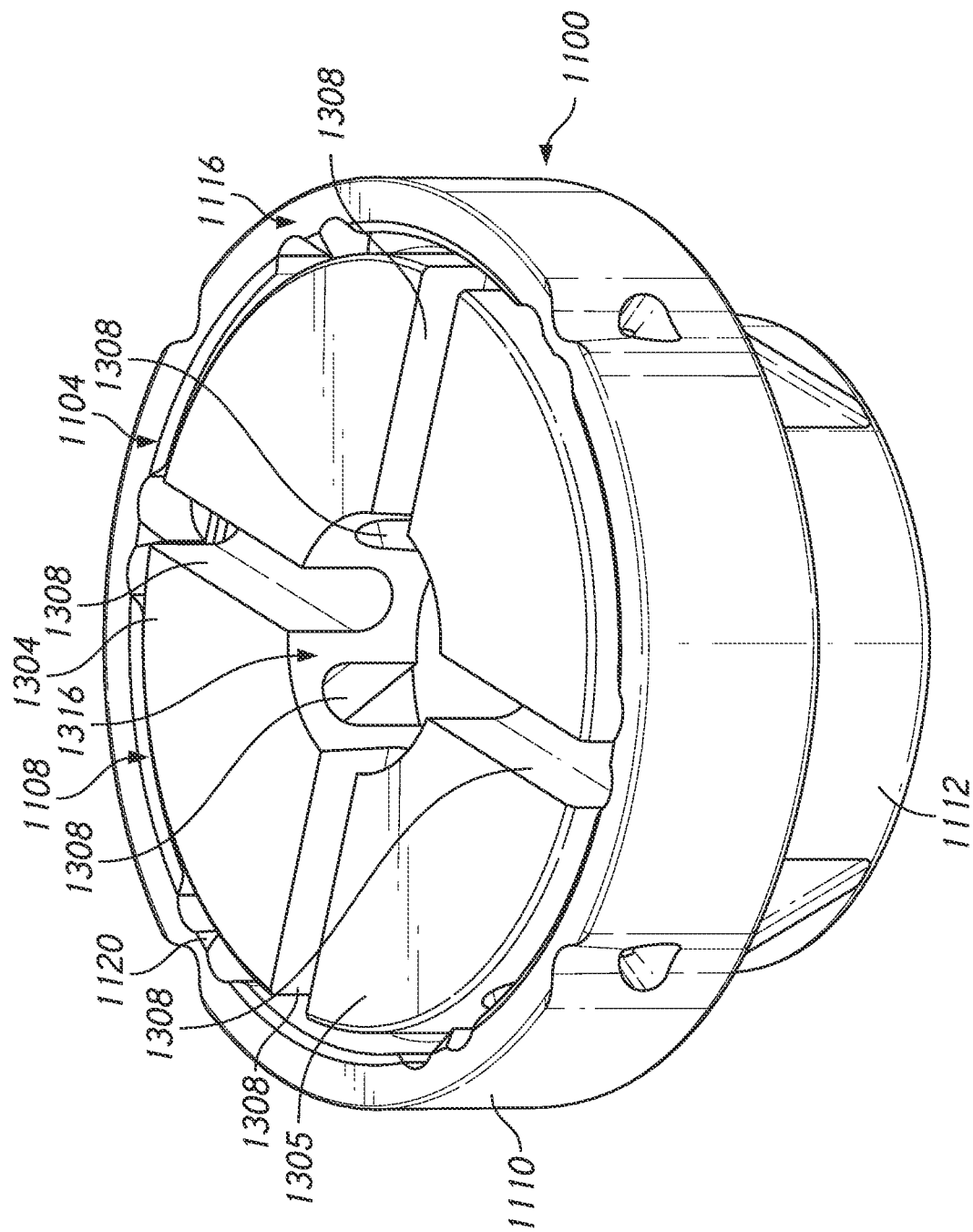
FIG. 44 is a perspective view of a collet lock assembly.

FIGS. 39-41 illustrate various views of the actuator 1232 while FIGS. 42-43 illustrate a perspective and side view of the securement portion 1264. The actuator 1232 can include a proximal end 1236, a collar 1256, and a distal end 1244.

The actuator 1232 can include some of the features of the actuator 1032 and the first portion 1008 of the coupler 1000. Like the first portion 1008 of the coupler 1000, the actuator 1232 can be configured to engage with the articular body of a humeral head assembly. In some embodiments, the proximal end 1236 can also include a tool interface 1240 that extends through a portion of the proximal end 1236. In some examples, the actuating surface 1240 is configured to engage with a tool such that the actuator 1232 can be rotated. As illustrated in FIG. 39, the actuating surface 1240 can have a hexagonal shape. The actuating surface 1240 can have any shape that allows a tool to engage with the actuator 1232, e.g., having at least one flat surface or at least one non-circular surface.

The actuator 1232 can also include a collar 1256 that is located between the proximal end 1236 and the distal end 1244. In some examples, as illustrated in FIGS. 32-36, the collar 1256 can have a radius greater than the proximal aperture 1216. This can allow the collar 1256 to rest above the surface of the expandable disc 1204. In some embodiments, the collar 1256 can include a radial protrusion 1260. The radial protrusion 1260 on the collar 1256 can provide for eccentricity adjustments of the humeral head assembly as illustrated in the various embodiments discussed above. For example, the radial protrusion 1260 of the collar 1256 can be configured to engage with an engagement portion that is located on a surface of an articular body of a humeral head assembly (e.g. humeral head assembly 100 or humeral head assembly formed from the kit 900), as illustrated in the embodiments shown in FIGS. 2-11 and 16-20 and as may be incorporated into the humeral head assembly 800 of FIGS. 1A, 1C and the reverse bearing assembly 800A of FIG. 15. In other examples, the radial protrusion 1260 of the collar 1256 can be configured to engage with an engagement portion that is located on a surface of an anchor as illustrated in the embodiment shown in FIGS. 13A-13C. As discussed in more detail above, by adjusting an articular body such as the articular body 804 to engage the radial protrusion 1260 of the collar 1256 at different positions, the relative positioning of the articular body to the actuator 1232 can provide different eccentricities to the anchor 830 or to the anchor 830A and to the humerus to which they are coupled.

As discussed above, the distal end 1244 of the actuator 1232 can be received in the proximal aperture 1216 of the expandable disc 1204 of the coupler 1200. In some embodiments, the distal end 1244 can have a radius that is smaller than the collar 1256 such that the collar 1256 rests above the proximal aperture 1216 of the expandable disc 1204. The distal end 1244 can be configured to engage the securement portion 1264 such that the actuator 1232 is secured within the expandable disc 1204 to form the cam assembly 1276. For example, the distal end 1244 can include a distal opening 1248 in the distal end 1244. As noted above, a first portion 1268 of the securement portion 1264 can engage with the distal opening 1248 to retain the actuator 1232 in the expandable disc 1204. The actuator 1232 can also include at least one radial protrusion 1246. In some embodiments, the radial protrusion 1246 extends from the distal end 1244 and is disposed on an outside of the distal end 1244 of the actuator 1232. In some examples the radial protrusion 1246 can have a shape inverse to that of the radial notch 1230 of the proximal aperture 1216. As will be discussed below, the inverse shape of the protrusion to the notch can allow the radial notch 1230 of the proximal aperture 1216 to receive the proximal end 1236 of the actuator 1232 in a secure manner.

Similar to the coupler 1000, the distal end 1244 of the actuator 1232 can have an oblong shape (e.g. oval) that is configured to secure the expandable disc 1204 with the anchor 1100 when the cam assembly 1276 is actuated. In some embodiments, the distal end 1244 of the actuator 1232 is longer along a major axis 1252 than a minor axis 1254. In the example illustrated in FIG. 40, the periphery of the distal end 1244 of the actuator 1232 is longest along the major axis 1252. As will be discussed in more detail below, by rotating the actuator 1232, the major axis 1252 of the actuator 1232 will cause the expandable disc 1204 to expand and engage the anchor 1100 (or the anchor 830 or the anchor 830A).

FIGS. 42-43 illustrate an embodiment of the securement portion 1264 that includes a first portion 1268 and a second portion 1272. In some examples, the first portion 1268 can be cylindrical and have a smaller radius than the second portion 1272. The first portion 1268 is configured to be received in the distal opening 1248 of the actuator 1232. The second portion 1272 is configured to be received in the distal aperture 1220 of the expandable disc 1204 of the coupler 1200.

Similar to the coupler 1000, the coupler 1200 is configured to provide an expandable fixation assembly for an orthopedic application (e.g. humeral head assembly). The expandable disc 1204 of the coupler 1200 is configured to fit into the anchor 1100 and expand/contract so as to engage a portion of an outside perimeter of the expandable disc 1204 (e.g., the spaced apart external engagement portions 1228) with the interior surface or perimeter of the recess in the anchor 1100. In some embodiments, the inside surface or perimeter of the recess in the anchor 1100 (e.g. the secondary features 1116) is configured be received above the external engagement portions 1228 on the outside surface of the expandable disc 1204 such that no contact is made between the secondary features 1116 and the coupler 1200. The expandable disc 1204 of the coupler 1200 includes the first slot 1208 and the second slot 1212. The proximal aperture 1216 located on the first surface 1205 of the expandable disc 1204 is oblong in order to receive the oblong profile of the distal end 1244 of the actuator 1232.

In some embodiments, when the actuator 1232 is rotated, the actuating surface of the distal end 1244 can force the expansion of the proximal aperture 1216 and the associated first slot 1208. In some examples, the actuator 1232 can be rotated 90 degrees such that the radial protrusion 1246 of the actuator 1232 can be retained in one of the radial notches 1230. In some embodiments, either of the radial notches 1230 can be configured to lock the actuator 1232 in place. The expansion of the proximal aperture 1216 and the first slot 1208 can cause the second slot 1212 to compress and to absorb any expansion the rotation of the actuator 1232. In some embodiments, the expansion of the first slot 1208 and the compression of the second slot 1212 can cause the outside perimeter of the expandable disc 1204 of the coupler 1200 to engage with the inside perimeter of the recess 1108 of the anchor 1100. The interior surface of the anchor 1100 can be spaced apart from the outer periphery of the expandable disc 1204 of the coupler 1200 prior to the expansion thereof. In one embodiment, the expanded state of the expandable disc 1204 causes the external engagement portion 1228 to engage a portion of the interior surface distal to the secondary features 1116 so that these features are not contacted by the expandable disc 1204 so that the ridge portion 1120 are not altered by engagement with the expandable disc 1204. In other embodiments, upon expansion, the expandable disc 1204 can be enlarged to be as large as or larger than a periphery intersecting the peaks of the ridge portion 1120. The external engagement portion 1228 can be disposed to the position of the ridge portion 1120. This can provide interference between the outer periphery of the expandable disc 1204 and the ridge portion 1120, thereby enhancing securement when the ridge portion 1120 is present.

After the coupler 1200 is secured in place, an anatomic articular body, e.g., similar to the articular body 804 can be secured to the proximal end 1236 of the actuator 1232.

In some embodiments, the coupler 1200 can be disengaged from the anchor 1100 by rotating the actuator 1232 another 90 degrees such that the oblong profile of the actuator 1232 is realigned with the profile of the proximal aperture 1216. In this way, the actuator 1232 no longer expands the proximal aperture 1216 and the first slot 1208 such that the first slot 1208 and the second slot 1212 can return to their original configuration. This enables the expandable disc 1204 to return to an un-expanded configuration.

In a revision procedure, the anatomic articular body (similar to the articular body 804) can be removed by forcing a wedge into the gap between the first surface 1205 and the side of the articular body opposite the convex articulating surface. The wedge can overcome the interference connection between the proximal end 1236 of the actuator 1232 and a tapered recess in the articular body such that the articular body is separated from the coupler 1200. Thereafter, the coupler 1200 can be removed by actuating the radial protrusion 1246 out of the radial notch 1230. The coupler 1200 can be removed once it is contracted.

In one embodiment, the ridge portion 1120 of the anchor 1100 remains out of contact with the coupler 1200 when the actuator 1232 is rotated to cause expansion of the expandable disc 1204. A gap extends between the radially inwardmost portion of the ridge portion 1120. In a revision procedure, after the anatomic head and the coupler 1200 are removed, a reverse articular body similar to the articular body 804A can be inserted into the recess 1108. As discussed above, the distal portion of the reverse articular body can also engage with the interior surface of the anchor 1100.

By configuring the coupler 1200 to be actuated from an enlarged state (with the radial protrusion 1246 engaged into the radial notch 1230) to a smaller configuration (with the radial protrusion 1246 out of the radial notch 1230, e.g., aligned with the first slot 1208) the expandable disc 1204 of the coupler 1200 can be removed from the recess 1108 without undue force being applied to the anchor 1100. This allows a reverse articular body to be applied with minimal disruption.

The anchor 1100 and the coupler 1200 enable both an anatomic articular body 804 and a reverse articular body 804A to be coupled to the anchor 1100 at the resection plane. The anchor 1100 and the reverse articular body 804A eliminate potential tolerance stackup that would normally arise due to an intervening tray between the reverse insert and the anchor.

D. Expanding Coupler with Collet Lock Coupler

FIGS. 44-50 illustrate an embodiment of a coupler 1304 that provides another embodiment of an expandable coupler for coupling an articular body to a humeral anchor. The coupler 1304 includes a collet lock coupler for securing an articular body to a humeral anchor. Similar to the coupler 1000 and coupler 1200 discussed above, the coupler 1304 is configured to be removably secured to the anchor 1100, the anchor 830, or the anchor 830A.

Figure 50:
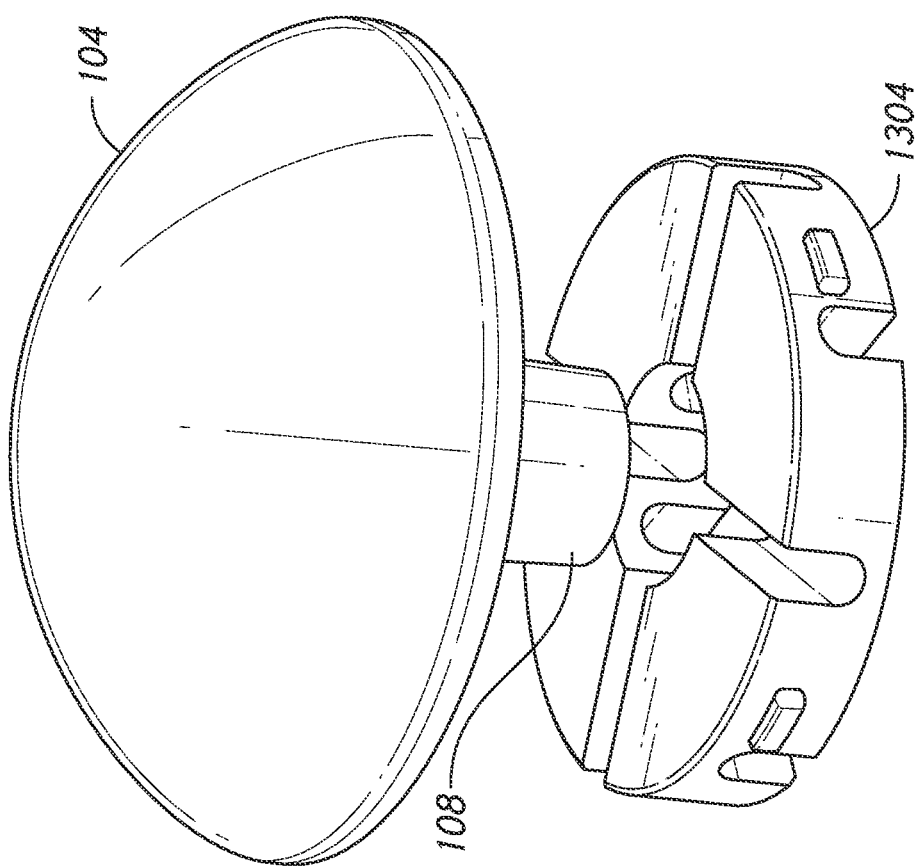
FIG. 50 shows a perspective view of the coupler of FIG. 48 engaging with a humeral head assembly.

As shown in FIGS. 44-47 the coupler 1304 differs from coupler 1000 and coupler 1200 discussed above in that the coupler 1304 is configured to expand without the use of a cam assembly. As will be discussed in more detail below, the coupler 1304 includes a tapered opening 1316 that is configured to receive a connection portion of a coupler of a humeral head assembly. For example, the coupler 1304 can be configured to receive the second portion 204 of the coupler 108 of the humeral head assembly 100 as illustrated in FIGS. 2-6. An exploded view of an example of a humeral head assembly configured to be engaged with the coupler 1304 is illustrated in FIG. 50 and includes the articular body 104 and the coupler 108 (though any articular body and coupler disclosed herein can be use).

FIGS. 32-47 illustrates the coupler 1304 engaged with the anchor 1100. As with the coupler 1000 and the coupler 1200, the coupler 1304 can be configured to engage with the anchor 1100. When positioned within the cylindrical portion 1110, the first surface 1305 of the coupler 1304 can be slightly below or aligned with the proximal face 1104 of the anchor 1100. In some examples, the coupler 1304 can be positioned such that the first surface 1305 can be slightly above the proximal face 1104 of the anchor 1100. For example, the associated humeral head can be adapted to receive the portion of the second portion 1012 that extends above the proximal face 1104 of the anchor 1100. In some embodiments, the second surface 1306 of the coupler 1304 can lie flush against a bottom surface (e.g. bottom surface 1111) of the cylindrical portion 1110. As noted above, by having the cylindrical portion 1110 secure the coupler 1304 at or below the resection level, this can position the base of an articular body (e.g. articular body 104 of FIG. 2) such that the anatomic head is flush or near flush with the resection.

In some embodiments, the coupler 1304 can include a plurality of external engagement portions 1312. As will be discussed in more detail below, when the coupler 1304 is placed into the cylindrical portion 1110 of the anchor 1100, each of the external engagement portions 1312 can be configured to engage the secondary features 1116 on the interior surface of the cylindrical portion 1110. In some embodiments, the external engagement portion 1312 are configured to engage with the slot 852 of the anchor 1100 that, as discussed above, can be configured to receive the C-ring 850. The engagement of the external engagement portion 1312 with the slot 852 can provide for a secondary locking mechanism that prevents the assembly from separating.

Figure 45:
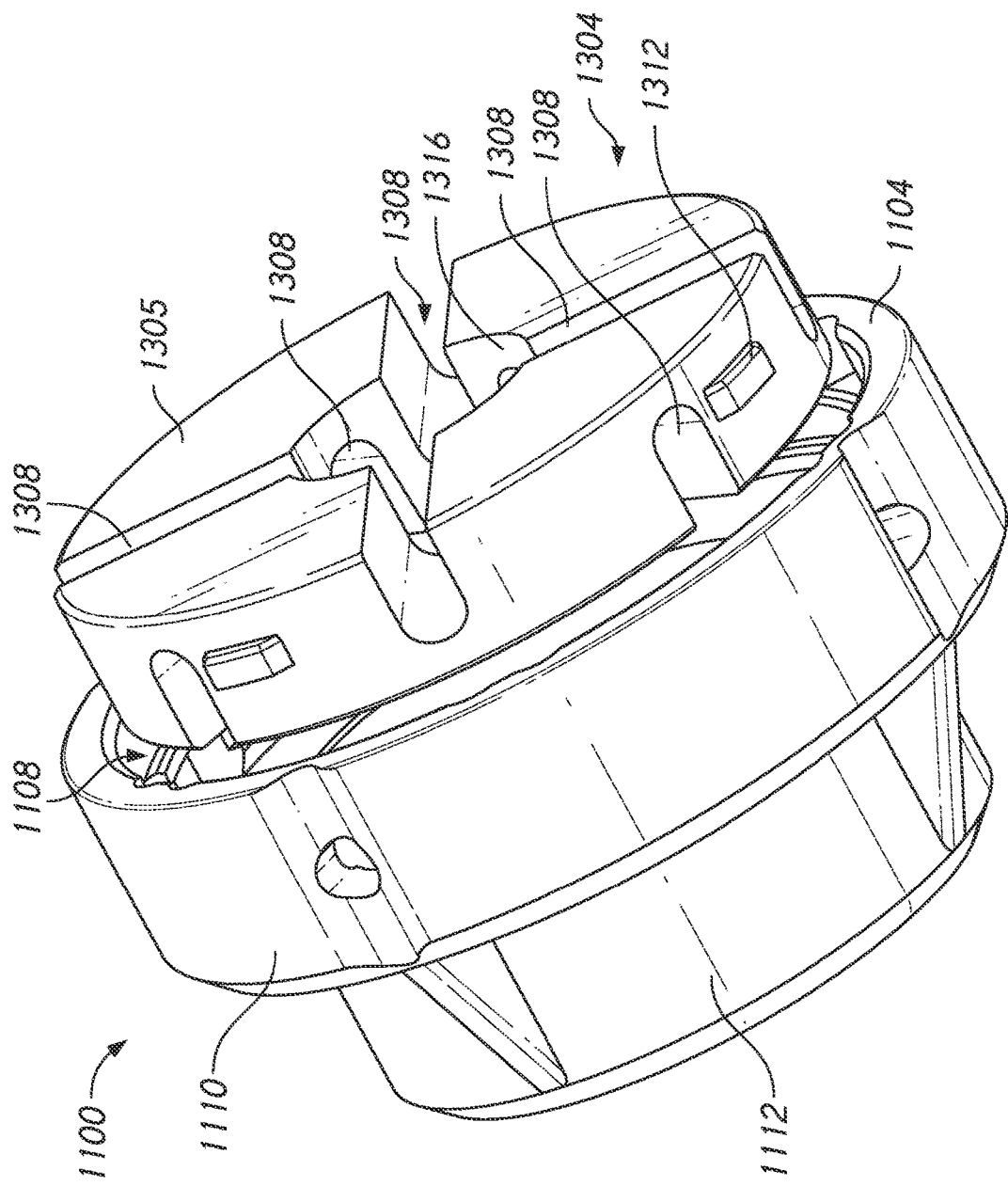
FIG. 45 is an exploded perspective view of the collet lock assembly of FIG. 44.

In some embodiments, the coupler 1304 is an expandable disc that include a plurality of flexible zones or living hinges 1308 (referred to as "hinges" below). FIGS. 45, 48, and 49 illustrate various views of the plurality of hinges 1308 in the coupler 1304. In some embodiments, the coupler 1304 can include a plurality of hinges 1308 on a first surface 1305 and/or a second surface 1306 of the coupler 1304. Each of the plurality hinges 1308 can extend between the tapered opening 1316 of the coupler 1304 and the exterior periphery of the coupler 1304. In some examples, each of the plurality of hinges 1308 are equidistantly spaced from each other. For example, each of the plurality of hinges 1308 on the first surface 1305 can be spaced 45° apart from each other and each of the plurality of hinges 1308 can be spaced 45° apart from each other. More or less than four hinges can be provided on the two opposing surfaces of the coupler 1304 spaced apart by larger or smaller equidistant angles. In some embodiments, the plurality of hinges 1308 on the first surface 1305 are in a staggered configuration with the plurality of hinges 1308 on the second surface 1306.

FIG. 49 illustrates a cross-sectional view of the coupler 1304 to show a cross section of each of the hinges 1308. As discussed, each of the plurality of hinges 1308 can include a channel 1308a that extends through a portion of the body of coupler 1304. In some embodiments, the channel 1308a extends through enough of the body of the coupler 1304 to form a bend 1308b. As will be discussed in more detail below, the bend 1308b can allow the channel 1308a of each of the hinges 1308 to widen or narrow.

Figure 47:
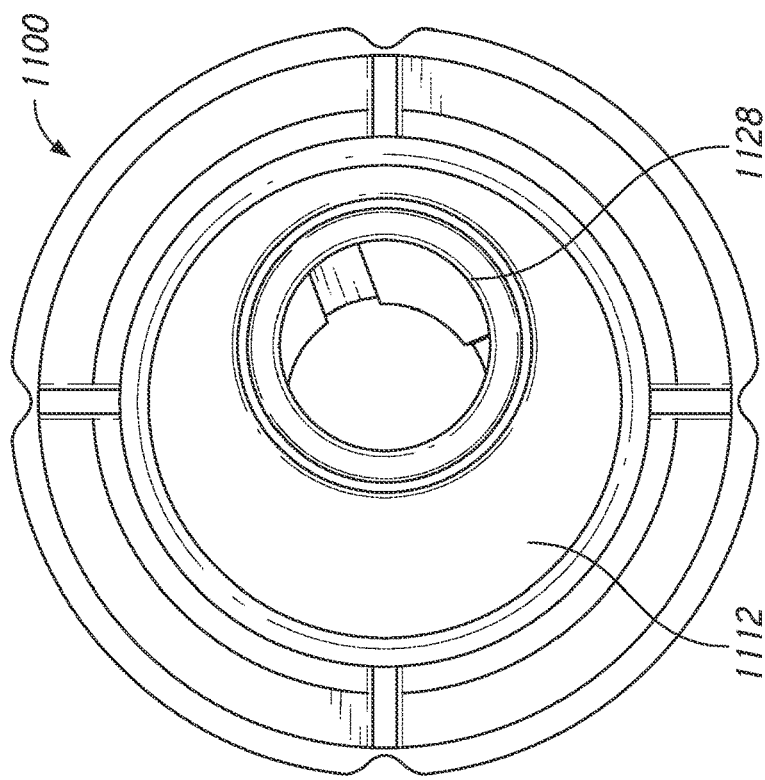
FIG. 47 is a bottom view of the collet lock assembly of FIG. 44.
Figure 46:
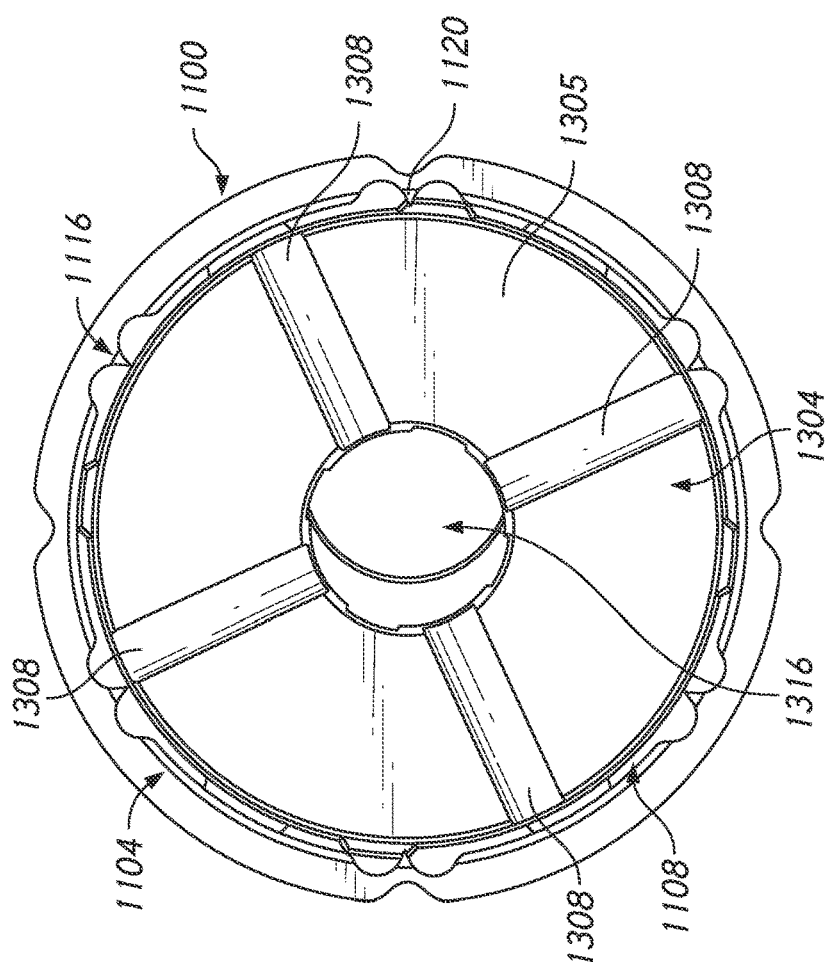
FIG. 46 is a top view of the collet lock assembly of FIG. 44.

In some embodiments, the coupler 1304 can include a tapered opening 1316. The tapered opening 1316 can extend through the coupler 1304. As noted above, the tapered opening 1316 is configured to receive a second portion of a coupler of a humeral head assembly. FIGS. 46-47 illustrates a top and bottom view of the coupler 1304 inserted in the anchor 1100. As shown in FIG. 47, in some embodiments the anchor 1100 can include an aperture 1128 that extends through distal end 1112 of the anchor 1100. The aperture 1128 can be partially overlapping with the tapered opening 1316 such that a second portion of a coupler can extend through both the coupler 1304 toward the aperture 1128 in the anchor 1100. The aperture 1128 can be used to connect the anchor 1100 to a stem by any of the techniques disclosed in application number PCT/US2017/028470, also published as WO 2017/184792. The tapered opening 1316 can have a radius that decrease as it extends between the first surface 1305 and the second surface 1306. As will be discussed in more detail below, the decreasing radius of the tapered opening 1316 can cause the coupler 1304 to expand and engage with the interior surface of the recess 1108 of the anchor 1100.

Like the coupler 1000 and the taper cam and slot assembly 1200, the coupler 1304 is configured to provide an expandable fixation assembly for an orthopedic application (e.g. humeral head assembly). A portion of the coupler 1304 is configured to fit into the anchor 1100 and expand/contract so as to engage the outside perimeter of the coupler 1304 with the interior surface or perimeter of the hinges 1308 in the anchor 1100. In some embodiments, the inside surface or perimeter of the recess in the anchor 1100 (e.g. the secondary features 1116) is configured to engage with the external engagement portions 1312 on the outside surface of the coupler 1304. As discussed above, the coupler 1304 include a plurality of hinges 1308 on the first surface 1305 and the second surface 1306 of the coupler 1304. The tapered opening 1316 is configured to receive a portion of the coupler of a humeral head assembly (e.g. a coupler 108 of the humeral head assembly 100). In some embodiments, the entrance of the tapered opening 1316 on the first surface 1305 has a radius that is the same or slightly larger than the radius of the portion of the coupler (e.g. the second portion 204) configured for insertion into the coupler 1304.

In some embodiments, when the coupler is inserted into the coupler 1304 (e.g. the second portion 204 of the coupler 108), the tapered opening 1316 can expand such that the radius of the tapered opening 1316 equals the radius of the inserted coupler (e.g. the second portion 204 of the coupler 108). The expansion of the tapered opening 1316 can force the channels 1308a of each of the plurality of hinges 1308 to widen. In some embodiments, the expansion of the tapered opening 1316 can cause the channels 1308a in the first surface 1305 of the coupler 1304 to expand while causing the channels 1308a in the second surface 1306 to contract. The expansion of the channels 1308a in the first surface 1305 and the contraction of the channels 1308a in the second surface 1306 is configured to allow a portion of the coupler of a humeral head assembly (e.g. a coupler 108 of the humeral head assembly 100) to enter into the tapered opening 1316 of the coupler 1304. The widening of each of the hinges 1308 can cause the outside perimeter of the coupler 1304 to engage with the inside perimeter of the recess 1108 of the anchor 1100. In some examples, the ridge portion 1120 of the secondary features 1116 and the external engagement portion 1312 of the coupler 1304 can be configured to provide additional engagement points to further secure the coupler 1304 within the anchor 1100. The ridge portion 1120 can be spaced apart from the outer surface of the coupler 1304 prior to the expansion thereof. Upon expansion, the coupler 1304 can be enlarged to be as large as or larger than a periphery intersecting the peaks of the ridge portion 1120. This can provide interference between the outer periphery of the coupler 1304 and the ridge portion 1120, thereby enhancing securement when the ridge portion 1120 is present.

FIG. 50 shows that after the coupler 1304 is secured in place, an anatomic articular body, e.g., similar to the articular body 104 can be secured adjacent to the first surface 1305 of the coupler 1304.

In some embodiments, the coupler 1304 can be disengaged from the anchor 1100 by pulling the coupler of the humeral head assembly from the tapered opening 1316. In this way, the coupler of the humeral head assembly (e.g. the second portion 204 Of the coupler 108) no longer expands the tapered opening 1316 such that each of the plurality of hinges 1308 can return to their original configuration. This enables the coupler 1304 to return to an un-expanded configuration.

In a revision procedure, the anatomic articular body (similar to the articular body 804) can be removed by forcing a wedge into the gap between the first surface 1305 and the side of the articular body opposite the convex articulating surface. The wedge can overcome the interference connection between the tapered opening 1316 of the coupler 1304 and the articular body 104, 804 such that the humeral head assembly 100 is separated from the coupler 1304. Thereafter, the coupler 1304 can be removed as it is contracted.

In one embodiment, the ridge portion 1120 of the anchor 1100 remains out of contact with the coupler 1304 when the coupler 1304 is in the expanded configuration. A gap extends between the radially inward-most portion of the ridge portion 1120. In a revision procedure, after the anatomic head and the coupler 1304 are removed, a reverse articular body similar to the articular body 804A can be inserted into the recess 1108. As discussed above, the distal portion of the reverse articular body can also engage with the interior surface of the anchor 1100.

By configuring the coupler 1304 to be actuated from an enlarged state (with the coupler of the humeral head assembly (e.g. the second portion 204 Of the coupler 108) inserted) to a smaller configuration (with the coupler of the humeral head assembly (e.g. the second portion 204 Of the coupler 108) out of the tapered opening 1316) the coupler 1304 can be removed from the recess 1108 without undue force being applied to the anchor 1100. This allows a reverse articular body to be applied with minimal disruption.

The anchor 1100 and the coupler 1304 enable both an anatomic articular body 804 and a reverse articular body 804A to be coupled to the anchor 1100 at the resection plane. The anchor 1100 and the reverse articular body 804A eliminate potential tolerance stackup that would normally arise due to an intervening tray between the reverse insert and the anchor.

V. Methods of Assembling and Disassembling Humeral Head and Reverse Bearing Assemblies The humeral head assembly 800 and the humeral head assembly 800A described allows a surgeon to treat a wider variety of patient anatomy with a kit that has fewer components than was possible in the past. The anchor 830 of the humeral head assembly 800 and the humeral head assembly 800A is configured to be able to receive a portion of an articular body below a humeral resection plane. As well, the anchor 830 is configured to allow a surgeon to reverse the articular surfaces of the shoulder while accommodating soft tissue of a wide variety of patients. Although the method below is discussed in connection with the humerus, as discussed herein the humeral head and reverse bearing assemblies, the anchors, and the couplers can be deployed in other orthopedic applications such as in implanting a glenosphere in a glenoid, a femoral articular body on an end of a femur (e.g., for hip or knee procedures) or for implanting a tibial articular body at an end of a tibia for a joint procedure.

The method of assembling the humeral head assembly 800 and the reverse bearing assembly 800A can first include resecting a humerus at a superior or proximal end thereof. The resection can be performed with a surgical guide. The surgeon may be provided with one or more sizing disks to determine a size of the metaphysis. The sizing disks can be configured to facilitate visualization of the space between the implant to be implanted and the cortical boundary of the bone. While preparing the glenoid or during other surgical steps not involving humeral preparation, an appropriately sized cut protector may be provided on the resection surface.

Figure 51:
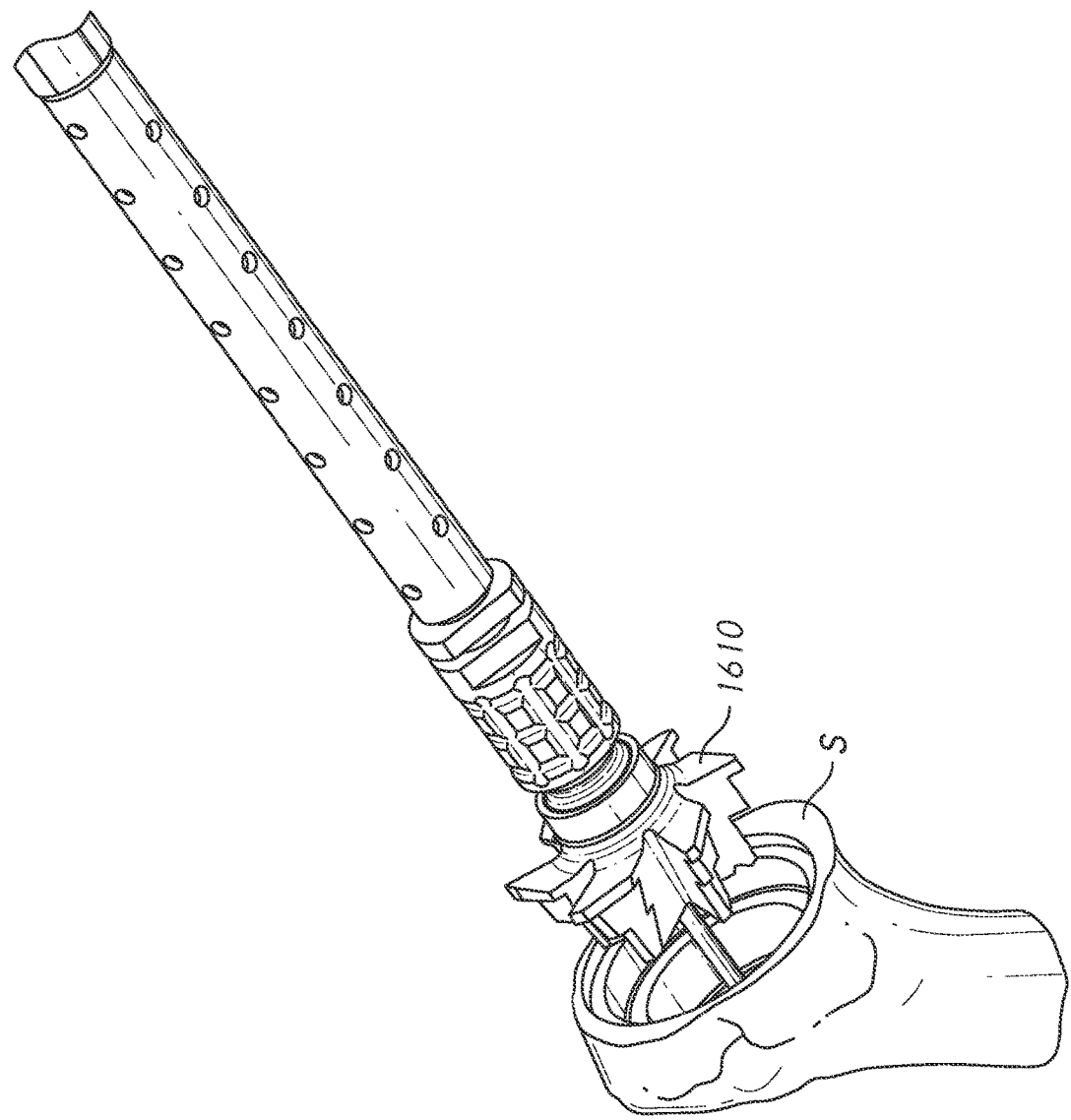
FIG. 51 shows a portion of a method of implanting a humeral anchor in which a reamer has been advanced into a surface of a resected humerus.

The method of assembling the humeral head assembly 800 can include selecting an appropriately sized reamer for the resected humerus. As illustrated in FIG. 51, a reamer 1610 is configured to produce a generally concave recessed surface S in the resected humerus.

Figure 52B:
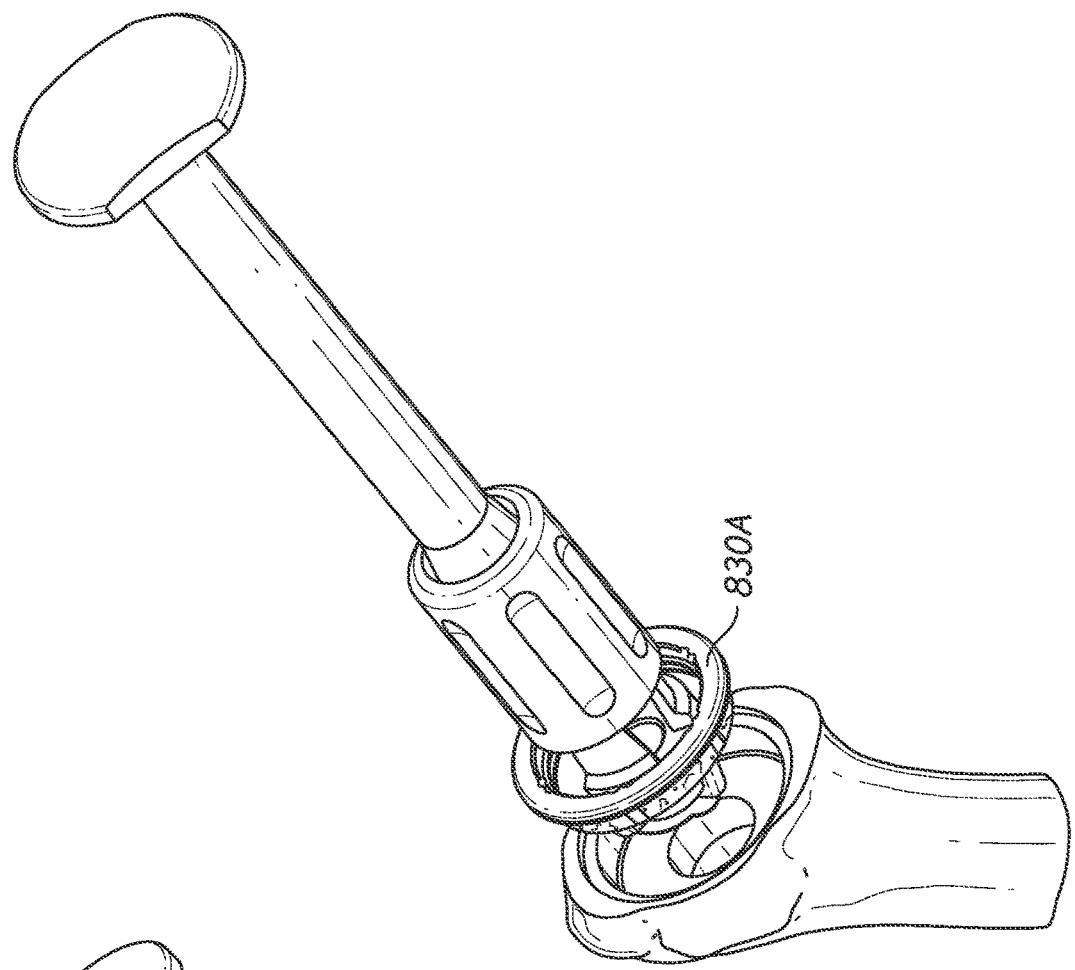
FIG. 52B shows a portion of a method following reaming as illustrated in FIG. 51 where another embodiment of an anchor is inserted into a surface of the resected humerus.
Figure 52A:
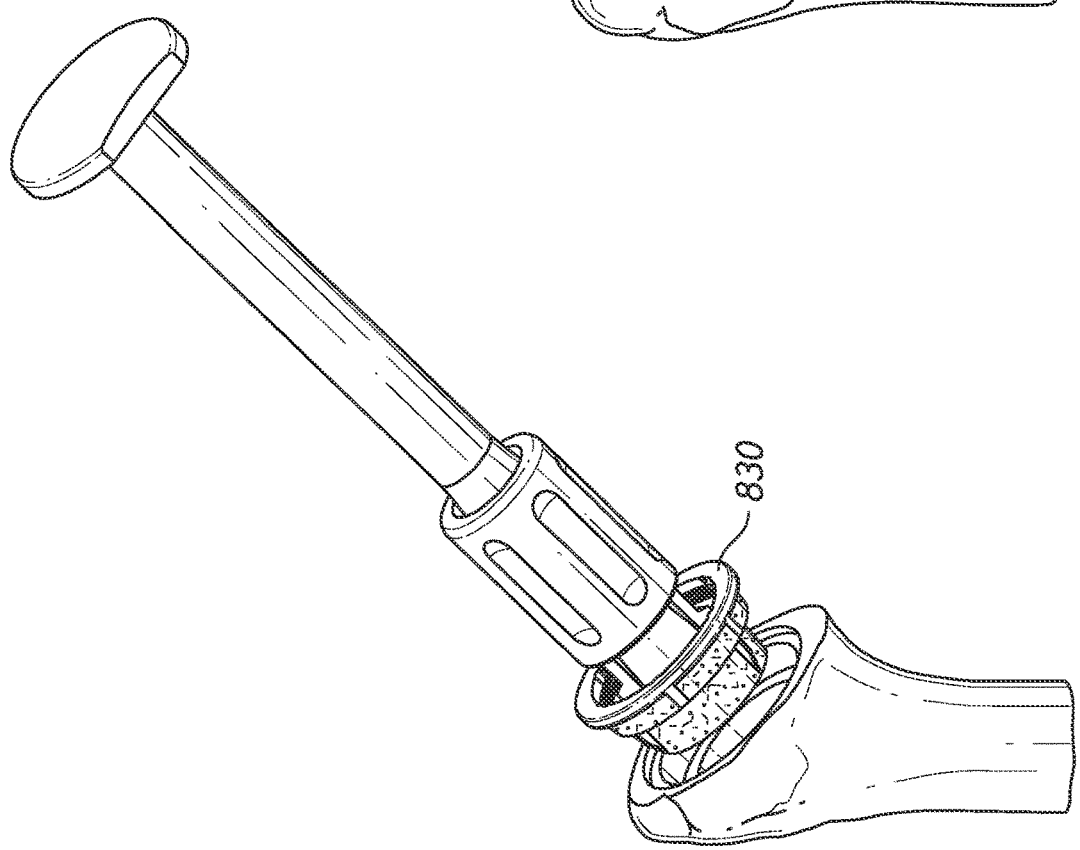
FIG. 52A shows a portion of a method following reaming as illustrated in FIG. 51 where an embodiment of an anchor is inserted into a surface of the resected humerus.

The method of assembling the humeral head assembly 800 can include insertion of an appropriate anchor. After reaming, an appropriate anchor can be selected for insertion into the prepared resected surface S of the humerus. FIGS. 52A-52B illustrate the anchor 830 and the anchor 830A being inserted into the recessed surface S of the resected humerus respectively. The anchor 830 of FIG. 52A is discussed above in FIG. 1A as part of the humeral head assembly 800. As illustrated in FIG. 52A, the anchor 830 can be configured to take up more space within the resected humerus. The anchor 830A of FIG. 52B is discussed above in FIG. 15 as part of the humeral head assembly 800B. As illustrated, in FIG. 52B, the anchor 830A can be configured to take up less space than the anchor 830 within the resected humerus. As described above, both of the anchor 830 and the anchor 830A are configured to couple with either the articular body 804 of the humeral head assembly 800 or the reverse articular body 804A of the reverse bearing assembly 800A. Both of the anchors 830, 830A include a receiving portion that can receive any of the couplers 924a, 924b, 924c or a portion of the reverse articular body 804A below the resection level of the humerus. The anchors 830, 830A eliminate a separate intermediate connector such as a tray between the anchors 830, 830A and the body 804A.

Figure 53:
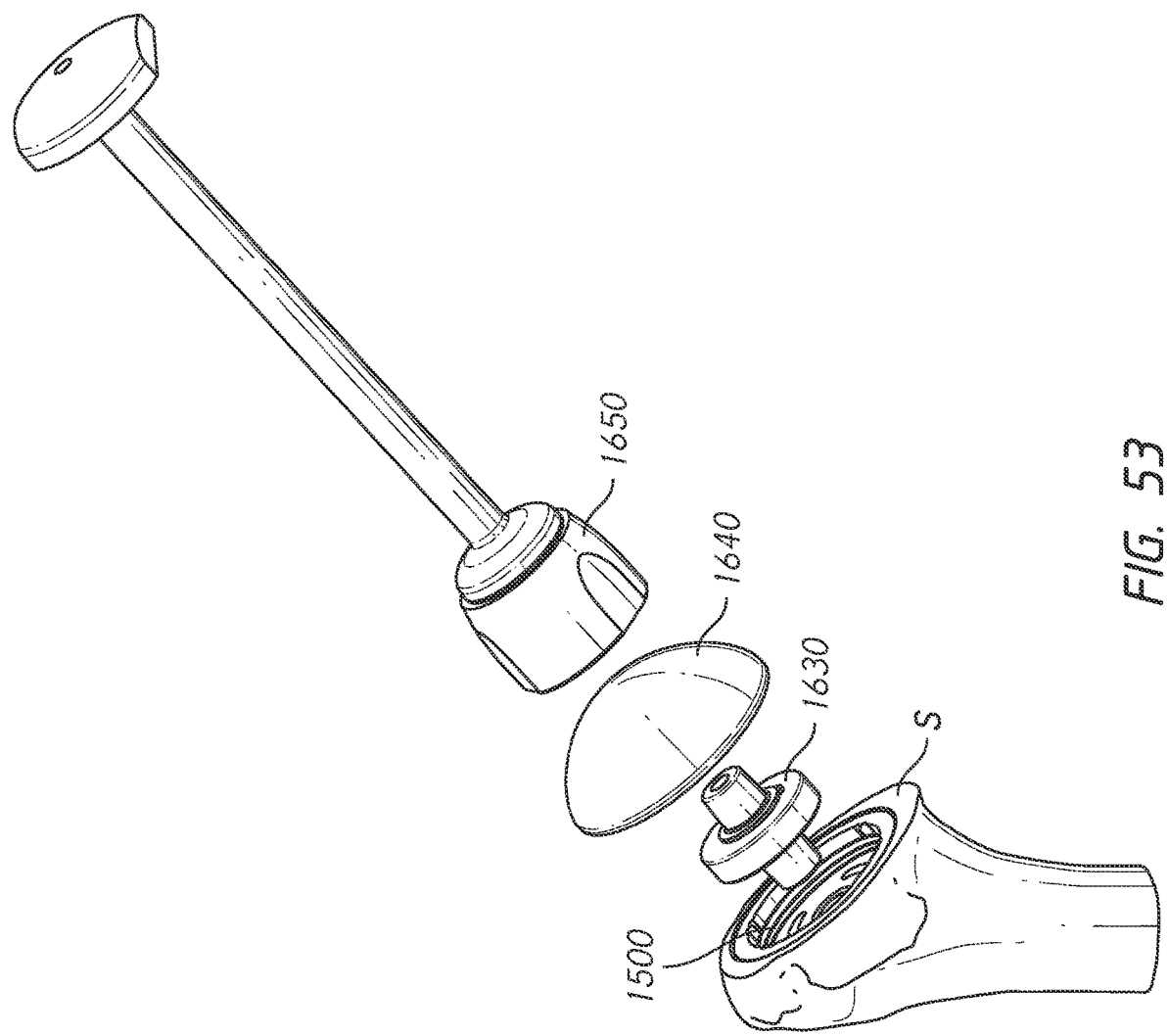
FIG. 53 shows an exploded view of the impacting of the components of the humeral head assembly into the inserted anchor in a surface of the resected humerus.

The method of assembling the humeral head assembly 800 can include impacting the components of the humeral head assembly 800 with either the anchor 830 or the anchor 830A illustrated in FIGS. 52A-52B. As illustrated in FIG. 53, the impactor 1650 can be configured to engage a coupler 1630 and an articular body 1440 with the inserted anchor. The coupler 1630 can be any of the couplers 924a, 924b, 924c. The coupler 1630 can include any of the couplers of FIGS. 19-20A. The coupler that is selected is based on the anatomy of the patient. In some embodiments, depending on the patient's anatomy, if a centered non-eccentric configuration is required, the coupler 924a can be selected to provide a first configuration 922a. In some examples, if a low eccentric configuration is required, the coupler 924b can be selected to provide a second configuration 922b. In some embodiments, if a high eccentric configuration is required, the coupler 924c can be selected to provide a third configuration 922c. As discussed above, as the inserted anchor 830, 830A has a receiving portion that is below surface S of the resected humerus, the impactor 1650 can impact the components of the humeral head assembly 800 such that the articular body 804, 904 is flush against the surface S of the resected humerus.

In another embodiment, the coupler 924a, 924b, 924c, can be impacted into the articular body 1640 on a back-table, e.g., in the operating room but not on the patient.

Prior to impacting the articular body 904, a first portion (any of the first portions 928a, 928b, 928c) is inserted into the second recess 916. A first alignment feature (e.g., any of the radial protrusion 944a, 944b, 944c) can be aligned with a second alignment feature (e.g., any of the notch 920). In aligning the first and second alignment features, the relative position of indicia (see FIG. 16A) on the body 904 can be used to provide proper positioning.

In another example, the method of assembling the humeral head assembly can involve impacting a coupler with the anchor first before impacting the articular body with the coupler. For example, as discussed above with regard to FIGS. 18-20A, the eccentricity of any one of the couplers 1424a, 1424b, 1424c can be adjusted relative to the humeral anchor 1500 before the articular body 1404 is attached. As illustrated in FIG. 18A, prior to impacting the articular body 1404, a first portion 1428 of the coupler 1424 (any of the first portions 1428a, 1428b, 1428c of the couplers 1424a, 1424b, 1424c) is inserted into the second recess portion 1524 of the humeral anchor 1500. Before any of the couplers 1424a, 1424b, 1424c is secured to the humeral anchor 1500, a first alignment feature (e.g., the window 1444 on any of the couplers 1424b, 1424c) can be aligned with a second alignment feature (e.g., any of the indicia on the coupling portion 1532 on the proximal face 1504 of the collar 1506 of the humeral anchor 1500). In aligning the first and second alignment features (e.g., wherein the indicia on the coupling portion 1532 of the humeral anchor 1500 is shown in the window 1444 of the coupler 1424) the relative position of indicia (see FIG. 18A) on the coupling portion 1532 of the humeral anchor 1500 can be used to provide proper positioning.

The method of assembling the humeral head assembly 800 can also include removing humeral head assembly 800 from the anchor 830, 830A and inserting the reverse bearing assembly 800A such that the articular surfaces of the shoulder is reversed. Removing a humeral head assembly can include separating one or more of the couplers 924a, 924b, and 924c from a corresponding articular body or anchor 500, 830, 830A. For example, as illustrated in FIGS. 17C, each of the couplers 924a, 924b, 924c includes a threaded channel 956. As discussed above, the threaded channel 956 can be configured to receive and/or threadingly engage a tool (e.g., a rod) or in some cases a tool similar to the coupler separator 1800 discussed below such that a load can be applied to disassemble the coupler 924a, 924b, 924c from the anchor 830, 830a. In some embodiments, the articular body 904 can first be removed from the coupler 924 (e.g., one of the couplers 924a, 924b, 924c). Once the articular body 904 is removed, a first end of the tool (e.g., a threaded rod as in the coupler separator 1800) can be inserted into the threaded channel 956 from a top surface of the disc member 932a, 932b, 932c such that the tool is advanced in a proximal to distal direction (e.g., from the first portion 928a, 928b, 928c towards the second portion 936a, 936b, 936c). In some embodiments, the tool is rotated to advance through the threaded channel 956 such that the tool emerges from a bottom surface of the disc member 932a, 932b, 932c. As the tool emerges from the bottom surface of the disc member 932a, 932b, 932c, an end of the tool engages the anchor 500, 830, 830a and additional rotation of the tool applies a load against a surface of the anchor 500, 830, 830a to disengage the coupler 924 (e.g., one of coupler 924a, 924b, 924c) from the anchor 500, 830, 830a. In other embodiments, the coupler 924 (e.g., one of the couplers 924a, 924b, 924c) with the attached articular body 904 can be first separated from the anchor 830, 830a. Once the anchor 500, 830, 830a is removed, a first end of the tool (e.g., a threaded rod) can be inserted into the threaded channel 956 from a bottom surface of the disc member 932a, 932b, 932c such that the tool is advanced in a distal to proximal direction (e.g., from the second portion 936a, 936b, 936c towards the first portion 928a, 928b, 928c). In some embodiments, the tool is rotated to advance through the threaded channel 956 such that the tool emerges from a top surface of the disc member 932a, 932b, 932c. As the tool emerges from the top surface of the disc member 932a, 932b, 932c, an end of the tool engages the lateral side of the articular body 904 to disengage the coupler 924 (e.g., one of coupler 924a, 924b, 924c) from the articular body 904. Alternatively, the method of assembling the humeral head assembly 800 can include removing the reverse articular body 804A from the anchor 830, 830A and inserting the humeral head assembly 800 to provide an anatomic configuration.

FIGS. 54-57C illustrates another embodiment of the method of removing the humeral head system 1400 from the humeral anchor 1500. As discussed above with regard to the humeral head assembly 800, removal of the humeral head system 1400 from the humeral anchor 1500 can either involve first disengaging one of the couplers 1424a, 1424b, 1424c from the humeral anchor 1500 or first disengaging one of the couplers 1424a, 1424b, 1424c from the articular body 1404. FIGS. 55A-55B illustrates an embodiment wherein the articular body 1404 is first removed from one of the couplers 1424a, 1424b, 1424c. FIGS. 57A-57C illustrates wherein one of the couplers 1424a, 1424b, 1424c is then removed from the humeral anchor 1500.

FIG. 54 illustrates a prying tool 1700 that can be configured to remove the articular body 1404 of the humeral head system 1400 from the attached coupler 1424. For the purposes of this discussion, reference to the coupler 1424 can refer to any one of couplers 924a, 924b, 924c. The prying tool 1700 can include a distal end 1710 and a proximal end 1720. In some examples, the proximal end 1710 of the prying tool 1700 forms a wedge portion 1730 that is attached to a distal end of a shaft 1740. In some embodiments, the wedge portion 1730 at the distal end 1710 of the prying tool 1700 can include an opening 1732 between a plurality of arms 1734. As illustrated in FIG. 54, the opening 1732 can form a "u-shape," although the opening 1732 and the plurality of arms 1734 can form any shape that can receive and engage with the disc member 1432 and ledge 1442 of the coupler 1424. In some examples, the wedge portion 1730 has a thickness that increases as the wedge portion 1730 extends from the distal end 1710 toward the proximal end 1720. As will be discussed in more detail below, the increasing thickness of the wedge portion 1730 (e.g., resulting in an inclined plane on a top surface of the wedge portion 1730) provides a mechanical advantage by reducing the force required to be applied to the end opposite the wedge portion 1730 to separate the articular body 1404 from the coupler 1424. In some embodiments, the wedge portion 1730 has a triangular cross-section. Furthermore, the shape of the wedge portion 1730 can allow the distal end 1710 of the wedge portion 1730 to fit between the ledge 1442 of the coupler 1424 and the humeral anchor 1500.

Figure 55A:
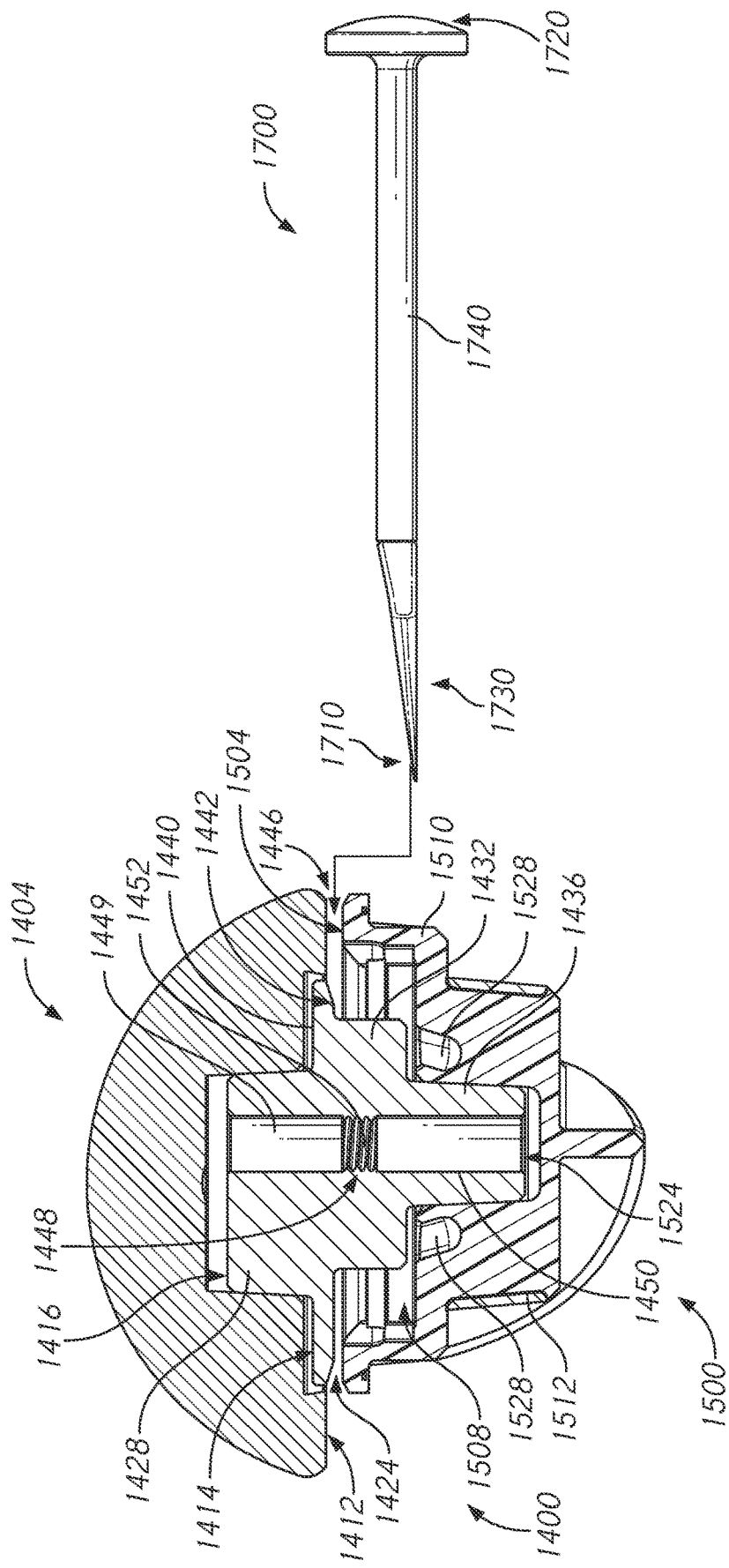
FIGS. 55A-55B illustrate a method of using the prying tool of FIG. 54 to separate components of the humeral head assembly of FIG. 18.
Figure 55B:
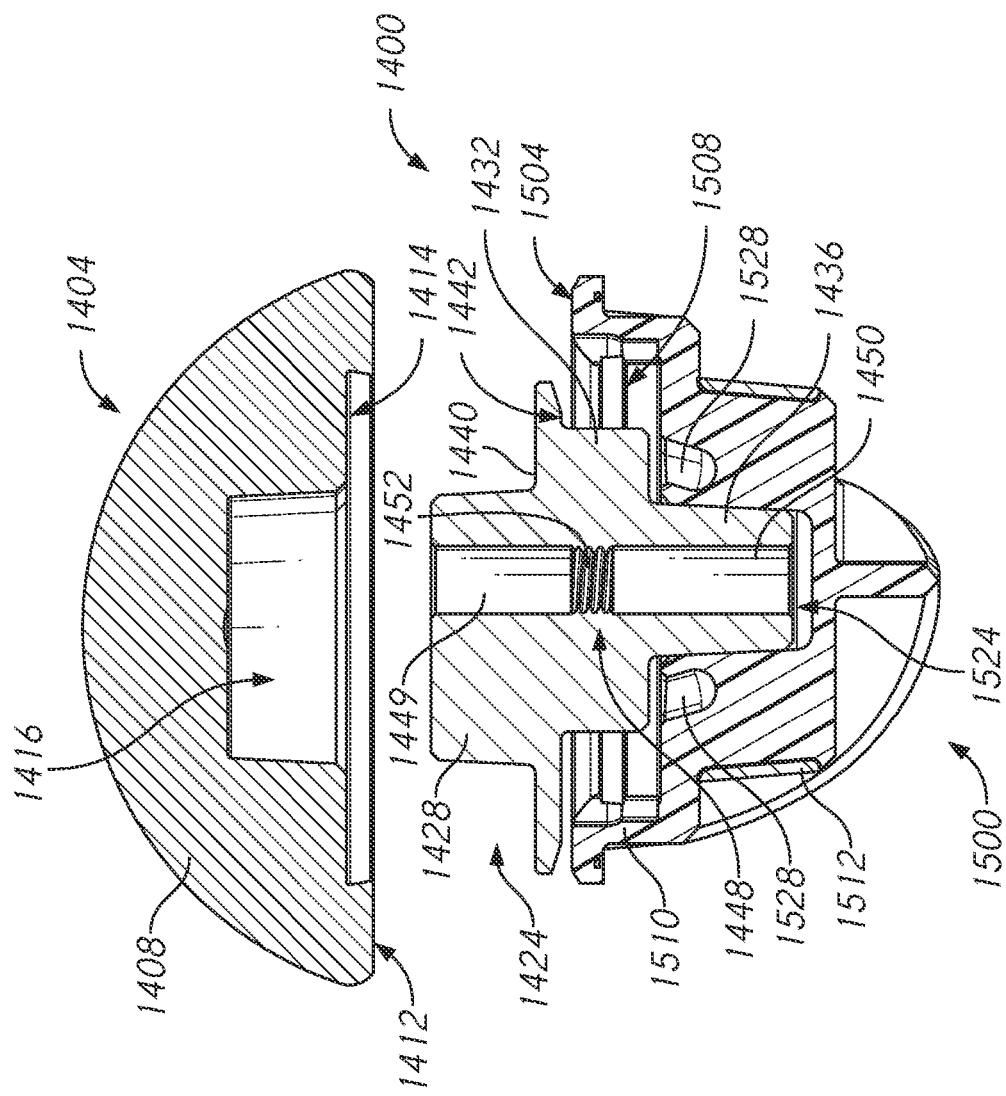

FIGS. 55A-55B illustrate a cross-sectional view of the humeral head system 1400 and the insertion of the prying tool 1700 to separate the articular body 1404 from the coupler 1424. As illustrated in FIG. 55A, the distal end 1710 of the wedge portion 1730 of the prying tool 1700 can be inserted into the gap 1446. As mentioned above, the triangular or wedge-shaped cross-section of the wedge portion 1730 separates the articular body 1404 from the coupler 1424 as the prying tool 1700 is advanced towards the coupler 1424. As the thicker portion of the wedge portion 1730 is advanced toward the coupler 1424, the articular body 1404 is pushed away from the proximal face 1504 of the collar 1506 to separate the articular body 1404 from the coupler 1424. In some embodiments, the angled ledge 1442 of the coupler 1424 can be configured to engage with and correspond the angled surface of the plurality of arms 1734 of the wedge portion 1730. In some examples, once the user advances the prying tool 1700 between the articular body 1404 and the humeral anchor 1500 using the shaft 1740 and engages the coupler 1424, the user can apply a load downward on the shaft 1740 to apply an upward force onto the articular body 1404 to separate the first portion 1428 of the articular body 1404 from the coupler 1424. As illustrated in FIG. 55B, in some embodiments, the articular body 1404 can be removed from the first portion 1428 of the coupler 1424 to expose the proximal end 1449 of the channel 1448 while the coupler 1424 remains in the anchor 1500.

Alternatively, in some embodiments, the prying tool 1700 can be configured to remove the coupler 1424 from the humeral anchor 1500. In some examples, the user can advance the prying tool 1700 between the articular body 1404 and the humeral anchor 1500 using the shaft 1740 to engage the 1424. Due to the wedge configuration the advancing of the wedge portion 1730 in the gap between the anchor 1500 and the prying ledge 1442 generates a medially oriented force that can separate the coupler 1424 from the anchor 1500. If needed, a user can then apply a load upward on the shaft 1740 to apply a downward force onto the articular body 1404 to generate more medially oriented force separate the coupler 1424 from the humeral anchor 1500. In some embodiments, the articular body 1404 can be removed from the second portion 1436 of the coupler 1424 to expose the distal end 1450 of the channel 1448. In some examples, this provides the user with the coupler 1424 attached to the humeral head system 1400 as shown in FIG. 18C.

Figure 56:
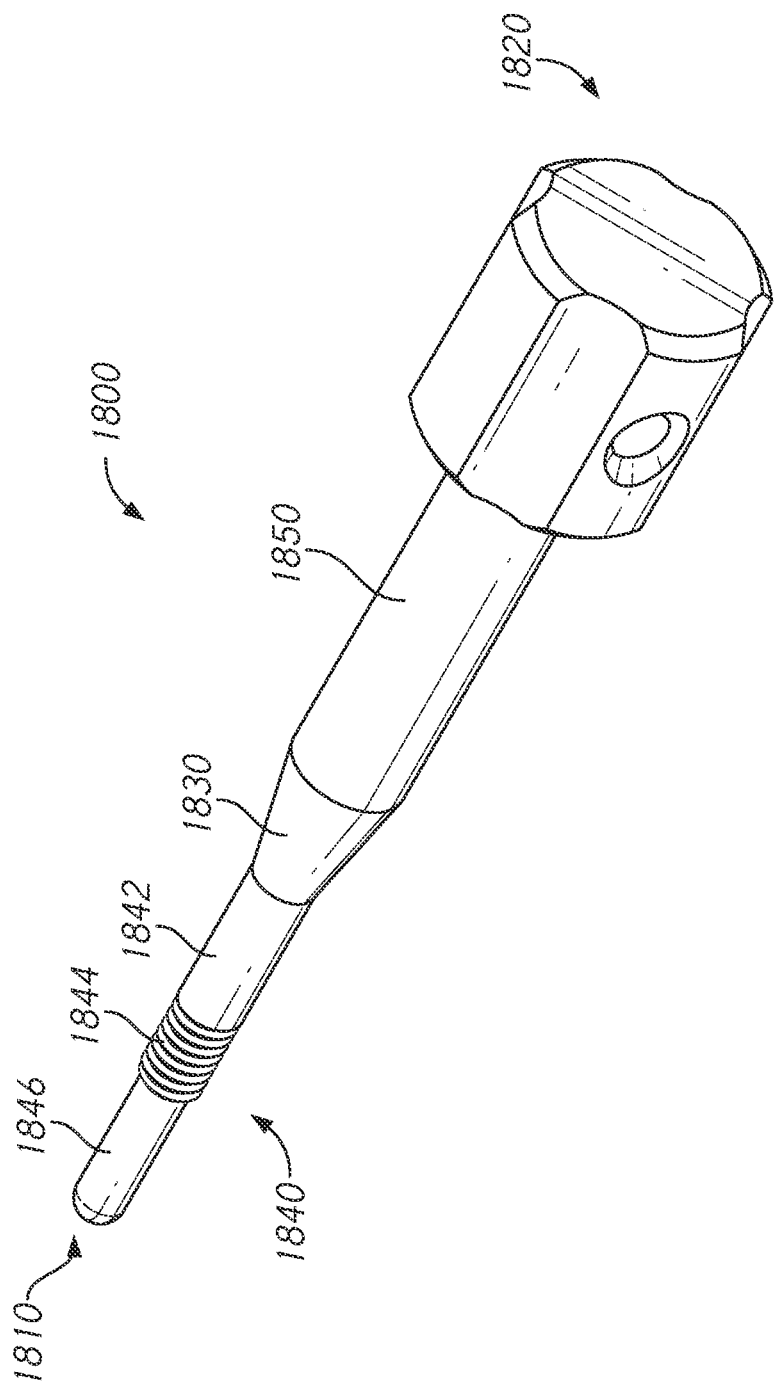
FIG. 56 shows a perspective view of a coupler separator for separating components of a humeral head assembly, for example, components of the humeral head assembly of FIG. 18.

FIG. 56 illustrates a coupler separator 1800 that can be configured to be inserted into the channel 1448 of the coupler 1424. For the purposes of this discussion, reference to the coupler 1424 can refer to any one of couplers 924a, 924b, 924c. The coupler separator 1800 can include a distal end 1810 and a proximal end 1820. In some examples, the coupler separator 1800 includes an elongate shaft 1840, a tapered portion 1830, and an actuation portion 1850. In some embodiments, the elongate shaft 1840 of the coupler separator 1800 is located at the distal end 1810 of the coupler separator 1800. The elongate shaft 1840 can include a distal portion 1846, a proximal portion 1842 and a threaded portion 1844 that extends between the distal portion 1846 and the proximal portion 1842. In some examples, the actuation portion 1850 of the coupler separator 1800 is located at the proximal end 1820 of the coupler separator 1800. As will be described in more detail below, the actuation portion 1850 can be grasped by a user to rotate the coupler separator 1800 to engage the threaded portion 1844 with the threaded portion 1452 of the channel 1448. In some embodiments, the tapered portion 1830 can extend between the elongate shaft 1840 and the actuation portion 1850. In some examples, the tapered portion 1830 can increase in diameter in a distal to distal direction.

FIGS. 57A-57C illustrate a cross-sectional view of the coupler 1424 attached to the humeral anchor 1500 and the insertion of the coupler separator 1800 to separate the coupler 1424 from the humeral anchor 1500. As illustrated in FIG. 57A, the distal end 1810 of the coupler separator 1800 can be inserted into the channel 1448. In some embodiments, the distal portion 1846 of the elongate shaft 1840 can be advanced through the proximal end 1449 and the threaded portion 1452 in a distal direction until the distal end of the threaded portion 1844 engages with the threaded portion 1452. In some examples, as the threaded portion 1844 engages with the threaded portion 1452, a user can rotate the actuation portion 1850 of the coupler separator 1800 such that the coupler separator 1800 rotates and causes the threaded portion 1844 to engage the threaded portion 1452. As the coupler separator 1800 is rotated, the coupler separator 1800 continues to advance the distal portion 1846 through the distal end 1450 towards the bottom of the second recess portion 1524. FIG. 57B shows the ends of the coupler separate 1800 and omits a central length thereof for clarity. The coupler separator 1800 can be rotated when in the position of FIG. 57B until a leading edge or portion of the threaded portion 1844 of the elongate shaft 1840 is advanced past the threaded portion 1452 of the channel 1448. When the leading portion of the threaded portion 1844 of the elongate shaft 1840 has been advanced past the threaded portion 1452 of the channel 1448, the distal end of the distal portion 1846 is engaged with the base of the second recess portion 1524, the proximal portion 1842 of the elongate shaft 1840 extends through the proximal end 1449 and a portion of the channel 1448, and a distal end of the tapered portion 1830 is advanced into a portion of the proximal end 1449. As the coupler separator 1800 is rotated such that a leading portion of the threaded portion 1844 moves past the channel 1448, the rotational force pushes the second portion 1436 of the coupler 1424 away from the second recess portion 1524. This can allow the coupler 1424 to separate from the humeral anchor 1500 such that the coupler 1424 can be removed from the humeral anchor 1500. As discussed above, in some embodiments the second recess portion 1524 is tapered. Therefore, movement of the second portion 1436 away from the base of the second recess portion 1524 can allow the coupler 1424 to be loosened from the humeral anchor 1500. In some embodiments, the tapered portion 1830 can limit how far the coupler separator 1800 is advanced through the channel 1448. As shown in FIG. 57C, once the second portion 1436 has been backed out of the second recess portion 1524, the coupler 1424 can be removed from the humeral anchor 1500.

Alternatively, in some embodiments wherein the humeral anchor 1500 is first removed from the coupler 1424 and the articular body 1404 remains attached from the coupler 1424, the distal end 1810 of the coupler separator 1800 can instead be inserted through the distal end 1450 of the channel 1448. In some embodiments, the distal end 1810 of the coupler separator 1800 can be inserted into the distal end 1450 of the channel 1448. In some examples, the distal portion 1846 of the elongate shaft 1840 can be advanced through the distal end 1450 and the threaded portion 1452 in a distal direction until the distal end of the threaded portion 1844 engages with the threaded portion 1452. In some embodiments, as the threaded portion 1844 engages with the threaded portion 1452, a user can rotate the actuation portion 1850 of the coupler separator 1800 such that the coupler separator 1800 rotates and causes the threaded portion 1844 to engage with the threaded portion 1452. As the coupler separator 1800 is rotated, the coupler separator 1800 continues to advance the distal portion 1846 through the proximal end 1449 towards a top or end wall of the second recess 1416 of the humeral head system 1400. In some embodiments, the coupler separator 1800 can be rotated until a leading portion of the threaded portion 1844 of the elongate shaft 1840 is advanced past the threaded portion 1452 of the channel 1448. As the threaded portion 1844 of the elongate shaft 1840 is advanced through or past the threaded portion 1452 of the channel 1448, the distal end of the distal portion 1846 is engaged with the top wall of the second recess 1416, the proximal portion 1842 of the elongate shaft 1840 extends through the distal end 1450 and a portion of the channel 1448, and a distal end of the tapered portion 1830 is advanced into a portion of the distal end 1450. As the coupler separator 1800 is rotated such that the threaded portion 1844 moves past the channel 1448, an axial force along the longitudinal axis of the channel 1448 pushes the first portion 1428 of the coupler 1424 away from the second recess 1416. This can allow the coupler 1424 to separate from the articular body 1404 such that the coupler 1424 can be removed from the articular body 1404. As discussed above, in some embodiments, the second recess 1416 is tapered. Therefore, movement of the first portion 1428 away from the top of the second recess 1416 can allow the first portion 1428 to be loosened from the humeral anchor 1500. In some examples, the tapered portion 1830 can limit how far the coupler separator 1800 is advanced through the channel 1448. As discussed with regard to FIG. 57C, once the first portion 1428 has been pushed out of the second recess 1416, the articular body 1404 can be removed from the coupler 1424.

In the past, commercial systems provided kits with multiple articular body/coupler combinations that were pre-assembled. Thus, the present application enables a wide range of patients to be treated with fewer components, simpler systems, and less cost.

Terminology

Although certain embodiments have been described herein, the implants and methods described herein can interchangeably use any articular component, as the context may dictate.

As used herein, the relative terms "proximal" and "distal" shall be defined from the perspective of the implant. Thus, proximal refers to the direction of the articular component and distal refers to the direction of an anchor component, such as a stem of a humeral anchor or a thread or porous surface or other anchoring structure of a stemless anchor when the implant is assembled.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "inserting a humeral stem into a humerus" include "instructing insertion of a humeral head into a humerus."

What is claimed is:

1. A humeral head system comprising:
    an articular body comprising a convex articular surface and a coupling portion, the coupling portion disposed on a side of the articular body opposite the convex articular surface;
    a coupler comprising a first portion configured to mate with the coupling portion and a second portion opposite the first portion, the second portion configured to mate with another member of a joint prosthesis;
        wherein the coupler is configured to provide a fixed rotational position between the articular body and the coupler to provide a selected degree of offset of the articular surface to the other member of the joint prosthesis, wherein the coupler comprises a threaded channel extending from a first end surface of the coupler to a second end surface of the coupler, the channel providing access to a surface of one or both of the articular body and the other member of the joint prosthesis, and wherein the threaded channel is configured to engage a tool to apply a load to the articular body;
        wherein the coupler comprises an offset window disposed between the first portion and the second portion of the coupler;
        wherein the coupler comprises a plate extending transverse to the second portion, the offset window comprising a slot formed in the plate configured to uncover indicia indicative of an extent of eccentricity of the articular body to the other member of the joint prosthesis; and
    a humeral anchor comprising the other member of the joint prosthesis, the humeral anchor comprising indicia of eccentricity, the slot uncovering different indicia in different rotational positions of the coupler to the humeral anchor, wherein the rotational positions are changed by rotation about a longitudinal axis extending through the second portion of the coupler.

2. The humeral head system of claim 1, wherein the threaded channel is formed through the first and second portions of the coupler.

3. The humeral head system of claim 1, wherein the coupler comprises a prying ledge comprising an angled surface disposed between the first portion and the second portion, the prying ledge responsive to a radial load being applied thereto to direct a longitudinal force along the longitudinal axis of the first portion or the second portion of the coupler.

4. The humeral head system of claim 3, wherein the prying ledge extends radially between a disc member of the coupler and a periphery of the coupler, the prying ledge being accessible from a periphery of the humeral head system when the humeral head system is fully assembled.

5. The humeral head system of claim 1, wherein the articular body comprises a recess comprising the coupling portion.

6. The humeral head system of claim 5, wherein the recess comprise a central axis that is offset from a central axis of the convex articular surface of the articular body.

7. The humeral head system of claim 5, wherein the recess comprises a tapered profile.

8. The humeral head system of claim 5, the first portion of the coupler comprises a projection configured to be mated with the recess.

9. The humeral head system of claim 8, wherein the projection is an axial projection and further comprising a radial protrusion, and the recess comprises at least one discrete position site that includes a radial notch, wherein the radial protrusion is configured to mate with the radial notch to define an amount of eccentricity adjustment.

10. The humeral head system of claim 9, wherein the coupling portion of the articular body comprises the radial notch.

11. The humeral head system of claim 1, wherein the coupler comprises a disc member having a first surface configured to mate with a recessed portion of the other member of a joint prosthesis and a second surface opposite the first surface configured to be disposed at or adjacent to an exposed surface of the other member.

12. The humeral head system of claim 1, further comprising at least one discrete position site disposed between the coupler and the convex articular surface, the discrete position site providing a fixed rotational position between the articular body and the coupler.

13. The humeral head system of claim 12, wherein the at least one discrete position site comprises a single radial notch for connection between the coupler and the articular body.

14. The humeral head system of claim 1, wherein the side of the articular body opposite the convex articular surface comprises indicia indicating orientation.

15. The humeral head system of claim 1, wherein the coupler comprises an annular projection disposed away from a surface of the coupler configured to face the side of the articular body opposite the convex articular surface, the annular projection being configured to engage a radial notch of the coupling portion at a single rotational orientation.

16. The humeral head system of claim 1, wherein the first portion of the coupler comprises a tapered protrusion that couples with the articular body by an interference fit.

17. The humeral head system of claim 1, wherein the second portion is tapered.

18. A kit comprising:
    the humeral head system of claim 1, wherein the coupler has a first offset between the first portion and the second portion; and
    the kit further comprises a second coupler that comprises a first portion configured to mate with the coupling portion of the articular body and a second portion configured to mate with the other member of the joint prosthesis, wherein the second coupler has a second offset between or no offset between the first portion and the second portion of the second coupler, the second offset being different from the first offset.

* * * * *